United States Patent
Rennie et al.

(10) Patent No.: US 11,180,493 B2
(45) Date of Patent: Nov. 23, 2021

(54) SGC STIMULATORS

(71) Applicant: Cyclerion Therapeutics, Inc., Cambridge, MA (US)

(72) Inventors: Glen Robert Rennie, Somerville, MA (US); Timothy Claude Barden, Salem, MA (US); Thomas Wai-Ho Lee, Lexington, MA (US); Rajesh R. Iyengar, West Newton, MA (US); Takashi Nakai, Newton, MA (US); Ara Mermerian, Waltham, MA (US); Lei Jia, Belmont, MA (US); Karthik Iyer, Cambridge, MA (US); G-Yoon Jamie Im, Cambridge, MA (US); Paul Allan Renhowe, Sudbury, MA (US); Joon Jung, Newton, MA (US); Peter Germano, Newton, MA (US); Kim Tang, Belmont, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/348,377

(22) PCT Filed: Nov. 7, 2017

(86) PCT No.: PCT/US2017/060305
§ 371 (c)(1),
(2) Date: May 8, 2019

(87) PCT Pub. No.: WO2018/089330
PCT Pub. Date: May 17, 2018

(65) Prior Publication Data
US 2020/0071318 A1    Mar. 5, 2020

Related U.S. Application Data

(60) Provisional application No. 62/419,086, filed on Nov. 8, 2016.

(51) Int. Cl.
*C07D 471/04* (2006.01)
*C07D 403/04* (2006.01)
*C07D 403/14* (2006.01)
*C07D 487/04* (2006.01)

(52) U.S. Cl.
CPC ......... *C07D 471/04* (2013.01); *C07D 403/04* (2013.01); *C07D 403/14* (2013.01); *C07D 487/04* (2013.01)

(58) Field of Classification Search
CPC .. C07D 471/04; C07D 403/14; C07D 487/04; A61K 31/437; A61K 31/416; A61K 31/5025; A61K 31/4985
USPC ........... 514/248, 249, 259.3, 300, 303, 406; 544/236, 281, 350, 333; 546/121, 119; 548/362.5
See application file for complete search history.

(56) References Cited

U.S. PATENT DOCUMENTS 6,833,364 B1  12/2004 Straub et al.
2010/0004235 A1  1/2010 Schirok et al.

FOREIGN PATENT DOCUMENTS

| CN | 1317005 A | 10/2001 | |
|---|---|---|---|
| CN | 1665811 A | 9/2005 | |
| CN | 105408328 A | 3/2016 | |
| CN | 105764893 A | 7/2016 | |
| WO | 2000/006569 A1 | 2/2000 | |
| WO | 2003/095451 A1 | 11/2003 | |
| WO | 2007/124854 A1 | 11/2007 | |
| WO | 2014/144100 A2 | 9/2014 | |
| WO | 2015/063003 A1 | 5/2015 | |
| WO | 2017108441 A1 | 6/2017 | |
| WO | WO207/106175 | * 6/2017 | ........... C07D 487/04 |
| WO | 2017/121700 A1 | 7/2017 | |

OTHER PUBLICATIONS

Purohit et al., YC-1 binding to the beta subunit of soluble guanylyl cyclase overcomes allosteric inhibition by the a subunit. Biochemistry. Jan. 14, 2014;53(1):101-14.
Roberts et al., Acidic triazoles as soluble guanylate cyclase stimulators. Bioorg Med Chem Lett. Nov. 1, 2011;21(21):6515-8.
International Search Report and Written Opinion for Application No. PCT/US2017/060305, dated Jun. 7, 2018, 15 pages.
Griebenow et al., Identification of acidic heterocycle-substituted 1 H-pyrazolo[3,4-b]pyridines as soluble guanylate cyclase stimulators. Bioorg Med Chem Lett. Mar. 1, 2013; 23(5):1197-200.
Chinese Office Action for Application No. 201780081092.2, dated Aug. 13, 2021, 20 pages.

* cited by examiner

*Primary Examiner* — Jeffrey H Murray
(74) *Attorney, Agent, or Firm* — McCarter & English, LLP; Steven G. Davis; Xin Zhang

(57) ABSTRACT

The present disclosure relates to stimulators of soluble guanylate cyclase (sGC), pharmaceutical formulations comprising them and their uses thereof, alone or in combination with one or more additional agents, for treating various diseases, wherein an increase in the concentration of nitric oxide (NO) and/or an increase in the concentration of cyclic Guanosine Monophosphate (cGMP) might be desirable. Various compounds are disclosed, including those of Formula (I).

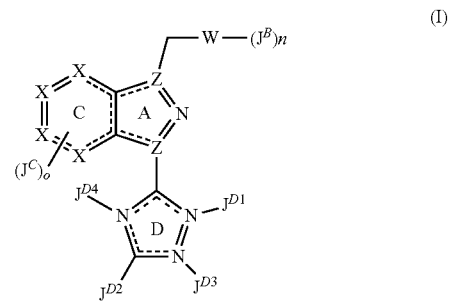

10 Claims, No Drawings

SGC STIMULATORS

RELATED APPLICATIONS

This application is a 35 U.S.C. § 371 national stage filing of International Application No. PCT/US2017/060305, filed Nov. 7, 2017, which claims the benefit of the filing date, under 35 U.S.C. § 119(e), of U.S. Provisional Application No. 62/419,086, filed Nov. 8, 2016. The entire contents of each of the foregoing applications are incorporated herein by reference.

FIELD OF THE INVENTION

The present disclosure relates to stimulators of soluble guanylate cyclase (sGC), pharmaceutical formulations comprising them and their uses thereof, alone or in combination with one or more additional agents, for treating various diseases, wherein an increase in the concentration of nitric oxide (NO) or an increase in the concentration of cyclic Guanosine 3',5'-Monophosphate (cGMP) or both, or an upregulation of the NO pathway is desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts guanosine 5'-triphosphate (GTP) into the secondary messenger cyclic guanosine 3',5'-monophosphate (cGMP). The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure. Experimental and clinical evidence indicates that reduced concentrations, bioavailability and/or responsiveness to endogenously produced NO contributes to the development of a number diseases.

NO-independent, heme-dependent, sGC stimulators, have several important differentiating characteristics, when compared to other types of sGC modulators, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed.

Compounds that stimulate sGC in an NO-independent manner offer considerable advantages over other current alternative therapies that either target the aberrant NO pathway or that may otherwise benefit from the upregulation of the NO pathway. There is a need to develop novel stimulators of sGC. These compounds are useful for treating various diseases, wherein the diseases or disorders are ones that benefit from sGC stimulation or from an increase in the concentration of NO or cGMP or both, or wherein an upregulation of the NO pathway is desirable.

sGC stimulators that can cross the blood-brain barrier and penetrate the brain provide additional benefits for the treatment of diseases of the central nervous system (CNS). sGC stimulators with the physicochemical properties necessary to cross the blood brain barrier have not been previously described. Compounds of the invention are useful for the treatment of diseases of the CNS due to their ability to cross the blood-brain barrier.

SUMMARY OF THE INVENTION

The present invention is directed to compounds of Formula I, or pharmaceutically acceptable salts thereof,

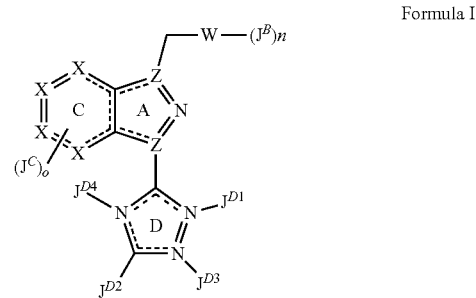

Formula I wherein:
rings A and C constitute the core of the molecule; rings A and D are heteroaryl rings; ring C may be a phenyl or a heteroaryl ring; each bond in these rings is either a single or a double bond depending on the substituents, so that each of said rings has aromatic character;
one instance of Z on ring A is N and the other instance of Z is C;
each instance of X on ring C is independently selected from C or N; wherein 0, 1 or 2 instances of X can simultaneously be N;
o is an integer selected from 2, 3 or 4;
each $J^C$ is a substituent on a carbon atom independently selected from hydrogen, halogen, —CN, $C_{1-4}$ aliphatic, $C_{1-4}$ haloalkyl or $C_{1-4}$ alkoxy;
W is either:
  i) absent, and $J^B$ is connected directly to the methylene group linked to the core; n is 1; and $J^B$ is a $C_{1-7}$ alkyl chain optionally substituted by up to 9 instances of fluorine; or
  ii) a ring B selected from phenyl or a 5 or 6-membered heteroaryl ring, containing 1 or 2 ring heteroatoms independently selected from N, O or S; wherein when W is ring B, n is 0 or an integer selected from 1, 2 or 3;
each $J^B$ is independently selected from halogen, —CN, a $C_{1-6}$ aliphatic, —$OR^B$ or a $C_{3-8}$ cycloaliphatic ring; wherein each said $C_{1-6}$ aliphatic and each said $C_{3-8}$ cycloaliphatic ring is optionally and independently substituted with up to 3 instances of $R^3$;
each $R^B$ is independently selected from a methyl, propyl, butyl, isopropyl, isobutyl or a $C_{3-8}$ cycloaliphatic ring; wherein each of said $R^B$ is optionally and independently substituted with up to 3 instances of $R^{3a}$;
each $R^3$ and each $R^{3a}$ is independently selected in each instance from halogen, —CN, $C_{1-4}$ alkyl, $C_{1-4}$ haloalkyl, —O($C_{1-4}$ alkyl) or —O($C_{1-4}$ haloalkyl);

$J^{D1}$ and $J^{D4}$ are independently selected from a lone pair on the nitrogen atom to which they are attached or hydrogen, wherein $J^{D1}$ and $J^{D4}$ are not both simultaneously hydrogen or both simultaneously a lone pair;

$J^{D3}$ is either a lone pair on the nitrogen atom to which it is attached, hydrogen, or a substituent selected from —C(O)$R^D$, a $C_{1-6}$ aliphatic, —($C_{1-6}$ aliphatic)-$R^D$, a $C_{3-8}$ cycloaliphatic ring, a phenyl ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^D$ moiety, said $C_{3-8}$ cycloaliphatic ring, said 4 to 8-membered heterocyclic ring, and said 5 or 6-membered heteroaryl ring is optionally and independently substituted with up to 5 instances of $R^5$; and wherein said phenyl ring is optionally and independently substituted with up to 5 instances of $R^{5a}$;

$J^{D1}$ and $J^{D3}$ cannot both simultaneously be hydrogen;

$J^{D2}$ is hydrogen, or a substituent selected from halogen, —CN, —NO$_2$, —OR$^{D1}$, —C(O)R$^D$, —C(O)N(R$^D$)$_2$, —N(R$^D$)$_2$, —N(R$^D$)C(O)R$^D$, —N(R$^D$)C(O)OR$^D$, —N(R$^D$)C(O)N(R$^D$)$_2$, —OC(O)N(R$^D$)$_2$, a $C_{1-6}$ aliphatic, —($C_{1-6}$ aliphatic)-R$^D$, a $C_{3-8}$ cycloaliphatic ring, a phenyl ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-R$^D$ moiety, said $C_{3-8}$ cycloaliphatic ring, said 4 to 8-membered heterocyclic ring and said 5 or 6-membered heteroaryl ring is optionally and independently substituted with up to 5 instances of $R^5$; and wherein said phenyl ring is optionally and independently substituted with up to 5 instances of $R^{5a}$;

each $R^D$ is independently selected from hydrogen, a $C_{1-6}$ aliphatic, —($C_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-R$^f$ moiety, each said $C_{3-8}$ cycloaliphatic ring, each said 4 to 8-membered heterocyclic ring and each said 5 to 6-membered heteroaryl ring is optionally and independently substituted with up to 5 instances of $R^5$; and wherein each said phenyl ring is optionally and independently substituted with up to 5 instances of $R^{5a}$;

$R^{D1}$ is selected from a $C_{1-6}$ aliphatic, —($C_{1-6}$ aliphatic)-R$^f$, a $C_{3-8}$ cycloaliphatic ring, a 4 to 8-membered heterocyclic ring, a phenyl ring or a 5 to 6-membered heteroaryl ring; wherein said 4 to 8-membered heterocyclic ring and said 5 to 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-R$^f$ moiety, said $C_{3-8}$ cycloaliphatic ring, said 4 to 8-membered heterocyclic ring and said 5 to 6-membered heteroaryl ring is optionally and independently substituted with up to 5 instances of $R^5$; wherein said phenyl ring is optionally and independently substituted with up to 5 instances of $R^{5a}$;

each R$^f$ is independently selected from a a $C_{3-8}$ cycloaliphatic ring, a 4 to 8-membered heterocyclic ring, a phenyl ring or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{3-8}$ cycloaliphatic ring, each said 4 to 8-membered heterocyclic ring and each said 5 to 6-membered heteroaryl ring is optionally and independently substituted by up to 5 instances of $R^5$; and wherein each said phenyl is optionally and independently substituted by up to 5 instances of $R^{5a}$;

each $R^5$ is independently selected from halogen, —CN, $C_{1-6}$ aliphatic, —($C_{1-6}$ alkyl)-R$^6$, —OR$^6$, —COR$_6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, a $C_{3-8}$ cycloalkyl ring, a 4 to 8-membered heterocyclic ring, a 5 or 6-membered heteroaryl ring, phenyl, benzyl or an oxo group; wherein if two instances of $R^5$ are oxo and —OH or oxo and —OR$^6$, they are not substituents on the same carbon atom; wherein each of said 5 or 6-membered heteroaryl ring or 4 to 8-membered heterocyclic ring contains up to 3 ring heteroatoms independently selected from N, O and S; and wherein each of said $C_{1-6}$ aliphatic, each said $C_{1-6}$ alkyl portion of the —($C_{1-6}$ alkyl)-R$^6$ moiety, each said $C_{3-8}$ cycloalkyl ring, each said 5 or 6-membered heteroaryl ring and each said 4 to 8-membered heterocyclic ring, is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —CONH$_2$, —O($C_{1-4}$ alkyl), —O($C_{1-4}$ haloalkyl) or oxo; wherein if two instances of a substituent on $R^5$ are a) oxo and —OH or b) oxo and —O($C_{1-4}$ alkyl) or c) oxo and —O($C_{1-4}$ haloalkyl), they are not substituents on the same carbon atom; wherein each said benzyl or phenyl is optionally and independently substituted with up to 3 instances of halogen, $C_{1-4}$ alkyl, —NH$_2$, —NH($C_{1-4}$ alkyl), —N($C_{1-4}$ alkyl)$_2$, —CN, —CONH$_2$, —O($C_{1-4}$ alkyl), —O($C_{1-4}$ haloalkyl);

each $R^{5a}$ is independently selected from halogen, —CN, $C_{1-6}$ aliphatic, —($C_{1-6}$ alkyl)-R$^6$, —OR$^{6a}$, —COR$_6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, a $C_{3-8}$ cycloalkyl ring, a 4 to 8-membered heterocyclic ring, a 5 or 6-membered heteroaryl ring, phenyl, benzyl or an oxo group; wherein each of said 5 or 6-membered heteroaryl ring and each of said 4 to 8-membered heterocyclic ring contains up to 3 ring heteroatoms independently selected from N, O and S; and wherein each of said $C_{1-6}$ aliphatic, each of said $C_{1-6}$ alkyl portion of the —($C_{1-6}$ alkyl)R$^6$ moiety, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —CONH$_2$, —O($C_{1-4}$ alkyl), —O($C_{1-4}$ haloalkyl) or oxo; wherein if two instances of a substituent on $R^{5a}$ are a) oxo and —OH or b) oxo and —O($C_{1-4}$ alkyl) or c) oxo and —O($C_{1-4}$ haloalkyl), they are not substituents on the same carbon atom; and wherein each of said benzyl and each of said phenyl is optionally and independently substituted with up to 3 instances of halogen, $C_{1-4}$ alkyl, $C_{1-4}$ haloalkyl —NH$_2$, —NH($C_{1-4}$ alkyl), —N($C_{1-4}$ alkyl)$_2$, —CN, —CONH$_2$, —O($C_{1-4}$ alkyl) or —O($C_{1-4}$ haloalkyl);

each $R^6$ is independently selected from hydrogen, a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring or 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo; wherein if two instances of a substituent on $R^6$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, $C_{1-4}$ haloalkyl, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo;

each $R^{6a}$ is independently selected from a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring and each of said 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo; wherein if two instances of $R^{6a}$ are a) oxo and —OH or b) oxo and —O($C_{1-4}$ alkyl) or c) oxo and —O($C_{1-4}$ haloalkyl), they are not substituents on the same carbon atom; wherein each of said phenyl now abandoned each of said benzyl is optionally and independently substituted with up to 3 instances of halogen, $C_{1-4}$ alkyl, $C_{1-4}$ haloalkyl, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo;

alternatively, $J^{D2}$ and $J^{D3}$, together with the atoms to which they are attached, form a 5 or 6-membered heteroaryl ring or a 5 to 8-membered heterocyclic ring; wherein said heteroaryl ring or heterocyclic ring contains between 1 and 3 heteroatoms independently selected from N, O or S, including the N to which $J^{D3}$ is attached; wherein said heterocyclic or heteroaryl ring can be substituted by up to three instances of $J^E$; and $J^E$ is selected from halogen, $C_{1-4}$ alkyl, $C_{1-4}$ haloalkyl or oxo; provided the compound is not one of the two depicted below, or any of their tautomeric forms:

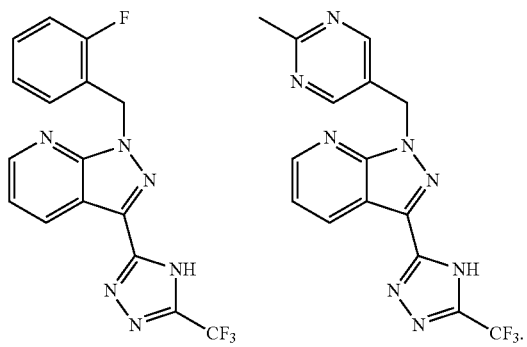 [SMILES: Fc1ccccc1Cn1nc(-c2nnc(C(F)(F)F)[nH]2)c2cccnc21 ; Cc1ncc(Cn2nc(-c3nnc(C(F)(F)F)[nH]3)c3cccnc32)cn1]

The invention is also directed to compounds of Formula I depicted in Table IA and their pharmaceutically acceptable salts thereof. The invention is also directed to compounds depicted in Table IB and their pharmaceutically acceptable salts thereof.

The invention is also directed to a pharmaceutical composition comprising a compound according to Formula I, Table IA or Table IB, or a pharmaceutically acceptable salt thereof, and at least one pharmaceutically acceptable excipient or carrier. The invention is also directed to a pharmaceutical dosage form comprising the pharmaceutical composition.

The invention also provides a method of treating or preventing a disease, health condition or disorder in a subject in need thereof, comprising administering, alone or in combination therapy, a therapeutically effective amount of a compound of Formula I, a compound from Table IA or a compound from Table IB, or a pharmaceutically acceptable salt thereof to the subject; wherein the disease is one that benefits from sGC stimulation or from an increase in the concentration of NO or cGMP or both, or from the upregulation of the NO pathway.

The invention also provides a method of treating or preventing a disease, health condition or disorder in a subject in need thereof, comprising administering, alone or in combination therapy, a pharmaceutical composition comprising a compound of Formula I, a compound of Table IA or a compound of Table IB, or a pharmaceutically acceptable salt thereof, or a dosage form comprising the pharmaceutical composition to the subject, wherein the disease is one that benefits from sGC stimulation or from an increase in the concentration of NO or cGMP or both, or from the upregulation of the NO pathway.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula I, Table IA or Table IB may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. As will be apparent to one of ordinary skill in the art, moieties such as —H, halogen, —$NO_2$, —CN, —OH, —$NH_2$ or —$OCF_3$ would not be substitutable groups. An alkyl chain, or a ring are non-limiting examples of substitutable moieties.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

A compound, such as the compounds of Formula I or Table IA or Table IB or other compounds herein disclosed, may be present in its free form (e.g., an amorphous form, or a crystalline form or a polymorph). Under certain conditions, compounds may also form co-forms. As used herein, the term co-form is synonymous with the term multi-component crystalline form. The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group" or "aliphatic chain", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 or 1-2 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. An aliphatic group will be represented by the term "$C_{x-y}$ aliphatic"; wherein x and y are the minimum and the maximum number of carbon atoms forming the aliphatic chain. The term "alkyl" (as in "alkyl chain" or "alkyl group"), as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like. An alkyl group will be represented by the term "$C_{x-y}$ alkyl"; wherein x and y are the minimum and the maximum number of carbon atoms forming the alkyl chain.

The term "alkenyl" (as in "alkenyl chain" or "alkenyl group"), refers to a linear or branched-chain monovalent hydrocarbon radical with at least one site of unsaturation, i.e., a carbon-carbon, $sp^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like. An alkenyl group will be represented by the term "$C_{x-y}$ alkenyl"; wherein x and y are the minimum and the maximum number of carbon atoms forming the alkenyl chain.

The term "alkynyl" (as in "alkynyl chain" or "alkynyl group"), refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like. An alkynyl group will be represented by the term "$C_{x-y}$ alkynyl"; wherein x and y are the minimum and the maximum number of carbon atoms forming the alkynyl chain.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term could be used in the phrase "aromatic carbocycle", and in this case it would refer to an "aryl group" as defined below.

The term "cycloaliphatic" (or "non-aromatic carbocycle", "non-aromatic carbocyclyl", "non-aromatic carbocyclic" or "cycloaliphatic ring") refers to a cyclic hydrocarbon that is completely saturated or that contains one or more units of unsaturation but which is not aromatic, and which has a single point of attachment to the rest of the molecule. In one embodiment, the term "cycloaliphatic" refers to a monocyclic $C_{3-12}$ hydrocarbon. A cycloaliphatic ring will be represented by the term "$C_{x-y}$ cycloaliphatic"; wherein x and y are the minimum and the maximum number of carbon atoms forming the cycloaliphatic ring. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

"Cycloalkyl" or "cycloalkyl ring", as used herein, refers to a ring system which is completely saturated and which has a single point of attachment to the rest of the molecule.

In one embodiment, the term "cycloalkyl" refers to a monocyclic $C_{3-12}$ saturated hydrocarbon. Suitable cycloalkyl groups include, but are not limited to, cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like. A cycloalkyl ring will be represented by the term "$C_{x-y}$ cycloalkyl"; wherein x and y are the minimum and the maximum number of carbon atoms forming the cycloalkyl ring.

"Heterocycle" (or "heterocyclyl" or "heterocyclic or "heterocyclic ring"), as used herein, refers to a ring system in which one or more ring members is an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term could be used in the phrase "aromatic heterocycle", and in this case it would refer to a "heteroaryl group" as defined below. In some embodiments, the heterocycle has 3-10 ring members in which one or more ring members is a heteroatom independently selected from oxygen, nitrogen or sulfur. In other embodiments, a heterocycle may be a monocycle having 3-7 ring members (2-6 carbon atoms and 1-4 heteroatoms).

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl.

The term "heteroaryl" (or "heteroaromatic" or "heteroaryl group" or "aromatic heterocycle" or "heteroaryl ring") used alone or as part of a larger moiety as in "heteroaralkyl" or "heteroarylalkoxy" refers to a ring which is aromatic and contains one or more heteroatoms, has between 5 and 6 ring members and which has a single point of attachment to the rest of the molecule. Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl.

The term "ring atom" refers to an atom such as C, N, O or S that is part of the ring of an aromatic ring, a cycloaliphatic ring, a cycloalkyl ring, a heterocyclic ring or a heteroaryl ring. A "substitutable ring atom" is a ring carbon or nitrogen atom bonded to at least one hydrogen atom. The hydrogen can be optionally replaced with a suitable substituent group.

Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, including any oxidized form of nitrogen or sulfur, the quaternized form of any basic nitrogen, or a substitutable nitrogen of a heterocyclic or heteroaryl ring, for example N (as in 3,4-dihydro-2H-pyrrolyl), NH (as in pyrrolidinyl) or $NR^+$ (as in N-substituted pyrrolidinyl).

In some embodiments, two independent occurrences of a variable may be taken together with the atom(s) to which each variable is bound to form a 5-8-membered aryl or heteroaryl ring or a 3-8-membered cycloaliphatic ring or heterocyclyl. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule.

It will be appreciated that a variety of other rings can be formed when two independent occurrences of a substituent are taken together with the atom(s) to which each substituent is bound and that the examples detailed above are not intended to be limiting.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

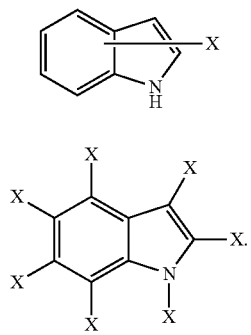

This also applies to multiple ring systems fused to optional ring systems (which would be represented by dotted lines). For example, in Formula D5, X is an optional substituent both for ring A and ring B.

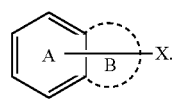

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

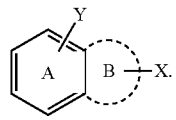

As used herein, the term "alkoxy" refers to an alkyl group, as previously defined, attached to the molecule, or to another chain or ring, through an oxygen ("alkoxy" i.e., —O-alkyl) atom.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH$_2$CHF$_2$ and a $C_{1-2}$ haloalkoxy could be —OC(Br) HCHF$_2$. This term includes perfluorinated alkyl groups, such as —CF$_3$ and —CF$_2$CF$_3$.

As used herein, the term "cyano" refers to —CN or —C≡N.

As used herein, an "amino" group refers to —NH$_2$.

The term "hydroxyl" or "hydroxy" refers to —OH.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$. When an "oxo' group is listed as a possible substituent on a ring or another moiety or group (e.g. an alkyl chain) it will be understood that the bond between the oxygen in said oxo group and the ring, or moiety it is attached to will be a double bond, even though sometimes it may be drawn generically with a single line. For example, in the example depicted below, J$^D$ attached to the ring may be selected from several different substituents. When J$^D$ is oxo, it will be understood that the bond between J$^D$ and the ring is a double bond. When J$^D$ is a halogen, it will be understood that the bond between J$^D$ and the ring is a single bond. In some instances, for example when the ring contains an unsaturation or it has aromatic character, the compound may exist in two or more possible tautomeric forms. In one of them the bond between the oxo group and the ring will be a double bond. In the other one, a hydrogen bond will be exchanged between atoms and substituents in the ring, so that the oxo becomes a hydroxy and an additional double bond is formed in the ring. Whereas the compound is depicted as D7 or D8, both will be taken to represent the set of all possible tautomers for that particular compound.

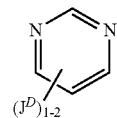

could be, for example:

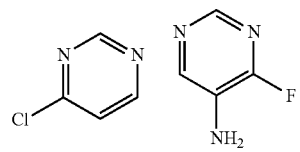

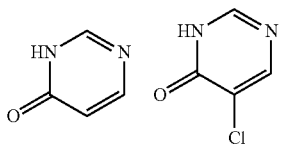

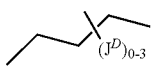

could be, for example

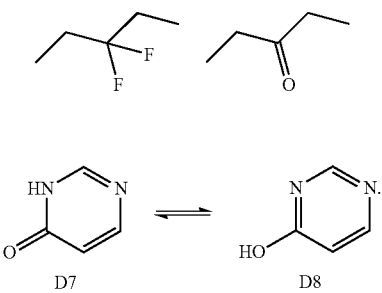

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—$CH_2$—) which can be substituted by two different groups, one for each of the free valences (e.g. as in Ph-$CH_2$-Ph, wherein methylene acts as a linker between two phenyl rings). Ethylene can be $C_2$ alkyl linker (—$CH_2CH_2$—) wherein the two free valences are on different atoms. The amide group, for example, can act as a linker when placed in an internal position of a chain (e.g. —CONH—). The compounds of the invention are defined herein by their chemical structures and/or chemical names. Where a compound is referred to by both a chemical structure and a chemical name, and the chemical structure and chemical name conflict, the chemical structure is determinative of the compound's identity.

Compound Embodiments

The present invention is directed to compounds of Formula I, or pharmaceutically acceptable salts thereof,

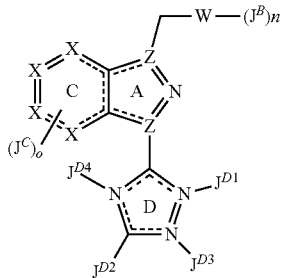

Formula I wherein:
rings A and C constitute the core of the molecule; rings A and D are heteroaryl rings; ring C may be a phenyl or a heteroaryl ring; each bond in these rings is either a single or a double bond depending on the substituents, so that each of said rings has aromatic character;
one instance of Z on ring A is N and the other instance of Z is C;
each instance of X on ring C is independently selected from C or N; wherein 0, 1 or 2 instances of X can simultaneously be N;
o is an integer selected from 2, 3 or 4;
each $J^C$ is a substituent on a carbon atom independently selected from hydrogen, halogen, —CN, $C_{1-4}$ aliphatic, $C_{1-4}$ haloalkyl or $C_{1-4}$ alkoxy;
W is either:
  i) absent, and $J^B$ is connected directly to the methylene group linked to the core; n is 1; and $J^B$ is a $C_{1-7}$ alkyl chain optionally substituted by up to 9 instances of fluorine; or
  ii) a ring B selected from phenyl or a 5 or 6-membered heteroaryl ring, containing 1 or 2 ring heteroatoms independently selected from N, O or S; wherein when W is ring B, n is 0 or an integer selected from 1, 2 or 3;
each $J^B$ is independently selected from halogen, —CN, a $C_{1-6}$ aliphatic, —$OR^B$ or a $C_{3-8}$ cycloaliphatic ring; wherein each said $C_{1-6}$ aliphatic and each said $C_{3-8}$ cycloaliphatic ring is optionally and independently substituted with up to 3 instances of $R^3$;
each $R^B$ is independently selected from a methyl, propyl, butyl, isopropyl, isobutyl or a $C_{3-8}$ cycloaliphatic ring; wherein each of said $R^B$ is optionally and independently substituted with up to 3 instances of $R^{3a}$;
each $R^3$ and each $R^{3a}$ is independently selected in each instance from halogen, —CN, $C_{1-4}$ alkyl, $C_{1-4}$ haloalkyl, —O($C_{1-4}$ alkyl) or —O($C_{1-4}$ haloalkyl);
$J^{D1}$ and $J^{D4}$ are independently selected from a lone pair on the nitrogen atom to which they are attached or hydrogen, wherein $J^{D1}$ and $J^{D4}$ are not both simultaneously hydrogen or both simultaneously a lone pair;
$J^{D3}$ is either a lone pair on the nitrogen atom to which it is attached, hydrogen, or a substituent selected from —C(O)$R^D$, a $C_{1-6}$ aliphatic, —($C_{1-6}$ aliphatic)-$R^D$, a $C_{3-8}$ cycloaliphatic ring, a phenyl ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^D$ moiety, said $C_{3-8}$ cycloaliphatic ring, said 4 to 8-membered heterocyclic ring, and said 5 or 6-membered heteroaryl ring is optionally and independently substituted with up to 5 instances of $R^5$; and wherein said phenyl ring is optionally and independently substituted with up to 5 instances of $R^{5a}$;
$J^{D1}$ and $J^{D3}$ cannot both simultaneously be hydrogen;
$J^{D2}$ is hydrogen, or a substituent selected from halogen, —CN, —$NO_2$, —$OR^{D1}$, —C(O)$R^D$, —C(O)N($R^D$)$_2$, —N($R^D$)$_2$, —N($R^D$)C(O)$R^D$, —N($R^D$)C(O)O$R^D$, —N($R^D$)C(O)N($R^D$)$_2$, —OC(O)N($R^D$)$_2$, a $C_{1-6}$ aliphatic, —($C_{1-6}$ aliphatic)-$R^D$, a $C_{3-8}$ cycloaliphatic ring, a phenyl ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^D$ moiety, said $C_{3-8}$ cycloaliphatic ring, said 4 to 8-membered heterocyclic ring and said 5 or 6-membered heteroaryl ring is optionally and independently substituted with up to 5 instances of $R^5$; and wherein said phenyl ring is optionally and independently substituted with up to 5 instances of $R^{5a}$;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring and each said 5 to 6-membered heteroaryl ring is optionally and independently substituted with up to 5 instances of $R^5$; and wherein each said phenyl ring is optionally and independently substituted with up to 5 instances of $R^{5a}$;

$R^{D1}$ is selected from a $C_{1-6}$ aliphatic, —($C_{1-6}$ aliphatic)-$R^f$, a $C_{3-8}$ cycloaliphatic ring, a 4 to 8-membered heterocyclic ring, a phenyl ring or a 5 to 6-membered heteroaryl ring; wherein said 4 to 8-membered heterocyclic ring and said 5 to 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^f$ moiety, said $C_{3-8}$ cycloaliphatic ring, said 4 to 8-membered heterocyclic ring and said 5 to 6-membered heteroaryl ring is optionally and independently substituted with up to 5 instances of $R^5$; wherein said phenyl ring is optionally and independently substituted with up to 5 instances of $R^{5a}$;

each $R^f$ is independently selected from a a $C_{3-8}$ cycloaliphatic ring, a 4 to 8-membered heterocyclic ring, a phenyl ring or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{3-8}$ cycloaliphatic ring, each said 4 to 8-membered heterocyclic ring and each said 5 to 6-membered heteroaryl ring is optionally and independently substituted by up to 5 instances of $R^5$; and wherein each said phenyl is optionally and independently substituted by up to 5 instances of $R^{5a}$;

each $R^5$ is independently selected from halogen, —CN, $C_{1-6}$ aliphatic, —($C_{1-6}$ alkyl)-$R^6$, —$OR^6$, —$COR_6$, —C(O)N($R^6$)$_2$, —N($R^6$)C(O)$R^6$, —N($R^6$)C(O)$OR^6$, —N($R^6$)C(O)N($R^6$)$_2$, —N($R^6$)$_2$, a $C_{3-8}$ cycloalkyl ring, a 4 to 8-membered heterocyclic ring, a 5 or 6-membered heteroaryl ring, phenyl, benzyl or an oxo group; wherein if two instances of $R^5$ are oxo and —OH or oxo and —$OR^6$, they are not substituents on the same carbon atom; wherein each of said 5 or 6-membered heteroaryl ring or 4 to 8-membered heterocyclic ring contains up to 3 ring heteroatoms independently selected from N, O and S; and wherein each of said $C_{1-6}$ aliphatic, each said $C_{1-6}$ alkyl portion of the —($C_{1-6}$ alkyl)-$R^6$ moiety, each said $C_{3-8}$ cycloalkyl ring, each said 5 or 6-membered heteroaryl ring and each said 4 to 8-membered heterocyclic ring, is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —$CONH_2$, —O($C_{1-4}$ alkyl), —O($C_{1-4}$ haloalkyl) or oxo; wherein if two instances of a substituent on $R^5$ are a) oxo and —OH or b) oxo and —O($C_{1-4}$ alkyl) or c) oxo and —O($C_{1-4}$ haloalkyl), they are not substituents on the same carbon atom; wherein each said benzyl or phenyl is optionally and independently substituted with up to 3 instances of halogen, $C_{1-4}$ alkyl, —$NH_2$, —NH($C_{1-4}$ alkyl), —N($C_{1-4}$ alkyl)$_2$, —CN, —$CONH_2$, —O($C_{1-4}$ alkyl), —O($C_{1-4}$ haloalkyl);

each $R^{5a}$ is independently selected from halogen, —CN, $C_{1-6}$ aliphatic, —($C_{1-6}$ alkyl)-$R^6$, —$OR^{6a}$, —$COR_6$, —C(O)N($R^6$)$_2$, —N($R^6$)C(O)$R^6$, —N($R^6$)C(O)$OR^6$, —N($R^6$)C(O)N($R^6$)$_2$, —N($R^6$)$_2$, a $C_{3-8}$ cycloalkyl ring, a 4 to 8-membered heterocyclic ring, a 5 or 6-membered heteroaryl ring, phenyl, benzyl or an oxo group; wherein each of said 5 or 6-membered heteroaryl ring and each of said 4 to 8-membered heterocyclic ring contains up to 3 ring heteroatoms independently selected from N, O and S; and wherein each of said $C_{1-6}$ aliphatic, each of said $C_{1-6}$ alkyl portion of the —($C_{1-6}$ alkyl)-$R^6$ moiety, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl, —OH, —$NH_2$, —NH($C_{1-4}$ alkyl), —N($C_{1-4}$ alkyl)$_2$, —CN, —$CONH_2$, —O($C_{1-4}$ alkyl), —O($C_{1-4}$ haloalkyl) or oxo; wherein if two instances of a substituent on $R^{5a}$ are a) oxo and —OH or b) oxo and —O($C_{1-4}$ alkyl) or c) oxo and —O($C_{1-4}$ haloalkyl), they are not substituents on the same carbon atom; and wherein each of said benzyl and each of said phenyl is optionally and independently substituted with up to 3 instances of halogen, $C_{1-4}$ alkyl, $C_{1-4}$ haloalkyl —$NH_2$, —NH($C_{1-4}$ alkyl), —N($C_{1-4}$ alkyl)$_2$, —CN, —$CONH_2$, —O($C_{1-4}$ alkyl) or —O($C_{1-4}$ haloalkyl);

each $R^6$ is independently selected from hydrogen, a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring or 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo; wherein if two instances of a substituent on $R^6$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, $C_{1-4}$ haloalkyl, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo;

each $R^{6a}$ is independently selected from a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring and each of said 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo; wherein if two instances of $R^{6a}$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, $C_{1-4}$ haloalkyl, —$NH_2$, —$NH(C_{1-4}$ alkyl), —$N(C_{1-4}$ alkyl)$_2$, —CN, —$C(O)NH_2$, —$O(C_{1-4}$ alkyl), —$O(C_{1-4}$ haloalkyl) or oxo;

alternatively, $J^{D2}$ and $J^{D3}$, together with the atoms to which they are attached, form a 5 or 6-membered heteroaryl ring or a 5 to 8-membered heterocyclic ring; wherein said heteroaryl ring or heterocyclic ring contains between 1 and 3 heteroatoms independently selected from N, O or S, including the N to which $J^{D3}$ is attached; wherein said heterocyclic or heteroaryl ring can be substituted by up to three instances of $J^E$; and $J^E$ is selected from halogen, $C_{1-4}$ alkyl, $C_{1-4}$ haloalkyl or oxo;

provided the compound is not one of the two depicted below, or any of their tautomers:

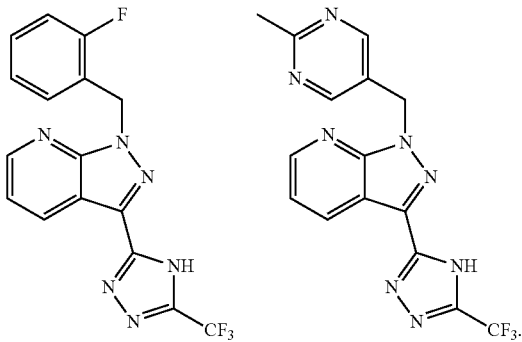 [SMILES: Fc1ccccc1Cn1nc(-c2nnc(C(F)(F)F)[nH]2)c2cccnc21 ; Cc1ncc(Cn2nc(-c3nnc(C(F)(F)F)[nH]3)c3cccnc32)cn1]

In some embodiments of Formula I, the compound is one of Formula IIA, Formula IIB or Formula IIC, or a pharmaceutically acceptable salt thereof:

Formula IIA
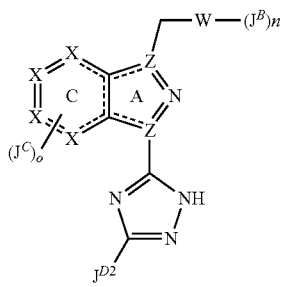

Formula IIB
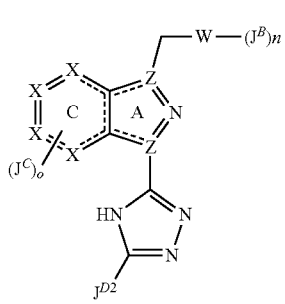

Formula IIC
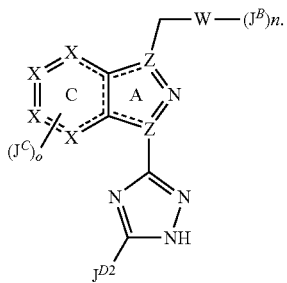

In some embodiments of Formula I, Formula IIA, Formula IIB or Formula IIC, $J^{D2}$ is selected from: hydrogen, halogen, —CN, —$OR^{D1}$, —$C(O)R^D$, —$C(O)N(R^D)_2$, —$N(R^D)_2$, —$N(R^D)C(O)R^D$, a $C_{1-6}$ aliphatic, —$(C_{1-6}$ aliphatic)-$R^D$, a $C_{3-8}$ cycloaliphatic ring, a phenyl ring, and a 4 to 8-membered heterocyclic ring containing between 1 and 3 heteroatoms independently selected from O, N or S. In some embodiments, the $C_{1-6}$ aliphatic, $C_{1-6}$ aliphatic portion of the —$(C_{1-6}$ aliphatic)-$R^D$ moiety, $C_{3-8}$ cycloaliphatic ring, 4 to 8-membered heterocyclic ring, or 5 or 6-membered heteroaryl ring may be substituted with up to 5 instances of $R^5$, and each instance of $R^5$ may be the same or different. In some of these embodiments, $R^5$ is selected in each instance from halogen, $C_{1-6}$ haloalkyl, —OH, —$OCH_3$, —$C(O)CF_3$, —$NH(CO)O(C_{1-6}$ aliphatic), —$NH_2$, phenyl, —$CH_2$_heteroaryl, —$N(CH_3)_2$, $C_{1-6}$ aliphatic, —$NH(CO)R^6$, or oxo. In other embodiments, the phenyl ring may be substituted with up to 5 instances of $R^{5a}$, and each instance of $R^{5a}$ may be the same or different. In some of these embodiments, $R^{5a}$ is selected in each instance from halogen, $C_{1-6}$ haloalkyl, —OH, —$OCH_3$, —$C(O)CF_3$, —$NH(CO)O(C_{1-6}$ aliphatic), —$NH_2$, phenyl, —$CH_2$_heteroaryl, —$N(CH_3)_2$, $C_{1-6}$ aliphatic, —$NH(CO)R^6$, or oxo.

In some embodiments, $J^{D3}$ is hydrogen or a lone pair of electrons on the nitrogen to which it is attached.

In some embodiments, the compound is one of Formula III, or a pharmaceutically acceptable salt thereof:

Formula III
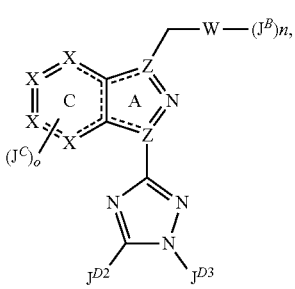

wherein $J^{D3}$ is not hydrogen or a lone pair on the N atom to which it is attached.

In some embodiments of Formula I or Formula III, $J^{D2}$ and $J^{D3}$, together with the atoms to which they are attached, form a 5 or 6-membered heteroaryl ring or a 5 to 8-membered heterocyclic ring; wherein said heteroaryl ring or heterocyclic ring contains between 1 and 3 heteroatoms independently selected from N, O or S, including the N to which $J^{D3}$ is attached. In some of these embodiments, the heterocyclic or heteroaryl ring can be substituted by up to three instances of $J^E$. In some of these embodiments, $J^E$ is selected from halogen, $C_{1-4}$ alkyl, $C_{1-4}$ haloalkyl or oxo. In other embodiments, $J^{D2}$ and $J^{D3}$, together with the atoms to which they are attached, form a ring selected from pyrrole, pyridine, oxazine, pyrimidine, diazepine, pyrazine, pyridazine, and imidazole. In these embodiments, the ring is partially or fully saturated and is optionally substituted by up to three instances of $J^E$.

In some embodiments of Formula I, Formula IIA, Formula IIB, Formula IIC and Formula III, $J^{D2}$ is selected from hydrogen, halogen, —NH$_2$, —CF$_3$, —CH$_3$, and —CH$_2$OH.

In some embodiments of Formula I or Formula III, $J^{D3}$ is a $C_{1-6}$ aliphatic. In some of these embodiments, the $C_{1-6}$ aliphatic may be substituted with up to 5 instances of $R^5$, and each instance of $R^5$ may be the same or different.

In some embodiments of Formula I or Formula II, $J^{D2}$ is selected from hydrogen, halogen, —NH$_2$, —CF$_3$, —CH$_3$, and —CH$_2$OH; and $J^{D3}$ is a $C_{1-6}$ aliphatic. In some of these embodiments, the $C_{1-6}$ aliphatic may be substituted with up to 5 instances of $R^5$, and each instance of $R^5$ may be the same or different. In some of these embodiments, each $R^5$ is independently selected from halogen, —CN, —OR$^6$, —C(O)N(R$^6$)$_2$, a 4 to 8-membered heterocyclic ring (containing up to 3 ring heteroatoms independently selected from N, O and S), or phenyl. In some embodiments, the 4 to 8-membered heterocyclic ring is optionally and independently substituted with up to 3 instances of halogen, —O(C$_{1-4}$ alkyl), or oxo. In some embodiments, the phenyl is optionally and independently substituted with up to 3 instances of halogen. In some of these embodiments, $J^{D3}$ is selected from —C$_{1-4}$ alkyl, —CH$_2$CF$_3$, —(CH$_2$)$_2$OH, —CH$_2$C(O)NH$_2$, —CH$_2$CN, —CH$_2$C(OH)CF$_3$, —(CH$_2$)$_2$ pyrrolidin-2-one, or benzyl optionally substituted with methoxy or halogen.

In some embodiments of Formula I, Formula IIA, Formula IIB, Formula IIC or Formula III, W is absent, and $J^B$ is connected directly to the methylene group linked to the core; n is 1; and $J^B$ is a $C_{1-7}$ alkyl chain optionally substituted by up to 9 instances of fluorine.

In some embodiments of Formula I, Formula IIA, Formula IIB, Formula IIC or Formula III, W is a ring B selected from phenyl or a 5 or 6-membered heteroaryl ring, and the compound is one of Formula IV, or a pharmaceutically acceptable salt thereof:

Formula IV

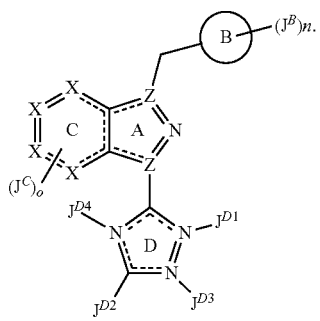

In other embodiments, ring B is selected from phenyl, pyridine, pyridazine, pyrazine, and pyrimidine. In still other embodiments, ring B is phenyl. In yet other embodiments, ring B is pyridine or pyrimidine In some embodiments of Formula I, Formula IIA, Formula IIB, Formula IIC, Formula III or Formula IV, n is 1. In other embodiments of Formula I, Formula IIA, Formula IIB, Formula IIC, Formula III or Formula IV, n is 2. In still other embodiments of Formula I, Formula IIA, Formula IIB, Formula IIC, Formula III or Formula IV, n is 0. In some embodiments of Formula I, Formula IIA, Formula IIB, Formula IIC, Formula III or Formula IV, n is 3.

In some embodiments of Formula I, Formula IIA, Formula IIB, Formula IIC, Formula III or Formula IV, each $J^B$ is independently selected from halogen and a $C_{1-6}$ aliphatic. In other embodiments, each $J^B$ is independently selected from halogen atoms. In still other embodiments, each $J^B$ is independently selected from fluoro or chloro. In yet other embodiments, each $J^B$ is fluoro. In some embodiments, each $J^B$ is a $C_{1-6}$ aliphatic. In other embodiments, each $J^B$ is methyl.

In some embodiments of Formula I, Formula IIA, Formula IIB, Formula IIC, Formula III or Formula IV, at least one $J^B$ is ortho to the attachment of the methylene linker between ring B and ring A. In some embodiments, one $J^B$ is ortho to the attachment of the methylene linker between rings B and Ring A and is fluoro.

In some embodiments of Formula I, Formula IIA, Formula IIB, Formula IIC, Formula III or Formula IV, the core formed by rings C and A is selected from:

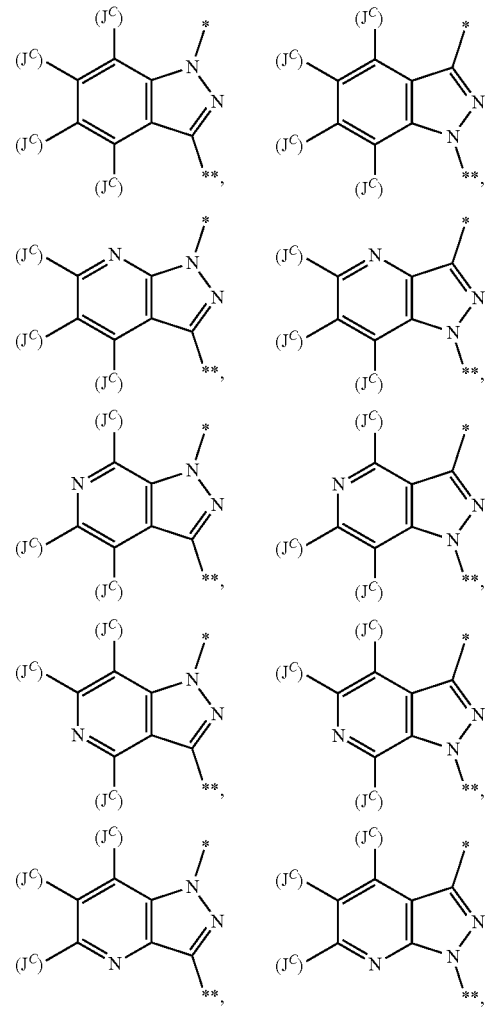

-continued

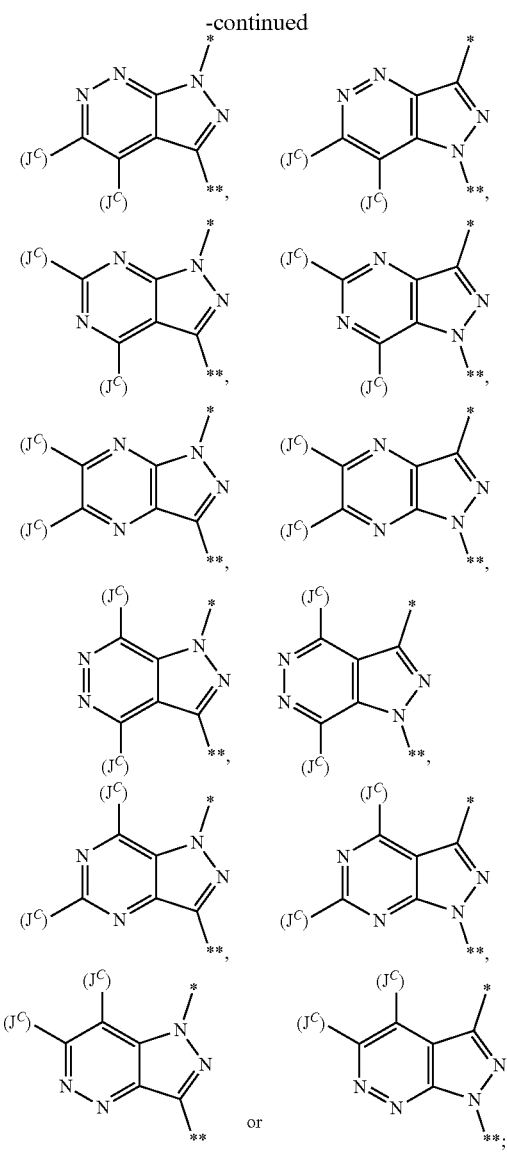

wherein the atom with a symbol * represents the attachment point to the methylene linker to W-(J$^B$)$_n$; and the atom with a symbol ** represents the point of attachment to ring D. In other embodiments, the core formed by rings C and A is selected from:

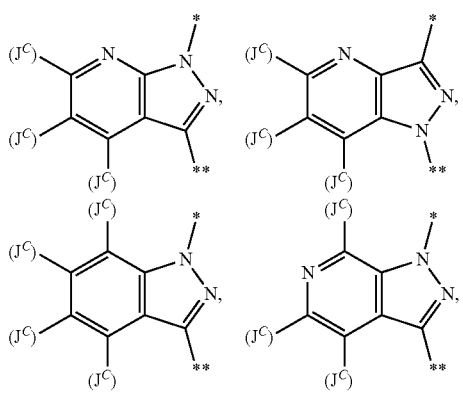

-continued

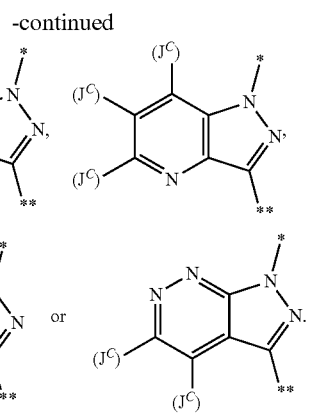

In still other embodiments, the core formed by rings C and A is selected from:

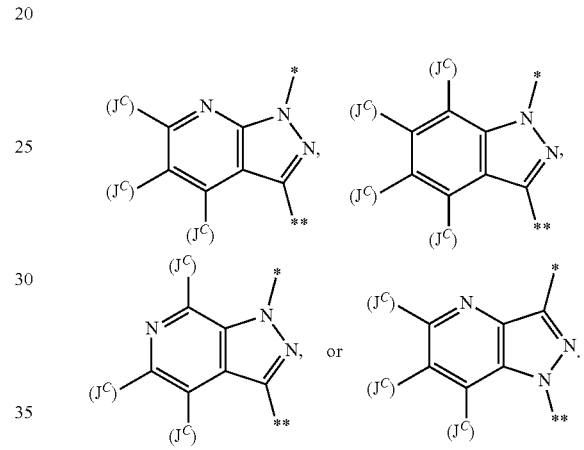

In some embodiments of Formula I, Formula IIA, Formula IIB, Formula IIC, Formula III or Formula IV, the core formed by rings C and A is selected from:

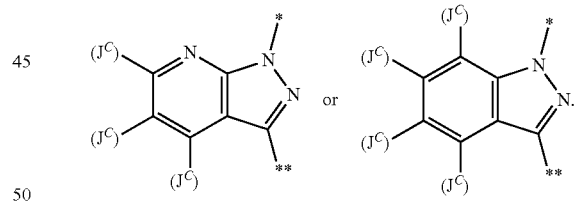

In other embodiments of Formula I, Formula IIA, Formula IIB, Formula IIC, Formula III or Formula IV, the core formed by rings C and A is selected from:

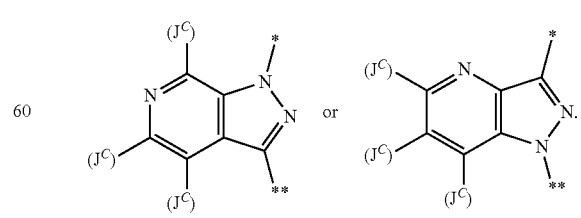

In some embodiments of Formula I, Formula IIA, Formula IIB, Formula IIC, Formula III or Formula IV, each J$^C$ is independently selected from hydrogen, halogen, or $C_{1-4}$ aliphatic. In other embodiments, each $J^C$ is independently selected from hydrogen, fluoro, chloro, or methyl.
In some embodiments, the compounds of Formula I are selected from those listed in Table IA.
TABLE IA
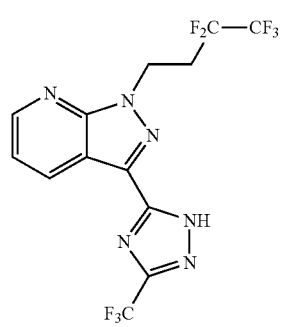 [SMILES: FC(F)(F)c1n[nH]c(-c2nn(CCC(F)(F)C(F)(F)F)c3ncccc23)n1]
I-1
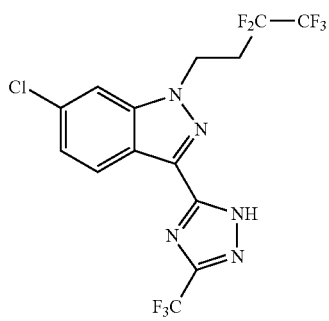 [SMILES: FC(F)(F)c1n[nH]c(-c2nn(CCC(F)(F)C(F)(F)F)c3cc(Cl)ccc23)n1]
I-2
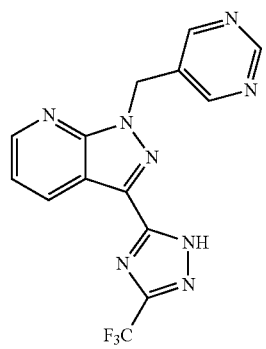 [SMILES: FC(F)(F)c1n[nH]c(-c2nn(Cc3cncnc3)c3ncccc23)n1]
I-3
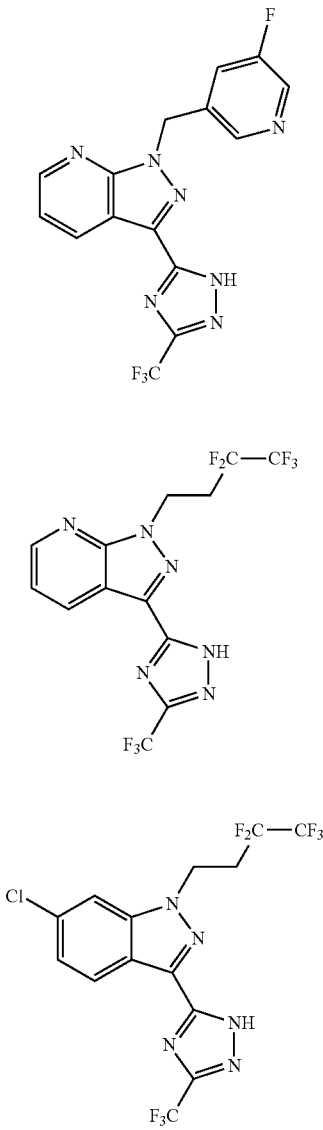
I-4
TABLE IA-continued
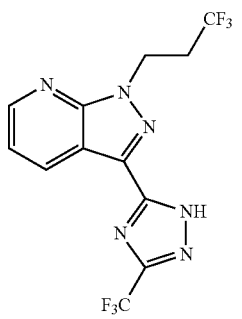 [SMILES: FC(F)(F)CCn1nc(-c2nc(C(F)(F)F)n[nH]2)c2cccnc21]
I-7
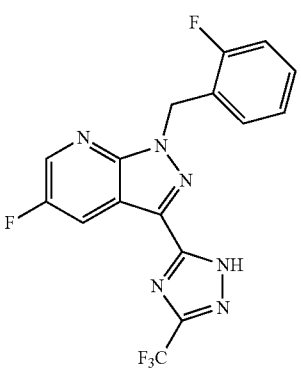 [SMILES: Fc1cnc2c(c1)c(-c1nc(C(F)(F)F)n[nH]1)nn2Cc1ccccc1F]
I-8
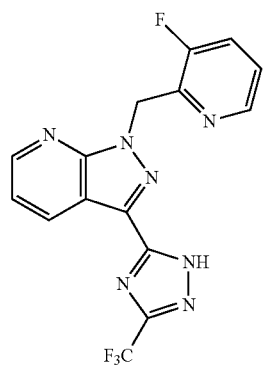 [SMILES: Fc1cccnc1Cn1nc(-c2nc(C(F)(F)F)n[nH]2)c2cccnc21]
I-13
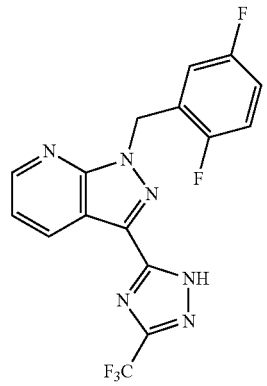 [SMILES: Fc1ccc(F)c(Cn2nc(-c3nc(C(F)(F)F)n[nH]3)c3cccnc32)c1]
I-14

TABLE IA-continued
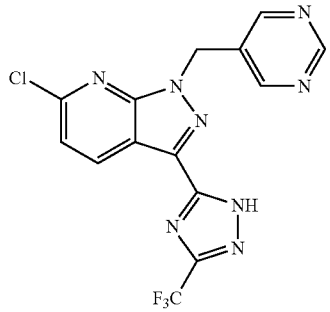 [SMILES: FC(F)(F)c1n[nH]c(-c2nn(Cc3cncnc3)c3nc(Cl)ccc23)n1] I-16
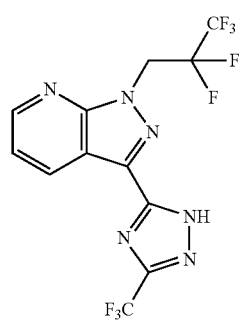 [SMILES: FC(F)(F)c1n[nH]c(-c2nn(CC(F)(F)C(F)(F)F)c3ncccc23)n1] I-19
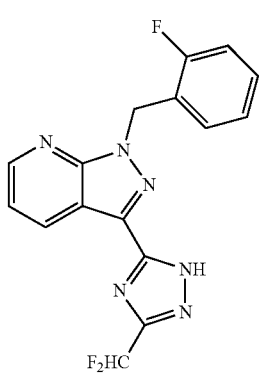 [SMILES: Fc1ccccc1Cn1nc(-c2nc(C(F)F)n[nH]2)c2cccnc21] I-20
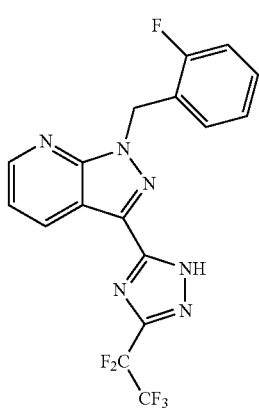 [SMILES: Fc1ccccc1Cn1nc(-c2nc(C(F)(F)C(F)(F)F)n[nH]2)c2cccnc21] I-21
TABLE IA-continued
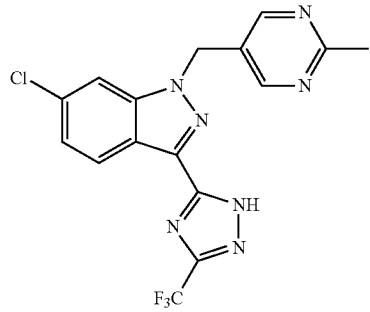 [SMILES: Cc1ncc(Cn2nc(-c3nc(C(F)(F)F)n[nH]3)c3ccc(Cl)cc32)cn1] I-22
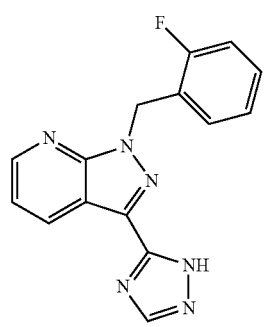 [SMILES: Fc1ccccc1Cn1nc(-c2ncn[nH]2)c2cccnc21] I-25
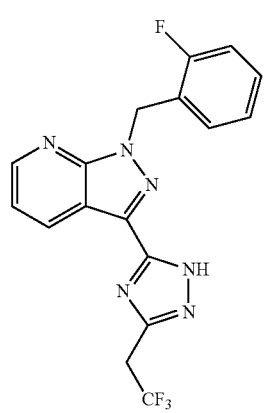 [SMILES: Fc1ccccc1Cn1nc(-c2nc(CC(F)(F)F)n[nH]2)c2cccnc21] I-26
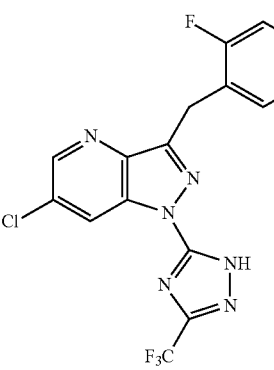 I-30

TABLE IA-continued
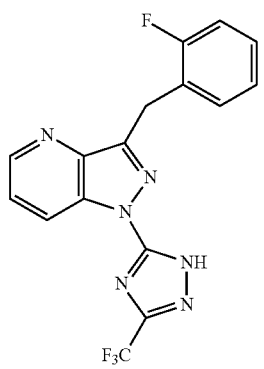
I-31
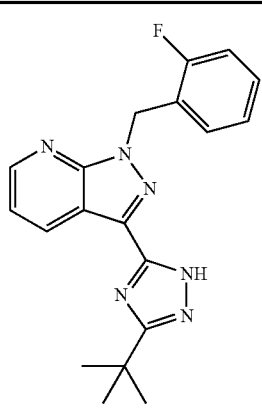
I-37
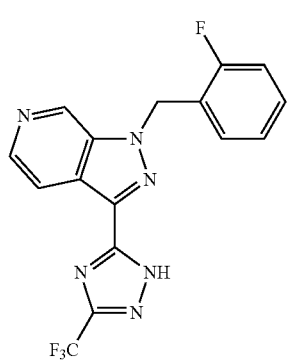 [SMILES: Fc1ccccc1Cn1nc(-c2nc(C(F)(F)F)n[nH]2)c2ccncc21]
I-32
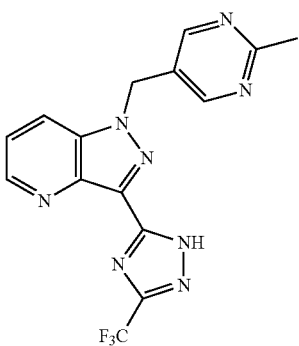
I-38
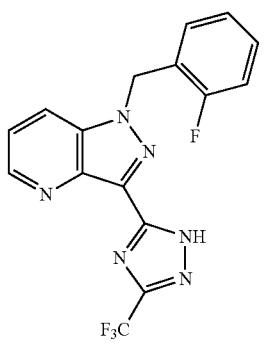 [SMILES: Fc1ccccc1Cn1nc(-c2nc(C(F)(F)F)n[nH]2)c2ncccc21]
I-35
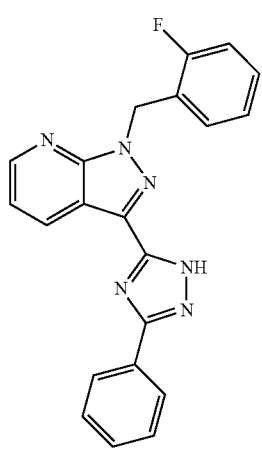
I-39
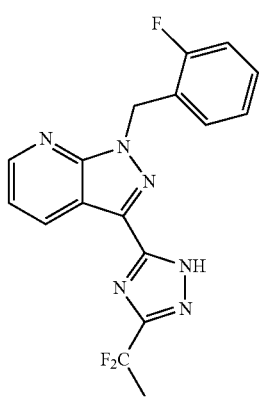 [SMILES: CC(F)(F)c1n[nH]c(-c2nn(Cc3ccccc3F)c3ncccc23)n1]
I-36
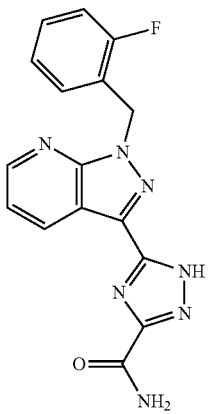 [SMILES: NC(=O)c1n[nH]c(-c2nn(Cc3ccccc3F)c3ncccc23)n1]
I-40

TABLE IA-continued
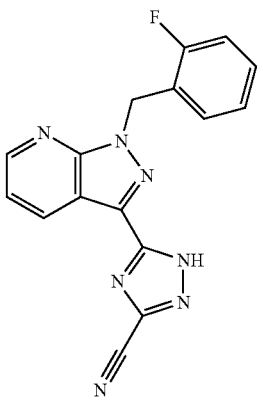 [SMILES: N#Cc1n[nH]c(-c2nn(Cc3ccccc3F)c3ncccc23)n1]
I-41
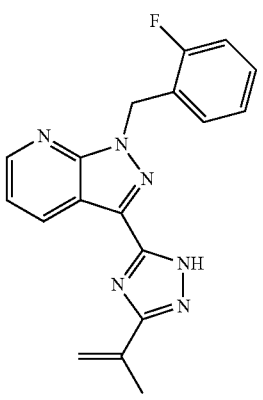 [SMILES: C=C(C)c1n[nH]c(-c2nn(Cc3ccccc3F)c3ncccc23)n1]
I-55
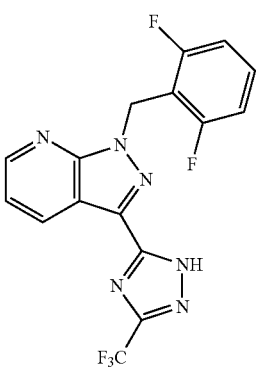 [SMILES: Fc1cccc(F)c1Cn1nc(-c2nc(C(F)(F)F)n[nH]2)c2cccnc21]
I-42
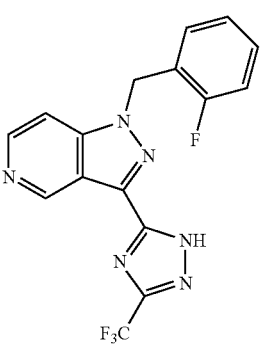 [SMILES: Fc1ccccc1Cn1nc(-c2nc(C(F)(F)F)n[nH]2)c2cnccc21]
I-43
TABLE IA-continued
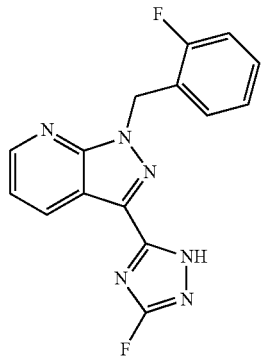 [SMILES: Fc1n[nH]c(-c2nn(Cc3ccccc3F)c3ncccc23)n1]
I-45

I-46
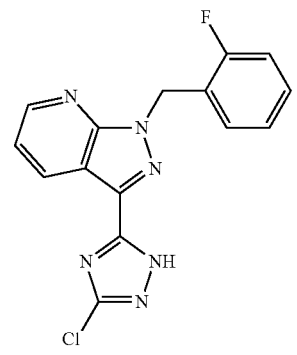 [SMILES: Fc1ccccc1Cn1nc(-c2nc(Cl)n[nH]2)c2cccnc21]
I-47
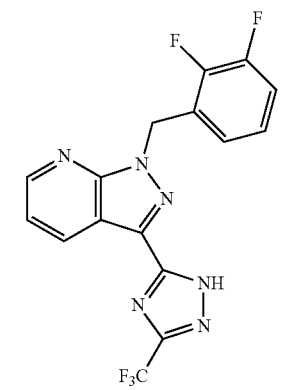 [SMILES: Fc1cccc(Cn2nc(-c3nc(C(F)(F)F)n[nH]3)c3cccnc32)c1F]
I-48

TABLE IA-continued
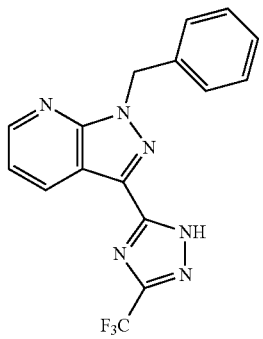 [SMILES: FC(F)(F)c1n[nH]c(-c2nn(Cc3ccccc3)c3ncccc23)n1]
I-49
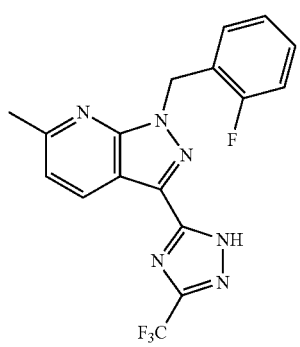 [SMILES: Cc1ccc2c(-c3nc(C(F)(F)F)n[nH]3)nn(Cc3ccccc3F)c2n1]
I-50
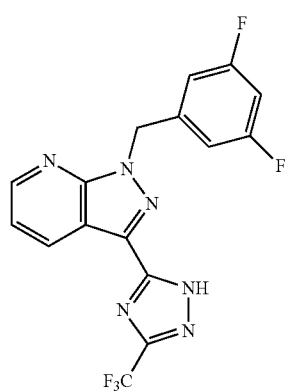 [SMILES: Fc1cc(F)cc(Cn2nc(-c3nc(C(F)(F)F)n[nH]3)c3cccnc32)c1]
I-51
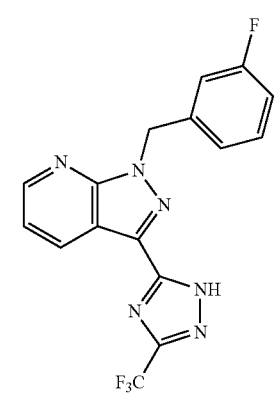 [SMILES: Fc1cccc(Cn2nc(-c3nc(C(F)(F)F)n[nH]3)c3cccnc32)c1]
I-52
TABLE IA-continued
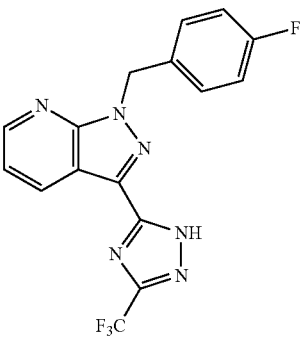 [SMILES: Fc1ccc(Cn2nc(-c3nc(C(F)(F)F)n[nH]3)c3cccnc32)cc1]
I-53
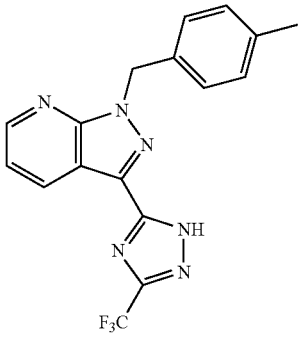 [SMILES: Cc1ccc(Cn2nc(-c3nc(C(F)(F)F)n[nH]3)c3cccnc32)cc1]
I-54
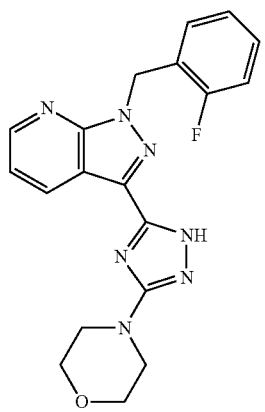 [SMILES: Fc1ccccc1Cn1nc(-c2nc(N3CCOCC3)n[nH]2)c2cccnc21]
I-57
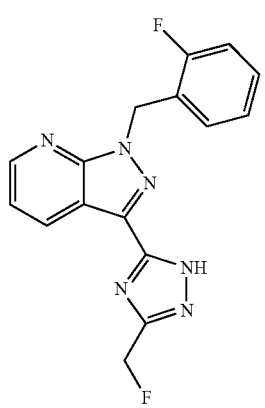 [SMILES: FCc1n[nH]c(-c2nn(Cc3ccccc3F)c3ncccc23)n1]
I-58

TABLE IA-continued
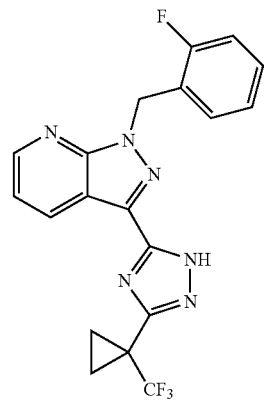 [SMILES: Fc1ccccc1Cn1nc(-c2nc(C3(C(F)(F)F)CC3)n[nH]2)c2cccnc21]
I-59
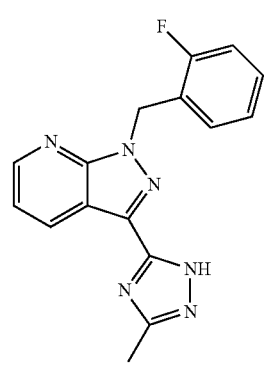 [SMILES: Cc1n[nH]c(-c2nn(Cc3ccccc3F)c3ncccc23)n1]
I-60
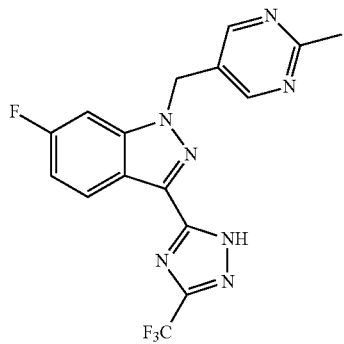 [SMILES: Cc1ncc(Cn2nc(-c3nc(C(F)(F)F)n[nH]3)c3ccc(F)cc32)cn1]
I-61
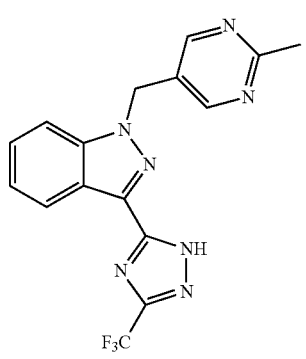 [SMILES: Cc1ncc(Cn2nc(-c3nc(C(F)(F)F)n[nH]3)c3ccccc32)cn1]
I-62
TABLE IA-continued
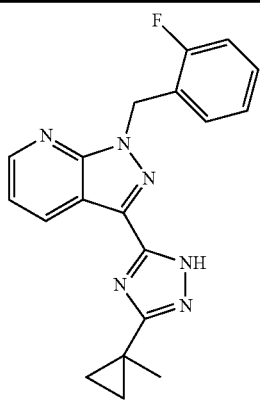
I-63
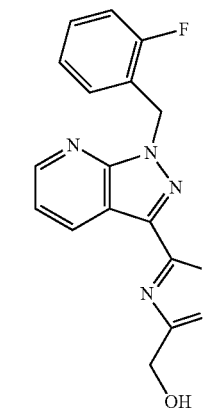
I-64
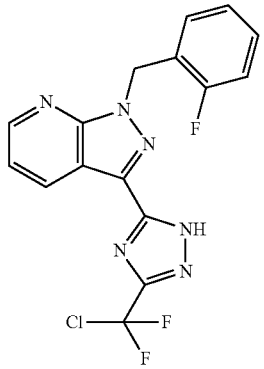 [SMILES: Fc1ccccc1Cn1nc(-c2nc(C(F)(F)Cl)n[nH]2)c2cccnc21]
I-65
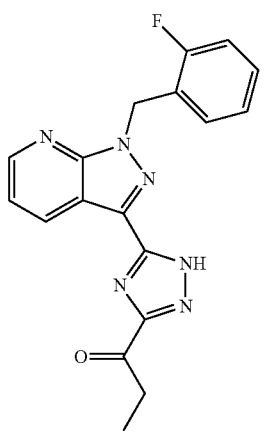 [SMILES: CCC(=O)c1n[nH]c(-c2nn(Cc3ccccc3F)c3ncccc23)n1]
I-66

TABLE IA-continued
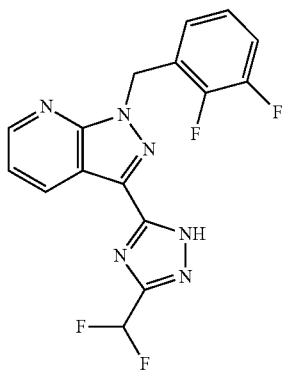 [SMILES: Fc1cccc(Cn2nc(-c3nc(C(F)F)n[nH]3)c3cccnc32)c1F]
I-67
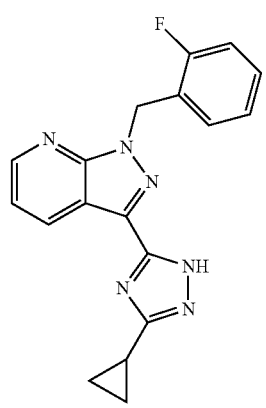 [SMILES: Fc1ccccc1Cn1nc(-c2nc(C3CC3)n[nH]2)c2cccnc21]
I-68
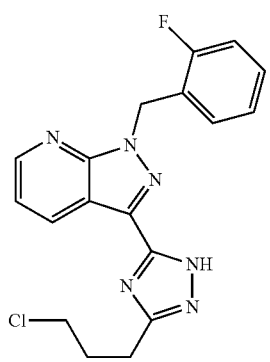 [SMILES: Fc1ccccc1Cn1nc(-c2nc(CCCCl)n[nH]2)c2cccnc21]
I-69
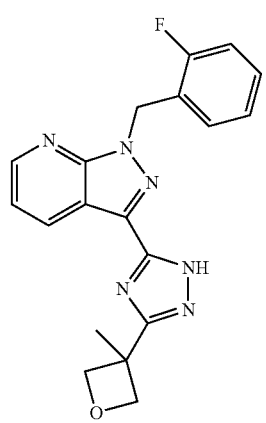 [SMILES: CC1(c2n[nH]c(-c3nn(Cc4ccccc4F)c4ncccc34)n2)COC1]
I-70
TABLE IA-continued
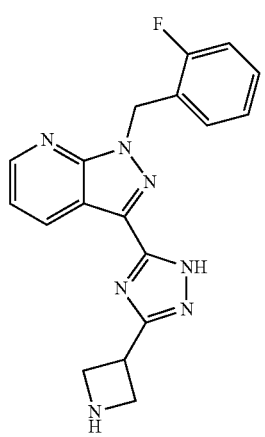 [SMILES: Fc1ccccc1Cn1nc(-c2nc(C3CNC3)n[nH]2)c2cccnc21]
I-73
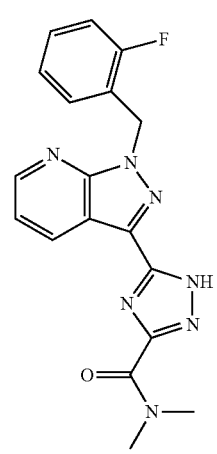 [SMILES: CN(C)C(=O)c1n[nH]c(-c2nn(Cc3ccccc3F)c3ncccc23)n1]
I-74
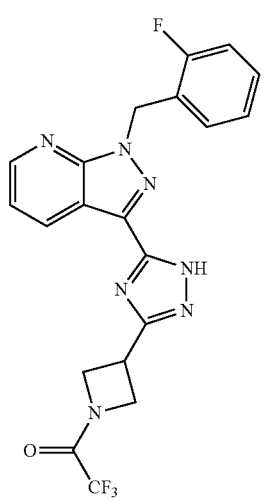 [SMILES: O=C(N1CC(c2n[nH]c(-c3nn(Cc4ccccc4F)c4ncccc34)n2)C1)C(F)(F)F]
I-75

TABLE IA-continued
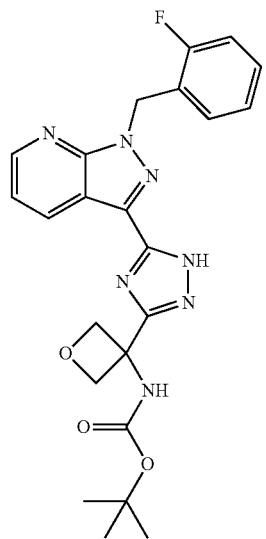 [SMILES: CC(C)(C)OC(=O)NC1(c2n[nH]c(-c3nn(Cc4ccccc4F)c4ncccc34)n2)COC1]
I-76
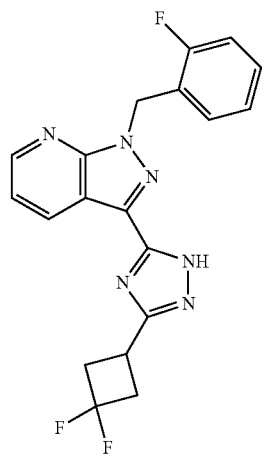 [SMILES: Fc1ccccc1Cn1nc(-c2nc(C3CC(F)(F)C3)n[nH]2)c2cccnc21]
I-77
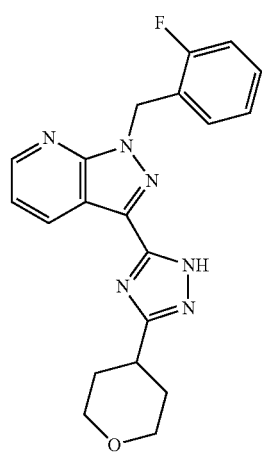 [SMILES: Fc1ccccc1Cn1nc(-c2nc(C3CCOCC3)n[nH]2)c2cccnc21]
I-78
TABLE IA-continued
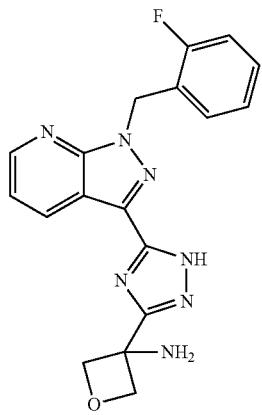 [SMILES: NC1(c2n[nH]c(-c3nn(Cc4ccccc4F)c4ncccc34)n2)COC1]
I-79
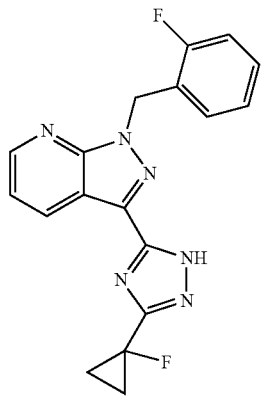 [SMILES: Fc1ccccc1Cn1nc(-c2nc(C3(F)CC3)n[nH]2)c2cccnc21]
I-80
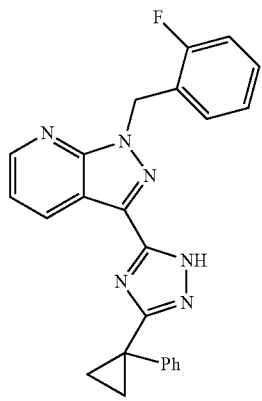 [SMILES: Fc1ccccc1Cn1nc(-c2nc(C3(c4ccccc4)CC3)n[nH]2)c2cccnc21]
I-81
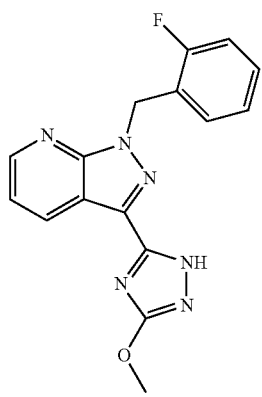 [SMILES: COc1n[nH]c(-c2nn(Cc3ccccc3F)c3ncccc23)n1]
I-82

TABLE IA-continued
I-83
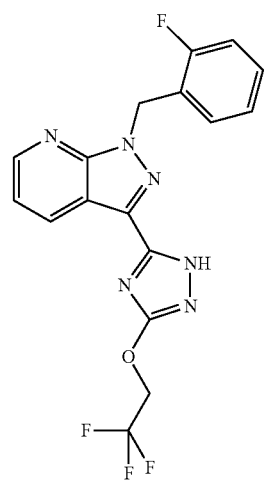 [SMILES: Fc1ccccc1Cn1nc(-c2nc(OCC(F)(F)F)n[nH]2)c2cccnc21]
I-84
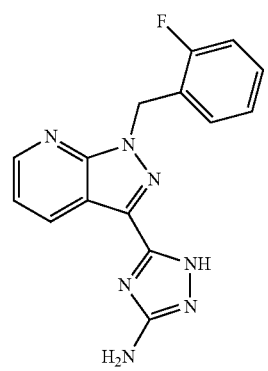 [SMILES: Nc1n[nH]c(-c2nn(Cc3ccccc3F)c3ncccc23)n1]
I-85
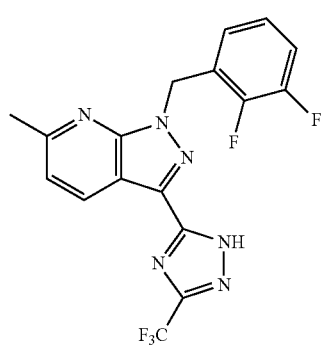 [SMILES: Cc1ccc2c(-c3nc(C(F)(F)F)n[nH]3)nn(Cc3cccc(F)c3F)c2n1]
I-86
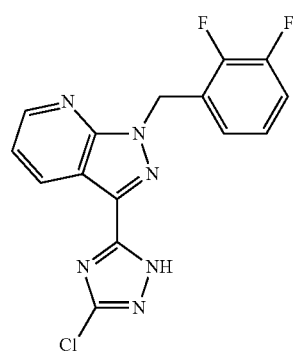 [SMILES: Fc1cccc(Cn2nc(-c3nc(Cl)n[nH]3)c3cccnc32)c1F]
TABLE IA-continued
I-87
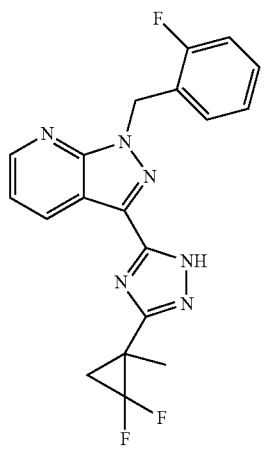 [SMILES: CC1(c2n[nH]c(-c3nn(Cc4ccccc4F)c4ncccc34)n2)CC1(F)F]
I-88
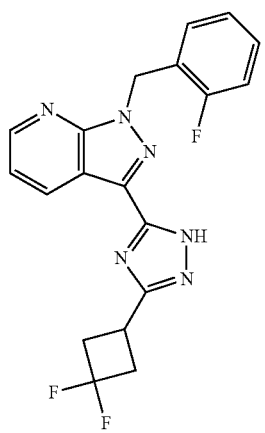 [SMILES: Fc1ccccc1Cn1nc(-c2nc(C3CC(F)(F)C3)n[nH]2)c2cccnc21]
I-89
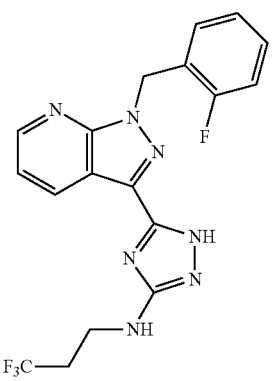 [SMILES: Fc1ccccc1Cn1nc(-c2nc(NCCC(F)(F)F)n[nH]2)c2cccnc21]
I-90
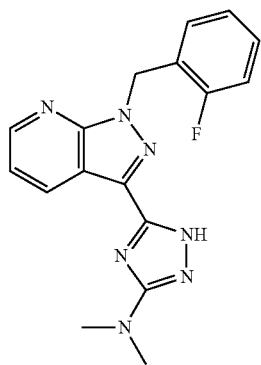 [SMILES: CN(C)c1n[nH]c(-c2nn(Cc3ccccc3F)c3ncccc23)n1]

TABLE IA-continued
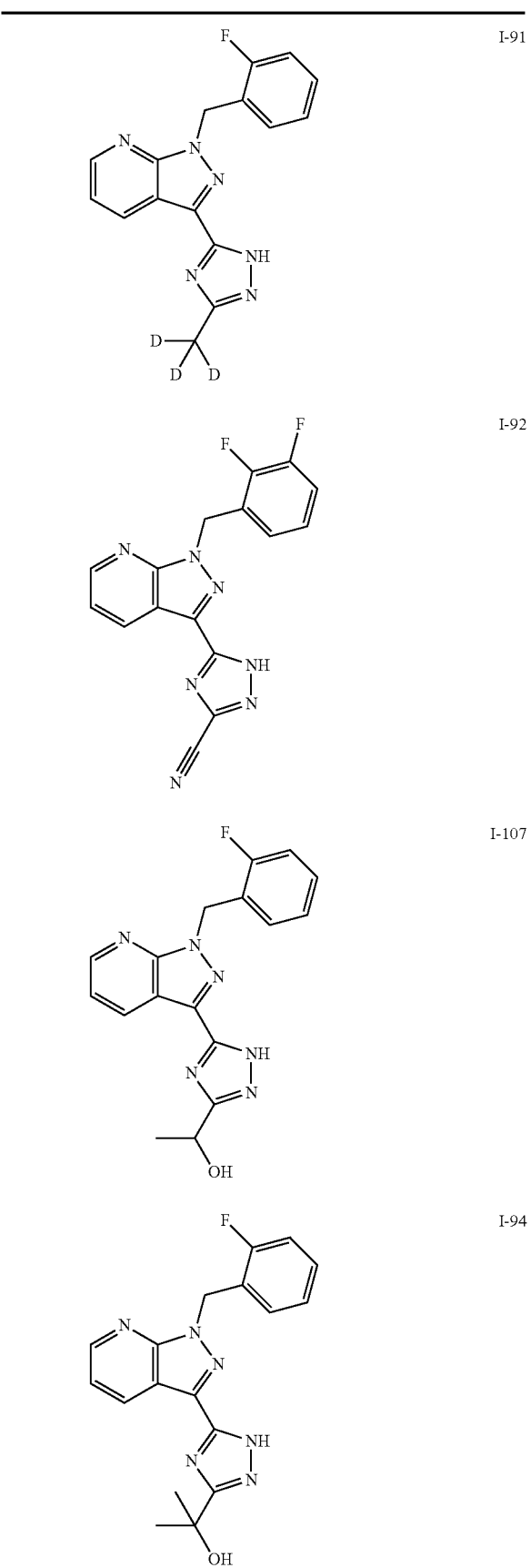
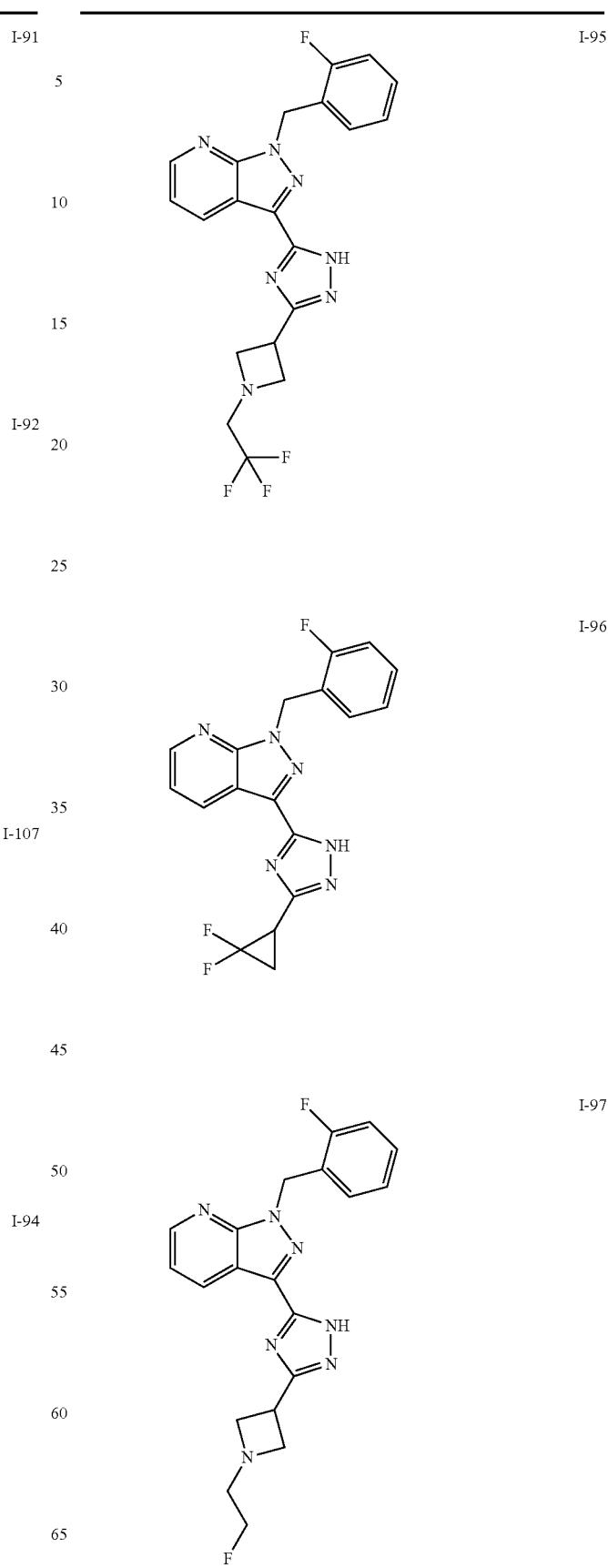

TABLE IA-continued
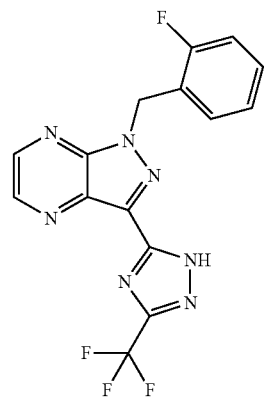 [SMILES: Fc1ccccc1Cn1nc(-c2nc(C(F)(F)F)n[nH]2)c2nccnc21]
I-98
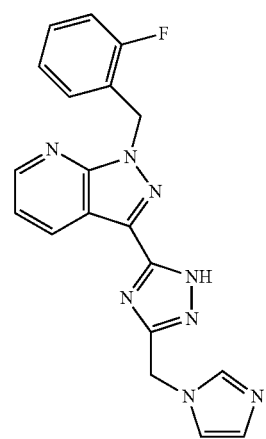 [SMILES: Fc1ccccc1Cn1nc(-c2nc(Cn3ccnc3)n[nH]2)c2cccnc21]
I-99
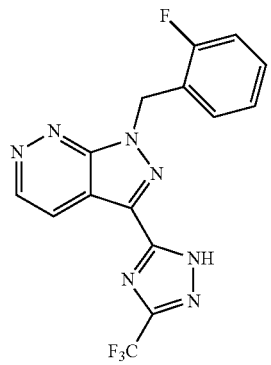 [SMILES: Fc1ccccc1Cn1nc(-c2nc(C(F)(F)F)n[nH]2)c2ccnnc21]
I-100
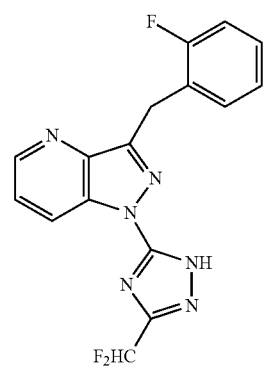 [SMILES: Fc1ccccc1Cc1nn(-c2nc(C(F)F)n[nH]2)c2cccnc12]
I-101
TABLE IA-continued
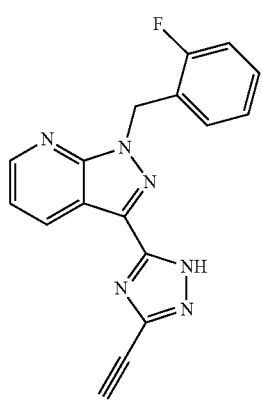 [SMILES: C#Cc1n[nH]c(-c2nn(Cc3ccccc3F)c3ncccc23)n1]
I-102
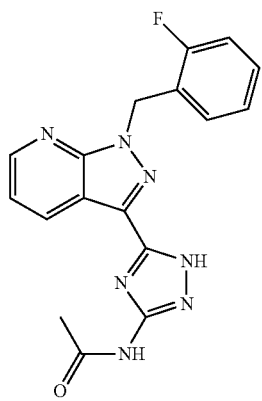 [SMILES: CC(=O)Nc1n[nH]c(-c2nn(Cc3ccccc3F)c3ncccc23)n1]
I-103
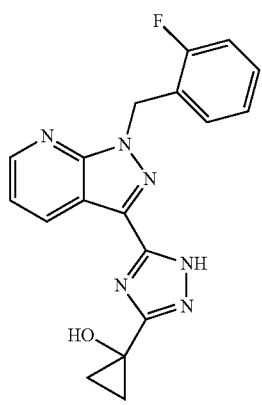 [SMILES: OC1(c2n[nH]c(-c3nn(Cc4ccccc4F)c4ncccc34)n2)CC1]
I-104
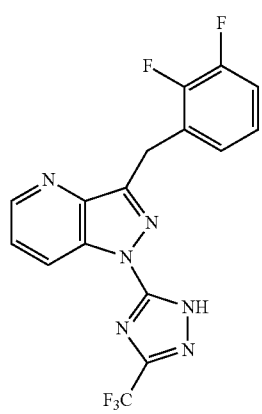 [SMILES: Fc1cccc(Cc2nn(-c3nc(C(F)(F)F)n[nH]3)c3cccnc23)c1F]
I-105

TABLE IA-continued
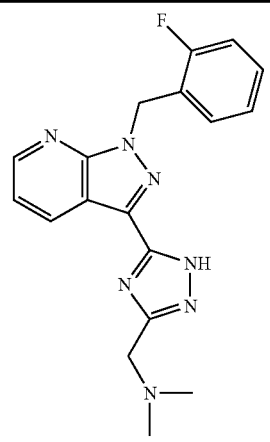
I-106
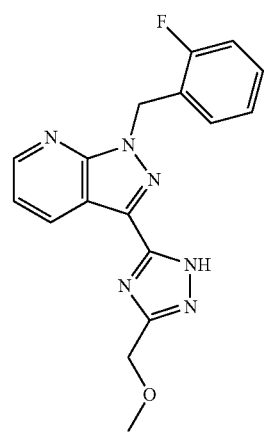 [SMILES: COCc1n[nH]c(-c2nn(Cc3ccccc3F)c3ncccc23)n1]
I-112
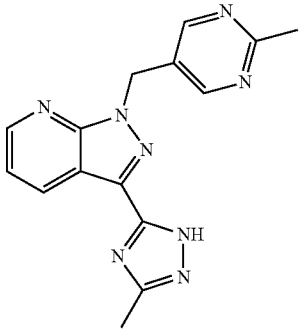 [SMILES: Cc1ncc(Cn2nc(-c3nc(C)n[nH]3)c3cccnc32)cn1]
I-113
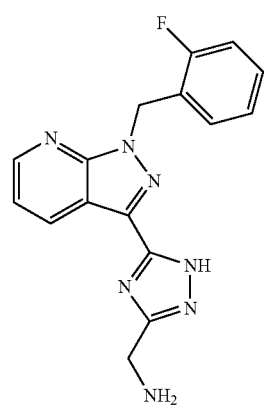
I-115
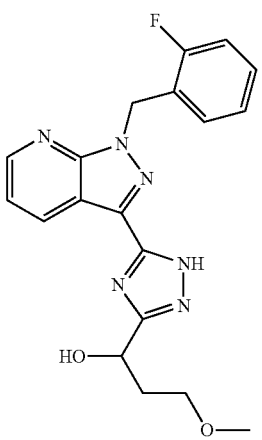 [SMILES: COCCC(O)c1n[nH]c(-c2nn(Cc3ccccc3F)c3ncccc23)n1]
I-116
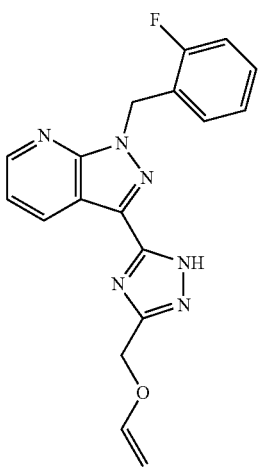 [SMILES: C=COCc1n[nH]c(-c2nn(Cc3ccccc3F)c3ncccc23)n1]
I-117
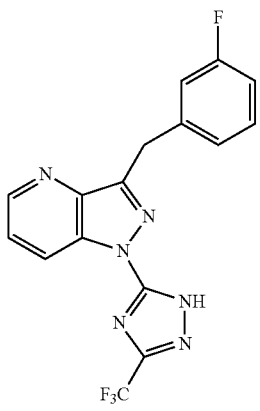 [SMILES: Fc1cccc(Cc2nn(-c3nc(C(F)(F)F)n[nH]3)c3cccnc23)c1]
I-120

TABLE IA-continued
I-121
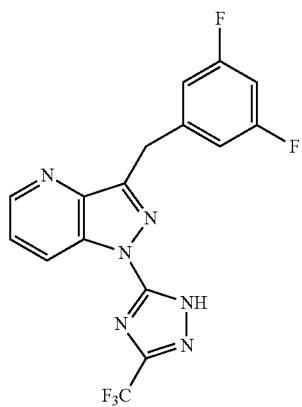 [SMILES: Fc1cc(F)cc(Cc2nn(-c3nc(C(F)(F)F)n[nH]3)c3cccnc23)c1]
I-122
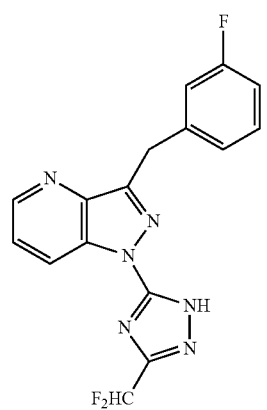 [SMILES: Fc1cccc(Cc2nn(-c3nc(C(F)F)n[nH]3)c3cccnc23)c1]
I-123
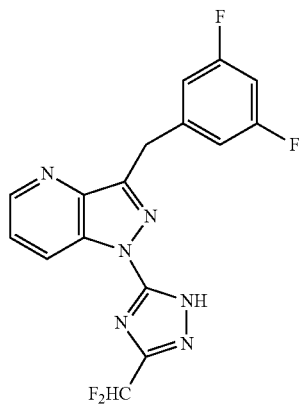 [SMILES: Fc1cc(F)cc(Cc2nn(-c3nc(C(F)F)n[nH]3)c3cccnc23)c1]
I-124
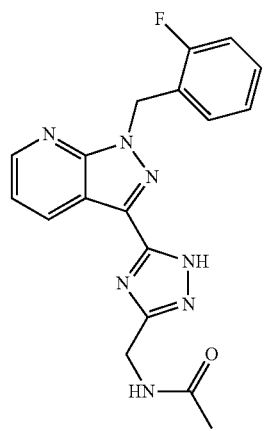 [SMILES: CC(=O)NCc1n[nH]c(-c2nn(Cc3ccccc3F)c3ncccc23)n1]
TABLE IA-continued
I-125
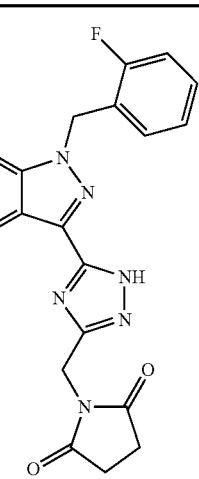
I-126
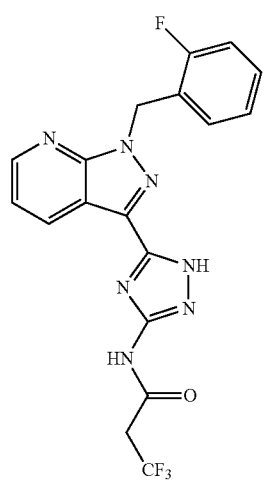 [SMILES: O=C(CC(F)(F)F)Nc1n[nH]c(-c2nn(Cc3ccccc3F)c3ncccc23)n1]
I-127
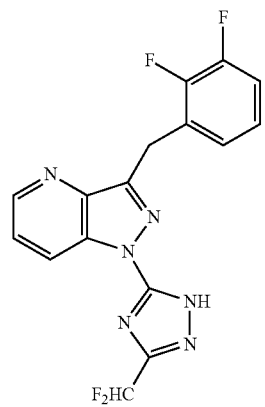 [SMILES: Fc1cccc(Cc2nn(-c3nc(C(F)F)n[nH]3)c3cccnc23)c1F]

TABLE IA-continued
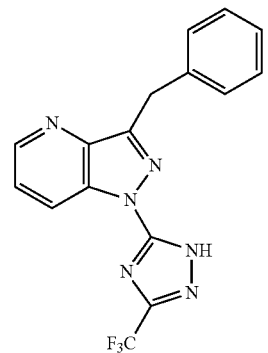 [SMILES: FC(F)(F)c1n[nH]c(-n2nc(Cc3ccccc3)c3ncccc32)n1]
I-128
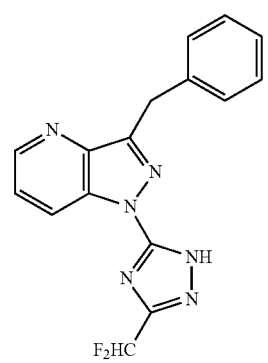 [SMILES: FC(F)c1n[nH]c(-n2nc(Cc3ccccc3)c3ncccc32)n1]
I-129
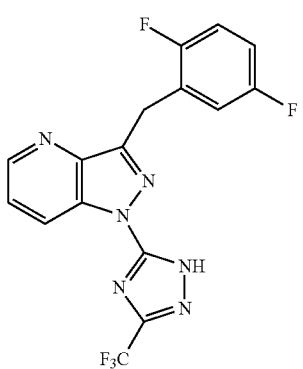 [SMILES: Fc1ccc(F)c(Cc2nn(-c3nc(C(F)(F)F)n[nH]3)c3cccnc23)c1]
I-130
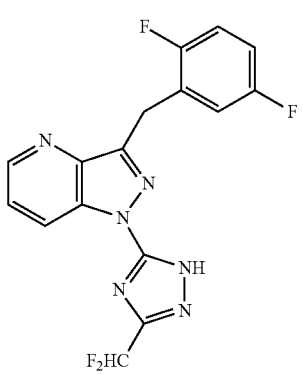 [SMILES: Fc1ccc(F)c(Cc2nn(-c3nc(C(F)F)n[nH]3)c3cccnc23)c1]
I-131
TABLE IA-continued
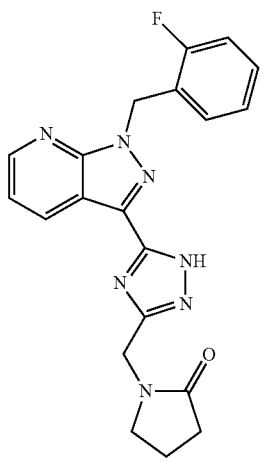 [SMILES: O=C1CCCN1Cc1n[nH]c(-c2nn(Cc3ccccc3F)c3ncccc23)n1]
I-132
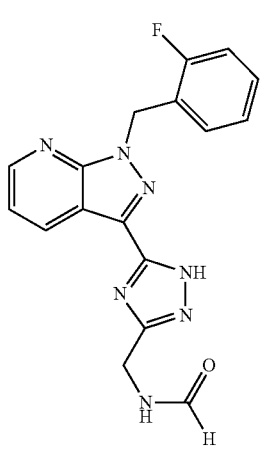 [SMILES: O=CNCc1n[nH]c(-c2nn(Cc3ccccc3F)c3ncccc23)n1]
I-133
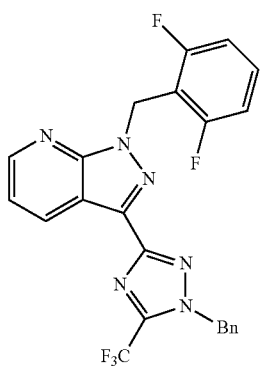 [SMILES: Fc1cccc(F)c1Cn1nc(-c2nc(C(F)(F)F)n(Cc3ccccc3)n2)c2cccnc21]
I-134
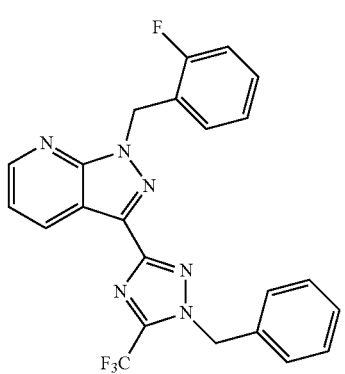 [SMILES: Fc1ccccc1Cn1nc(-c2nc(C(F)(F)F)n(Cc3ccccc3)n2)c2cccnc21]
I-135

In some embodiments, the compounds are selected from those listed in Table IB:
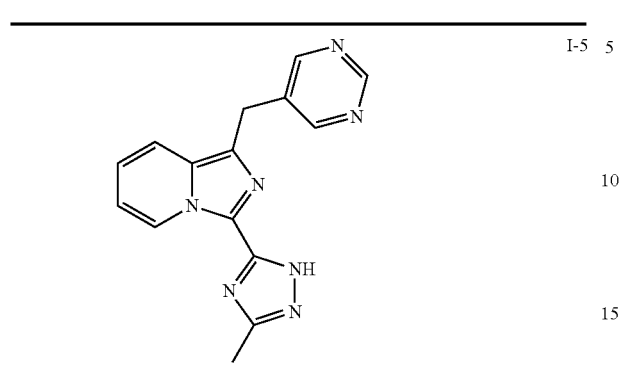
I-5
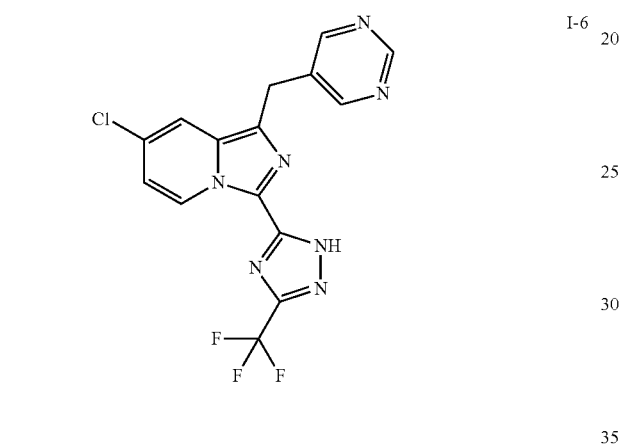
I-6
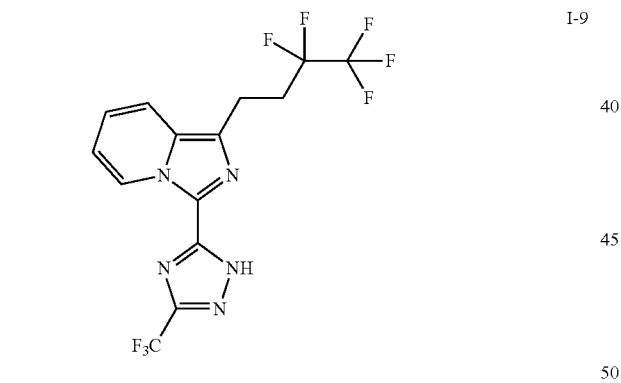
I-9
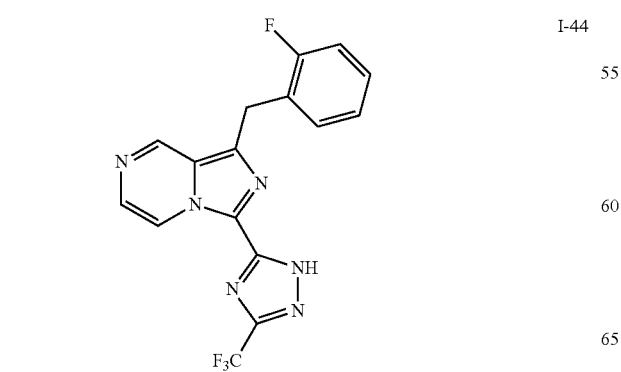
I-44
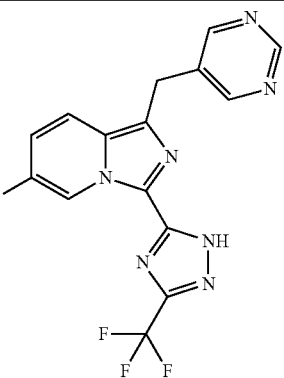
I-12
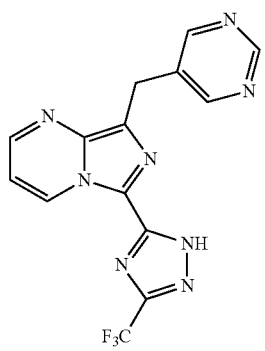 [SMILES: FC(F)(F)c1n[nH]c(-c2nc(Cc3cncnc3)c3ncccn23)n1]
I-15
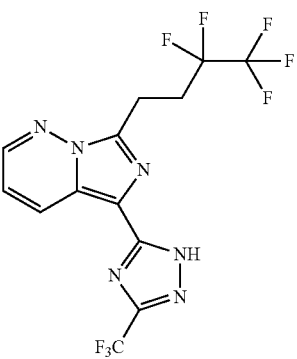 [SMILES: FC(F)(F)c1n[nH]c(-c2nc(CCC(F)(F)C(F)(F)F)n3ncccc23)n1]
I-17
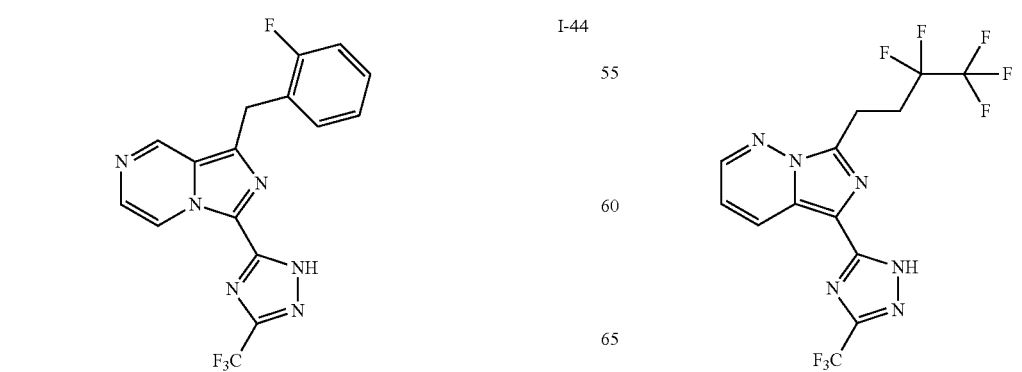
I-18

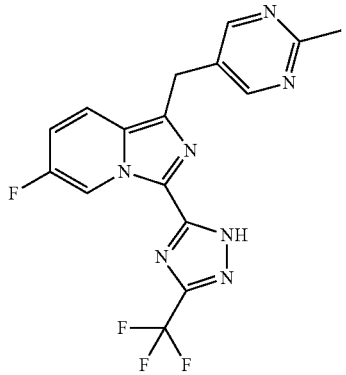 [SMILES: Cc1ncc(Cc2nc(-c3nc(C(F)(F)F)n[nH]3)n3cc(F)ccc23)cn1]

I-23

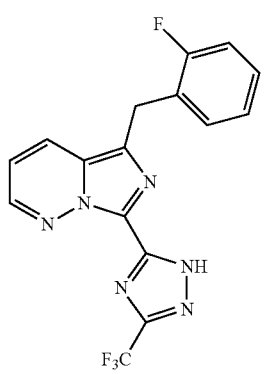 [SMILES: Fc1ccccc1Cc1nc(-c2nc(C(F)(F)F)n[nH]2)n2ncccc12]

I-24

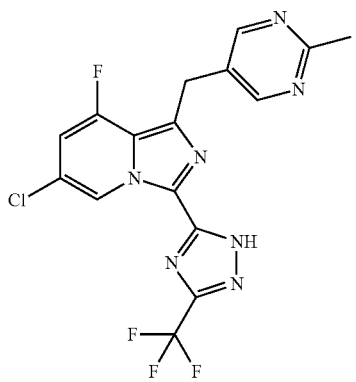 [SMILES: Cc1ncc(Cc2nc(-c3nc(C(F)(F)F)n[nH]3)n3cc(Cl)cc(F)c23)cn1]

I-27

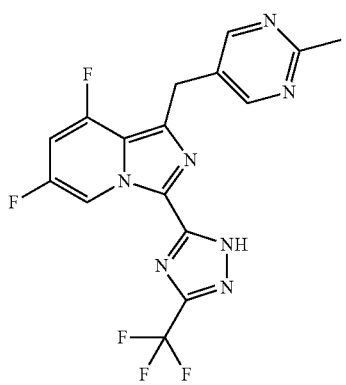 [SMILES: Cc1ncc(Cc2nc(-c3nc(C(F)(F)F)n[nH]3)n3cc(F)cc(F)c23)cn1]

I-28

I-29

I-34

Pharmaceutically Acceptable Salts of the Invention

The phrase "pharmaceutically acceptable salt," as used herein, refers to pharmaceutically acceptable organic or inorganic salts of a compound of Formula I, Table IA or Table IB. The pharmaceutically acceptable salts of a compound of Formula I, Table IA or Table IB are used in medicine. Salts that are not pharmaceutically acceptable may, however, be useful in the preparation of a compound of Formula I, Table IA or Table IB or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from the compounds with inorganic acids, organic acids or bases. In some embodiments, the salts can be prepared in situ during the final isolation and purification of the compounds. In other embodiments the salts can be prepared from the free form of the compound in a separate synthetic step.

When a compound of Formula I, Table IA or Table IB is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N.sup. 1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Formula I, Table IA or Table IB is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

Pharmaceutical Compositions and Methods of Administration.

In another aspect, the invention is also directed to a pharmaceutical composition comprising a compound according to Formula I, Table IA or Table IB, or a pharmaceutically acceptable salt thereof, and at least one pharmaceutically acceptable excipient or carrier. The invention is also directed to a pharmaceutical dosage form comprising the pharmaceutical composition.

The compounds herein disclosed, and their pharmaceutically acceptable salts thereof may be formulated as pharmaceutical compositions or "formulations".

A typical formulation is prepared by mixing a compound of Formula I, Table IA or Table IB, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I, Table IA or Table IB is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I, Table IA or Table IB or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Formula I, Table IA or Table IB, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I, Table IA or Table IB or a pharmaceutically acceptable salt thereof is typically formulated into pharmaceutical dosage forms to provide an easily controllable dosage of the drug and to enable patient compliance with the prescribed regimen. Pharmaceutical formulations of a compound of Formula I, Table IA or Table IB, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I, Table IA or Table IB will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nanoparticles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g., methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semipermeable membrane. The osmotic agent contained in the core of this device may be an aqueous-swellable hydrophilic polymer or it may be an osmogen, also known as an osmagent.

Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including, for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolate. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e. g., Explotab™ CLV), microcrystalline cellulose (e. g., Avicel™), microcrystalline silicified cellulose (e. g., Pro-Solv™) and croscarmellose sodium (e. g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. Nos. 6,419,952, 6,342,249, 5,324,280, 4,672,850, 4,627,850, 4,203,440, and 3,995,631.

As further noted above, the agents described herein may be provided in the form of microparticulates, generally ranging in size from about 10 am to about 2 mm (including, for example, from about 100 µm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 µm) can be designed using polymers able to be degraded in vivo (e.g. biodegradable polyalkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein.

The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intra-hepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I, Table IA or Table IB that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Formula I, Table IA or Table IB in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as butylated hydroxyanisol or alpha-tocopherol.

Aqueous suspensions of a compound of Formula I, Table IA or Table IB contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I, Table IA or Table IB may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I, Table IA or Table IB include Tween™-60, Span™-80, cetostearyl alcohol, benzyl alcohol, myristyl alcohol, glyceryl monostearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I, Table IA or Table IB or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

In another aspect, the invention also provides a method of treating or preventing a disease, health condition or disorder in a subject in need thereof, comprising administering, alone or in combination therapy, a therapeutically effective amount of a compound of Formula I, a compound from Table IA or a compound from Table IB, or a pharmaceutically acceptable salt thereof, to the subject; wherein the disease is one that benefits from sGC stimulation or from an increase in the concentration of NO or cGMP or both, or from the upregulation of the NO pathway.

The invention also provides a method of treating or preventing a disease, health condition or disorder in a subject in need thereof, comprising administering, alone or in combination therapy, a pharmaceutical composition comprising a compound of Formula I, a compound of Table IA or a compound of Table IB, or a pharmaceutically acceptable salt thereof, to the subject or a dosage form comprising the pharmaceutical composition, wherein the disease is one that benefits from sGC stimulation or from an increase in the concentration of NO or cGMP or both, or from the upregulation of the NO pathway.

The invention relates to the treatment of certain disorders by using sGC stimulators, either alone or in combination, or their pharmaceutically acceptable salts or pharmaceutical compositions comprising them, in a patient in need thereof.

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO or an increase in the concentration of cGMP might be desirable. The diseases that can be treated include but are not limited to pulmonary hypertension, arterial hypertension, heart failure, atherosclerosis, inflammation, thrombosis, renal fibrosis and failure, liver cirrhosis, erectile dysfunction, female sexual disorders, disorders related to diabetes, ocular disorders and other related cardiovascular disorders.

Increased concentration of cGMP leads to vasodilation, inhibition of platelet aggregation and adhesion, anti-hypertensive effects, anti-remodeling effects, anti-apoptotic effects, anti-inflammatory, anti-fibrotic effects and neuronal signal transmission effects. Thus, sGC stimulators may be used to treat and/or prevent a range of diseases and disorders, including but not limited to a peripheral, pulmonary, hepatic, liver, cardiac or cerebrovascular/endothelial disorders or conditions, a urogenital-gynecological or sexual disorder or condition, a thromboembolic disease, an ischemic disease, a fibrotic disorder, a topical or skin disorder, a pulmonary or respiratory disorder, a renal or hepatic disorder, a metabolic disorder, atherosclerosis, or a lipid related disorder.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

In other embodiments, the compounds here disclosed are sGC stimulators that may be useful in the prevention and/or treatment of diseases and disorders characterized by increased neuroinflammation. One embodiment of the invention is a method of decreasing neuroinflammation in a subject in need thereof by administering to the subject any one of the compounds of Formula I, Table IA or Table IB or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by increased neurotoxicity. One embodiment of the invention is a method of reducing neurotoxicity in a subject in need thereof by administering to the subject any one of the compounds of Formula I, Table IA or Table IB, or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by impaired neurorengeneration. One embodiment of the invention is a method of restoring neuroregeneration in a subject in need thereof by administering to the subject any one of the compounds of Formula I, Table IA or Table IB, or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by impaired synaptic function. One embodiment of the invention is a method of restoring synaptic function in a subject in need thereof by administering to the subject any one of the compounds of Formula I, Table IA or Table IB, or a pharmaceutically acceptable salt thereof. In particular the diseases and disorders is a CNS disease or disorder as described in sections (9)-(16), below.

In other embodiments, the compounds here disclosed are sGC stimulators that may be useful in the prevention and/or treatment of diseases and disorders characterized by down-regulated neurotransmitters. One embodiment of the invention is a method of normalizing neurotransmitter in a subject in need thereof by administering to the subject any one of the compounds of Formula I, Table IA or Table IB, or a pharmaceutically acceptable salt thereof. In particular the diseases and disorders is a CNS disease or disorder as described in sections (9)-(16), below. Specifically, the disease is Alzheimer's Disease. Specifically, the disease is Mixed Dementia.

In other embodiments, the compounds here disclosed are sGC stimulators that may be useful in the prevention and/or treatment of diseases and disorders characterized by impaired cerebral blood flow. One embodiment of the invention is a method of restoring cerebral blood flow in a subject in need thereof by administering to the subject any one of the compounds of Formula I, Table IA or Table IB, or a pharmaceutically acceptable salt thereof. In particular the diseases and disorders is a CNS disease or disorder as described in sections (9)-(16), below. Specifically, the disease is Vascular Dementia or Alzheimer's Disease. Specifically, the disease is Mixed Dementia. In other embodiments CNS disorder is selected from either traumatic (closed or open, penetrating head injuries), traumatic brain injury (TBI), or nontraumatic (stroke, aneurism, hypoxia) injury to the brain or cognitive impairment or dysfunction resulting from brain injuries or neurodegenerative disorders.

In other embodiments, the compounds here disclosed are sGC stimulators that may be useful in the prevention and/or treatment of diseases and disorders characterized by increased neurodegeneration. One embodiment of the invention is a method of decreasing neurodegeneration in a subject in need thereof by administering to the subject any one of the compounds of Formula I, Table IA or Table IB, or a pharmaceutically acceptable salt thereof. In particular the diseases and disorders is a CNS disease or disorder as described in sections (9)-(16), below.

In other embodiments, the compounds here disclosed are sGC stimulators are neuroprotective. In particular, the compounds of Formula I, Table IA or Table IB, or a pharmaceutically acceptable salt thereof may be useful protect the neurons in a subject in need thereof. In particular, the diseases and disorders is a CNS disease or disorder as described in sections (9)-(16), below.

In other embodiments, the compounds here disclosed are sGC stimulators that may be useful in the prevention and/or treatment orphan pain indications. One embodiment of the invention is a method of treating an orphan pain indication in a subject in need thereof by administering to the subject any one of the compounds of Formula I, Table IA or Table IB, or a pharmaceutically acceptable salt thereof. In particular, the orphan pain indication is selected from Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, and Tolosa-Hunt syndrome.

Throughout this disclosure, the terms "hypertension", "arterial hypertension" or "high blood pressure (HBP)" are used interchangeable and refer to an extremely common and highly preventable chronic condition in which blood pressure (BP) in the arteries is higher than normal. If not properly controlled, it represents a significant risk factor for several serious cardiovascular and renal conditions. Hypertension may be a primary disease, called "essential hypertension" or "idiopathic hypertension", or it may be caused by other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension. Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

As used herein "heart failure" is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neurohormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness, edema of the feet, ankles and legs, rapid weight gain, chronic cough, including that producing mucus or blood. Depending on its clinical presentation, heart failure is classified as de novo, transient or chronic. Acute heart failure, i.e. the rapid or gradual onset of symptoms requiring urgent therapy, may develop de novo or as a result of chronic heart failure becoming decompensated. Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, nonvoluntary loss of at least 6% of body weight over a period of six months.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p 13.1-13.3). "Hyperglyceridemia" refers to elevated levels of glycerides (e.g., "hypertrigliceridemia" involves elevated levels of triglycerides). "Hyperlipoproteinemia" refers to elevated levels of lipoproteins (usually LDL unless otherwise specified).

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or brain. PVD can result from atherosclerosis, inflammatory processes leading to stenosis, an embolism, or thrombus formation. It causes either acute or chronic "ischemia (lack of blood supply)". Often PVD is a term used to refer to atherosclerotic blockages found in the lower extremity. PVD also includes a subset of diseases classified as microvascular diseases resulting from episodal narrowing of the arteries (e.g., "Raynaud's phenomenon"), or widening thereof (erythromelalgia), i.e. vascular spasms.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen, and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin.

A "stroke", or cerebrovascular accident (CVA), is the rapid loss of brain function(s) due to disturbance in the blood supply to the brain. This can be due to "ischemia" (lack of blood flow) caused by blockage (thrombosis, arterial embolism), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Ischemia" is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism).

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

As used herein, the term "bronchoconstriction" is used to define the constriction of the airways in the lungs due to the tightening of surrounding smooth muscle, with consequent coughing, wheezing, and shortness of breath. The condition has a number of causes, the most common being as well as asthma. Exercise and allergies can bring on the symptoms in an otherwise asymptomatic individual. Other conditions such as chronic obstructive pulmonary disease (COPD) can also present with bronchoconstriction.

Specific diseases of disorders which may be treated and/or prevented by administering an sGC stimulator of the invention, include but are not limited to: hypertension (e.g., diabetic hypertension, arterial hypertension, pulmonary hypertension, resistant hypertension, peripheral artery disease, etc.), heart failure (e.g., left ventricular diastolic dysfunction (LVDD) and left ventricular systolic dysfunction (LVSD), sleep apnea associated with heart failure), arteriosclerotic disease (e.g., atherosclerosis), thromboembolic disorders (e.g., chronic thromboembolic pulmonary hypertension, thrombosis, stroke (in particular, ischemic stroke), embolism, pulmonary embolism), Alzheimer's disease, renal or kidney diseases (e.g., renal fibrosis, ischemic renal disease, renal failure, renal insufficiency, chronic kidney disease), hepatic disease (e.g., liver fibrosis or cirrhosis, non-alcoholic steatohepatitis (NASH)), respiratory disease (e.g., pulmonary fibrosis, asthma, chronic obstructive pulmonary disease, interstitial lung disease), sexual disorders (e.g., erectile dysfunction, male and female sexual dysfunction, vaginal atrophy), sickle cell anemia, sickle cell disease (SCD), neuro inflammatory diseases or disorders, CNS disease and disorders, gastro intestinal disorders (e.g., achalasia or esophageal achalasia), and metabolic disorders (e.g., lipid related disorders).

Further specific diseases of disorders which may be treated and/or prevented by administering an sGC stimulator of the invention, include but are not limited to: age-associated memory impairment, mixed dementia, sleep wake disorders, and Sneddon's syndrome.

Further specific diseases of disorders which may be treated and/or prevented by administering an sGC stimulator of the invention, include but are not limited to: acute pain, central pain syndrome, chemotherapy induced neuropathy and neuropathic pain, diabetic neuropathy, fibromyalgia, inflammatory pain, neuropathic pain, neuropathic pain associated with a CNS disease, painful diabetic peripheral neuropathy, post-operative pain, tonic pain, and visceral pain.

Further specific diseases of disorders which may be treated and/or prevented by administering an sGC stimulator of the invention, include but are not limited to: altitude (mountain) sickness, cerebral small vessel disease, cerebral vasculitis, cerebral vasospasm, diabetic heart failure (diabetic HF), diabetic angiopathy, diabetic macular edema, diabetic microangiopathies, Heart failure with preserved ejection fraction (HFpEF), hepatic encephalopathy, moyamoya, non-diabetic nephropathy, and Parkinson's Dysphagia.

Further specific diseases of disorders which may be treated and/or prevented by administering an sGC stimulator of the invention, include but are not limited to: angina, ataxia telangliectasia, autism spectrum disorder, chronic fatigue, chronic traumatic encephalopathy (CTE), cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell, concussion, dysphagia, eye fibrosis, Fabry Disease, Gaucher Disease, glioblastoma, inflammation caused by cerebral malaria (SoC), inflammation caused by infectious disease, intellectual disability, microvascular angina, myopic choroidal neovascularization, neuromyelitis optica, neuropathic pain with Multiple Sclerosis, neuropathic pain with shingles (herpes zoster), neuropathic pain with spine surgery, Parkinson's Dementia, peripheral and autonomic neuropathies, peripheral retinal degeneration, post-traumatic stress syndrome, post herpetic neuralgia, post-operative dementia, proliferative vitroretinopathy, radiation induced fibrosis, radiculopathy, refractory epilepsy, retinal vein occlusion, Sjogren's syndrome, spinal cord injury, spinal muscular atrophy, spinal subluxations, tauopathies, ulcers, and wet age-related macular degeneration.

The compounds of Formula I, Table IA or Table IB as well as pharmaceutically acceptable salts thereof, as stimulators of sGC, are useful in the prevention and/or treatment of the following types of diseases, conditions and disorders which can benefit from sGC stimulation or an upregulation of the NO pathway:

(1) Peripheral, pulmonary, hepatic, kidney, cardiac or cerebral vascular/endothelial disorders/conditions or diseases otherwise related to circulation:
  disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); resistant hypertension, diabetic hypertension, congestive heart failure; diastolic or systolic dysfunction; coronary insufficiency; arrhythmias; reduction of ventricular preload; cardiac hypertrophy; heart failure/cardiorenal syndrome; portal hypertension; endothelial dysfunction or injury;

thromboembolic disorders and ischemias such as myocardial infarction, stroke (in particular, ischemic stroke), transient ischemic attacks (TIAs); obstructive thromboanginitis; stable or unstable angina pectoris; coronary spasms, variant angina, Prinzmetal's angina; prevention of restenosis after thrombolysis therapies; thrombogenic disorders;

dementia, vascular dementia, cerebral vasospasm;

peripheral arterial disease, peripheral occlusive arterial disease; peripheral vascular disease; hypertonia; Raynaud's syndrome or phenomenon, critical limb ischemia, vasculitis; peripheral embolism; intermittent claudication; vaso-occlusive crisis; Duchenne's and Becker muscular dystrophies; microcirculation abnormalities; control of vascular leakage or permeability;

shock; sepsis; cardiogenic shock; control of leukocyte activation; inhibition or modulation of platelet aggregation;

pulmonary/respiratory conditions such as pulmonary hypertension, pulmonary arterial hypertension, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, precapillary pulmonary hypertension, idiopathic pulmonary hypertension, thrombotic pulmonary arteriopathy, plexogenic pulmonary arteriopathy; cystic fibrosis; bronchoconstriction or pulmonary bronchoconstriction; acute respiratory distress syndrome; lung fibrosis, lung transplant;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venooclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schistosomiasis, sarcoidosis, chronic obstructive pulmonary disease, asthma, emphysema, chronic bronchitis, pulmonary capillary hemangiomatosis; histiocytosis X, lymphangiomatosis and compressed pulmonary vessels (such as due to adenopathy, tumor or fibrosing mediastinitis);

arterosclerotic diseases or conditions such as atherosclerosis (e.g., associated with endothelial injury, platelet and monocyte adhesion and aggregation, smooth muscle proliferation and migration); restenosis (e.g. developed after thrombolysis therapies, percutaneous transluminal angioplasties (PTAs), percutaneous transluminal coronary angioplasties (PTCAs) and bypass); inflammation;

cardiovascular disease associated with metabolic syndrome (e.g., obesity, dyslipidemia, diabetes, high blood pressure); lipid related disorders such as dyslipidemia, hypercholerolemia, hypertriglyceridemia, sitosterolemia, fatty liver disease, steatosis, steatohepatitis, non-alcoholic steatohepatitis (NASH), and hepatitis; preeclampsia; polycystic kidney disease progression; subcutaneous fat; obesity;

liver cirrhosis, associated with chronic liver disease, hepatic fibrosis, liver fibrosis, hepatic stellate cell activation, hepatic fibrous collagen and total collagen accumulation; liver disease of necro-inflammatory and/ or of immunological origin; and urogenital system disorders, such as renal fibrosis and renal failure resulting from chronic kidney diseases or insufficiency (e.g. due to accumulation/deposition and tissue injury, progressive sclerosis, glomerulonephritis); prostate hypertrophy; non-alcoholic steatohepatitis or NASH;

systemic sclerosis;

cardiac interstitial fibrosis; cardiac remodeling and fibrosis; cardiac hypertrophy;

gastrointestinal disease such as achalasia or esophageal achalasia; and other diseases or conditions: cancer metastasis, osteoporosis, gastroparesis; functional dyspepsia; diabetic complications, diseases associated with endothelial dysfunction, and neurologic disorders associated with decreased nitric oxide production.

(2) ischemia, reperfusion damage; ischemia/reperfusion associated with organ transplant, lung transplant, pulmonary transplant, cardiac transplant; conserving blood substituents in trauma patients;

(3) sexual, gynecological and urological disorders of conditions: erectile dysfunction; impotence; premature ejaculation; female sexual dysfunction (e.g., female sexual arousal dysfunction, hypoactive sexual arousal disorder), vaginal atrophy, dyspaneuria, atrophic vaginitis; benign prostatic hyperplasia (BPH) or hypertrophy or enlargement, bladder outlet obstruction; bladder pain syndrome (BPS), interstitial cystitis (IC), overactive bladder, neurogenic bladder and incontinence; diabetic nephropathy;

(4) ocular diseases or disorders: glaucoma, retinopathy, diabetic retinopathy, (including proliferative and non-proliferative), blepharitis, dry eye syndrome, Sjigren's Syndrome;

(5) hearing diseases or disorders: hearing impairment, partial or total hearing loss; partial or total deafness; tinnitus; noise-induced hearing loss;

(6) topical or skin disorders or conditions: dermal fibrosis, scleroderma, skin fibrosis;

(7) wound healing: for instance in diabetics; microvascular perfusion improvement (e.g., following injury, to counteract the inflammatory response in perioperative care), anal fissures, diabetic ulcers;

(8) other diseases or conditions: cancer metastasis, osteoporosis, gastroparesis; functional dyspepsia; diabetic complications, diseases associated with endothelial dysfunction, and neurologic disorders associated with decreased nitric oxide production; achalasia or esophageal achalasia.

(9) CNS diseases, health conditions or disorders, for instance: Alzheimer's disease (AD), amyotrophic lateral sclerosis (ALS or Lou Gehrig's disease), Down's syndrome, dementia, vascular dementia (VD), vascular cognitive impairment, Mixed Dementia, Binswanger's dementia (subcortical arteriosclerotic encephalopathy), cerebral autosomal-dominant arteriopathy with subcortical infarcts and leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment or MCI), glaucoma, Huntington's disease (or Huntington's chorea, HD), or a cognitive defect associated with HD; multiple sclerosis (MS) (including Clinically isolated syndrome (CIS), Relapsing-remitting MS (RRMS), Primary progressive MS (PPMS), and Secondary progressive MS (SPMS), multiple system atrophy (MSA), Parkinson's disease (PD), Parkinsonism Plus, spinocerebellar ataxias, Steel-Richardson-Olszewski disease (progressive supranuclear palsy), attention deficit disorder (ADD) and attention deficit hyperactivity disorder (ADHD);

(10) a CNS disorder or condition selected from Alzheimer's disease or pre-Alzheimer's disease, mild to moderate Alzheimer's disease or moderate to severe Alzheimer's disease

(11) a CNS disorder is selected from either traumatic (closed or open), penetrating head injuries, traumatic brain injury (TBI) including, for example, concussions and Chronic traumatic encephalopathy (CTE)), non traumatic injury to the brain (e.g., stroke (including ischemic stroke), aneurism, hypoxia) or cognitive impairment or dysfunction resulting from brain injuries or neurodegenerative disorders;

(12) a CNS disease or disorder is selected from dystonias, including for example, generalized, focal, segmental, sexual, intermediate, acute dystonic reaction, and genetic/primary dystonia; and dyskinesias, including for example, acute, chronic/tardive, and non-motor and levo-dopa induced dyskinesia (LID);

(13) a CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders, including autism, Asperger's syndrome, pervasive development disorder and childhood disintegrative disorder;

(14) a CNS disorder is neuropathic pain;

(15) a CNS disorder is a psychiatric, mental, mood or affective disorder selected from a bipolar disorder, schizophrenia, general psychosis, drug-induced psychosis, a delusional disorder, a schizoaffective disorder, obsessive compulsive disorder (OCD), a depressive disorder, an anxiety disorder, a panic disorder, post-traumatic stress disorder (PTSD); and

(16) a CNS disorder is selected from chemo brain, levo-dopa induced addictive behavior, alcoholism, narcotic dependence (including but not limited to amphetamine, opiates or other substances) and substance abuse.

In some embodiments, the invention relates to a method of treating a disease, health condition or disorder in a subject, comprising administering a therapeutically effective amount of a compound of any of the above depicted Formulae, or a pharmaceutically acceptable salt thereof, to the subject in need of treatment, wherein the disease, health condition or disorder is selected from one of the diseases listed above.

In other embodiments the disease, health condition or disorder is selected from a peripheral, pulmonary, hepatic, kidney, cardiac or cerebralvascular/endothelial disorder or condition, or a disease otherwise related to circulation selected from: increased acute and chronic coronary blood pressure, arterial hypertension and vascular disorder resulting from cardiac and renal complications, heart disease, stroke (in particular, ischemic stroke), cerebral ischemia, renal failure; resistant hypertension, diabetic hypertension, congestive heart failure; diastolic or systolic dysfunction; coronary insufficiency; arrhythmias; reduction of ventricular preload; cardiac hypertrophy; heart failure/cardiorenal syndrome; portal hypertension; endothelial dysfunction or injury; myocardial infarction; stroke or transient ischemic attacks (TIAs); obstructive thromboanginitis; stable or unstable angina pectoris; coronary spasms, variant angina, Prinzmetal's angina; restenosis as a result of thrombolysis therapies and thrombogenic disorders.

In still other embodiments, the disease, health condition or disorder is selected from a peripheral vascular/endothelial disorder or condition or a disease otherwise related to circulation selected from: peripheral arterial disease, peripheral occlusive arterial disease; peripheral vascular disease; hypertonias; Raynaud's syndrome or phenomenon or disease; critical limb ischemia; vasculitis; peripheral embolism; intermittent claudication; vaso-occlusive crisis; Duchenne's and Becker muscular dystrophies; microcirculation abnormalities; and vascular leakage or permeability issues.

In further embodiments, the disease, health condition or disorder is a pulmonary disorder or condition or a disease otherwise related to circulation selected from: pulmonary hypertension; pulmonary arterial hypertension and associated pulmonary vascular remodeling; localized thrombosis; right heart hypertrophy; pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; cystic fibrosis; bronchoconstriction or pulmonary bronchoconstriction; acute respiratory distress syndrome; lung fibrosis and lung transplant. In some of these embodiments, the pulmonary hypertension is pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, coagulation disorders, chronic thromboembolism; pulmonary embolism, due to tumor, parasites or foreign material; connective tissue disease, lupus, schistosomiasis, sarcoidosis, chronic obstructive pulmonary disease, asthma, emphysema, chronic bronchitis, pulmonary capillary hemangiomatosis; histiocytosis X; lymphangiomatosis and compressed pulmonary vessels due to adenopathy, tumor or fibrosing mediastinitis.

In still other embodiments, the health condition or disorder is a vascular or endothelial disorder or condition or a disease otherwise related to circulation selected from: arterosclerotic diseases; atherosclerosis, atherosclerosis associated with endothelial injury, atherosclerosis associated with platelet and monocyte adhesion and aggregation, atherosclerosis associated with smooth muscle proliferation and migration; restenosis, restenosis developed after thrombolysis therapies; restenosis developed after percutaneous transluminal angioplasties; restenosis developed after percutaneous transluminal coronary angioplasties and bypass; inflammation; cardiovascular disease associated with metabolic syndrome (e.g., obesity, dyslipidemia, diabetes, high blood pressure); lipid related disorders such as dyslipidemia, hypercholesterolemia, hypertriglyceridemia, sitosterolemia, fatty liver disease, steatosis, steatohepatitis, non-alcoholic steatohepatitis (NASH), and hepatitis; preeclampsia; polycystic kidney disease progression; subcutaneous fat; and obesity.

In other embodiments, the disease, health condition or disorder is selected from dementia, vascular dementia or cerebral vasospasm.

In yet other embodiments, the disease, health condition or disorder selected from liver cirrhosis, liver cirrhosis associated with chronic liver disease, hepatic fibrosis, hepatic stellate cell activation, hepatic fibrous collagen and total collagen accumulation; and liver disease of necro-inflammatory or of immunological origin.

In further embodiments, the disease, health condition or disorder is a urogenital system disorder selected from renal fibrosis; renal failure resulting from chronic kidney diseases or insufficiency; renal failure due to accumulation or deposition and tissue injury, progressive sclerosis or glomerulonephritis; and prostatic hypertrophy.

In some embodiments, the disorder is a CNS disease, health condition or disorder selected from Alzheimer's disease, amyotrophic lateral sclerosis (ALS or Lou Gehrig's disease), Down syndrome, dementia, vascular dementia, Mixed Dementia, vascular cognitive impairment, Binswanger's dementia (subcortical arteriosclerotic encephalopathy), Cerebral Autosomal-Dominant Arteriopathy with Subcortical Infarcts and Leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment, MCI), glaucoma, Huntington's diseases (or chorea, HD), or a cognitive defect associated with HD; multiple sclerosis (MS), multiple system atrophy (MSA), Parkinson's disease, Parkinsonism Plus, spinocerebellar ataxias, Steel-Richardson-Olszewski disease (progressive supranuclear palsy), attention deficit disorder (ADD) and attention deficit hyperactivity disorder (ADHD).

In further embodiments, the disease, health condition or disorder is a CNS disorder or condition selected from Alzheimer's disease or pre-Alzheimer's disease, mild to moderate Alzheimer's disease or moderate to severe Alzheimer's disease.

In other embodiments, the CNS disorder is selected from either traumatic (closed or open, penetrating head injuries), traumatic brain injury (TBI), or nontraumatic (stroke (in particular, ischemic stroke), aneurism, hypoxia) injury to the brain or cognitive impairment or dysfunction resulting from brain injuries or neurodegenerative disorders.

In other embodiments, the CNS disease or disorder is selected from dystonias, including for example, generalized, focal, segmental, sexual, intermediate, acute dystonic reaction, and genetic/primary dystonia; and dyskinesias, including for example, acute, chronic/tardive, and non-motor and levo-dopa induced dyskinesia (LID).

In other embodiments, the CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders, including autism, Asperger's syndrome, pervasive development disorder and childhood disintegrative disorder.

In other embodiments, the CNS disorder is neuropathic pain.

In other embodiments, the CNS disorder is a psychiatric, mental, mood or affective disorder selected from a bipolar disorder, schizophrenia, general psychosis, drug-induced psychosis, a delusional disorder, schizoaffective disorder, obsessive compulsive disorder (OCD), a depressive disorder, an anxiety disorder, a panic disorder, post-traumatic stress disorder (PTSD).

In other embodiments, the CNS disorder is selected from chemo brain, levo-dopa induced addictive behavior, alcoholism, narcotic dependence (including but not limited to amphetamine, opiates or other substances) and substance abuse.

In some embodiments, the disease or disorder is achalasia or esophageal achalasia.

In other embodiments, the disease or disorder is non-alcoholic steatohepatitis or NASH.

In further embodiments, the disease, health condition or disorder is systemic sclerosis.

In further embodiments, the disease, health condition or disorder is a cardiac disorder selected from cardiac interstitial fibrosis; cardiac remodeling and fibrosis and cardiac hypertrophy.

In further embodiments, the disease, health condition or disorder is selected from ischemia, reperfusion damage; ischemia/reperfusion associated with organ transplant, lung transplant, pulmonary transplant or cardiac transplant; conserving blood substituents in trauma patients.

In further embodiments, the disease, health condition or disorder is a sexual, gynecological or urological disorder of condition selected from erectile dysfunction; impotence; premature ejaculation; female sexual dysfunction; female sexual arousal dysfunction; hypoactive sexual arousal disorder; vaginal atrophy, dyspaneuria, atrophic vaginitis; benign prostatic hyperplasia (BPH) or hypertrophy or enlargement; bladder outlet obstruction; bladder pain syndrome (BPS); interstitial cystitis (IC); overactive bladder, neurogenic bladder and incontinence; diabetic nephropathy.

In further embodiments, the disease, health condition or disorder is selected from vaginal atrophy, dyspaneuria and atrophic vaginitis.

In further embodiments, the disease, health condition or disorder is selected from benign prostatic hyperplasia (BPH) or hypertrophy or enlargement; bladder outlet obstruction; bladder pain syndrome (BPS); interstitial cystitis (IC); overactive bladder, neurogenic bladder and incontinence.

In further embodiments, the disease, health condition or disorder is a sexual, condition selected from erectile dysfunction; impotence; premature ejaculation; female sexual dysfunction; female sexual arousal dysfunction and hypoactive sexual arousal disorder.

In further embodiments, the disease or disorder is diabetic nephropathy.

In further embodiments, the disease, health condition or disorder is Duchenne's and Becker muscular dystrophies.

In further embodiments, the disease is an ocular diseases or disorder selected from glaucoma, retinopathy, diabetic retinopathy (including proliferative and non-proliferative), blepharitis, dry eye syndrome and Sjigren's Syndrome.

In further embodiments, the disease is a hearing diseases or disorder selected from hearing impairment, partial or total hearing loss; partial or total deafness; tinnitus; and noise-induced hearing loss.

In further embodiments, the disease is a topical or skin disorders or condition selected from dermal fibrosis, scleroderma and skin fibrosis.

In further embodiments, the treatment involves wound healing; wound healing in diabetics; improvement of microvascular perfusion; improvement of microvascular perfusion issues following injury; treatment of anal fissures; and treatment of diabetic ulcers.

In further embodiments, the disease or condition is selected from cancer metastasis; osteoporosis; gastroparesis; functional dyspepsia; diabetic complications; diseases associated with endothelial dysfunction and neurologic disorders associated with decreased nitric oxide production.

In other embodiments, the disease, or condition is a CNS disease. In some embodiments, the CNS disease, health condition or disorder is selected from Alzheimer's disease (AD), amyotrophic lateral sclerosis (ALS or Lou Gehrig's disease), Down's syndrome, dementia, vascular dementia (VD), vascular cognitive impairment, Binswanger's dementia (subcortical arteriosclerotic encephalopathy), cerebral autosomal-dominant arteriopathy with subcortical infarcts and leukoencephalopathy (CADASIL or CADASIL syndrome), frontotemporal lobar degeneration or dementia, HIV-associated dementia, Lewy body dementia, pre-senile dementia (mild cognitive impairment or MCI), glaucoma, Huntington's disease (or Huntington's chorea, HD), multiple sclerosis (MS), multiple system atrophy (MSA), Parkinson's disease (PD), Parkinsonism Plus, spinocerebellar ataxias, Steel-Richardson-Olszewski disease (progressive supranuclear palsy), attention deficit disorder (ADD) and attention deficit hyperactivity disorder (ADHD).

In other embodiments, the disease, health condition or disorder is a CNS disorder or condition selected from Alzheimer's disease or pre-Alzheimer's disease, mild to moderate Alzheimer's disease or moderate to severe Alzheimer's disease.

In other embodiments, the CNS disorder is selected from either traumatic (closed or open) penetrating head injuries, traumatic brain injury (TBI), non-traumatic injury to the brain (e.g., stroke, aneurism, hypoxia) or cognitive impairment or dysfunction resulting from brain injuries or neurodegenerative disorders.

In other embodiments, the CNS disease or disorder is selected from a dystonia, including for example, generalized, focal, segmental, sexual, intermediate, genetic/primary dystonia or acute dystonic reaction; or a dyskinesia, including for example, acute, chronic/tardive, and non-motor and levo-dopa induced dyskinesia (LID).

In other embodiments, the CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders (ASD), autism, Asperger's syndrome, pervasive development disorder or childhood disintegrative disorder.

In other embodiments, the CNS disorder is neuropathic pain.

In other embodiments, the CNS disorder is a psychiatric, mental, mood or affective disorder selected from a bipolar disorder, schizophrenia, general psychosis, drug-induced psychosis, a delusional disorder, a schizoaffective disorder, obsessive compulsive disorder (OCD), a depressive disorder, an anxiety disorder, a panic disorder, post-traumatic stress disorder (PTSD).

In other embodiments, the CNS disorder is selected from chemo brain, levo-dopa induced addictive behavior, alcoholism, narcotic dependence (including but not limited to amphetamine, opiates or other substances) and substance abuse.

In further embodiments, the disease or condition is selected from cancer metastasis; osteoporosis; gastroparesis; functional dyspepsia; diabetic complications; diseases associated with endothelial dysfunction and neurologic disorders associated with decreased nitric oxide production.

In further embodiments, the disease or condition is selected from age-associated memory impairment, mixed dementia, sleep wake disorders, and Sneddon's syndrome.

In further embodiments, the disease or condition is selected from acute pain, central pain syndrome, chemotherapy induced neuropathy and neuropathic pain, diabetic neuropathy, fibromyalgia, Inflammatory pain, neuropathic pain, neuropathic pain associated with a CNS disease, painful diabetic peripheral neuropathy, post-operative pain, tonic pain, and visceral pain.

In further embodiments, the disease or condition is selected from altitude (mountain) sickness, cerebral small vessel disease, cerebral vasculitis, cerebral vasospasm, diabetic heart failure (diabetic HF), diabetic angiopathy, diabetic macular edema, diabetic microangiopathies, Heart failure with preserved ejection fraction (HFpEF), hepatic encephalopathy, moyamoya, non-diabetic nephropathy, and Parkinson's Dysphagia.

In further embodiments, the disease or condition is selected from angina, ataxia telangliectasia, autism spectrum disorder, chronic fatigue, chronic traumatic encephalopathy (CTE), cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell, concussion, dysphagia, eye fibrosis, Fabry Disease, Gaucher Disease, glioblastoma, inflammation caused by cerebral malaria (SoC), inflammation caused by infectious disease, intellectual disability, microvascular angina, myopic choroidal neovascularization, neuromyelitis optica, neuropathic pain with Multiple Sclerosis, neuropathic pain with shingles (herpes zoster), neuropathic pain with spine surgery, Parkinson's Dementia, peripheral and autonomic neuropathies, peripheral retinal degeneration, post-traumatic stress syndrome, post herpetic neuralgia, post-operative dementia, proliferative vitroretinopathy, radiation induced fibrosis, radiculopathy, refractory epilepsy, retinal vein occlusion, Sjogren's syndrome, spinal cord injury, spinal muscular atrophy, spinal subluxations, tauopathies, ulcers, and wet age-related macular degeneration.

In further embodiments, the disease or condition is selected from an orphan pain indication. In particular, the orphan pain indication is selected from Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, and Tolosa-Hunt syndrome.

In another embodiment, compounds of the invention can be delivered in the form of implanted devices, such as stents. A stent is a mesh 'tube' inserted into a natural passage/conduit in the body to prevent or counteract a disease-induced, localized flow constriction. The term may also refer to a tube used to temporarily hold such a natural conduit open to allow access for surgery.

A drug-eluting stent (DES) is a peripheral or coronary stent (a scaffold) placed into narrowed, diseased peripheral or coronary arteries that slowly releases a drug to block cell proliferation, usually smooth muscle cell proliferation. This prevents fibrosis that, together with clots (thrombus), could otherwise block the stented artery, a process called restenosis. The stent is usually placed within the peripheral or coronary artery by an Interventional cardiologist or Interventional Radiologist during an angioplasty procedure. Drugs commonly used in DES in order to block cell proliferation include paclitaxel or rapamycin analogues In some embodiments of the invention, a sGC stimulator of the invention can be delivered by means of a drug-eluting stent coated with said sGC stimulator. A drug-eluting stent coated with a sGC stimulator of the invention may be useful in the prevention of stent restenosis and thrombosis during percutaneous coronary interventions. A drug-eluting stent coated with a sGC stimulator of the invention may be able to prevent smooth cell proliferation as well as to assist re-vascularization and re-generation of the endothelial tissue of the artery in which the stent is inserted.

An alternative to percutaneous coronary intervention for the treatment of intractable angina due to coronary artery occlusive disease is the procedure named Coronary Artery Bypass Grafting (CABG). CABG provides only palliation of an ongoing process that is further complicated by the rapid development of graft atherosclerosis. The saphenous vein graft is the most commonly used conduit in CABG surgery. The long-term clinical success of venous CABG is hampered for three main reasons: accelerated graft atherosclerosis, incomplete endothelialization and thrombosis.

In some embodiments, a sGC stimulator of the invention can be used for the prevention of saphenous graft failure during CABG. Compounds of the invention may assist the process of endothelialization and help prevent thrombosis. In this indication, the sGC stimulator is delivered locally in the form of a gel.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Formula I, Table IA or Table IB, or a pharmaceutically acceptable salt thereof, to the subject in need of the treatment. Alternatively, the invention provides the use of a compound of Formula I, Table IA or Table IB, or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Formula I, Table IA or Table IB, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, cerebrospinal fluid (CSF), or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernible symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments, the terms "treat", "treatment" and "treating" refer to the inhibition of the progression of an sGC, cGMP and/or NO mediated condition, either physically by, e.g., stabilization of a discernible symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g. a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I or a pharmaceutically acceptable salt thereof and a second amount of an additional suitable therapeutic agent.

In one embodiment of this invention, a compound of Formula I, or a pharmaceutically acceptable salt thereof, and the additional therapeutic agent are each administered in an effective amount (i.e., each in an amount which would be therapeutically effective if administered alone). In another embodiment, the compound of Formula I and the additional therapeutic agent are each administered in an amount which alone does not provide a therapeutic effect (a sub-therapeutic dose). In yet another embodiment, the compound of Formula I can be administered in an effective amount, while the additional therapeutic agent is administered in a sub-therapeutic dose. In still another embodiment, the compound of Formula I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Formula I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of Formula I, or a pharmaceutically acceptable salt thereof, either administered separately or in the same pharmaceutical composition include, but are not limited to:

(1) Endothelium-derived releasing factor (EDRF) or NO gas.
(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholinosydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.
(3) Other substances that enhance cGMP concentrations such as protoporphyrin IX, arachidonic acid and phenyl hydrazine derivatives.
(4) Nitric Oxide Synthase substrates: for example, N-hydroxyguanidine based analogs, such as N[G]-hydroxy-L-arginine (NOHA), 1-(3,4-dimethoxy-2-chlorobenzylideneamino)-3-hydroxyguanidine, and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl) oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.
(5) Compounds which enhance eNOS transcription.
(6) NO independent heme-independent sGC activators, including, but not limited to: BAY 58-2667 (described in patent publication DE19943635)

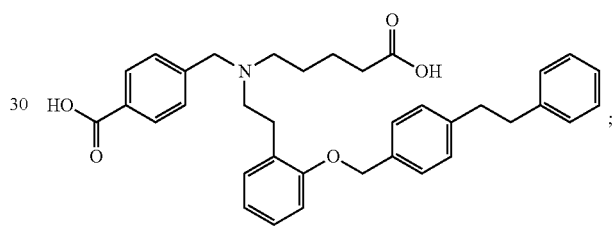

HMR-1766 (ataciguat sodium, described in patent publication WO2000002851)

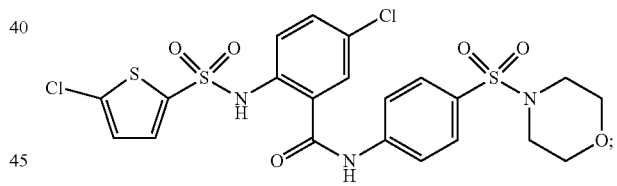

S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851)

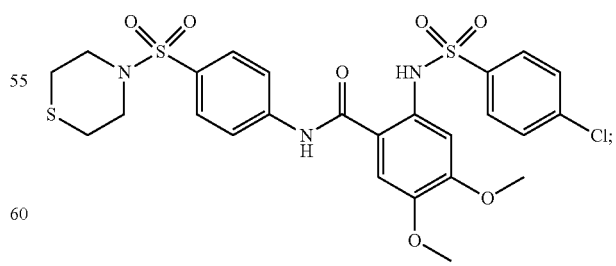

and
HMR-1069 (Sanofi-Aventis).
(7) Heme-dependent, NO-independent sGC stimulators including, but not limited to: YC-1 (see patent publications EP667345 and DE19744026)

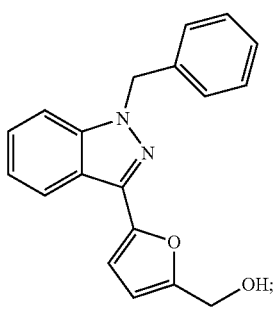 [SMILES: OCc1ccc(-c2nn(Cc3ccccc3)c3ccccc23)o1]
riociguat (BAY 63-2521, Adempas®, described in DE19834044)
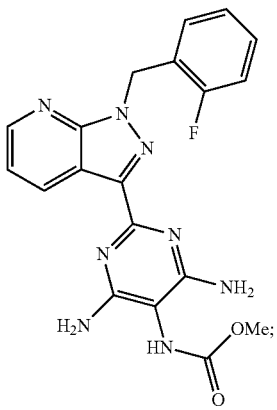 [SMILES: COC(=O)Nc1c(N)nc(-c2nn(Cc3ccccc3F)c3ncccc23)nc1N]
neliciguat (BAY 60-4552, described in WO 2003095451)
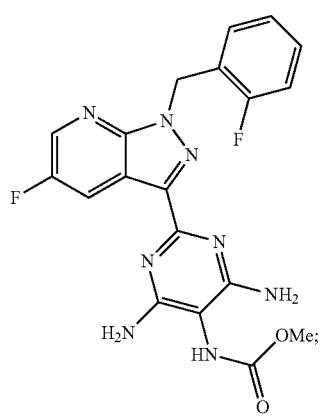 [SMILES: COC(=O)Nc1c(N)nc(-c2nn(Cc3ccccc3F)c3ncc(F)cc23)nc1N]
vericiguat (BAY 1021189)
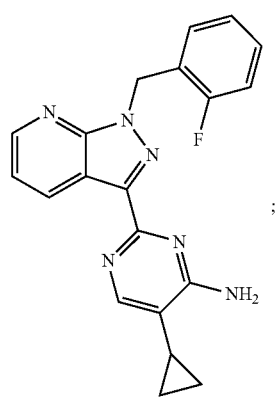 [SMILES: Nc1nc(-c2nn(Cc3ccccc3F)c3ncccc23)ncc1C1CC1]
BAY 41-2272 (described in DE19834047 and DE19942809)
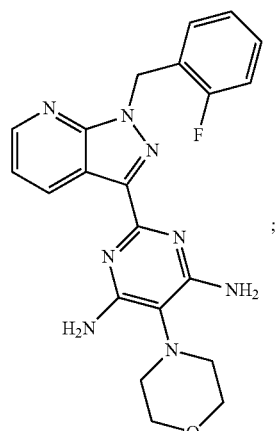
BAY 41-8543 (described in DE19834044)
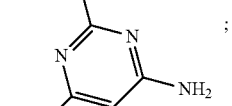
etriciguat (described in WO 2003086407)
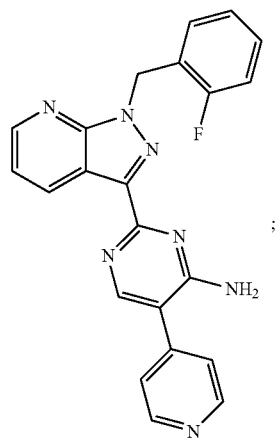 [SMILES: Nc1nc(-c2nn(Cc3ccccc3F)c3ncccc23)ncc1-c1ccncc1]
CFM-1571 (described in patent publication WO2000027394)
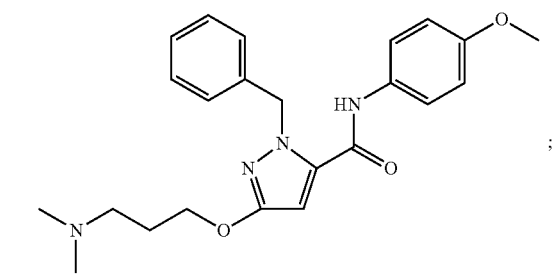

A-344905, its acrylamide analogue A-350619 and the aminopyrimidine analogue A-778935

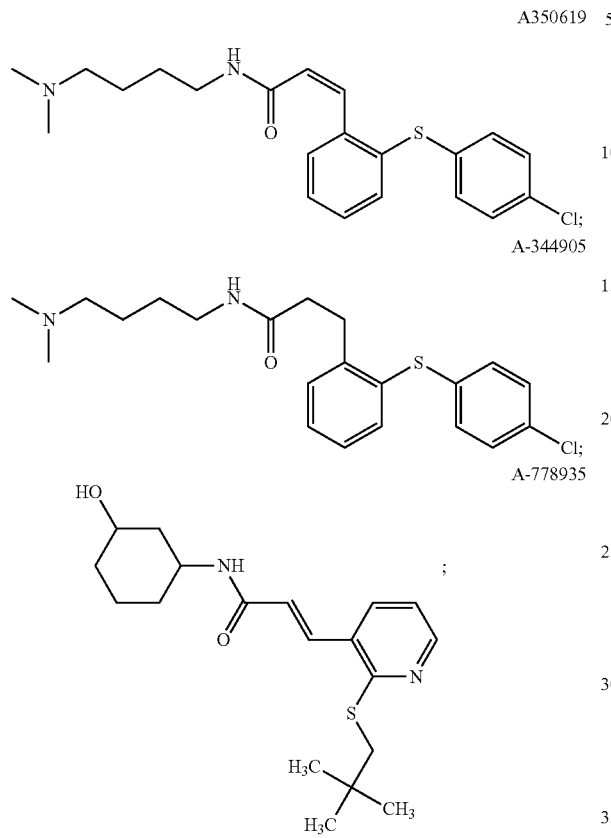

and other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds described in Tetrahedron Letters (2003), 44(48): 8661-8663.

(8) Compounds that inhibit the degradation of cGMP, such as:
PDE5 inhibitors, such as, for example, sildenafil (Viagra®) and related agents such as avanafil, lodenafil, mirodenafil, sildenafil citrate (Revatio®), tadalafil (Cialis® or Adcirca®), vardenafil (Levitra®) and udenafil; alprostadil; dipyridamole and PF-00489791;
PDE9 inhibitors, such as, for example, PF-04447943; and PDE10 inhibitors such as, for example, PF-02545920 (PF-10).

(9) Calcium channel blockers of the following types:
dihydropyridine calcium channel blockers such asamlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), isradipine (Lomir®);
phenylalkylamine calcium channel blockers such as verapamil (Calan®, Isoptin®)

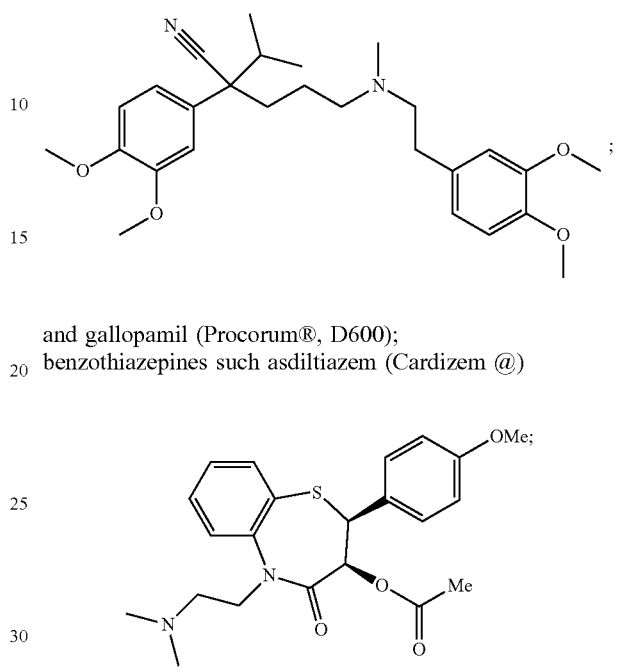

and gallopamil (Procorum®, D600);
benzothiazepines such asdiltiazem (Cardizem @)

and
nonselective calcium channel inhibitors such as mibefradil, bepridil, fluspirilene, and fendiline.

(10) Endothelin receptor antagonists (ERAs) such as the dual ($ET_A$ and $ET_B$) endothelin receptor antagonist bosentan (Tracleer®), sitaxentan (Thelin®) or ambrisentan (Letairis®).

(11) Prostacyclin derivatives or analogues, such asprostacyclin (prostaglandin $I_2$), epoprostenol (synthetic prostacyclin, Flolan®), treprostinil (Remodulin®), iloprost (Ilomedin®), iloprost (Ventavis®); and oral and inhaled forms of Remodulin® under development.

(12) Antihyperlipidemics such as the following types:
bile acid sequestrants like cholestyramine, colestipol, colestilan, colesevelam or sevelamer;
statins like atorvastatin, simvastatin, lovastatin, fluvastatin, pitavastatin, rosuvastatin and pravastatin;
cholesterol absorption inhibitors such as ezetimibe;
other lipid lowering agents such as icosapent ethyl ester, omega-3-acid ethyl esters, reducol;
fibric acid derivatives such as clofibrate, bezafibrate, clinofibrate, gemfibrozil, ronifibrate, binifibrate, fenofibrate, ciprofibrate, choline fenofibrate;
nicotinic acid derivatives such as acipimox and niacin;
combinations of statins, niacin and intestinal cholesterol absorption-inhibiting supplements (ezetimibe and others) and fibrates; and
antiplatelet therapies such as clopidogrel bisulfate.

(13) Anticoagulants, such as the following types:
coumarines (Vitamin K antagonists) such as warfarin (Coumadin®), cenocoumarol, phenprocoumon and phenindione;
heparin and derivatives such as low molecular weight heparin, fondaparinux and idraparinux;

direct thrombin inhibitors such as argatroban, lepirudin, bivalirudin, dabigatran and ximelagatran (Exanta®); and tissue-plasminogen activators, used to dissolve clots and unblock arteries, such as alteplase.

(14) Antiplatelet drugs such as, for instance, topidogrel, ticlopidine, dipyridamole and aspirin.

(15) ACE inhibitors, for example the following types:
sulfhydryl-containing agents such as captopril (Capoten®) and zofenopril;
dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);
phosphonate-containing agents such as fosinopril;
naturally occurring ACE inhibitors such as casokinins and lactokinins, which are breakdown products of casein and whey that occur naturally after ingestion of milk products, especially cultured milk;
the lactotripeptides Val-Pro-Pro and Ile-Pro-Pro produced by the probiotic *Lactobacillus helveticus* or derived from casein also having ACE-inhibiting and antihypertensive functions; other ACE inhibitors such as alacepril, delapril, cilazapril, imidapril, trandolapril, temocapril, moexipril and pirapril.

(16) Supplemental oxygen therapy.

(17) Beta blockers, such as the following types:
non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;
$\beta_1$-Selective agents such as cebutolol, atenolol, betaxolol, bisoprolol, celiprolol, dobutamine hydrochloride, irsogladine maleate, carvedilol, talinolol, esmolol, metoprolol and nebivolol; and
$\beta_2$-Selective agents such as butaxamine.

(18) Antiarrhythmic agents such as the following types:
Type I (sodium channel blockers) such as quinidine, lidocaine, phenytoin, propafenone;
Type III (potassium channel blockers) such as amiodarone, dofetilide and sotalol; and
Type V such as adenosine and digoxin.

(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.

(20) Direct-acting vasodilators such as hydralazine hydrochloride, diazoxide, sodium nitroprusside, cadralazine; other vasodilators such as isosorbide dinitrate and isosorbide 5-mononitrate.

(21) Exogenous vasodilators such as Adenocard® and alpha blockers.

(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.

(23) Bronchodilators of the following types:
short acting $\beta_2$ agonists, such as albutamol or albuterol (Ventolin®) and terbutaline;
long acting $\beta_2$ agonists (LABAs) such as salmeterol and formoterol;
anticholinergics such as pratropium and tiotropium; and theophylline, a bronchodilator and phosphodiesterase inhibitor.

(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.

(25) Dietary supplements such as, for example omega-3 oils; folic acid, niacin, zinc, copper, Korean red *ginseng* root, ginkgo, pine bark, Tribulus *terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(26) PGD2 receptor antagonists.

(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as β2-agonists like terbutaline, metaproterenol, fenoterol, isoetharine, albuterol, salmeterol, bitolterol and pirbuterol; β2-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine.

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; dipeptidyl peptidase IV inhibitors such as sitagliptin, vildagliptin, saxagliptin, alogliptin and linagliptin.

(32) HDL cholesterol-increasing agents such as anacetrapib and dalcetrapib.

(33) Antiobesity drugs such as methamphetamine hydrochloride, amfepramone hydrochloride (Tenuate®), phentermine (Ionamin®), benzfetamine hydrochloride (Didrex®), phendimetrazine tartrate (Bontril®, Prelu-2 ®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, metformin hydrochloride, sibutramine/metformin, bupropion SR/zonisamide SR, CORT-108297, canagliflozin, chromium picolinate, GSK-1521498, LY-377604, metreleptin, obinepitide, P-57AS3, PSN-821, salmeterol xinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and betalapachone.

(34) Angiotensin receptor blockers such as losartan, valsartan, candesartan, cilexetil, eprosaran, irbesartan, telmisartan, olmesartran, medoxomil, azilsartan and medoxomil.

(35) Renin inhibitors such as aliskiren hemifumirate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) PDE-3 inhibitors such as amrinone, milrinone, enoximone, vesnarinone, pimobendan, and olprinone.

(46) Adenylate cyclase activators such as colforsin dapropate hydrochloride.

(47) Positive inotropic agents such as digoxin and metildigoxin; metabolic cardiotonic agents such as ubidecarenone; brain natriuretic peptides such as nesiritide.

(48) Drugs used for the treatment of erectile dysfunction such as alprostadil, aviptadil, and phentolamine mesilate.

(49) Drugs used in the treatment of obesity, including but not limited to, methamphetamine hydrochloride (Desoxyn®), amfepramone hydrochloride (Tenuate®), phentermine (Ionamin®), benzfetamine hydrochloride (Didrex®), phendimetrazine hydrochloride (Bontril®, Prelu-2®, Plegine®), mazindol (Sanorex®) and orlistat (Xenical®).

(50) Drugs used for the treatment of Alzheimer's disease and dementias such as the following types:

acetyl cholinesterase inhibitors including galantamine (Razadyne®), rivastigmine (Exelon®), donepezil (Aricept®) and tacrine (Cognex®);

NMDA receptor antagonists such as mernantine (Namenda®); and oxidoreductase inhibitors such as idebenone.

(51) Psychiatric medications such as the following types: ziprasidone (Geodon™), risperidone (Risperdal™), olanzapine (Zyprexa™), valproate;

dopamine D4 receptor antagonists such as clozapine;

dopamine D2 receptor antagonists such as nemonapride;

mixed dopamine D1/D2 receptor antagonists such as zuclopenthixol;

GABA A receptor modulators such as carbamazepine;

sodium channel inhibitors such as lamotrigine;

monoamine oxidase inhibitors such as moclobemide and indeloxazine;

primavanserin, perospirone; and

PDE4 inhibitors such as rolumilast.

(52) Drugs used for the treatment of movement disorders or symptoms such as the following types:

catechol-O-methyl transferase inhibitors such as entacapone;

monoamine oxidase B inhibitors such as selegiline;

dopamine receptor modulators such as levodopa;

dopamine D3 receptor agonists such as pramipexole;

decarboxylase inhibitors such as carbidopa;

other dopamine receptor agonists such as pergolide, ropinirole, cabergoline;

ritigonide, istradefylline, talipexole; zonisamide and safinamide; and synaptic vesicular amine transporter inhibitors such as tetrabenazine.

(53) Drugs used for the treatment of mood or affective disorders or OCD such as the following types tricyclic antidepressants such as amitriptyline (Elavil®), desipramine (Norpramin®), imipramine (Tofranil®), amoxapine (Asendin®), nortriptyline and clomipramine;

selective serotonin reuptake inhibitors (SSRIs) such as paroxetine (Paxil®), fluoxetine (Prozac®), sertraline (Zoloft®), and citralopram (Celexa®);

doxepin (Sinequan®), trazodone (Desyrel®) and agomelatine;

selective norepinephrine reuptake inhibitors (SNRIs) such as venlafaxine, reboxetine and atomoxetine; dopaminergic antidepressants such as bupropion and amineptine.

(54) Drugs for the enhancement of synaptic plasticity such as the following types: nicotinic receptor antagonists such as mecamylamine; and mixed 5-HT, dopamine and norepinephrine receptor agonists such as lurasidone.

(55) Drugs used for the treatment of ADHD such as amphetamine; 5-HT receptor modulators such as vortioxetine and alpha-2 adrenoceptor agonists such as clonidine.

(56) Neutral endopeptidase (NEP) inhibitors such as sacubitril, omapatrilat; and

(57) Methylene blue (MB).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet.

Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Example 1: Compound Syntheses 1-((5-Fluoropyridin-3-yl)methyl)-1H-pyrazolo[3,4-b]pyridine-3-carbonitrile (Intermediate 1)

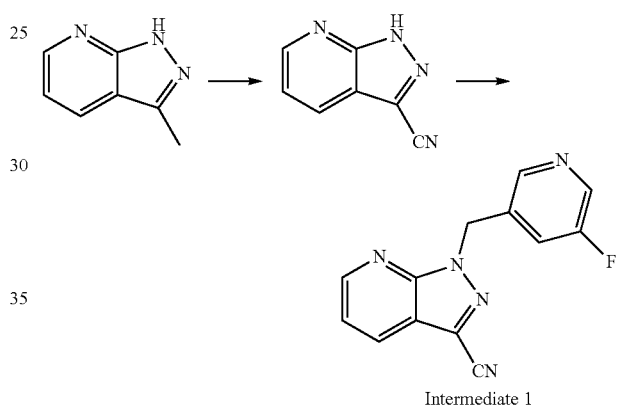

Intermediate 1

The title compound was synthesized in 2 steps.

Step 1: Synthesis of 1H-pyrazolo[3,4-b]pyridine-3-carbonitrile

Zinc(II) cyanide (1.0 g, 8.6 mmol) and 2-iodo-1H-pyrazolo[3,4-b]pyridine (1.4 g, 5.7 mmol) were mixed in DMF (40 mL) at ambient temperature and a stream of nitrogen was bubbled through the solution for 5 minutes. [1,1'-Bis(diphenylphosphino)ferrocene]dichloro-palladium(II) dichloromethane complex (Pd(dppf)Cl$_2$.CH$_2$Cl$_2$) (0.33 g, 0.40 mmol) was added and the solution was degassed for another 10 minutes. The reaction was maintained under a positive nitrogen atmosphere and heated at 130° C. for 48 hours. The mixture was cooled to ambient temperature, filtered and the filter cake was washed with EtOAc. The combined filtrates were concentrated onto Celite and purified by silica gel chromatography (20 to 70% EtOAc/hexanes gradient) to afford the title compound as a light yellow solid (0.51 g, 62% yield).

$^1$H NMR (500 MHz, methanol-d$_4$) δ (ppm) 8.67 (dd, 1H), 8.34 (dd, 1H), 7.44 (dd, 1H).

Step 2: Synthesis of 1-((5-fluoropyridin-3-yl)methyl)-1H-pyrazolo[3,4-b]pyridine-3-carbonitrile 3-Bromomethyl-5-fluoropyridine hydrobromide (150 mg, 0.56 mmol), 1H-pyrazolo[3,4-b]pyridine-3-carbonitrile (80 mg, 0.56 mmol) and freshly ground $K_2CO_3$ (230 mg, 1.7 mmol) were mixed in DMF (3.0 mL) and stirred at ambient temperature overnight. The mixture was diluted with EtOAc (70 mL) and washed with water (3×10 mL) and brine. The organic phase was dried over $Na_2SO_4$, filtered and concentrated in vacuo. The product was purified by silica gel chromatography (5 to 15% EtOAc/dichloromethane gradient) to afford the title compound as a white solid (120 mg, 85% yield).

$^1$H NMR (500 MHz, methanol-$d_4$) δ (ppm) 8.73 (dd, 1H), 8.60 (s, 1H), 8.46 (s, 1H), 8.24 (dd, 1H), 7.52 (dt, 1H), 7.42 (dd, 1H), 5.84 (s, 2H).

Using a similar procedure for the synthesis of Intermediate 1, the following nitrile intermediates were prepared. The reaction conditions (such as reagents ratio, temperature and reaction time) were modified as needed.

1-((3-Fluoropyridin-2-yl)methyl)-1H-pyrazolo[3,4-b]pyridine-3-carbonitrile;
1-(2,5-Difluorobenzyl)-1H-pyrazolo[3,4-b]pyridine-3-carbonitrile;
1-(2-Fluorobenzyl)-1H-pyrazolo[4,3-b]pyridine-3-carbonitrile;
1-(2,3-Difluorobenzyl)-1H-pyrazolo[3,4-b]pyridine-3-carbonitrile;
1-Benzyl-1H-pyrazolo[3,4-b]pyridine-3-carbonitrile;
1-(3,5-Difluorobenzyl)-1H-pyrazolo[3,4-b]pyridine-3-carbonitrile;
1-(3-Fluorobenzyl)-1H-pyrazolo[3,4-b]pyridine-3-carbonitrile;
1-(4-Fluorobenzyl)-1H-pyrazolo[3,4-b]pyridine-3-carbonitrile;
1-(4-Methylbenzyl)-1H-pyrazolo[3,4-b]pyridine-3-carbonitrile.

1-(Pyrimidin-5-ylmethyl)-1H-pyrazolo[3,4-b]pyridine-3-carbonitrile (Intermediate 2)

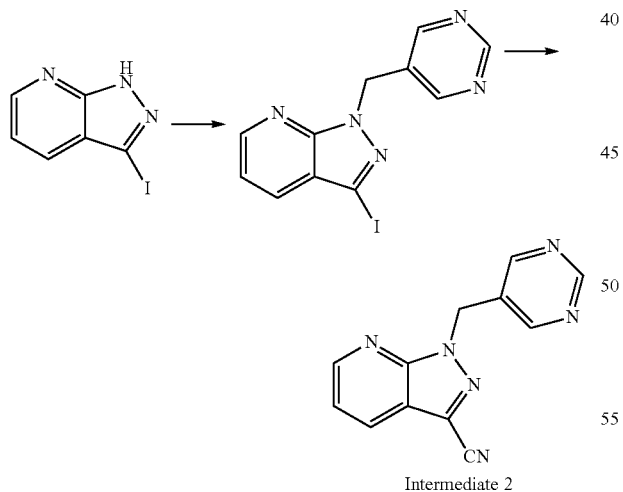

Intermediate 2

The title compound was synthesized in 2 steps.

Step 1: Synthesis of 3-iodo-1-(pyrimidin-5-ylmethyl)-1H-pyrazolo[3,4-b]pyridine

A solution of triphenylphosphine (2.4 g, 9.2 mmol) in dichloromethane/THF (1:1, 30 mL) was cooled to 0° C. was treated dropwise with diisopropylazodicarboxylate (DIAD) (1.8 mL, 9.2 mmol). After 60 minutes, the reaction mixture was added to a solution of pyrimidin-5-ylmethanol (1.0 g, 9.2 mmol) and 3-iodo-1H-pyrazolo[3,4-b]pyridine (1.5 g, 6.1 mmol) in THF (15 mL) at 0° C. The resultant mixture was allowed to warm to ambient temperature and stirred for 3 hours. The reaction was concentrated in vacuo and purified using reverse phase preparative HPLC (5-40% acetonitrile/water gradient with 0.1% TFA as additive) to isolate the title compound as a white solid (880 mg, 42% yield).

Step 2: Synthesis of 1-(pyrimidin-5-ylmethyl)-1H-pyrazolo[3,4-b]pyridine-3-carbonitrile A suspension of copper(I) cyanide (220 mg, 2.5 mmol) and 3-iodo-1-(pyrimidin-5-ylmethyl)-1H-pyrazolo[3,4-b]pyridine (640 mg, 1.9 mmol) in DMSO (5.0 mL) was heated at 160° C. in a microwave for 30 minutes. The mixture was cooled to ambient temperature, filtered through Celite and the filter cake was washed with THF and EtOAc. The filtrate was washed with ammonium hydroxide solution (28-30% w/w, 3×40 mL) and brine (3×40 mL). The organic phase was dried over $Na_2SO_4$, filtered and concentrated in vacuo to afford the title compound as an off-white solid (0.41 g, 78% yield).

$^1$H NMR (500 MHz, methanol-$d_4$) δ (ppm) 9.11 (s, 1H), 8.90 (s, 2H), 8.77 (dd, 1H), 8.37 (dd, 1H), 7.50 (dd, 1H), 5.92 (s, 2H).

Using a similar procedure for the synthesis of Intermediate 2, the following nitrile intermediate was prepared. The reaction conditions (such as reagents ratio, temperature and reaction time) were modified as needed.

7-Chloro-1-((2-methylpyrimidin-5-yl)methyl)-1H-indazole-3-carbonitrile

Synthesis of 6-Chloro-1-(pyrimidin-5-ylmethyl)-1H-indazole-3-carbonitrile (Intermediate 3)

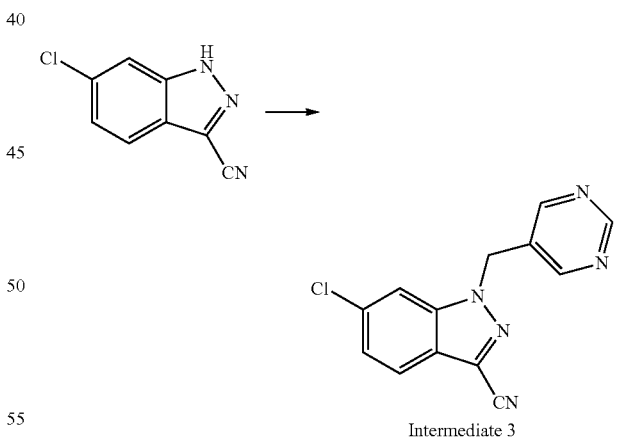

Intermediate 3

A solution of triphenylphosphine (1.1 g, 4.1 mmol) in dichloromethane/THF (1:1, 6 mL) was cooled to 0° C. was treated dropwise with diisopropylazodicarboxylate (DIAD) (0.85 mL, 4.1 mmol). After 60 minutes, the reaction mixture was added to a solution of pyrimidin-5-ylmethanol (0.47 g, 4.1 mmol) and 6-chloro-1H-indazole-3-carbonitrile (0.50 g, 2.7 mmol) in dichloromethane/THF (1:1, 5 mL) at 0° C. The resultant mixture was allowed to warm to ambient temperature and stirred for 3 hours. The reaction was concentrated in vacuo and purified using reverse phase preparative HPLC to isolate the title compound (700 mg, white solid) as a mixture enriched in the desired product. This material was used in the next step without further purification.

LCMS m/z=270.0 [M+H].

Using a similar procedure for the synthesis of Intermediate 3, the following nitrile intermediates were prepared. The reaction conditions (such as reagents ratio, temperature and reaction time) were modified as needed.

1-(2,2,3,3,3-Pentafluoropropyl)-1H-pyrazolo[3,4-b]pyridine-3-carbonitrile;

6-Chloro-1-((2-methylpyrimidin-5-yl)methyl)-1H-indazole-3-carbonitrile;

1-((2-Methylpyrimidin-5-yl)methyl)-1H-pyrazolo[4,3-b]pyridine-3-carbonitrile;

1-((2-Methylpyrimidin-5-yl)methyl)-1H-indazole-3-carbonitrile;

6-Fluoro-1-((2-methylpyrimidin-5-yl)methyl)-1H-indazole-3-carbonitrile;

1-((2-Methylpyrimidin-5-yl)methyl)-1H-pyrazolo[3,4-b]pyridine-3-carbonitrile 7-(3,3,4,4,4-Pentafluorobutyl)imidazo[1,5-b]pyridazine-5-carbonitrile (Intermediate 4)

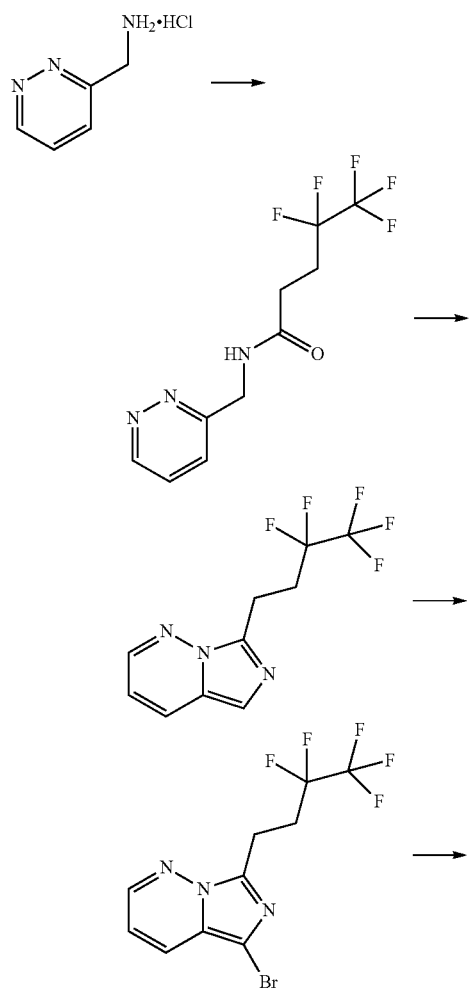

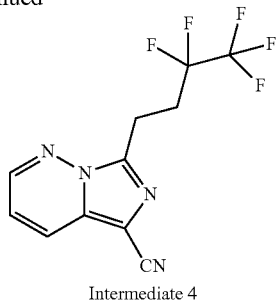

Intermediate 4

The title compound was synthesized in 4 steps.

Step 1: Synthesis of 4,4,5,5,5-pentafluoro-N-(pyridazin-3-ylmethyl)pentanamide

Into a suspension of pyridazin-3-ylmethanamine hydrochloride (170 mg, 1.2 mmol) and 4,4,5,5,5-pentafluoropentanoic acid (220 mg, 1.2 mmol) was added Hunig's Base (610 µL, 3.5 mmol). Contents were stirred for 1 minute, then PyAOP (610 mg, 1.2 mmol) was added to the reaction mixture. After 10 minutes at ambient temperature, the contents were concentrated in vacuo. The resulting residue was purified twice via silica gel chromatography, first utilizing a 0-10% MeOH/dichloromethane gradient, then utilizing a 10-100% EtOAc/hexanes gradient.

Step 2: Synthesis of 7-(3,3,4,4,4-pentafluorobutyl)imidazo[1,5-b]pyridazine

Into a 20 mL vial was added 4,4,5,5,5-pentafluoro-N-(pyridazin-3-ylmethyl)pentanamide (330 mg, 1.20 mmol) as a solution in 1,2-dichloroethane (2.9 mL). Contents were treated with phosphoryl trichloride (620 µL, 6.6 mmol), sealed, and heated to reflux for 3.5 hours. After cooling to ambient temperature, the mixture was concentrated in vacuo. The resulting residue was treated carefully with water and stirred vigorously for 5 minutes. The solution was then extracted with EtOAc. The aqueous layer was treated with saturated sodium bicarbonate solution (20 mL) and back-extracted with EtOAc (3×30 mL). The combined organic layers were washed with brine (20 mL), dried over MgSO$_4$, filtered, and concentrated in vacuo. The resulting residue was purified via silica gel chromatography, utilizing a 10-100% EtOAc/hexanes gradient to deliver 7-(3,3,4,4,4-pentafluorobutyl)imidazo[1,5-b]pyridazine (150 mg, 45% yield) as a dark yellow oil.

$^1$H NMR (500 MHz, chloroform-d) δ (ppm) 8.17 (d, 1H), 7.85 (dd, 1H), 7.51 (s, 1H), 6.64 (dd, 1H), 3.48-3.56 (m, 2H), 2.69-2.83 (m, 2H).

Step 3: Synthesis of 5-bromo-7-(3,3,4,4,4-pentafluorobutyl)imidazo[1,5-b]pyridazine Into a 20 mL vial was added 7-(3,3,4,4,4-pentafluorobutyl)imidazo[1,5-b]pyridazine (150 mg, 0.55 mmol) as a solution in dichloromethane (2.7 mL). The reaction was treated with N-bromosuccinimide (97 mg, 0.55 mmol) and stirred at ambient temperature for 15 minutes.

Water (5.0 mL) was added to the reaction, and the resulting layers were separated. The organic layer was washed with water (10 mL), and the combined aqueous layers were back-extracted with dichloromethane (2×10 mL). Combined organic layers were washed with brine (10 mL), dried over MgSO$_4$, filtered, and concentrated in vacuo to yield 5-bromo-7-(3,3,4,4,4-pentafluorobutyl)imidazo[1,5-b]pyridazine (160 mg, 87% yield) as a yellow solid. 1H NMR (500 MHz, chloroform-d) δ (ppm) 8.10 (dd, 1H), 7.70-7.75 (m, 1H), 6.58-6.64 (m, 1H), 3.37-3.46 (m, 2H), 2.63-2.76 (m, 2H).

Step 4: Synthesis of 7-(3,3,4,4,4-pentafluorobutyl)imidazo[1,5-b]pyridazine-5-carbonitrile Into a microwave vial was added 5-bromo-7-(3,3,4,4,4-pentafluorobutyl)imidazo[1,5-b]pyridazine (160 mg, 0.47 mmol) as a solution in DMSO (3.2 mL) followed by copper(I) cyanide (170 mg, 1.9 mmol). The vial was sealed and heated at 180° C. in the microwave for 2.5 hours. Contents were then filtered through a pad of Celite and the filter cake was washed with EtOAc and THF. The resulting dark brown filtrate was washed with ammonium hydroxide solution (28-30%, 3×20 mL) and brine (2×20 mL). The organic layer was dried over MgSO$_4$, filtered, and concentrated in vacuo. The crude material was purified via silica gel chromatography, utilizing a 10-100% EtOAc/hexanes gradient to deliver the title compound (23 mg, 17% yield).

$^1$H NMR (500 MHz, chloroform-d) δ (ppm) 8.32 (dd, 1H), 8.05 (dd, 1H), 6.98 (dd, 1H), 3.40-3.48 (m, 2H), 2.65-2.79 (m, 2H).

5-(2-Fluorobenzyl)imidazo[1,5-b]pyridazine-7-carbonitrile (Intermediate 5)

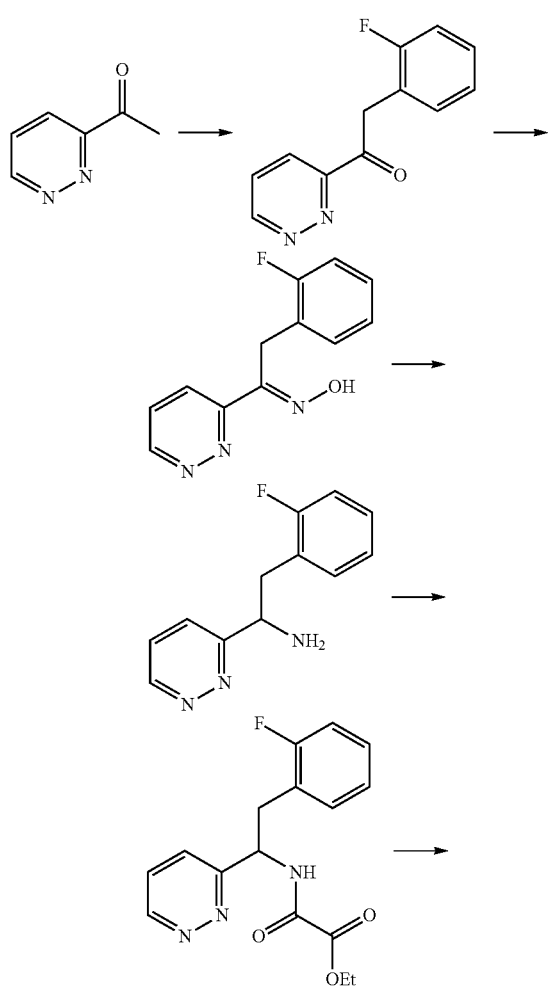

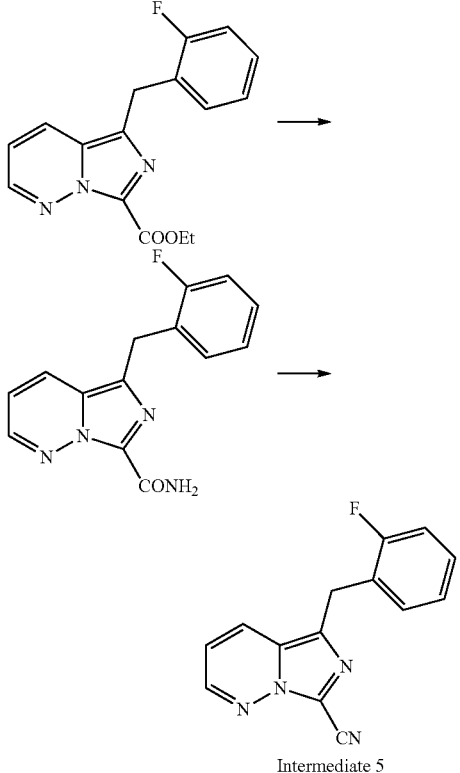

Intermediate 5

The title compound was synthesized in 7 steps.

Step 1: Synthesis of 2-(2-fluorophenyl)-1-(pyridazin-3-yl)ethanone

To a suspension of palladium (II) acetate (340 mg, 1.5 mmol), XANTPHOS (660 mg, 1.1 mmol) and tripotassium phosphate (4.5 g, 21 mmol) in dioxane (13 mL)/THF (3.2 mL)/toluene (3.2 mL) was added 1-(pyridazin-3-yl)ethanone (930 mg, 7.6 mmol) and 1-bromo-2-fluorobenzene (1.7 ml, 15 mmol). The reaction mixture was degassed with nitrogen, sealed, and heated to 100° C. for 18 hours, after which it was filtered through Celite and washed with several volumes of EtOAc. The filtrate was concentrated and purified using silica gel chromatography utilizing a gradient of 1 to 5% methanol in dichloromethane to afford 2-(2-fluorophenyl)-1-(pyridazin-3-yl)ethanone (190 mg, 12% yield) as light tan solid.

$^1$H NMR (500 MHz, methanol-d$_4$) δ (ppm) 9.39 (dd, 1H), 8.25 (dd, 1H), 7.91 (dd, 1H), 7.29-7.36 (m, 2H), 7.13-7.17 (m, 1H), 7.08-7.12 (m, 1H), 4.75 (s, 2H).

Step 2: Synthesis of 2-(2-fluorophenyl)-1-(pyridazin-3-yl)ethanone oxime

A solution of 2-(2-fluorophenyl)-1-(pyridazin-3-yl)ethanone (190 mg, 0.88 mmol) in methanol (4.0 mL) was treated with a 50% aqueous solution of hydroxylamine (0.21 ml, 3.5 mmol). The reaction mixture was stirred at ambient temperature for 24 hours, after which the reaction mixture was concentrated to afford 2-(2-fluorophenyl)-1-(pyridazin-3-yl)ethanone oxime (200 mg, 96% yield) as a light tan solid.

¹H NMR (500 MHz, methanol-d₄), δ (ppm) 9.08 (dd, 1H), 8.23 (dd, 1H), 7.68 (dd, 1H), 7.13-7.17 (m, 2H), 6.96-7.02 (m, 2H), 4.44 (s, 2H).

Step 3: Synthesis of 2-(2-fluorophenyl)-1-(pyridazin-3-yl)ethanamine

To a suspension of 2-(2-fluorophenyl)-1-(pyridazin-3-yl)ethanone oxime (200 mg, 0.84 mmol) in methanol (1.0 mL) was added zinc flakes (220 mg, 3.4 mmol) followed by ammonium acetate (72 mg, 0.93 mmol). Concentrated ammonium hydroxide (28-30% w/w in water) was added (1.0 mL) and the reaction was heated to 90° C. for 2 hours. The reaction mixture was filtered through Celite using several volumes of methanol and concentrated to afford 2-(2-fluorophenyl)-1-(pyridazin-3-yl)ethanamine as a crude mixture (180 mg) that was not purified.

Step 4: Synthesis of ethyl 2-((2-(2-fluorophenyl)-1-(pyridazin-3-yl)ethyl)amino)-2-oxoacetate To a suspension of 2-(2-fluorophenyl)-1-(pyridazin-3-yl)ethanamine (170 mg, 0.80 mmol) in dichloromethane (20 mL) was added ethyl 2-chloro-2-oxoacetate (0.10 mL, 0.87 mmol), followed by triethylamine (0.34 mL, 2.4 mmol). After 1 hour, an additional 0.50 equiv. of ethyl 2-chloro-2-oxoacetate was added. The reaction mixture was allowed to stir for another hour, after which it was concentrated to a brown residue. The crude material was purified by silica gel chromatography utilizing a gradient of 1 to 10% methanol in dichloromethane to deliver ethyl 2-((2-(2-fluorophenyl)-1-(pyridazin-3-yl)ethyl)amino)-2-oxoacetate (180 mg) as a mixture enriched in the desired product. This material was used in the next step without further purification.

Step 5: Synthesis of ethyl 5-(2-fluorobenzyl)imidazo[1,5-b]pyridazine-7-carboxylate To a solution of crude ethyl 2-((2-(2-fluorophenyl)-1-(pyridazin-3-yl)ethyl)amino)-2-oxoacetate (180 mg) in phosphorus oxychloride (2.7 mL, 29 mmol) was added phosphorus pentoxide (410 mg, 1.5 mmol). The reaction mixture was heated to 110° C. for 2 hours, after which it was cooled to ambient temperature. The reaction mixture was poured onto ice, adjusted to pH ~8 using 1N sodium hydroxide solution, extracted with dichloromethane (3×30 mL), dried over Na₂SO₄, filtered, and concentrated to afford a residue. The crude product was purified by silica gel chromatography utilizing a gradient of 1 to 10% methanol in dichloromethane to deliver ethyl 5-(2-fluorobenzyl)imidazo[1,5-b]pyridazine-7-carboxylate (93 mg, 54% yield) as a tan solid.

Step 6: Synthesis of 5-(2-fluorobenzyl)imidazo[1,5-b]pyridazine-7-carboxamide

A solution of ethyl 5-(2-fluorobenzyl)imidazo[1,5-b]pyridazine-7-carboxylate (200 mg, 0.67 mmol) in methanol (3.0 mL) was treated with a 7.0 N ammonia solution in methanol (5.3 mL, 37 mmol). The reaction was allowed to stir at ambient temperature for 16 hours, after which the conversion was complete. The reaction mixture was concentrated to afford 5-(2-fluorobenzyl)imidazo[1,5-b]pyridazine-7-carboxamide (170 mg, 91% yield) as a brown solid that was used in the subsequent step without further purification.

Step 7: Synthesis of 5-(2-fluorobenzyl)imidazo[1,5-b]pyridazine-7-carbonitrile

A suspension of 5-(2-fluorobenzyl)imidazo[1,5-b]pyridazine-7-carboxamide (170 mg, 0.61 mmol) in phosphorus oxychloride (2.8 mL, 31 mmol) and phosphorus pentoxide (430 mg, 1.5 mmol) was heated to 110° C. for 2 hours, after which it was poured over ice, neutralized by the addition of 1N aqueous sodium hydroxide solution, extracted with 5:1 dichloromethane/isopropanol (5×30 mL), dried over Na₂SO₄, filtered and concentrated to afford a brown residue. The crude material was purified by silica gel chromatography utilizing a gradient of 1 to 10% methanol in dichloromethane to afford the title compound (34 mg, 22% yield) as an off-white solid.

¹H NMR (500 MHz, methanol-d₄) δ (ppm) 8.48 (m, 1H), 8.13 (m, 1H), 7.31-7.35 (m, 1H), 7.24-7.30 (m, 1H), 7.11-7.14 (m, 1H), 7.05-7.09 (m, 1H), 6.98-7.02 (m, 1H), 4.31 (s, 2H).

1-(2-Fluorobenzyl)imidazo[1,5-a]pyrazine-3-carbonitrile (Intermediate 6)

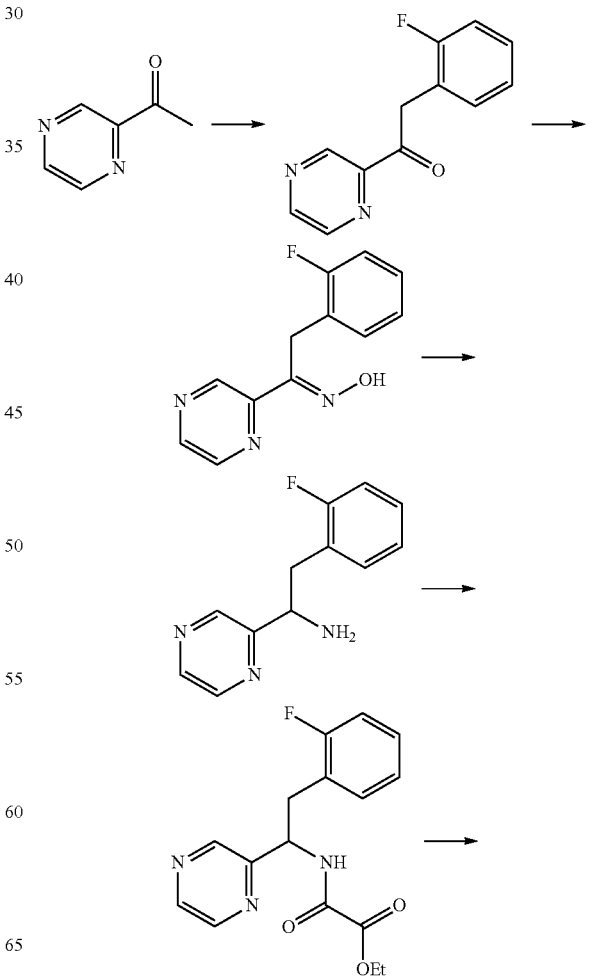

-continued

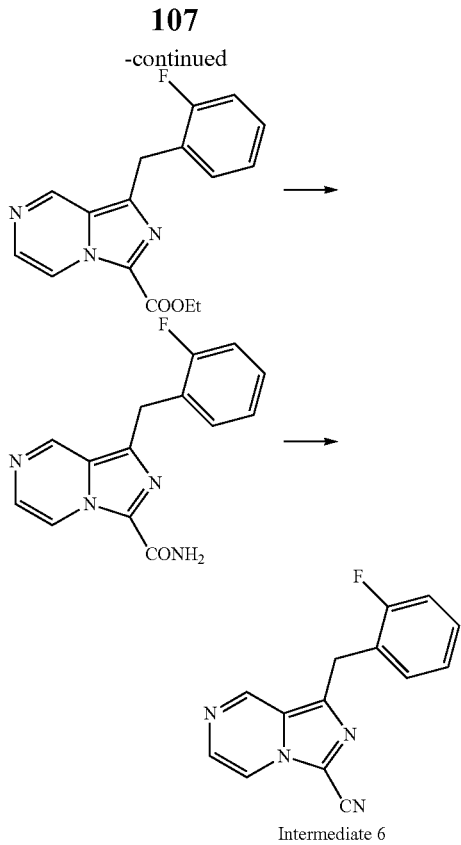

Intermediate 6

The title compound was synthesized in 7 steps.

Step 1: Synthesis of 2-(2-fluorophenyl)-1-(pyrazin-2-yl)ethanone

To a suspension of palladium (II) acetate (59 mg, 0.26 mmol), XANTPHOS (76 mg, 0.13 mmol) and tripotassium phosphate (3.9 g, 18 mmol) in dioxane (10 mL)/THF (2.7 mL)/toluene (2.7 mL) was added 1-(pyrazin-2-yl)ethanone (1.6 g, 13 mmol) and 1-bromo-2-fluorobenzene (0.72 mL, 6.6 mmol). The reaction mixture was degassed with nitrogen, sealed, and heated to 100° C. for 18 hours, after which it was filtered through Celite and washed with several volumes of EtOAc. The filtrate was concentrated to a residue which was purified using silica gel chromatography utilizing a gradient of 1 to 10% methanol in dichloromethane to afford 2-(2-fluorophenyl)-1-(pyrazin-2-yl)ethanone (250 mg, 17% yield) as an orange solid.

$^1$H NMR (500 MHz, methanol-$d_4$) δ (ppm) 9.19 (s, 1H), 8.85 (d, 1H), 8.80 (m, 1H), 7.31-7.34 (m, 2H), 7.15-7.18 (m, 1H), 7.09-7.13 (m, 1H), 4.62 (s, 2H).

Step 2: Synthesis of 2-(2-fluorophenyl)-1-(pyrazin-2-yl)ethanone oxime

A solution of 2-(2-fluorophenyl)-1-(pyrazin-2-yl)ethanone (250 mg, 1.1 mmol) in methanol (5.0 mL) was treated with a 50% aqueous solution of hydroxylamine (0.27 mL, 4.5 mmol). The reaction mixture was stirred at ambient temperature for 40 hours, after which it was concentrated to afford 2-(2-fluorophenyl)-1-(pyrazin-2-yl)ethanone oxime (270 mg, >99% yield) as a yellow solid (7:1 mixture of oxime isomers observed by $^1$H NMR). This material was used without purification in the following step.

$^1$H NMR (500 MHz, methanol-$d_4$) δ (ppm) 9.11 (d, 1H), 8.55 (m, 1H), 8.47 (d, 1H), 7.13-7.17 (m, 2H), 6.96-7.01 (m, 2H), 4.30 (s, 2H).

Step 3: Synthesis of -(2-fluorophenyl)-1-(pyrazin-2-yl)ethanamine

To a suspension of 2-(2-fluorophenyl)-1-(pyrazin-2-yl)ethanone oxime (270 mg, 1.2 mmol) in methanol (4.0 mL) and water (4.0 mL) was added zinc flakes (400 mg, 6.2 mmol) followed by ammonium acetate (110 mg, 1.4 mmol). Concentrated ammonium hydroxide (28-30% w/w, 4.0 mL) was added and the reaction was heated to 80° C. for 1 hour. The reaction mixture was filtered through Celite using several volumes of methanol and concentrated to afford (2-fluorophenyl)-1-(pyrazin-2-yl)ethanamine as a crude brown gummy mixture (420 mg). This material was used without purification in the following step.

Step 4: Synthesis of ethyl 2-((2-(2-fluorophenyl)-1-(pyrazin-2-yl)ethyl)amino)-2-oxoacetate To a suspension of crude 2-(2-fluorophenyl)-1-(pyrazin-2-yl)ethanamine (420 mg, 1.2 mmol) in dichloromethane (8.0 mL) was added ethyl 2-chloro-2-oxoacetate (0.13 mL, 1.1 mmol), followed by triethylamine (0.32 mL, 2.3 mmol). The reaction mixture was allowed to stir at ambient temperature for 1 hour after which it was concentrated to afford a brown residue. The crude material was purified by silica gel chromatography utilizing a gradient of 1 to 10% methanol in dichloromethane to deliver ethyl 2-((2-(2-fluorophenyl)-1-(pyrazin-2-yl)ethyl)amino)-2-oxoacetate (130 mg) as a mixture enriched in the desired product. Used in the next step without further manipulation.

Step 5: Synthesis of ethyl 1-(2-fluorobenzyl)imidazo[1,5-a]pyrazine-3-carboxylate To a solution of crude ethyl 2-((2-(2-fluorophenyl)-1-(pyrazin-2-yl)ethyl)amino)-2-oxoacetate (130 mg) in phosphorus oxychloride (940 µL, 10 mmol) was added phosphorus pentoxide (300 mg, 1.1 mmol). The reaction mixture was heated to 100° C. for 4 hours, after which the reaction was cooled to ambient temperature. The reaction mixture was poured onto ice, adjusted to pH~8 using 1N sodium hydroxide solution, extracted with dichloromethane (4×30 mL), dried over $Na_2SO_4$, filtered, and concentrated to afford ethyl 1-(2-fluorobenzyl)imidazo[1,5-a]pyrazine-3-carboxylate (110 mg, 85% yield) as a tan solid which was used in the next step without purification.

Step 6: Synthesis of 1-(2-fluorobenzyl)imidazo[1,5-a]pyrazine-3-carboxamide

A solution of ethyl 1-(2-fluorobenzyl)imidazo[1,5-a]pyrazine-3-carboxylate (110 mg, 0.36 mmol) in methanol (8.0 mL) was treated with ammonia (7.0 N in methanol, 2.6 mL, 18 mmol). The reaction was allowed to stir at ambient temperature for 12 hours, after which the reaction mixture was concentrated to afford 1-(2-fluorobenzyl)imidazo[1,5-a]pyrazine-3-carboxamide (94 mg, 97% yield) as a brown solid that was used in the following step without purification.

Step 7: Synthesis of 1-(2-fluorobenzyl)imidazo[1,5-a]pyrazine-3-carbonitrile

To a solution of crude 1-(2-fluorobenzyl)imidazo[1,5-a]pyrazine-3-carboxamide (94 mg, 0.35 mmol) in dichloromethane (5.0 mL) was added pyridine (0.08 mL, 1.0 mmol), followed by 2,2,2-trifluoroacetic anhydride (0.07 mL, 0.52 mmol). The reaction mixture was stirred at ambient temperature for 2 hours after which additional pyridine (3.0 equiv.) and 2,2,2-trifluoroacetic anhydride (1.5 equiv.) were added. After 20 minutes of stirring, the reaction mixture was concentrated to dryness, then purified by silica gel chromatography utilizing a gradient of 1 to 10% methanol in dichloromethane to afford a mixture of compounds enriched in 1-(2-fluorobenzyl)imidazo[1,5-a]pyrazine-3-carbonitrile (28 mg).

LCMS m/z=253.1 [M+H].

3-(3,5-Difluorobenzyl)-1H-pyrazolo[4,3-b]pyridine-1-carbonitrile (Intermediate 7)

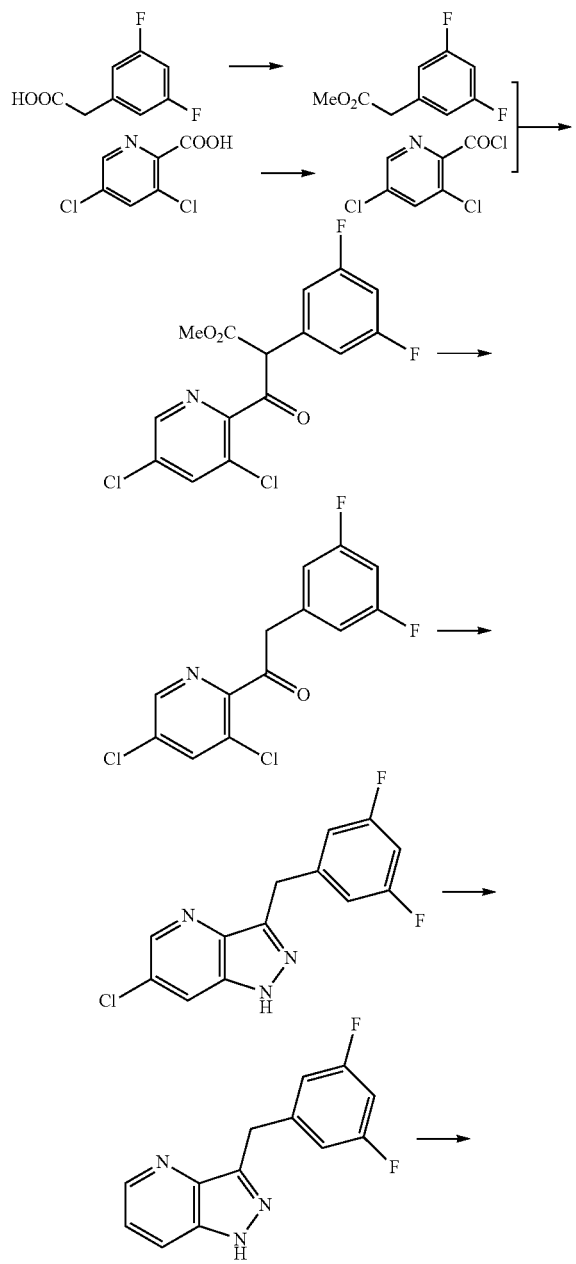

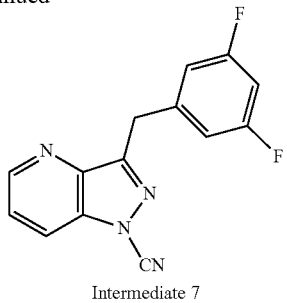

Intermediate 7

The title compound was synthesized in 7 steps.

Step 1: Synthesis of methyl 2-(3,5-difluorophenyl)acetate

A solution of 2-(3,5-difluorophenyl)acetic acid (10 g, 58 mmol) in anhydrous methanol (100 mL) was stirred at ambient temperature as concentrated sulfuric acid (0.50 mL, 9.4 mmol) was added. After stirring for 4 hours, the reaction mixture was cooled in ice and 10% aqueous $NaHCO_3$ solution (50 mL) and solid $NaHCO_3$ (10 g) were carefully added. The mixture was stirred for another 1 hour at ambient temperature. The methanol solvent was removed in vacuo. The residue was extracted with EtOAc (200 mL) and the organic phase was washed with water (3×20 mL), brine, dried over $Na_2SO_4$, filtered and concentrated in vacuo to afford methyl 2-(3,5-difluorophenyl)acetate as a colorless liquid (9.6 g, 89% yield).

$^1$H NMR (500 MHz, chloroform-d) δ (ppm) 6.84 (dd, 1H), 6.75 (tt, 2H), 3.74 (s, 3H), 3.63 (s, 2H).

Step 2: Synthesis of methyl 3,5-dichloropicolinic acid chloride

N,N-Dimethylformamide (0.05 mL, 0.60 mmol) was added to 3,5-dichloropicolinic acid (15 g, 78 mmol). The mixture was treated with thionyl chloride (45 mL, 620 mmol) and heated at 60° C. for 2 hours. The solution was cooled to ambient temperature and concentrated in vacuo. Toluene (50 mL) was added and the mixture was concentrated and dried in vacuo to afford methyl 3,5-dichloropicolinic acid chloride as a light tan solid (17 g, 100% yield).

$^1$H NMR (500 MHz, chloroform-d) δ (ppm) 8.64 (d, 1H), 7.93 (d, 1H).

Step 3: Synthesis of methyl 3-(3,5-dichloropyridin-2-yl)-2-(3,5-difluorophenyl)-3-oxopropanoate A solution of lithium bis(trimethylsilyl)amide (LiHMDS) (1.0M in THF, 42 mL, 42 mmol) was cooled to in a dry ice/acetone bath and treated with a solution of methyl 2-(3,5-difluorophenyl)acetate (6.5 g, 35 mmol) in THF (15 mL) over 10 minutes. After stirring at −70° C. for an hour, a solution of 3,5-dichloropicolinic acid chloride (8.1 g, 38 mmol) in THF (10 mL) was added to the cold reaction mixture over 10 minutes followed by another 30 minutes of stirring at −70° C. The mixture was allowed to warm to ambient temperature. It was then cooled in ice again and treated with saturated aqueous $NH_4Cl$ solution (50 mL) over 5 min. The mixture was further diluted with water (50 mL) and extracted with EtOAc (400 mL). The organic phase was washed with saturated aqueous $NH_4Cl$ solution (3×30 mL) and brine, dried over $Na_2SO_4$, filtered and concentrated in vacuo. Purification by silica gel chromatography (0 to 10% methanol/dichloromethane gradient) gave methyl 3-(3,5-dichloropyridin-2-yl)-2-(3,5-difluorophenyl)-3-oxopropanoate as light yellow solid (11 g, 90% yield). (Note: this particular product existed almost exclusively in the keto form in CDCl$_3$. In some other cases, they may appear as a mixture of keto-enol tautomers).

$^1$H NMR (500 MHz, chloroform-d) δ (ppm) 8.53 (d, 1H), 7.87 (d, 1H), 6.97 (dd, 2H), 6.79 (tt, 1H), 6.02 (s, 1H), 3.76 (s, 3H) ppm.

Step 4: Synthesis of 1-(3,5-dichloropyridin-2-yl)-2-(3,5-difluorophenyl)ethan-1-one The following reaction was run in five batches (methyl 3-(3,5-dichloropyridin-2-yl)-2-(3,5-difluorophenyl)-3-oxopropanoate, 11 g, 31 mmol total). A 35-mL microwave reaction vial was charged with methyl 3-(3,5-dichloropyridin-2-yl)-2-(3,5-difluorophenyl)-3-oxopropanoate (2.2 g, 6.1 mmol), freshly-ground NaCl (0.49 g, 8.4 mmol), water (0.25 mL, 14 mmol) and DMSO (10 mL). The contents were heated in a microwave reactor at 150° C. for 10 minutes. The five batches of crude reaction mixtures were combined and diluted with EtOAc (400 mL). The organic solution was washed with water (100 mL+5×50 mL), brine, dried over Na$_2$SO$_4$, filtered and concentrated in vacuo. Purification by silica gel chromatography (10% dichloromethane/hexanes) gave 1-(3,5-dichloropyridin-2-yl)-2-(3,5-difluorophenyl)ethan-1-one as a light pink solid (4.3 g, 47% yield).

$^1$H NMR (500 MHz, chloroform-d) δ (ppm) 8.55 (d, 1H), 7.85 (d, 1H), 6.84 (dd, 2H), 6.72 (tt, 1H), 4.43 (s, 2H) ppm.

Step 5: Synthesis of 6-chloro-3-(3,5-difluorobenzyl)-1H-pyrazolo[4,3-b]pyridine

The following reaction was run in 2 batches (1-(3,5-dichloropyridin-2-yl)-2-(3,5-difluorophenyl)ethan-1-one, 4.3 g, 14 mmol total). A 35-mL microwave reaction vial was charged with a solution of 1-(3,5-dichloropyridin-2-yl)-2-(3,5-difluorophenyl)ethan-1-one (2.2 g, 7.1 mmol) in absolute ethanol (15 mL). N,N-Dimethylpyridin-4-amine (DMAP) (0.43 g, 3.5 mmol) and hydrazine (3.4 mL, 110 mmol) were added and the microwave reaction vial was sealed under a nitrogen atmosphere. The reaction was heated in a microwave reactor at 160° C. for 90 minutes. The two batches of crude reaction mixtures were combined and concentrated in vacuo. The residue was partitioned between EtOAc (200 mL) and water (10 mL). The organic phase was washed with water (2×10 mL) and brine, dried over Na$_2$SO$_4$, filtered and the crude product was concentrated onto Celite. Purification by silica gel chromatography (0 to 20% EtOAc/dichloromethane gradient) gave 6-chloro-3-(3,5-difluorobenzyl)-1H-pyrazolo[4,3-b]pyridine as a light yellow solid (2.0 g, 50% yield).

$^1$H NMR (500 MHz, chloroform-d) δ (ppm) 8.55 (d, 1H), 7.81 (d, 1H), 6.93 (dd, 2H), 6.66 (tt, 1H), 4.43 (s, 2H) ppm.

Step 6: Synthesis of 3-(3,5-difluorobenzyl)-1H-pyrazolo[4,3-b]pyridine

To a solution of 6-chloro-3-(3,5-difluorobenzyl)-1H-pyrazolo[4,3-b]pyridine (2.0 g, 7.2 mmol) in absolute ethanol (60 mL) in a 250-mL round-bottom flask was added triethylamine (1.0 mL, 7.2 mmol) and palladium on charcoal (10% w/w containing ~50% H$_2$O, 0.40 g).

The vessel was purged with hydrogen gas, sealed and kept under positive hydrogen pressure with a balloon filled with hydrogen gas. After stirring rapidly at ambient temperature overnight, the reaction mixture was filtered through Celite and the filter cake was washed with EtOAc. The crude product was concentrated onto Celite. Purification by silica gel chromatography (10 to 90% EtOAc/hexanes gradient) gave 3-(3,5-difluorobenzyl)-1H-pyrazolo[4,3-b]pyridine as a white solid (1.5 g, 86% yield).

$^1$H NMR (500 MHz, chloroform-d) δ (ppm) 10.1 (br s, 1H), 8.64 (d, 1H), 7.83 (d, 1H), 7.36 (dd, 1H), 6.96 (d, 2H), 6.65 (t, 1H), 4.48 (s, 2H).

Step 7: Synthesis of 3-(3,5-difluorobenzyl)-1H-pyrazolo[4,3-b]pyridine-1-carbonitrile A solution of 3-(3,5-difluorobenzyl)-1H-pyrazolo[4,3-b]pyridine (0.40 g, 1.6 mmol), triethylamine (0.30 mL, 2.1 mmol) and N,N-dimethylpyridin-4-amine (DMAP) (0.04 g, 0.30 mmol) in dichloromethane (10 mL) was treated with cyanogen bromide (0.26 g, 2.4 mmol). After stirring for 15 minutes at ambient temperature, the reaction was diluted with dichloromethane (50 mL) and washed with 10% aqueous NaHCO$_3$ solution, water and brine. The organic phase was dried over Na$_2$SO$_4$, filtered and concentrated in vacuo. Purification by silica gel chromatography (5 to 30% EtOAc/hexanes gradient) gave the title compound as a white solid (0.32 g, 73% yield).

$^1$H NMR (500 MHz, chloroform-d) δ (ppm) 8.80 (d, 1H), 8.01 (d, 1H), 7.58 (dd, 1H), 6.98 (d, 2H), 6.69 (t, 1H), 4.43 (s, 2H).

Using a similar procedure for the synthesis of Intermediate 7, the following nitrile intermediates were prepared. The reaction conditions (such as reagents ratio, temperature and reaction time) were modified as needed.

6-Chloro-3-(2-fluorobenzyl)-1H-pyrazolo[4,3-b]pyridine-1-carbonitrile;

3-(2-Fluorobenzyl)-1H-pyrazolo[4,3-b]pyridine-1-carbonitrile;

3-(2,3-Difluorobenzyl)-1H-pyrazolo[4,3-b]pyridine-1-carbonitrile;

3-(3-Fluorobenzyl)-1H-pyrazolo[4,3-b]pyridine-1-carbonitrile;

3-(2,5-Difluorobenzyl)-1H-pyrazolo[4,3-b]pyridine-1-carbonitrile;

3-Benzyl-1H-pyrazolo[4,3-b]pyridine-1-carbonitrile.

1-(2-Fluorobenzyl)-1H-pyrazolo[3,4-b]pyridine-3-carboximidhydrazide (Intermediate 8)

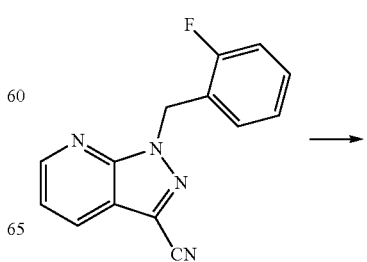

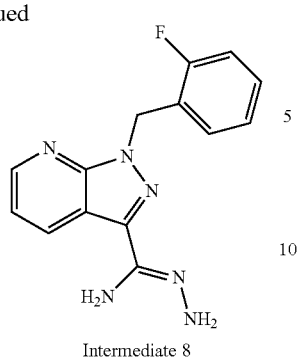

Intermediate 8

To a solution of 1-(2-fluorobenzyl)-1H-pyrazolo[3,4-b]pyridine-3-carbonitrile (50 g, 200 mmol) in ethanol (700 mL) was added anhydrous hydrazine (68 mL, 2.2 mol). After stirring at 60° C. overnight, complete disappearance of starting material was observed. The reaction was concentrated in vacuo, residual hydrazine was removed with methanol chasing, and the resultant solid was dried under vacuum overnight to obtain the title compound (56 g, 99% yield) as a yellow powder.

$^1$H NMR (500 MHz, DMSO-$d_6$) δ (ppm) 8.57 (dd, 1H), 8.52 (dd, 1H), 7.31-7.37 (m, 1H), 7.27 (dd, 1H), 7.22 (t, 1H), 7.09-7.14 (m, 1H), 7.05-7.09 (m, 1H), 5.73 (s, 2H), 5.51 (s, 2H), 5.37 (br s, 2H).

Using a similar procedure for the synthesis of Intermediate 8, the following intermediate was prepared. The reaction conditions (such as reagents ratio, temperature and reaction time) were modified as needed.

1-(2,3-Difluorobenzyl)-1H-pyrazolo[3,4-b]pyridine-3-carboximidhydrazide.

1-(2-Fluorobenzyl)-1H-pyrazolo[4,3-c]pyridine-3-carbonitrile (Intermediate 9)

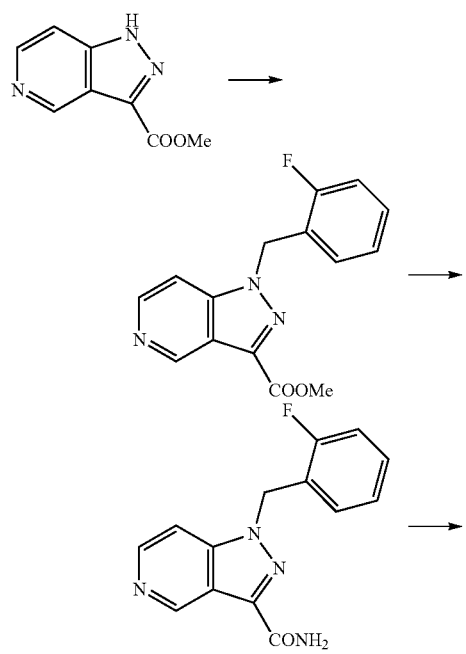

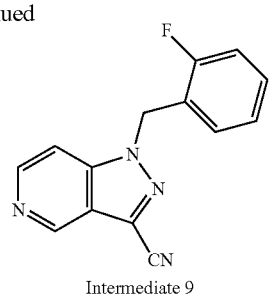

Intermediate 9

The title compound was synthesized in 3 steps.

Step 1: Synthesis of methyl 1-(2-fluorobenzyl)-1H-pyrazolo[4,3-c]pyridine-3-carboxylate 1-(Bromomethyl)-2-fluorobenzene (110 mg, 0.58 mmol), methyl 1H-pyrazolo[4,3-c]pyridine-3-carboxylate (98 mg, 0.55 mmol) and $K_2CO_3$ (230 mg, 1.7 mmol) were mixed in DMF (4.0 mL) and stirred at ambient temperature for 3 days. The mixture was diluted with EtOAc (30 mL) and washed with water (10 mL) and brine. The organic phase was dried over $Na_2SO_4$, filtered and concentrated in vacuo. The product was purified by silica gel chromatography (0 to 10% methanol/dichloromethane gradient) to afford methyl 1-(2-fluorobenzyl)-1H-pyrazolo[4,3-c]pyridine-3-carboxylate (42 mg, 27% yield).

Step 2: Synthesis of 1-(2-fluorobenzyl)-1H-pyrazolo[4,3-c]pyridine-3-carboxamide A solution of methyl 1-(2-fluorobenzyl)-1H-pyrazolo[4,3-c]pyridine-3-carboxylate (42 mg, 0.15 mmol) in methanol (1.0 mL) was treated with a 7.0 N ammonia solution in methanol (3.0 mL, 21 mmol). The reaction was allowed to stir at ambient temperature for 18 hours, after which the conversion was complete. The reaction mixture was concentrated to afford 1-(2-fluorobenzyl)-1H-pyrazolo[4,3-c]pyridine-3-carboxamide (40 mg, >99% yield) that was used in the subsequent step without further purification.

Step 3: Synthesis of 1-(2-fluorobenzyl)-1H-pyrazolo[4,3-c]pyridine-3-carbonitrile A solution of 1-(2-fluorobenzyl)-1H-pyrazolo[4,3-c]pyridine-3-carboxamide (40 mg, 0.15 mmol) and pyridine (36 μL, 0.44 mmol) in dichloromethane (1.5 mL) was treated with 2,2,2-trifluoroacetic anhydride (31 μL, 0.22 mmol) and stirred at ambient temperature overnight.

The reaction mixture was concentrated to dryness, dissolved in dichloromethane (5.0 mL) and washed with saturated aqueous $NaHCO_3$ solution (2.0 mL). The organic layer was dried over $Na_2SO_4$, filtered and concentrated in vacuo. The crude material was purified by silica gel chromatography utilizing a gradient of 1 to 10% methanol in dichloromethane to afford the title compound (21 mg, 56% yield).

LCMS m/z=253.1 [M+H].

1-(2-Fluorobenzyl)-3-(4,4,5,5-tetramethyl-1,3,2-dioxaborolan-2-yl)-1H-pyrazolo[3,4-b]pyridine (Intermediate 10)

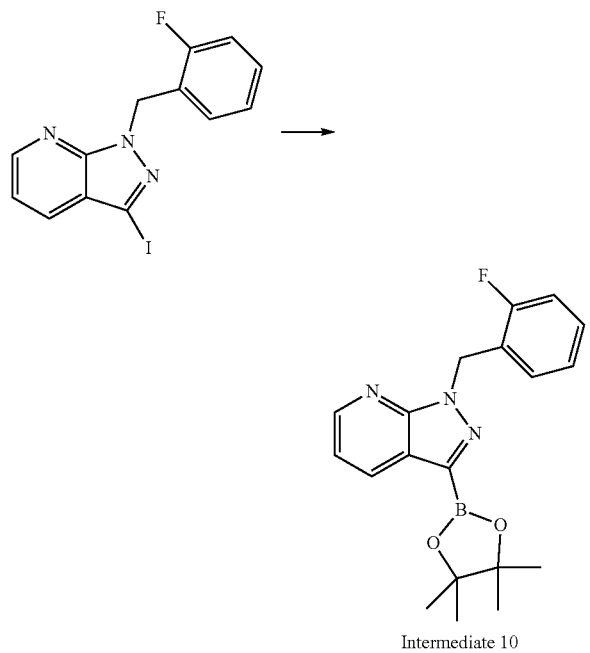

Intermediate 10

Into a vial was added 1-(2-fluorobenzyl)-3-iodo-H-pyrazolo[3,4-b]pyridine (1.5 g, 4.3 mmol), potassium acetate (1.3 g, 13 mmol), and bis(pinacolato)diboron (1.6 g, 6.4 mmol). DMF (28 mL) was added and the vial was flushed with argon for 20 minutes. [1,1'-Bis(diphenylphosphino)ferrocene]dichloro-palladium(II) dichloromethane complex (Pd(dppf)Cl$_2$—CH$_2$Cl$_2$) (0.35 g, 0.43 mmol) was added. The reaction vial was sealed and heated at 100° C. for 2 hours. The contents were cooled to ambient temperature and partitioned between water and EtOAc (200 mL total). The aqueous layer was extracted with EtOAc (3×40 mL). The combined organic layers were washed with brine (20 mL), dried over MgSO$_4$, filtered and concentrated in vacuo. The resulting residue was purified by silica gel chromatography (0-80% acetonitrile/methanol (7:1) in dichloromethane gradient) to deliver the title compound (180 mg, 16% yield) as a brown oil.

$^1$H NMR (500 MHz, chloroform-d) δ (ppm) 8.56 (s, 1H), 8.43 (d, 1H), 7.17-7.24 (m, 2H), 7.00-7.07 (m, 1H), 6.94-6.98 (m, 1H), 6.87-6.93 (m, 1H), 5.92 (s, 2H), 1.41 (s, 12H).

1-(2-Fluorobenzyl)-6-methyl-1H-pyrazolo[3,4-b]pyridine-3-carbonitrile (Intermediate 11)

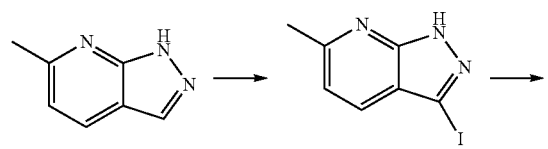

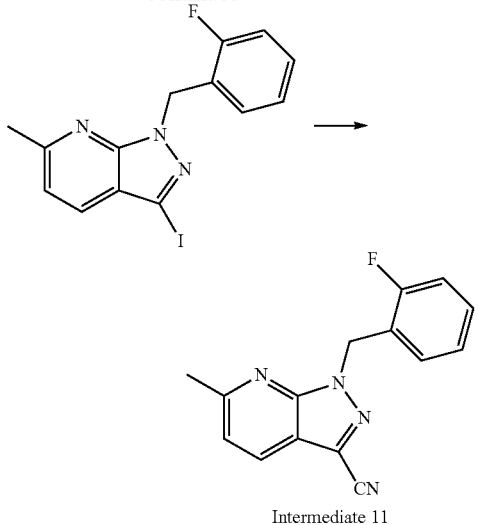

Intermediate 11

The title compound was synthesized in 3 steps.

Step 1: Synthesis of 3-iodo-6-methyl-1H-pyrazolo[3,4-b]pyridine (WO2014/42263A1)

To a brown solution of 6-methyl-1H-pyrazolo[3,4-b]pyridine (1.3 g, 9.4 mmol) and iodine (4.8 g, 19 mmol) in DMF (30 mL) at 0° C. was KOH (2.1 g, 38 mmol). The reaction was allowed to warm to ambient temperature and stir for an hour. The resultant mixture was poured into ice/water (200 mL) and extracted with EtOAc (3×200 mL). The combined organic layers were dried over Na$_2$SO$_4$, filtered and concentrated in vacuo. Purification using silica gel chromatography (30-50% EtOAc/hexanes gradient) afforded 3-iodo-6-methyl-1H-pyrazolo[3,4-b]pyridine as a light yellow solid (1.8 g, 74% yield).

Step 2: Synthesis of 1-(2-fluorobenzyl)-3-iodo-6-methyl-1H-pyrazolo[3,4-b]pyridine To a solution of 3-iodo-6-methyl-1H-pyrazolo[3,4-b]pyridine (810 mg, 3.1 mmol) in DMF (30 mL) was added K$_2$CO$_3$ (1.3 g, 9.4 mmol) followed by 1-bromomethyl-2-fluorobenzene (0.45 mL, 3.8 mmol) dropwise. After stirring at ambient temperature for 4.5 hours, the mixture was poured into water (75 mL) and extracted with dichloromethane (2×100 mL). The combined organic layers were dried over Na$_2$SO$_4$, filtered and concentrated in vacuo. Purification using silica gel chromatography (0-5% EtOAc/hexanes gradient) afforded 1-(2-fluorobenzyl)-3-iodo-6-methyl-1H-pyrazolo[3,4-b]pyridine as a white solid (990 mg, 86% yield).

Step 3: Synthesis of 1-(2-fluorobenzyl)-6-methyl-1H-pyrazolo[3,4-b]pyridine-3-carbonitrile A suspension of copper(I) cyanide (170 mg, 1.8 mmol) and 1-(2-fluorobenzyl)-3-iodo-6-methyl-1H-pyrazolo[3,4-b]pyridine (450 mg, 1.2 mmol) in DMSO (4.0 mL) was heated at 180° C. in a microwave for 30 minutes. The mixture was cooled to ambient temperature, filtered through Celite and the filter cake was washed with THF (20 mL) and EtOAc (80 mL). The filtrate was washed twice with a mixture of ammonium hydroxide solution (28-30% w/w, 10 mL)/water (40 mL) and saturated aqueous NaHCO₃ solution (30 mL). The organic phase was dried over Na₂SO₄, filtered and concentrated in vacuo. Purification using silica gel chromatography (5-10% EtOAc/hexanes gradient) afforded the title compound as a white solid (290 mg, 90% yield).

LCMS m/z=267.1 [M+H].

Using a similar procedure for the synthesis of Intermediate 11, the following nitrile intermediates were prepared. The reaction conditions (such as reagents ratio, temperature and reaction time) were modified as needed.

1-(2,3-Difluorobenzyl)-6-methyl-1H-pyrazolo[3,4-b]pyridine-3-carbonitrile
1-(2-Fluorobenzyl)-1H-pyrazolo[3,4-b]pyrazine-3-carbonitrile.

Synthesis of sodium 1-(2,2,2-trifluoroethyl azetidine-3-carboxylate (Intermediate 12)

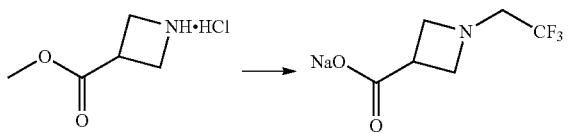

A mixture containing 2,2,2-trifluoroethyl trifluoromethanesulfonate (0.52 mL, 3.6 mmol), Hunig's Base (1.2 mL, 6.6 mmol) and methyl azetidine-3-carboxylate hydrochloride (0.50 g, 3.3 mmol) in methanol (16 mL) was heated at 90° C. for 1 hour. The mixture was cooled to ambient temperature and treated with sodium hydroxide (3.0 N aqueous solution, 3.3 mL, 9.9 mmol). After 3 hours, the mixture was concentrated in vacuo and dried further using benzene and methanol as azeotropes to give sodium 1-(2,2,2-trifluoroethyl)azetidine-3-carboxylate (649 mg, 95% yield) as a white solid.

¹H NMR (500 MHz, DMSO-d₆) δ (ppm) 3.37-3.45 (m, 2H), 3.23-3.30 (m, 2H), 3.00-3.10 (m, 2H), 2.77-2.90 (m, 1H).

Synthesis of sodium 1-(2-fluoroethyl)azetidine-3-carboxylate (Intermediate 13)

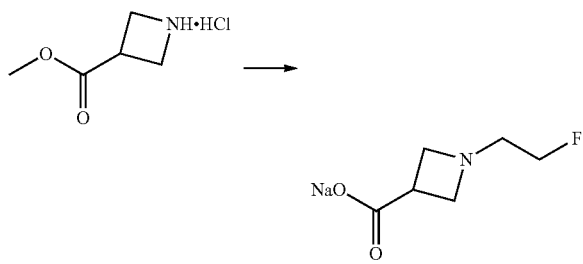

A mixture containing 2-fluoroethyl 4-toluenesulfonate (0.72 mL, 3.3 mmol), Hunig's Base (1.1 mL, 6.6 mmol) and methyl azetidine-3-carboxylate hydrochloride (0.50 g, 3.3 mmol) in methanol (16 mL) was heated at 100° C. for 24 hours. The mixture was cooled to ambient temperature and treated with sodium hydroxide (3.0 N aqueous solution, 3.3 mL, 9.9 mmol). After 3 hours, the mixture was concentrated in vacuo and dried further using benzene and methanol as azeotropes to give sodium 1-(2-fluoroethyl)azetidine-3-carboxylate (560 mg, >99% yield) as a white solid.

¹H NMR (500 MHz, DMSO-d₆) δ (ppm) 4.20-4.45 (m, 2H), 3.29 (m, 2H), 3.07 (m, 2H), 2.75 (m, 1H), 2.51-2.55 (m, 2H).

1-(2-Fluorobenzyl)-1H-pyrazolo[3,4-c]pyridazine-3-carbonitrile (Intermediate 14)

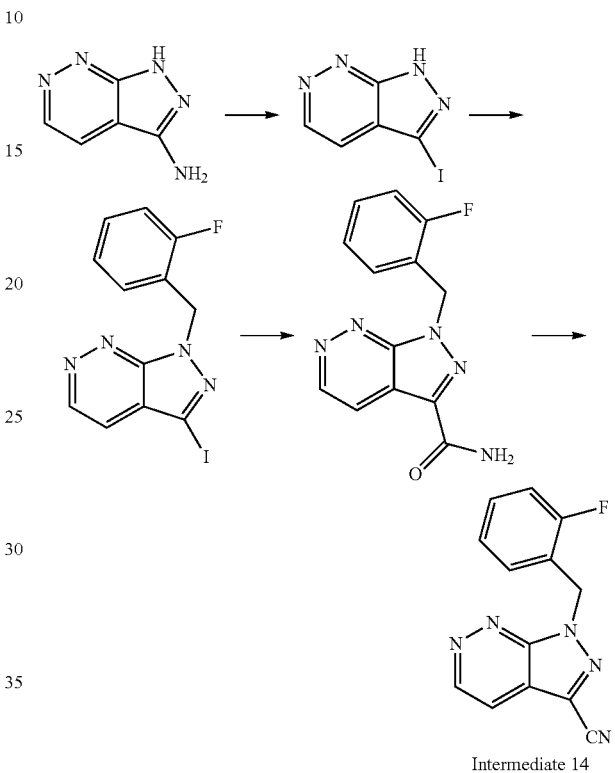

Intermediate 14

The title compound was synthesized in 4 steps.

Step 1: Synthesis of 3-iodo-1H-pyrazolo[3,4-c]pyridazine

To a 0° C. solution of 1H-pyrazolo[3,4-c]pyridazin-3-amine (270 mg, 2.0 mmol) in THF (9.0 mL) was added boron trifluoride diethyl etherate (0.50 mL, 3.9 mmol). The reaction mixture was cooled to −10° C. after which a solution of isoamyl nitrite (0.34 mL, 2.6 mmol) in THF (9.0 mL) was added. The reaction was allowed to stir for 30 minutes, after which the mixture was diluted with cold diethyl ether and filtered. The solid was dissolved in acetone (20 mL) and cooled to −10° C., after which a solution of sodium iodide (380 mg, 2.6 mmol) in acetone (10 mL) was cautiously added. The reaction mixture was warmed to ambient temperature and stirred for 30 minutes, after which it was poured into ice water, extracted with EtOAc (2×50 mL), dried over Na₂SO₄, and filtered to afford 3-iodo-1H-pyrazolo[3,4-c]pyridazine (280 mg, 59% yield) as a brown solid.

¹H NMR (500 MHz, methanol-d₄) δ (ppm) 9.16 (d, 1H), 7.94 (d, 1H).

Step 2: Synthesis of 1-(2-fluorobenzyl)-3-iodo-1H-pyrazolo[3,4-c]pyridazine

A suspension of 3-iodo-1H-pyrazolo[3,4-c]pyridazine (280 mg, 1.2 mmol), potassium carbonate (480 mg, 3.5 mmol)

and 1-(bromomethyl)-2-fluorobenzene (0.15 ml, 1.2 mmol) in N,N-dimethylformamide (10 mL) was stirred at ambient temperature for 12 hours. The reaction was then diluted with water, extracted with dichloromethane (3×50 mL), dried over Na$_2$SO$_4$, filtered, and concentrated to afford a brown liquid. The crude material was purified by silica gel chromatography (0 to 90% EtOAc/hexanes gradient) to deliver 1-(2-fluorobenzyl)-3-iodo-1H-pyrazolo[3,4-c]pyridazine (100 mg, 26% yield) as a light tan solid.

$^1$H NMR (500 MHz, methanol-d$_4$) δ (ppm) 9.18 (d, 1H), 7.88 (d, 1H), 7.32-7.37 (m, 2H), 7.11-7.16 (m, 2H), 5.99 (s, 2H).

Step 3: Synthesis of 1-(2-fluorobenzyl)-1H-pyrazolo[3,4-c]pyridazine-3-carboxamide A vial containing 1-(2-fluorobenzyl)-3-iodo-H-pyrazolo[3,4-c]pyridazine (100 mg, 0.29 mmol) and copper (I) cyanide (320 mg, 3.5 mmol) in N-methyl pyrrolidinone (4.0 mL) was heated at 160° C. for 1 hour in the microwave. The reaction mixture was filtered through Celite using several volumes of methanol and concentrated to a residue. This residue was extracted with dichloromethane (3×50 mL), washed with ammonium hydroxide solution (2×30 mL), dried over Na$_2$SO$_4$, filtered and concentrated to a residue. This material was flushed through a plug of silica gel and concentrated to afford crude 1-(2-fluorobenzyl)-1H-pyrazolo[3,4-c]pyridazine-3-carboxamide (80 mg) as a brown oil. This material was not purified and used in directly in the subsequent step.

Step 4: Synthesis of 1-(2-fluorobenzyl)-1H-pyrazolo[3,4-c]pyridazine-3-carbonitrile To an ambient temperature solution of crude 1-(2-fluorobenzyl)-1H-pyrazolo[3,4-c]pyridazine-3-carboxamide (80 mg, 0.30 mmol) in dichloromethane (6.0 mL) was added pyridine (0.07 mL, 0.89 mmol) followed by neat 2,2,2-trifluoroacetic anhydride (0.06 mL, 0.44 mmol). After 10 minutes, the reaction mixture was concentrated to dryness and purified directly using silica gel chromatography (0 to 100% EtOAc/hexanes gradient) to deliver the title compound as a yellow residue.

LCMS m/z=254.1 [M+H].

The following intermediates were synthesized according to general synthetic schemes described in the literature (Roberts, L. R. et al. *Bioorg. Med. Chem. Lett.* 2011, 21, 6515-6518). The reaction conditions (such as reagents ratio, temperature and reaction time) were modified as needed.

1-(Pyrimidin-5-ylmethyl)imidazo[1,5-a]pyridine-3-carbonitrile;
7-Chloro-1-(pyrimidin-5-ylmethyl)imidazo[1,5-a]pyridine-3-carbonitrile;
6-Fluoro-1-(pyrimidin-5-ylmethyl)imidazo[1,5-a]pyridine-3-carbonitrile;
8-Fluoro-1-(pyrimidin-5-ylmethyl)imidazo[1,5-a]pyridine-3-carbonitrile;
8-(Pyrimidin-5-ylmethyl)imidazo[1,5-a]pyrimidine-6-carbonitrile;
6-Fluoro-1-((2-methylpyrimidin-5-yl)methyl)imidazo[1,5-a]pyridine-3-carbonitrile;
6-Chloro-8-fluoro-1-((2-methylpyrimidin-5-yl)methyl)imidazo[1,5-a]pyridine-3-carbonitrile;
6,8-Difluoro-1-(pyrimidin-5-ylmethyl)imidazo[1,5-a]pyridine-3-carbonitrile;
7-Chloro-1-((2-methylpyrimidin-5-yl)methyl)imidazo[1,5-a]pyridine-3-carbonitrile;
6-Chloro-1-((2-methylpyrimidin-5-yl)methyl)imidazo[1,5-a]pyridine-3-carbonitrile.

Compound I-1

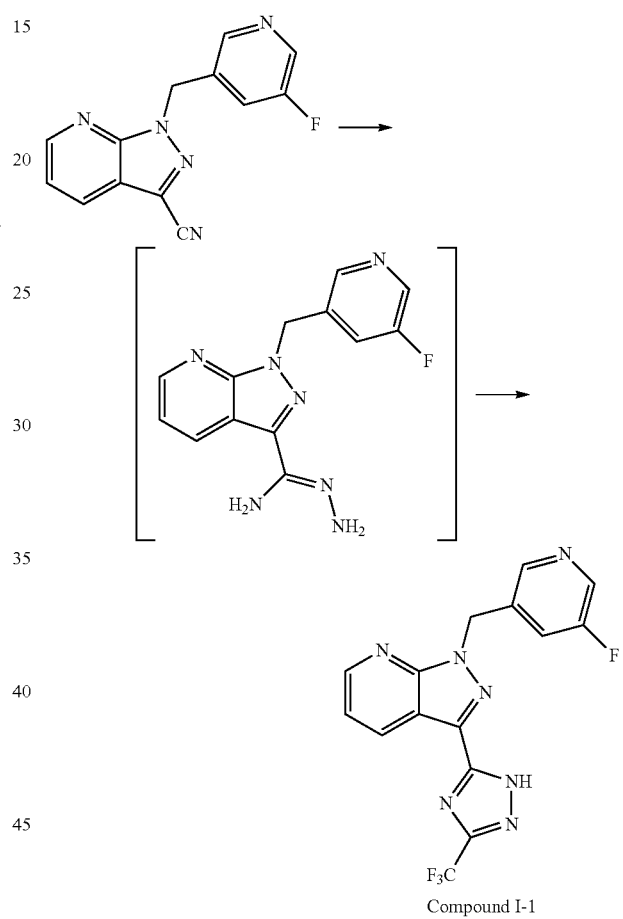

Compound I-1

General Procedure A: 1-((5-fluoropyridin-3-yl)methyl)-3-(3-(trifluoromethyl)-1H-1,2,4-triazol-5-yl)-1H-pyrazolo[3,4-b]pyridine To a solution of 1-((5-fluoropyridin-3-yl)methyl)-1H-pyrazolo[3,4-b]pyridine-3-carbonitrile (120 mg, 0.47 mmol) in absolute ethanol (3.0 mL) (note: anhydrous methanol could also be used as a solvent) was added anhydrous hydrazine (0.15 mL, 4.8 mmol). After stirring at 60° C. overnight, complete disappearance of starting material was observed. The reaction was concentrated and the residue was dried in vacuo overnight. The residue was taken up in dichloromethane (5.0 mL) and 2,2,2-trifluoroacetic anhydride (0.10 mL, 0.71 mmol) was added dropwise. The reaction was stirred at ambient temperature until complete consumption of the amidrazone intermediate. The solvent was removed in vacuo and toluene (5.0 mL) was added followed by dropwise addition of phosphoryl trichloride (0.13 mL, 1.4 mmol). The resultant mixture was heated at 85° C. for 60 min in a sealed vial. The reaction mixture was poured into EtOAc (100 mL) and washed with 10% aqueous NaHCO$_3$ solution (2×10 mL), water (10 mL) and brine (10 mL). The organic layer was dried over Na$_2$SO$_4$, filtered and concentrated in vacuo. Purification by silica gel chromatography (10 to 100% EtOAc/dichloromethane gradient) afforded the title compound as a white solid (110 mg, 63% yield).

$^1$H NMR (500 MHz, acetone-d$_6$) δ (ppm) 14.2 (br s, 1H), 8.76 (dd, 1H), 8.73 (dd, 1H), 8.58 (br t, 1H), 8.46 (d, 1H), 7.65 (dt, 1H), 7.50 (dd, 1H), 5.95 (s, 2H).

Compound I-4

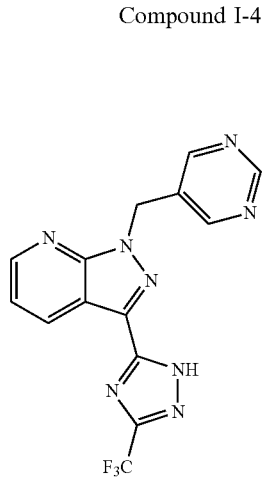

Compound I-4

1-(Pyrimidin-5-ylmethyl)-3-(3-(trifluoromethyl)-1H-1,2,4-triazol-5-yl)-1H-pyrazolo[3,4-b]pyridine was synthesized from 1-(pyrimidin-5-ylmethyl)-1H-pyrazolo[3,4-b]pyridine-3-carbonitrile according to General Procedure A as an off-white solid (180 mg, 27% yield). The reaction conditions (such as reagents ratio, temperature and reaction time) were modified as needed.

$^1$H NMR (500 MHz, DMSO-d$_6$) δ (ppm) 15.8 (s, 1H), 9.15 (s, 1H), 8.86 (s, 2H), 8.77 (dd, 1H), 8.66 (dd, 1H), 7.51 (dd, 1H), 5.93 (s, 2H).

Compound I-8

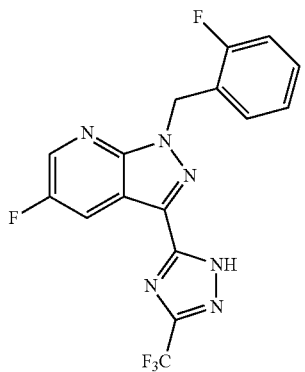

Compound I-8

5-Fluoro-1-(2-fluorobenzyl)-3-(3-(trifluoromethyl)-1H-1,2,4-triazol-5-yl)-1H-pyrazolo[3,4-b]pyridine was synthesized from 5-fluoro-1-(2-fluorobenzyl)-1H-pyrazolo[3,4-b]pyridine-3-carbonitrile (US2013/338137A1) according to General Procedure A as a white solid (35 mg, 24% yield). The reaction conditions (such as reagents ratio, temperature and reaction time) were modified as needed.

$^1$H NMR (500 MHz, chloroform-d) δ (ppm) 11.9 (br s, 1H), 8.50 (dd, 1H), 8.33 (dd, 1H), 7.20-7.26 (m, 1H), 7.14-7.18 (m, 1H), 6.98-7.05 (m, 2H), 5.76 (s, 2H).

Compound I-13

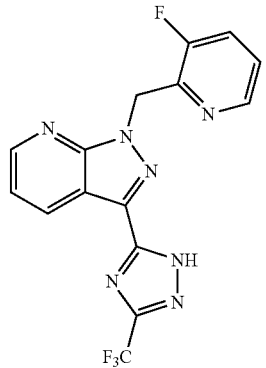

Compound I-13

1-((3-Fluoropyridin-2-yl)methyl)-3-(3-(trifluoromethyl)-1H-1,2,4-triazol-5-yl)-1H-pyrazolo[3,4-b]pyridine was synthesized according to General Procedure A as a white solid (71 mg, 62% yield). The reaction conditions (such as reagents ratio, temperature and reaction time) were modified as needed.

$^1$H NMR (500 MHz, chloroform-d) δ (ppm) 13.4 (br s, 1H), 8.68 (d, 1H), 8.57 (d, 1H), 8.35 (d, 1H), 7.47 (t, 1H), 7.28-7.34 (m, 2H), 5.97 (s, 2H).

Compound I-14

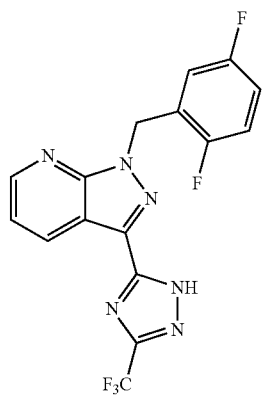

Compound I-14

1-(2,5-Difluorobenzyl)-3-(3-(trifluoromethyl)-1H-1,2,4-triazol-5-yl)-1H-pyrazolo[3,4-b]pyridine was synthesized according to General Procedure A as a white solid (110 mg, 62% yield). The reaction conditions (such as reagents ratio, temperature and reaction time) were modified as needed.

$^1$H NMR (500 MHz, chloroform-d) δ (ppm) 12.6 (br s, 1H), 8.81 (dd, 1H), 8.74 (dd, 1H), 7.40 (dd, 1H), 7.00 (td, 1H), 6.90-6.95 (m, 1H), 6.79-6.83 (m, 1H), 5.86 (s, 2H).

Compound I-15

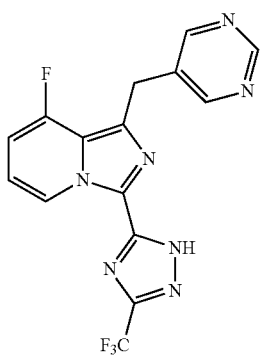

Compound I-15

8-Fluoro-1-(pyrimidin-5-ylmethyl)-3-(3-(trifluoromethyl)-1H-1,2,4-triazol-5-yl)imidazo[1,5-a]pyridine was synthesized according to General Procedure A as a pale green solid (41 mg, 25% yield). The reaction conditions (such as reagents ratio, temperature and reaction time) were modified as needed.

$^1$H NMR (500 MHz, DMSO-d$_6$) δ (ppm) 15.8 (br s, 1H), 9.05-9.10 (m, 2H), 8.77 (s, 2H), 7.03-7.08 (m, 1H), 6.97 (dd, 1H), 4.43 (s, 2H).

Compound I-16

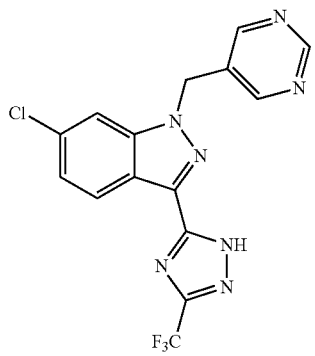

Compound I-16

6-Chloro-1-(pyrimidin-5-ylmethyl)-3-(3-(trifluoromethyl)-1H-1,2,4-triazol-5-yl)-1H-indazole was synthesized according to General Procedure A as an off-white solid (41 mg, 40% yield). The reaction conditions (such as reagents ratio, temperature and reaction time) were modified as needed.

$^1$H NMR (500 MHz, DMSO-d$_6$) δ (ppm) 15.7 (br s, 1H), 9.16 (s, 1H), 8.87 (s, 2H), 8.25-8.29 (m, 2H), 7.43 (dd, 1H), 5.90 (s, 2H).

Compound I-19

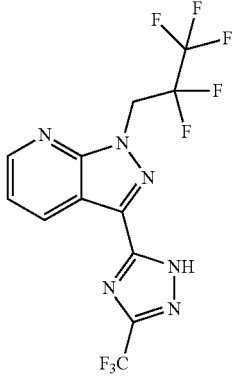

Compound I-19

1-(2,2,3,3,3-Pentafluoropropyl)-3-(3-(trifluoromethyl)-1H-1,2,4-triazol-5-yl)-1H-pyrazolo[3,4-b]pyridine was synthesized according to General Procedure A as a white solid (100 mg, 81% yield). The reaction conditions (such as reagents ratio, temperature and reaction time) were modified as needed.

$^1$H NMR (500 MHz, chloroform-d) δ (ppm) 12.1 (br s, 1H), 8.80 (d, 1H), 8.72 (d, 1H), 7.42 (dd, 1H), 5.26 (t, 2H).

Compound I-20

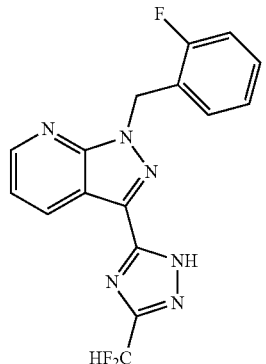

Compound I-20

3-(3-(Difluoromethyl)-1H-1,2,4-triazol-5-yl)-1-(2-fluorobenzyl)-1H-pyrazolo[3,4-b]pyridine was synthesized according to General Procedure A, with the exception that 2,2-difluoroacetic anhydride was used as the acylating agent, as a white solid (51 mg, 40% yield). The reaction conditions (such as reagents ratio, temperature and reaction time) were modified as needed.

$^1$H NMR (500 MHz, DMSO-d$_6$) δ (ppm) 15.3 (br s, 1H), 8.67 (d, 1H), 8.61 (d, 1H), 7.41 (m, 1H), 7.27-7.34 (m, 1H), 7.10-7.21 (m, 3H), 7.05-7.10 (m, 1H), 5.82 (s, 2H).

Compound I-21

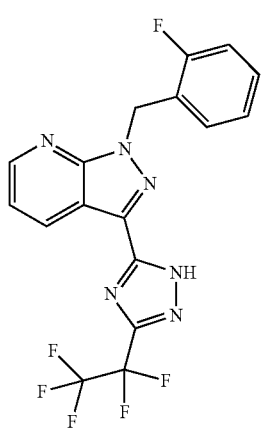

3-(3-(Difluoromethyl)-1H-1,2,4-triazol-5-yl)-1-(2-fluorobenzyl)-1H-pyrazolo[3,4-b]pyridine was synthesized according to General Procedure A, with the exception that 2,2,3,3,3-pentafluoropropanoic anhydride was used as the acylating agent, as a white solid (25 mg, 16% yield). The reaction conditions (such as reagents ratio, temperature and reaction time) were modified as needed.

$^{1}$H NMR (500 MHz, DMSO-d$_{6}$) δ (ppm) 15.9 (br s, 1H), 8.75-8.77 (m, 1H), 8.65 (d, 1H), 7.51 (dd, 1H), 7.35-7.40 (m, 1H), 7.23-7.28 (m, 1H), 7.18-7.22 (m, 1H), 7.12-7.17 (m, 1H), 5.91 (s, 2H).

Compound I-26

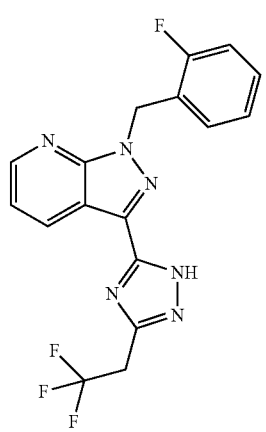

1-(2-Fluorobenzyl)-3-(3-(2,2,2-trifluoroethyl)-1H-1,2,4-triazol-5-yl)-1H-pyrazolo[3,4-b]pyridine was synthesized according to General Procedure A, with the exception that 3,3,3-trifluoropropanoic anhydride was used as the acylating agent, as a white solid (41 mg, 20% yield). The reaction conditions (such as reagents ratio, temperature and reaction time) were modified as needed.

$^{1}$H NMR (500 MHz, DMSO-d$_{6}$) δ (ppm) 14.8 (br s, 1H), 8.71 (d, 1H), 8.65 (d, 1H), 7.45 (dd, 1H), 7.33-7.40 (m, 1H), 7.21-7.27 (m, 1H), 7.12-7.21 (m, 2H), 5.86 (s, 2H), 3.90-4.01 (m, 2H).

Compound I-22

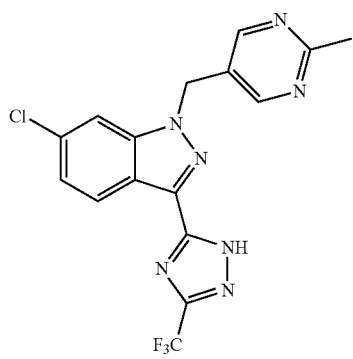

6-Chloro-1-((2-methylpyrimidin-5-yl)methyl)-3-(3-(trifluoromethyl)-1H-1,2,4-triazol-5-yl)-1H-indazole was synthesized according to General Procedure A as a white solid (48 mg, 24% yield). The reaction conditions (such as reagents ratio, temperature and reaction time) were modified as needed.

$^{1}$H NMR (500 MHz, DMSO-d$_{6}$) δ (ppm) 15.7 (br s, 1H), 8.77 (s, 2H), 8.24-8.28 (m, 2H), 7.42 (dd, 1H), 5.83 (s, 2H), 2.59 (s, 3H).

Compound I-29

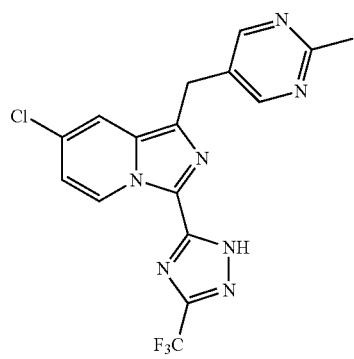

7-Chloro-1-((2-methylpyrimidin-5-yl)methyl)-3-(3-(trifluoromethyl)-1H-1,2,4-triazol-5-yl)imidazo[1,5-a]pyridine was synthesized according to General Procedure A as an off-white solid (49 mg, 67% yield). The reaction conditions (such as reagents ratio, temperature and reaction time) were modified as needed.

$^{1}$H NMR (500 MHz, DMSO-d$_{6}$) δ (ppm) 15.7 (s, 1H), 9.17 (d, 1H), 8.67 (s, 2H), 8.24 (d, 1H), 7.13 (dd, 1H), 4.31 (s, 2H), 2.56 (s, 3H).

Compound I-30

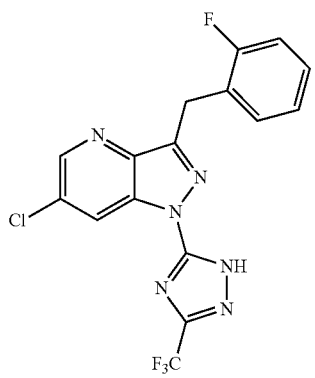

Compound I-30

6-Chloro-3-(2-fluorobenzyl)-1-(3-(trifluoromethyl)-1H-1,2,4-triazol-5-yl)-1H-pyrazolo[3,4-b]pyridine was synthesized according to General Procedure A as a white solid (14 mg, 38% yield). The reaction conditions (such as reagents ratio, temperature and reaction time) were modified as needed.

¹H NMR (500 MHz, chloroform-d) δ (ppm) 11.9 (br s, 1H), 8.74 (s, 1H), 8.69 (s, 1H), 7.32 (t, 1H), 7.17 (q, 1H), 6.95-7.04 (m, 2H), 4.49 (s, 2H).

Compound I-31

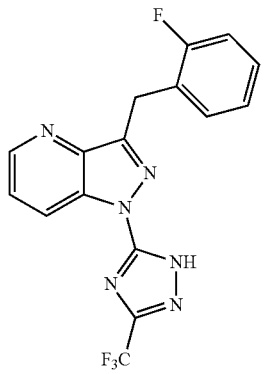

3-(2-Fluorobenzyl)-1-(3-(trifluoromethyl)-1H-1,2,4-triazol-5-yl)-1H-pyrazolo[4,3-b]pyridine was synthesized according to General Procedure A as a white solid (42 mg, 57% yield). The reaction conditions (such as reagents ratio, temperature and reaction time) were modified as needed.

¹H NMR (500 MHz, chloroform-d) δ (ppm) 11.7 (br s, 1H), 8.79 (d, 1H), 8.76 (d, 1H), 7.58 (dd, 1H), 7.38 (t, 1H), 7.23 (q, 1H), 7.03-7.09 (m, 2H), 4.45 (s, 2H).

Compound I-35

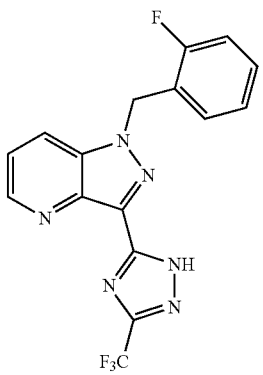

1-(2-Fluorobenzyl)-3-(3-(trifluoromethyl)-1H-1,2,4-triazol-5-yl)-1H-pyrazolo[4,3-b]pyridine was synthesized according to General Procedure A as a white solid (6.1 mg, 7.4% yield). The reaction conditions (such as reagents ratio, temperature and reaction time) were modified as needed.

¹H NMR (500 MHz, methanol-$d_4$) δ (ppm) 8.73 (d, 1H), 8.21 (d, 1H), 7.54 (dd, 1H), 7.34 (m, 2H), 7.14 (m, 2H), 5.86 (s, 2H).

Compound I-37

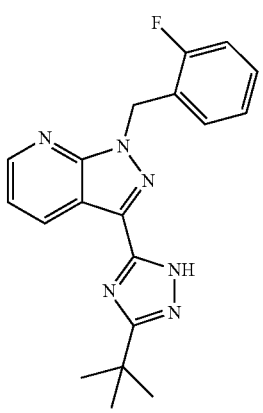

3-(3-(tert-Butyl)-1H-1,2,4-triazol-5-yl)-1-(2-fluorobenzyl)-1H-pyrazolo[3,4-b]pyridine was synthesized according to General Procedure A as a white solid (190 mg, 56% yield). The reaction conditions (such as reagents ratio, temperature and reaction time) were modified as needed.

¹H NMR (500 MHz, DMSO-$d_6$) δ (ppm) 13.9 (br s, 1H), 8.66 (d, 2H), 7.31-7.44 (m, 2H), 7.23 (t, 1H), 7.10-7.16 (m, 2H), 5.82 (s, 2H), 1.39 (s, 9H).

Compound I-38

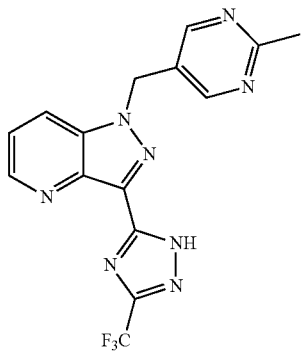
Compound I-38

This compound was synthesized according to General Procedure A as an off-white solid (7.4 mg, 3.3% yield). The reaction conditions (such as reagents ratio, temperature and reaction time) were modified as needed.

$^1$H NMR (500 MHz, methanol-$d_4$) δ (ppm) 8.80 (s, 2H), 8.77 (d, 1H), 8.36 (d, 1H), 7.60 (dd, 1H), 5.85 (s, 2H), 2.67 (s, 3H).

Compound I-39

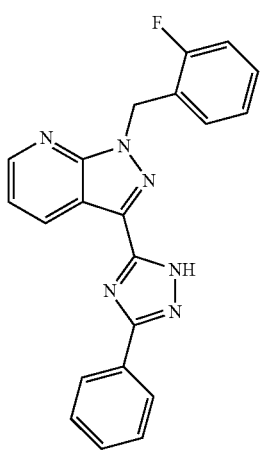
Compound I-39

This compound was synthesized according to General Procedure A as a white solid (130 mg, 36% yield). The reaction conditions (such as reagents ratio, temperature and reaction time) were modified as needed.

$^1$H NMR (500 MHz, DMSO-$d_6$ with a drop of TFA) δ (ppm) 8.80 (dd, 1H), 8.71 (dd, 1H), 8.14 (d, 2H), 7.54-7.58 (m, 2H), 7.49-7.53 (m, 1H), 7.45 (dd, 1H), 7.34-7.40 (m, 1H), 7.22-7.27 (m, 1H), 7.17-7.22 (m, 1H), 7.12-7.17 (m, 1H), 5.87 (s, 2H).

Compound I-43

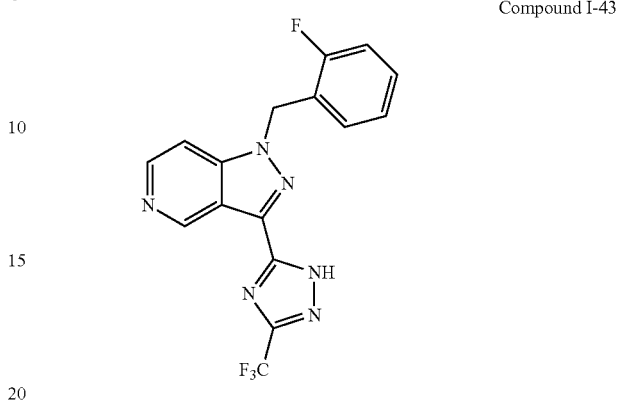
Compound I-43

1-(2-Fluorobenzyl)-3-(3-(trifluoromethyl)-1H-1,2,4-triazol-5-yl)-1H-pyrazolo[4,3-c]pyridine was synthesized according to General Procedure A as a light yellow solid (20 mg, 53% yield). The reaction conditions (such as reagents ratio, temperature and reaction time) were modified as needed.

$^1$H NMR (500 MHz, DMSO-$d_6$) δ (ppm) 15.8 (br s, 1H), 9.52 (s, 1H), 8.56 (d, 1H), 7.93 (d, 1H), 7.40 (m, 1H), 7.27-7.20 (m, 2H), 7.18 (app. t, 1H), 5.91 (s, 2H).

Compound I-44

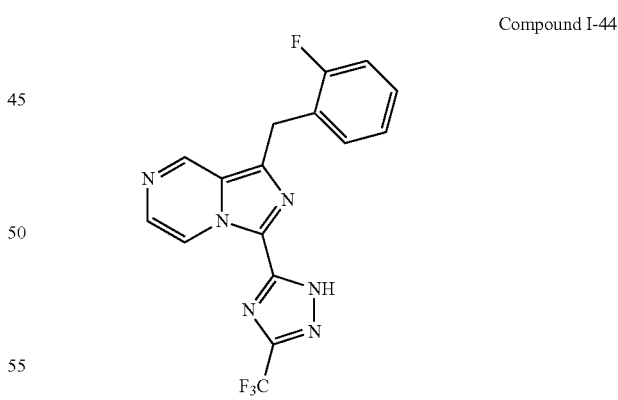
Compound I-44

1-(2-Fluorobenzyl)-3-(3-(trifluoromethyl)-1H-1,2,4-triazol-5-yl)imidazo[1,5-a]pyrazine was synthesized according to General Procedure A as a yellow-green solid (4.7 mg, 12% yield).

$^1$H NMR (500 MHz, methanol-$d_4$) δ (ppm) 9.19 (d, 1H), 9.12 (s, 1H), 7.79 (d, 1H), 7.41-7.44 (m, 1H), 7.27-7.31 (m, 1H), 7.13-7.16 (m, 1H), 7.08-7.12 (m, 1H), 4.51 (s, 2H).

Compound I-46

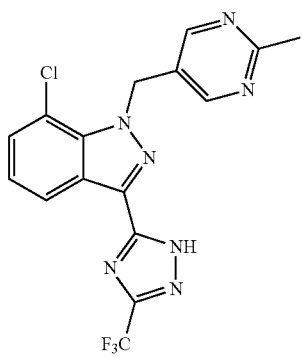

Compound I-46

7-Chloro-1-((2-methylpyrimidin-5-yl)methyl)-3-(3-(trifluoromethyl)-1H-1,2,4-triazol-5-yl)-1H-indazole was synthesized according to General Procedure A as a white solid (50 mg, 62% yield). The reaction conditions (such as reagents ratio, temperature and reaction time) were modified as needed.

$^1$H NMR (500 MHz, DMSO-$d_6$) δ (ppm) 8.63 (s, 2H), 8.31 (d, 1H), 7.65 (d, 1H), 7.38 (t, 1H), 6.11 (s, 2H), 2.59 (s, 3H).

Compound I-49

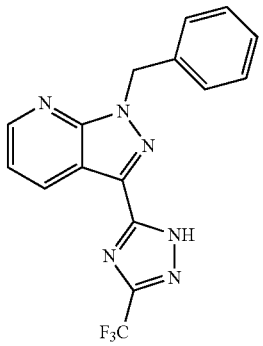

Compound I-49

1-Benzyl-3-(3-(trifluoromethyl)-1H-1,2,4-triazol-5-yl)-1H-pyrazolo[3,4-b]pyridine was synthesized according to General Procedure A as a white solid (87 mg, 84% yield). The reaction conditions (such as reagents ratio, temperature and reaction time) were modified as needed.

$^1$H NMR (500 MHz, chloroform-d) δ (ppm) 12.0 (br s, 1H), 8.77 (dd, 1H), 8.72 (dd, 1H), 7.37 (dd, 1H), 7.25-7.34 (m, 5H), 5.81 (s, 2H).

Compound I-48

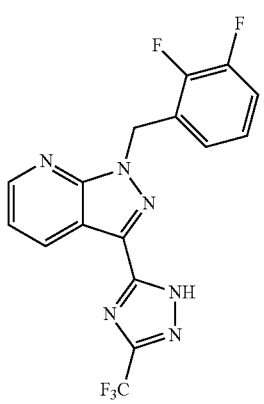

Compound I-48

1-(2,3-Difluorobenzyl)-3-(3-(trifluoromethyl)-1H-1,2,4-triazol-5-yl)-1H-pyrazolo[3,4-b]pyridine was synthesized according to General Procedure A as a white solid (87 mg, 62% yield). The reaction conditions (such as reagents ratio, temperature and reaction time) were modified as needed.

$^1$H NMR (500 MHz, chloroform-d) δ (ppm) 11.9 (br s, 1H), 8.79 (dd, 1H), 8.73 (dd, 1H), 7.39 (dd, 1H), 7.04-7.15 (m, 1H), 6.93-7.03 (m, 2H), 5.91 (s, 2H).

Compound I-50

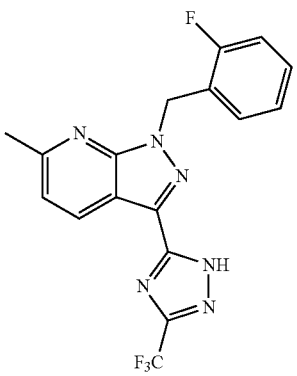

Compound I-50

1-(2-Fluorobenzyl)-6-methyl-3-(3-(trifluoromethyl)-1H-1,2,4-triazol-5-yl)-1H-pyrazolo[3,4-b]pyridine was synthesized according to General Procedure A as an off-white solid (90 mg, 74% yield). The reaction conditions (such as reagents ratio, temperature and reaction time) were modified as needed.

$^1$H NMR (500 MHz, DMSO-$d_6$) δ (ppm) 15.7 (br s, 1H), 8.52 (d, 1H), 7.38 (d, 1H), 7.37 (m, 1H), 7.25 (m, 1H), 7.14 (m, 2H), 5.85 (s, 2H), 2.68 (s, 3H).

Compound I-51

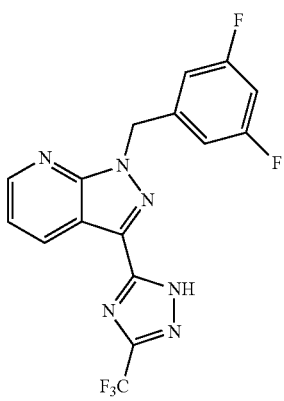

Compound I-51

1-(3,5-Difluorobenzyl)-3-(3-(trifluoromethyl)-1H-1,2,4-triazol-5-yl)-1H-pyrazolo[3,4-b]pyridine was synthesized according to General Procedure A as a white solid (81 mg, 57% yield). The reaction conditions (such as reagents ratio, temperature and reaction time) were modified as needed.

$^1$H NMR (500 MHz, chloroform-d) δ (ppm) 12.1 (br s, 1H), 8.80 (dd, 1H), 8.72 (dd, 1H), 7.40 (dd, 1H), 6.80-6.86 (m, 2H), 6.72 (tt, 1H), 5.78 (s, 2H).

Compound I-52

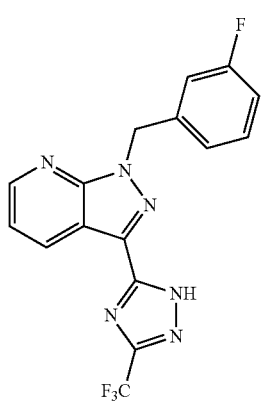

Compound I-52

1-(3-Fluorobenzyl)-3-(3-(trifluoromethyl)-1H-1,2,4-triazol-5-yl)-1H-pyrazolo[3,4-b]pyridine was synthesized according to General Procedure A as a white solid (89 mg, 74% yield). The reaction conditions (such as reagents ratio, temperature and reaction time) were modified as needed.

$^1$H NMR (500 MHz, chloroform-d) δ (ppm) 12.2 (br s, 1H), 8.79 (dd, 1H), 8.72 (dd, 1H), 7.39 (dd, 1H), 7.25 (ddd, 1H), 7.08 (d, 1H), 6.92-6.99 (m, 2H), 5.80 (s, 2H).

Compound I-53

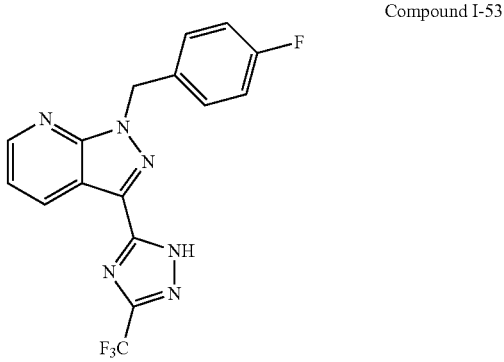 [SMILES: Fc1ccc(Cn2nc(-c3nc(C(F)(F)F)n[nH]3)c3cccnc32)cc1]

Compound I-53

1-(4-Fluorobenzyl)-3-(3-(trifluoromethyl)-1H-1,2,4-triazol-5-yl)-1H-pyrazolo[3,4-b]pyridine was synthesized according to General Procedure A as a white solid (82 mg, 69% yield). The reaction conditions (such as reagents ratio, temperature and reaction time) were modified as needed.

$^1$H NMR (500 MHz, chloroform-d) δ (ppm) 12.2 (br s, 1H), 8.78 (dd, 1H), 8.72 (dd, 1H), 7.38 (dd, 1H), 7.30 (dd, 2H), 6.96 (t, 2H), 5.78 (s, 2H).

Compound I-54

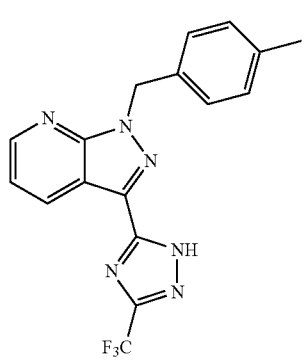

Compound I-54

1-(4-Methylbenzyl)-3-(3-(trifluoromethyl)-1H-1,2,4-triazol-5-yl)-1H-pyrazolo[3,4-b]pyridine was synthesized according to General Procedure A as a white solid (80 mg, 67% yield). The reaction conditions (such as reagents ratio, temperature and reaction time) were modified as needed.

$^1$H NMR (500 MHz, chloroform-d) δ (ppm) 12.3 (br s, 1H), 8.77 (dd, 1H), 8.72 (dd, 1H), 7.37 (dd, 1H), 7.18 (d, 2H), 7.05 (d, 2H), 5.76 (s, 2H), 2.26 (s, 3H).

Compound I-60

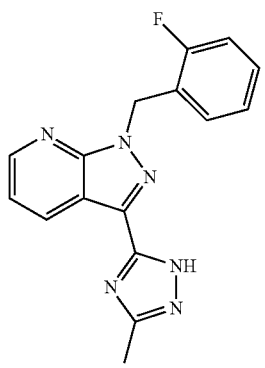

Compound I-60

1-(2-Fluorobenzyl)-3-(3-methyl-1H-1,2,4-triazol-5-yl)-1H-pyrazolo[3,4-b]pyridine was synthesized according to General Procedure A as a white solid (87 mg, 80% yield). The reaction conditions (such as reagents ratio, temperature and reaction time) were modified as needed.

$^1$H NMR (500 MHz, DMSO-$d_6$) δ (ppm) 13.9 (br s, 1H), 8.63-8.69 (m, 2H), 7.33-7.41 (m, 2H), 7.17-7.25 (m, 2H), 7.12-7.16 (m, 1H), 5.80 (s, 2H), 2.43 (s, 3H).

Compound I-61

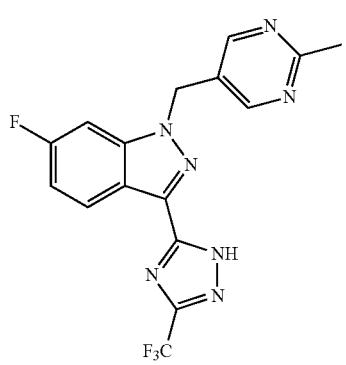

Compound I-61

6-Fluoro-1-((2-methylpyrimidin-5-yl)methyl)-3-(3-(trifluoromethyl)-1H-1,2,4-triazol-5-yl)-1H-indazole was synthesized according to General Procedure A, with the exception that phosphoryl trichloride was used as a solvent in the triazole cyclization step, as a cream colored solid (5.1 mg, 3.1% yield). The reaction conditions (such as reagents ratio, temperature and reaction time) were modified as needed.

$^1$H NMR (500 MHz, DMSO-$d_6$) δ (ppm) 15.7 (s, 1H), 8.76 (s, 2H), 8.26 (dd, 1H), 7.98 (d, 1H), 7.29 (td, 1H), 5.80 (s, 2H), 2.59 (s, 3H).

Compound I-65

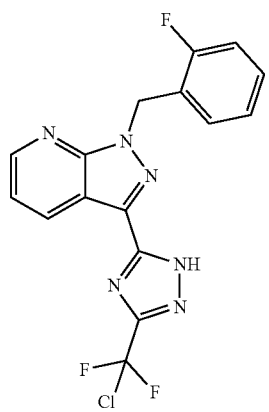

Compound I-65

3-(3-(Chlorodifluoromethyl)-1H-1,2,4-triazol-5-yl)-1-(2-fluorobenzyl)-1H-pyrazolo[3,4-b]pyridine was synthesized according to General Procedure A, with the exception that 2-chloro-2,2-difluoroacetyl chloride was used as the acylating agent and sodium carbonate (2 equiv.) was used as a base for that step, as a white solid (7.9 mg, 5.9% yield). The reaction conditions (such as reagents ratio, temperature and reaction time) were modified as needed.

$^1$H NMR (500 MHz, methanol-$d_4$) δ (ppm) 8.76 (dd, 1H), 8.70 (dd, 1H), 7.44 (dd, 1H), 7.33 (s, 1H), 7.24 (t, 1H), 7.13 (m, 2H), 5.92 (s, 2H).

Compound I-67

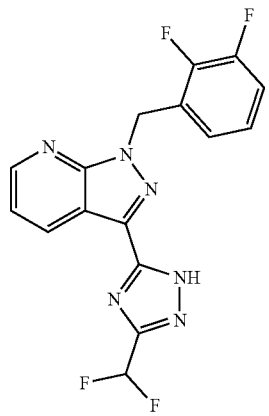

Compound I-67

1-(2,3-Difluorobenzyl)-3-(3-(difluoromethyl)-1H-1,2,4-triazol-5-yl)-1H-pyrazolo[3,4-b]pyridine was synthesized according to General Procedure A, with the exception that 2,2-difluoroacetic anhydride was used as the acylating agent, as a light yellow solid (130 mg, 85% yield). The reaction conditions (such as reagents ratio, temperature and reaction time) were modified as needed.

$^1$H NMR (500 MHz, DMSO-$d_6$) δ (ppm) 15.4 (br s, 1H), 8.75 (d, 1H), 8.68 (d, 1H), 7.49 (m, 1H), 7.40 (m, 1H), 7.20 (t, 1H), 7.17 (m, 1H), 7.03 (app. t, 1H), 5.93 (s, 2H).

Compound I-68 and Compound I-69

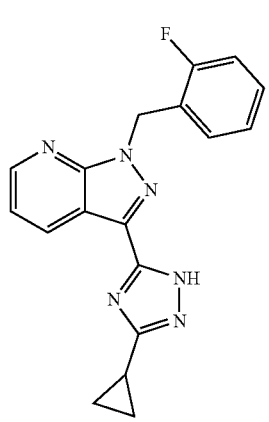
Compound I-68

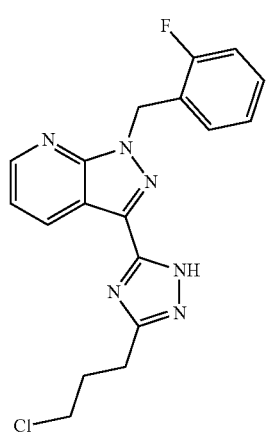
Compound I-69

3-(3-Cyclopropyl-1H-1,2,4-triazol-5-yl)-1-(2-fluorobenzyl)-1H-pyrazolo[3,4-b]pyridine (Compound I-68) and 3-(3-(3-chloropropyl)-1H-1,2,4-triazol-5-yl)-1-(2-fluorobenzyl)-1H-pyrazolo[3,4-b]pyridine (Compound I-69) were synthesized according to General Procedure A with the exception that cyclopropanecarbonyl chloride was used as the acylating agent to afford Compound I-68 as a white solid (32 mg, 28% yield) and Compound 1-69 as a white solid (31 mg, 23% yield). The reaction conditions (such as reagents ratio, temperature and reaction time) were modified as needed.

Compound I-68: $^1$H NMR (500 MHz, DMSO-$d_6$) δ (ppm) 8.62-8.67 (m, 2H), 7.33-7.39 (m, 2H), 7.23 (t, 1H), 7.12-7.16 (m, 2H), 5.80 (s, 2H), 2.08-2.13 (m, 1H), 0.97-1.08 (m, 4H).

Compound I-69: $^1$H NMR (500 MHz, DMSO-$d_6$) δ (ppm) 8.64-8.68 (m, 2H), 7.33-7.41 (m, 2H), 7.21-7.26 (m, 1H), 7.12-7.19 (m, 2H), 5.82 (s, 2H), 3.76 (t, 2H), 2.93 (t, 2H), 2.21 (quin, 2H).

Compound I-85

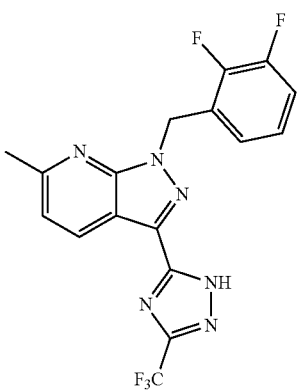
Compound I-85

1-(2,3-Difluorobenzyl)-6-methyl-3-(3-(trifluoromethyl)-1H-1,2,4-triazol-5-yl)-1H-pyrazolo[3,4-b]pyridine was synthesized according to General Procedure A as a colorless solid (2.2 mg, 40% yield). The reaction conditions (such as reagents ratio, temperature and reaction time) were modified as needed.

$^1$H NMR (500 MHz, methanol-$d_4$) δ (ppm) 8.59 (d, 1H), 7.33 (d, 1H), 7.21 (m, 1H), 7.08 (m, 1H), 6.98 (app. t, 1H), 5.91 (s, 2H), 2.73 (s, 3H).

Compound I-98

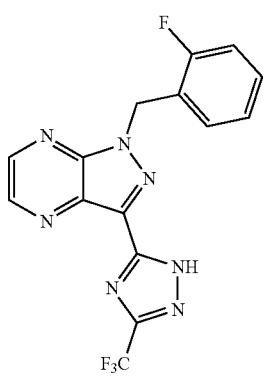
Compound I-98

1-(2-Fluorobenzyl)-3-(3-(trifluoromethyl)-1H-1,2,4-triazol-5-yl)-1H-pyrazolo[3,4-b]pyrazine was synthesized according to General Procedure A as a white solid (11 mg, 18% yield). The reaction conditions (such as reagents ratio, temperature and reaction time) were modified as needed.

$^1$H NMR (500 MHz, methanol-$d_4$) δ (ppm) 8.72 (d, 1H), 8.63 (d, 1H), 7.22-7.31 (m, 2H), 7.00-7.09 (m, 2H), 5.83 (s, 2H).

Compound I-100

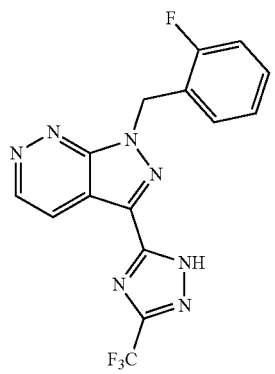

Compound I-100

1-(2-Fluorobenzyl)-3-(3-(trifluoromethyl)-1H-1,2,4-triazol-5-yl)-1H-pyrazolo[3,4-c]pyridazine was synthesized according to General Procedure A, with the exception that phosphorus pentoxide (2.0 equiv.) was added in addition to phosphoryl trichloride in the triazole cyclization step, as an off-white solid (10 mg, 12% yield). The reaction conditions (such as reagents ratio, temperature and reaction time) were modified as needed.

$^1$H NMR (500 MHz, methanol-$d_4$) δ (ppm) 9.32 (d, 1H), 8.62 (d, 1H), 7.43-7.46 (m, 1H), 7.34-7.38 (m, 1H), 7.13-7.17 (m, 2H), 6.13 (s, 2H).

Compound I-101

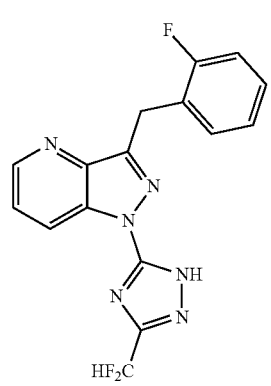

Compound I-101

1-(3-(Difluoromethyl)-1H-1,2,4-triazol-5-yl)-3-(2-fluorobenzyl)-1H-pyrazolo[4,3-b]pyridine was synthesized according to General Procedure A, with the exception that 2,2-difluoroacetic anhydride was used as the acylating agent, as a white solid (32 mg, 45% yield). The reaction conditions (such as reagents ratio, temperature and reaction time) were modified as needed.

$^1$H NMR (500 MHz, DMSO-$d_6$) δ (ppm) 15.2 (br s, 1H), 8.73 (s, 1H), 8.65 (s, 1H), 7.69 (s, 1H), 7.41 (t, 1H), 6.97-7.35 (m, 4H), 4.50 (s, 2H).

Compound I-105

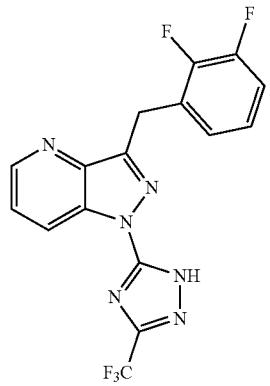

3-(2,3-Difluorobenzyl)-1-(3-(trifluoromethyl)-1H-1,2,4-triazol-5-yl)-1H-pyrazolo[4,3-b]pyridine was synthesized according to General Procedure A as a white solid (150 mg, 40% yield). The reaction conditions (such as reagents ratio, temperature and reaction time) were modified as needed.

$^1$H NMR (500 MHz, chloroform-d) δ (ppm) 11.8 (br s, 1H), 8.70-8.85 (m, 2H), 7.53-7.65 (m, 1H), 7.08-7.17 (m, 1H), 6.91-7.07 (m, 2H), 4.56 (s, 2H).

Compound I-2

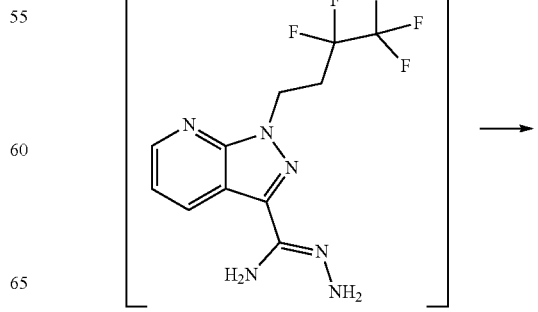

-continued

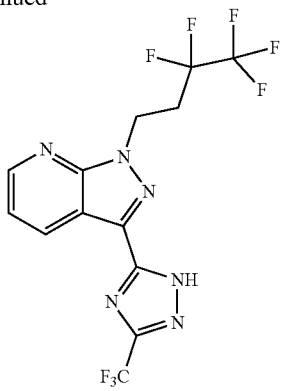

Compound I-2

Compound I-2

General Procedure B: 1-(3,3,4,4,4-pentafluorobutyl)-3-(3-(trifluoromethyl)-1H-1,2,4-triazol-5-yl)-1H-pyrazolo[3,4-b]pyridine

To a solution of 1-(3,3,4,4,4-pentafluorobutyl)-1H-pyrazolo[3,4-b]pyridine-3-carboximidamide hydrochloride (WO2011/149921A1) (200 mg, 0.58 mmol) and triethylamine (0.24 mL, 1.7 mmol) (Note: triethylamine was not necessary if the amidine starting material existed as the free base form) in ethanol (10 mL) was added hydrazine hydrate (0.03 mL, 0.64 mmol). After stirring at ambient temperature overnight, complete disappearance of starting material was observed. The reaction was concentrated and the residue was dried in vacuo overnight. A portion of the residue (77 mg, 0.24 mmol) was taken up in dichloromethane (2.0 mL) and 2,2,2-trifluoroacetic anhydride (0.04 mL, 0.26 mmol) was added dropwise. The reaction was stirred at ambient temperature until complete consumption of the amidrazone intermediate. The solvent was removed in vacuo and toluene (2.0 mL) was added followed by dropwise addition of phosphoryl trichloride (0.07 mL, 0.72 mmol) was added and the resultant mixture was heated at 85° C. for 45 min. The reaction was concentrated in vacuo and the residue was purified using reverse phase preparative HPLC (5-95% acetonitrile/water gradient with 0.1% TFA as additive) to isolate the title compound (30 mg, 31% yield) as an off-white solid.

$^1$H NMR (500 MHz, chloroform-d) δ (ppm) 8.80 (dd, 1H), 8.73 (dd, 1H), 7.40 (dd, 1H), 4.97 (m, 2H), 2.84 (m, 2H).

Compound I-7

Compound I-7

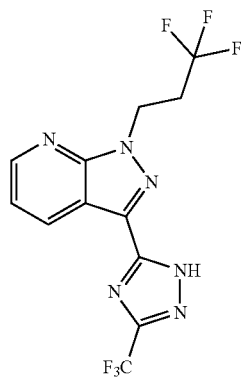

3-(3-(Trifluoromethyl)-1H-1,2,4-triazol-5-yl)-1-(3,3,3-trifluoropropyl)-1H-pyrazolo[3,4-b]pyridine was synthesized from 1-(3,3,3-trifluoropropyl)-1H-pyrazolo[3,4-b]pyridine-3-carboximidamide (WO2011/149921A1) according to General Procedure B as a white solid (110 mg, 40% yield). The reaction conditions (such as reagents ratio, temperature and reaction time) were modified as needed.

$^1$H NMR (500 MHz, DMSO-$d_6$) δ (ppm) 8.75 (dd, 1H), 8.65 (dd, 1H), 7.48 (dd, 1H), 4.88 (t, 2H), 3.03-3.14 (m, 2H).

Compound I-3

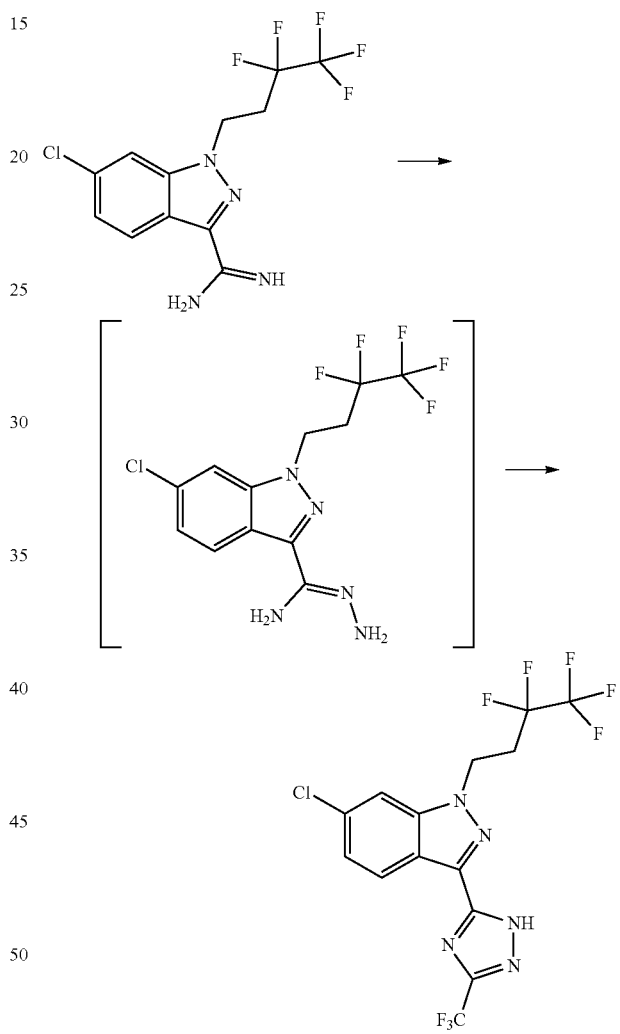

Compound I-3

General Procedure C: 6-chloro-1-(3,3,4,4,4-pentafluorobutyl)-3-(3-(trifluoromethyl)-1H-1,2,4-triazol-5-yl)-1H-indazole

To a solution of 6-chloro-1-(3,3,4,4,4-pentafluorobutyl)-1H-indazole-3-carboximidamide (WO2011/149921A1) (100 mg, 0.29 mmol) in ethanol (2.0 mL) was added hydrazine hydrate (0.03 mL, 0.64 mmol) (Note: anhydrous hydrazine could also be used). After stirring at ambient temperature overnight, complete disappearance of starting material was observed. The reaction was concentrated and the residue was dried in vacuo overnight. The residue was taken up in THF (2.0 mL) and 2,2,2-trifluoroacetic anhydride (0.05 mL, 0.34 mmol) was added dropwise. The reaction was stirred at ambient temperature until complete consumption of the amidrazone intermediate. Phosphoryl trichloride (0.08 mL, 0.84 mmol) was added and the resultant mixture was heated at 145° C. in a microwave for 30 min. The reaction was concentrated in vacuo and the residue was purified using reverse phase preparative HPLC (5-95% acetonitrile/water gradient with 0.1% TFA as additive) to isolate the title compound (54 mg, 44% yield) as an off-white solid.

$^1$H NMR (500 MHz, chloroform-d) δ (ppm) 8.41 (d, 1H), 7.52 (s, 1H), 7.37 (d, 1H), 4.73 (t, 2H), 2.81 (m, 2H).

Compound I-5 in a microwave for 15 min. The reaction mixture was poured into EtOAc (100 mL) and washed with saturated NaHCO$_3$ solution (50 mL), dried, filtered and concentrated in vacuo. The crude material was purified using silica gel chromatography (0-10% MeOH/dichloromethane gradient) to isolate the title compound (61 mg, 49% yield) as a light orange solid.

$^1$H NMR (500 MHz, methanol-d$_4$) δ (ppm) 9.22 (d, 1H), 8.96-9.00 (m, 1H), 8.77-8.82 (m, 2H), 7.69 (d, 1H), 6.89-6.95 (m, 1H), 6.78-6.85 (m, 1H), 4.34 (s, 2H), 2.51 (s, 3H).

Compound I-27

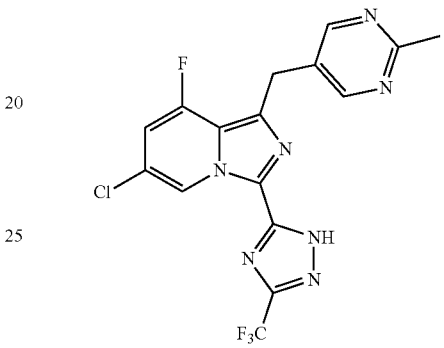

Compound I-27

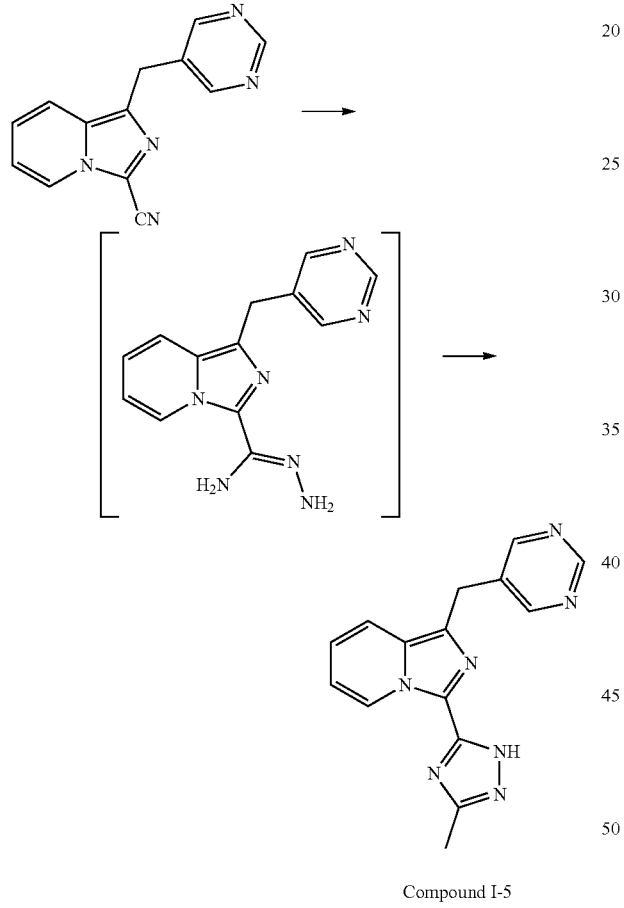

Compound I-5

6-Chloro-8-fluoro-1-((2-methylpyrimidin-5-yl)methyl)-3-(3-(trifluoromethyl)-1H-1,2,4-triazol-5-yl)imidazo[1,5-a]pyridine was synthesized according to General Procedure D as a white solid (10 mg, 48% yield). The reaction conditions (such as reagents ratio, temperature and reaction time) were modified as needed.

$^1$H NMR (500 MHz, chloroform-d) δ (ppm) 9.25-9.43 (m, 1H), 8.98 (s, 2H), 6.65-6.81 (m, 1H), 4.47 (s, 2H), 2.87 (s, 3H).

Compound I-34

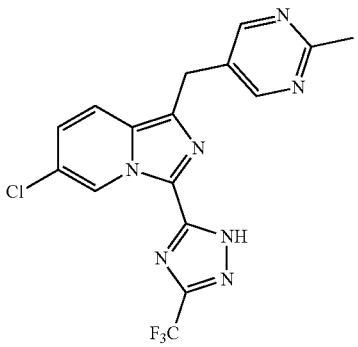

Compound I-34

General Procedure D: 3-(3-methyl-1H-1,2,4-triazol-5-yl)-1-(pyrimidin-5-ylmethyl)imidazo[1,5-a]pyridine To a solution of 1-(pyrimidin-5-ylmethyl)imidazo[1,5-a]pyridine-3-carbonitrile (100 mg, 0.43 mmol) in methanol (1.2 mL) was added anhydrous hydrazine (0.13 mL, 4.3 mmol). After stirring at ambient temperature overnight for 24 hours, complete disappearance of starting material was observed. The reaction was concentrated in vacuo. Toluene (25 mL), pyridine (0.41 mL, 5.1 mmol) and N,N-dimethylaniline (0.26 mL, 2.0 mmol) were added and the resultant mixture was cooled to 0° C. and treated with acetic anhydride (0.05 mL, 0.56 mmol). The reaction was stirred at ambient temperature for 30 min and then heated at 190° C.

6-Chloro-1-((2-methylpyrimidin-5-yl)methyl)-3-(3-(trifluoromethyl)-1H-1,2,4-triazol-5-yl)imidazo[1,5-a]pyridine was synthesized according to General Procedure D, with the exception that N,N-dimethylaniline was not used in this experiment, as a light yellow solid (100 mg, 24% yield). The reaction conditions (such as reagents ratio, temperature and reaction time) were modified as needed.

¹H NMR (500 MHz, methanol-d₄) δ (ppm) 9.37 (s, 1H), 8.82-8.90 (m, 2H), 7.83 (d, 1H), 7.04 (dd, 1H), 4.41 (s, 2H), 2.67-2.75 (s, 3H).

Compound I-12

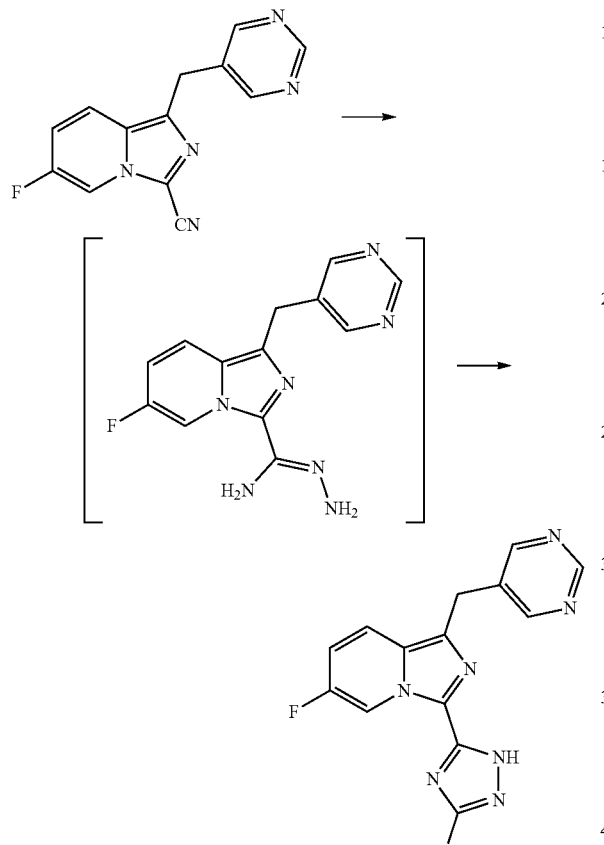

Compound I-12

General Procedure E: 6-fluoro-1-(pyrimidin-5-ylmethyl)-3-(3-(trifluoromethyl)-1H-1,2,4-triazol-5-yl)imidazo[1,5-a]pyridine To a solution of 6-fluoro-1-(pyrimidin-5-ylmethyl)imidazo[1,5-a]pyridine-3-carbonitrile (490 mg, 1.9 mmol) in methanol (9.7 mL) was added anhydrous hydrazine (0.36 mL, 12 mmol). After stirring at ambient temperature overnight for 24 hours, complete disappearance of starting material was observed. The reaction was concentrated in vacuo to afford an orange solid. Toluene (9.8 mL), N,N-dimethylaniline (1.0 mL, 7.9 mmol) were added and the resultant mixture was treated with 2,2,2-trifluoroacetic anhydride (0.42 mL, 2.9 mmol). The reaction was stirred at ambient temperature for 30 min. The reaction mixture was poured into EtOAc (100 mL) and washed with saturated NaHCO₃ solution (100 mL), dried, filtered and concentrated in vacuo. The crude material was purified using silica gel chromatography (0-5% MeOH/dichloromethane gradient) to isolate the title compound (80 mg, 11% yield) as a yellow solid.

¹H NMR (500 MHz, methanol-d₄) δ (ppm) 9.29-9.33 (m, 1H), 9.02 (s, 1H), 8.85 (s, 2H), 7.88-7.96 (m, 1H), 7.09 (ddd, 1H), 4.40 (s, 2H).

Compound I-6

Compound I-6

7-Chloro-1-(pyrimidin-5-ylmethyl)-3-(3-(trifluoromethyl)-1H-1,2,4-triazol-5-yl)imidazo[1,5-a]pyridine was synthesized according to General Procedure E as a white solid (7.4 mg, 5.1% yield). The reaction conditions (such as reagents ratio, temperature and reaction time) were modified as needed.

¹H NMR (500 MHz, methanol-d₄) δ (ppm) 9.23-9.40 (m, 1H), 9.02 (s, 1H), 8.85 (s, 2H), 7.90-8.03 (m, 1H), 6.98 (dd, 1H), 4.36 (s, 2H).

Compound I-23

Compound I-23

6-Fluoro-1-((2-methylpyrimidin-5-yl)methyl)-3-(3-(trifluoromethyl)-1H-1,2,4-triazol-5-yl)imidazo[1,5-a]pyridine pyridine was synthesized according to General Procedure E as a white solid (18 mg, 2.1% yield). The reaction conditions (such as reagents ratio, temperature and reaction time) were modified as needed.

¹H NMR (500 MHz, methanol-d₄) δ (ppm) 9.23-9.36 (m, 1H), 8.73 (s, 2H), 7.91 (dd, 1H), 7.01-7.14 (m, 1H), 4.31-4.40 (m, 2H), 2.65 (s, 3H).

Compound I-28

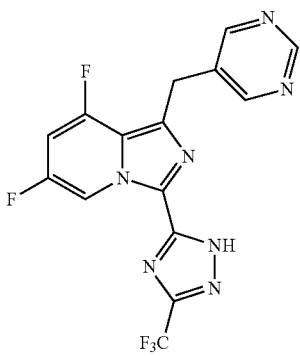

Compound I-28

6,8-Difluoro-1-(pyrimidin-5-ylmethyl)-3-(3-(trifluoromethyl)-1H-1,2,4-triazol-5-yl)imidazo[1,5-a]pyridine was synthesized according to General Procedure E as a white solid (4.3 mg, 16% yield). The reaction conditions (such as reagents ratio, temperature and reaction time) were modified as needed.

$^1$H NMR (500 MHz, methanol-$d_4$) δ (ppm) 9.23 (d, 1H), 9.03 (s, 1H), 8.86 (s, 1H), 7.15 (s, 2H), 4.53 (s, 2H).

Compound I-18

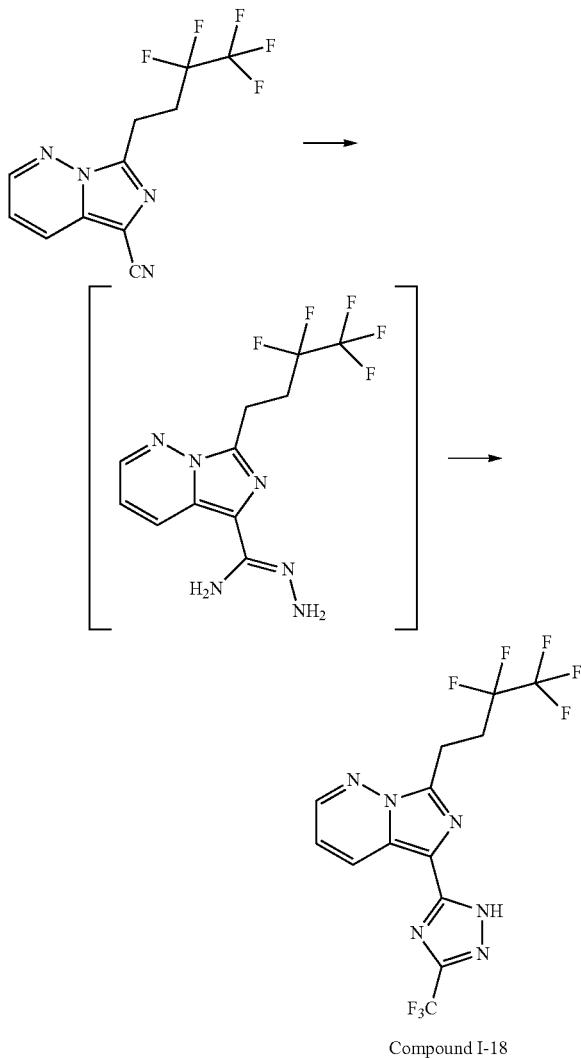

Compound I-18

General Procedure F: 7-(3,3,4,4,4-pentafluorobutyl)-5-(3-(trifluoromethyl)-1H-1,2,4-triazol-5-yl)imidazo[1,5-b]pyridazine To a solution of 7-(3,3,4,4,4-pentafluorobutyl)imidazo[1,5-b]pyridazine-5-carbonitrile (23 mg, 0.08 mmol) in methanol (0.40 mL) was added sodium methoxide (5.4 M solution in methanol, 29 μL, 0.16 mmol). After stirring at 60° C. for 3.5 hours, hydrazine hydrate (39 μl, 0.40 mmol) was added and the reaction was stirred at 60° C. for 18 hours. The reaction was concentrated in vacuo. The residue was taken up in dichloromethane (0.79 mL) and cooled to 0° C. 2,2,2-Trifluoroacetic anhydride (45 μL, 0.32 mmol) was added dropwise. The reaction was warmed to ambient temperature and stirred until complete consumption of the amidrazone intermediate. The solvent was removed in vacuo and toluene (0.80 mL) was added followed by dropwise addition of phosphoryl trichloride (22 μL, 0.24 mmol) and the resultant mixture was heated at 75° C. for 18 hours. The reaction mixture was partitioned between water and dichloromethane (1:1 ratio, 20 mL). The aqueous layer was back-extracted with dichloromethane (3×10 mL), neutralized to pH ~6 and further extracted with dichloromethane (2×10 mL). The combined organic phases were dried over MgSO$_4$, filtered and concentrated in vacuo. The crude material was purified using silica gel chromatography (0-80% acetonitrile/MeOH (7:1) in dichloromethane gradient) to afford the title compound (14 mg, 44% yield) as a pale yellow solid.

$^1$H NMR (500 MHz, methanol-$d_4$) δ (ppm) 8.60 (dd, 1H), 8.40 (dd, 1H), 7.02 (dd, 1H), 3.48-3.54 (m, 2H), 2.82-2.95 (m, 2H).

Compound I-24

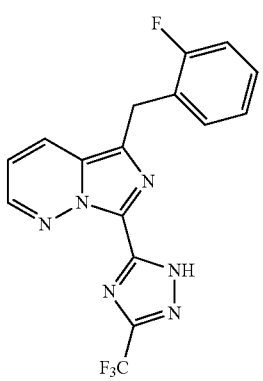

Compound I-24

5-(2-Fluorobenzyl)-7-(3-(trifluoromethyl)-1H-1,2,4-triazol-5-yl)imidazo[1,5-b]pyridazine was synthesized according to General Procedure F as a pale yellow-green solid (7.1 mg, 15% yield). The reaction conditions (such as reagents ratio, temperature and reaction time) were modified as needed.

$^1$H NMR (500 MHz, methanol-$d_4$) δ (ppm) 8.49 (dd, 1H), 8.08 (d, 1H), 7.38-7.41 (m, 1H), 7.23-7.27 (m, 1H), 7.10-7.13 (m, 1H), 7.05-7.09 (m, 1H), 6.91 (dd, 1H), 4.37 (s, 2H).

Compound I-36

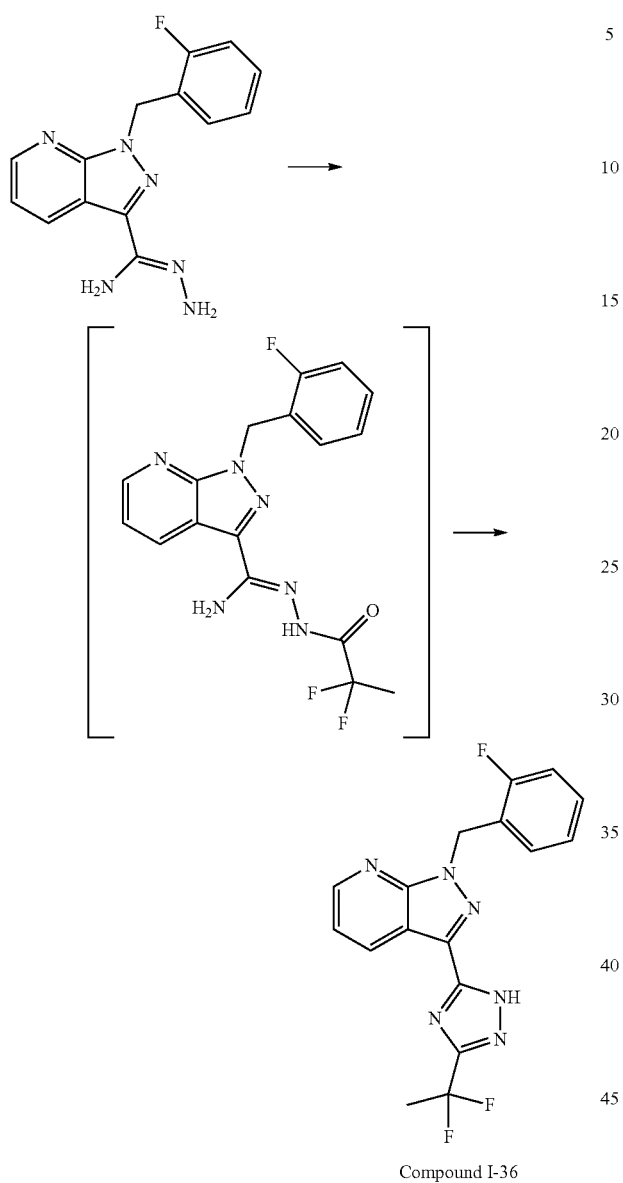

Compound I-36

General Procedure G: 3-(3-(1,1-difluoroethyl)-1H-1,2,4-triazol-5-yl)-1-(2-fluorobenzyl)-1H-pyrazolo[3,4-b]pyridine A mixture of 1-(2-fluorobenzyl)-1H-pyrazolo[3,4-b]pyridine-3-carboximidhydrazide (150 mg, 0.53 mmol) and 2,2-difluoropropanoic acid (70 mg, 0.63 mmol) in DMF (5.0 mL) was treated with Hunig's Base (280 µL, 1.6 mmol) and PyAOP (280 mg, 0.53 mmol). After stirring overnight at ambient temperature, the contents were concentrated in vacuo. The residue was dissolved in EtOAc and washed with water and brine. The organic phase was dried over $Na_2SO_4$, filtered and concentrated in vacuo. Toluene (5.0 mL) was added followed by dropwise addition of phosphoryl trichloride (0.49 mL, 5.3 mmol). The resultant mixture was heated at 80° C. overnight. The reaction mixture concentrated in vacuo and purified by reverse phase preparative HPLC to afford the title compound (11 mg, 5.3% yield) as a pale blue solid.

$^1$H NMR (500 MHz, methanol-$d_4$) δ (ppm) 8.66 (dd, 1H), 8.57 (d, 1H), 7.32 (dd, 1H), 7.19-7.25 (m, 1H), 7.10 (t, 1H), 6.96-7.05 (m, 2H), 5.80 (s, 2H), 2.02 (t, 3H).

Compound I-58

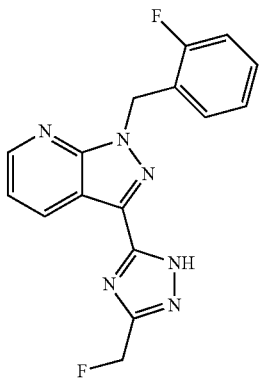

Compound I-58

1-(2-Fluorobenzyl)-3-(3-(fluoromethyl)-1H-1,2,4-triazol-5-yl)-1H-pyrazolo[3,4-b]pyridine was synthesized according to General Procedure G, with the exception that phosphoryl trichloride was used as the solvent in the triazole cyclization step, as a white solid (19 mg, 37% yield). The reaction conditions (such as reagents ratio, temperature and reaction time) were modified as needed.

$^1$H NMR (500 MHz, DMSO-$d_6$) δ (ppm) 14.9 (br s, 1H), 8.66-8.73 (m, 2H), 7.44 (dd, 1H), 7.37 (q, 1H), 7.17-7.27 (m, 2H), 7.12-7.17 (m, 1H), 5.86 (s, 2H), 5.55 (d, 2H).

Compound I-77

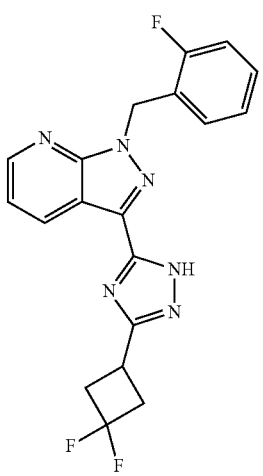

Compound I-77

3-(3-(3,3-Difluorocyclobutyl)-1H-1,2,4-triazol-5-yl)-1-(2-fluorobenzyl)-1H-pyrazolo[3,4-b]pyridine was synthesized according to General Procedure G as a white solid (14 mg, 21% yield). The reaction conditions (such as reagents ratio, temperature and reaction time) were modified as needed.

$^1$H NMR (500 MHz, chloroform-d) δ (ppm) 8.76 (d, 1H), 8.69 (s, 1H), 7.25-7.38 (m, 2H), 7.00-7.15 (m, 3H), 5.88 (s, 2H), 3.62, (m, 1H), 3.00-3.18 (m, 4H).

Compound I-78

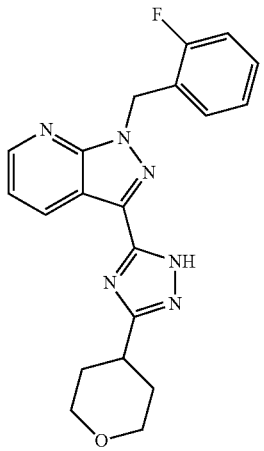

Compound I-78

1-(2-Fluorobenzyl)-3-(3-(tetrahydro-2H-pyran-4-yl)-1H-1,2,4-triazol-5-yl)-1H-pyrazolo[3,4-b]pyridine was synthesized according to General Procedure G as a white solid (11 mg, 15% yield). The reaction conditions (such as reagents ratio, temperature and reaction time) were modified as needed.

$^1$H NMR (500 MHz, chloroform-d) δ (ppm) 8.75 (d, 1H), 8.66 (d, 1H), 7.30 (dd, 1H), 7.22 (q, 1H), 6.95-7.08 (m, 3H), 5.89 (s, 2H), 4.09 (d, 2H), 3.59 (app. t, 2H), 3.16-3.24 (m, 1H), 2.00-2.13 (m, 4H).

Compound I-59

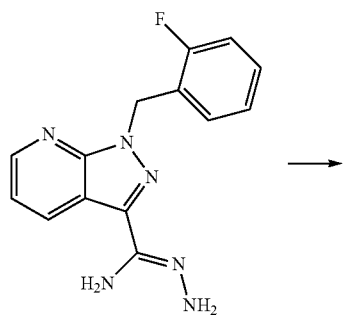

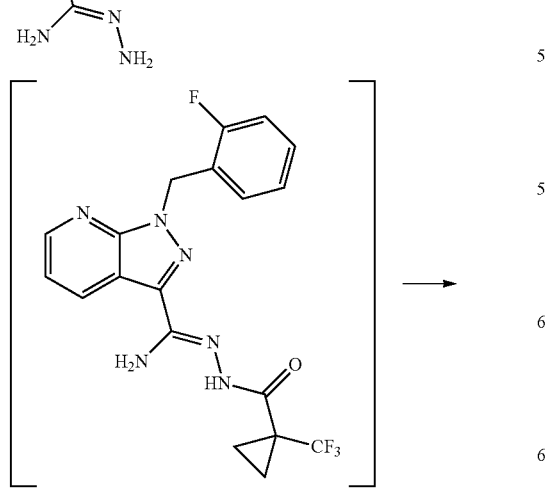

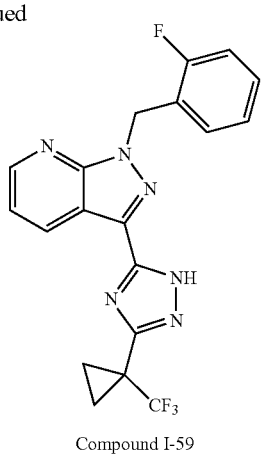

Compound I-59

General Procedure H: 1-(2-fluorobenzyl)-3-(3-(1-(trifluoromethyl)cyclopropyl)-1H-1,2,4-triazol-5-yl)-1H-pyrazolo[3,4-b]pyridine A mixture containing 1-(trifluoromethyl)cyclopropanecarboxylic acid (140 mg, 0.88 mmol), HATU (500 mg, 1.3 mmol), and 4-methylmorpholine (0.29 mL, 2.6 mmol) in DMF (15 mL) was stirred at ambient temperature for 15 minutes and then treated with 1-(2-fluorobenzyl)-1H-pyrazolo[3,4-b]pyridine-3-carboximidhydrazide (250 mg, 0.88 mmol). After stirring at ambient temperature overnight for 18 hours, complete disappearance of starting material was observed. The reaction was diluted with EtOAc (75 mL) and washed with water (50 mL) and brine (15 mL), dried over Na$_2$SO$_4$, filtered and concentrated to yield a crude residue. Phosphoryl trichloride (15 mL, 0.16 mmol) was added and the reaction was heated at 100° C. for 4 hours. The reaction was then concentrated and dried in vacuo overnight. The crude orange residue was purified by reverse phase preparative HPLC (5-95% acetonitrile in water gradient with 0.1% formic acid as additive) to obtain 1-(2-fluorobenzyl)-3-(3-(1-(trifluoromethyl)cyclopropyl)-1H-1,2,4-triazol-5-yl)-1H-pyrazolo[3,4-b]pyridine (180 mg, 51% yield) as a white solid after lyophilization.

$^1$H NMR (500 MHz, DMSO-d$_6$) δ (ppm) 14.7 (br s, 1H), 8.70 (d, 1H), 8.66 (d, 1H), 7.44 (dd, 1H), 7.32-7.39 (m, 1H), 7.20-7.27 (m, 1H), 7.11-7.16 (m, 2H), 5.85 (s, 2H), 1.48 (s, 4H).

Compound I-63

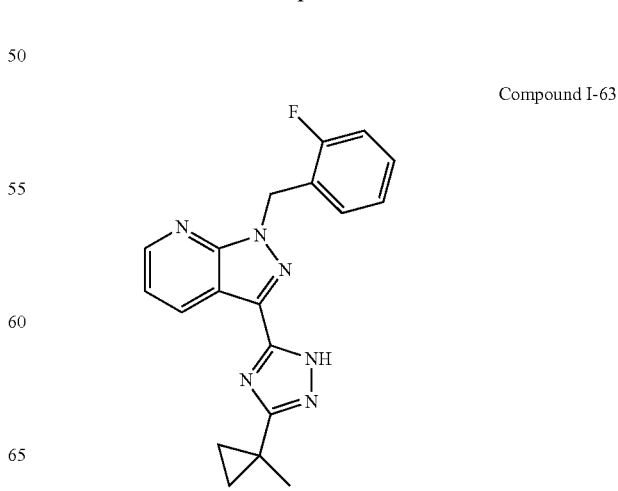

Compound I-63

1-(2-Fluorobenzyl)-3-(3-(1-methylcyclopropyl)-1H-1,2,4-triazol-5-yl)-1H-pyrazolo[3,4-b]pyridine was synthesized according to General Procedure H, with the exception that phosphoryl trichloride (4 equiv.) in toluene was used in the triazole cyclization step, as a pale brown solid (22 mg, 16% yield). The reaction conditions (such as reagents ratio, temperature and reaction time) were modified as needed.

$^1$H NMR (500 MHz, methanol-$d_4$) δ (ppm) 8.71 (d, 1H), 8.61 (d, 1H), 7.25-7.37 (m, 2H), 7.02-7.15 (m, 3H), 5.84-5.89 (m, 2H), 1.58 (s, 3H), 1.32 (s, 2H), 0.92-0.99 (m, 2H).

Compound I-80

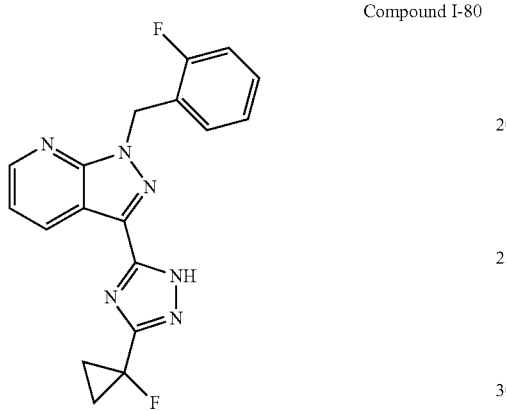

Compound I-80

1-(2-Fluorobenzyl)-3-(3-(1-fluorocyclopropyl)-1H-1,2,4-triazol-5-yl)-1H-pyrazolo[3,4-b]pyridine was synthesized according to General Procedure H, with the exception that phosphoryl trichloride (3 equiv.) in toluene was used in the triazole cyclization step, as a white film (1.5 mg, 1.6% yield). The reaction conditions (such as reagents ratio, temperature and reaction time) were modified as needed.

$^1$H NMR (500 MHz, methanol-$d_4$) δ (ppm) 8.73 (d, 1H), 8.64 (d, 1H), 7.38 (dd, 1H), 7.28-7.34 (m, 1H), 7.10-7.18 (m, 2H), 7.05-7.09 (m, 1H), 5.88 (s, 2H), 1.56-1.64 (m, 2H), 1.43-1.49 (m, 2H).

Compound I-81

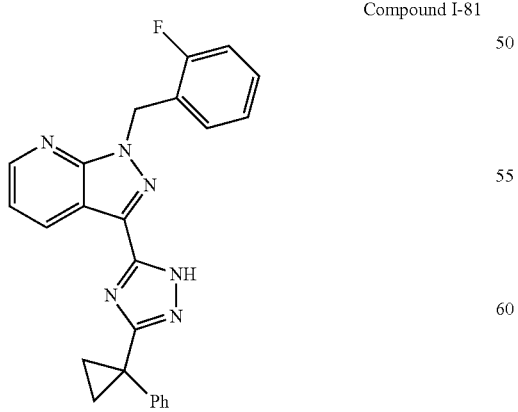

Compound I-81

1-(2-Fluorobenzyl)-3-(3-(1-phenylcyclopropyl)-1H-1,2,4-triazol-5-yl)-1H-pyrazolo[3,4-b]pyridine was synthesized according to General Procedure H, with the exception that Hunig's base (3 equiv.) was the base used in the coupling step and phosphoryl trichloride (3 equiv.) in toluene was used in the triazole cyclization step, as a yellow brown solid (22 mg, 30% yield). The reaction conditions (such as reagents ratio, temperature and reaction time) were modified as needed.

$^1$H NMR (500 MHz, methanol-$d_4$) δ (ppm) 8.77 (dd, 1H), 8.72 (dd, 1H), 7.49-7.54 (m, 3H), 7.33-7.39 (m, 3H), 7.28-7.32 (m, 2H), 7.15-7.20 (m, 2H), 5.91 (s, 2H), 1.80-1.83 (m, 2H), 1.47-1.50 (m, 2H).

Compound I-87

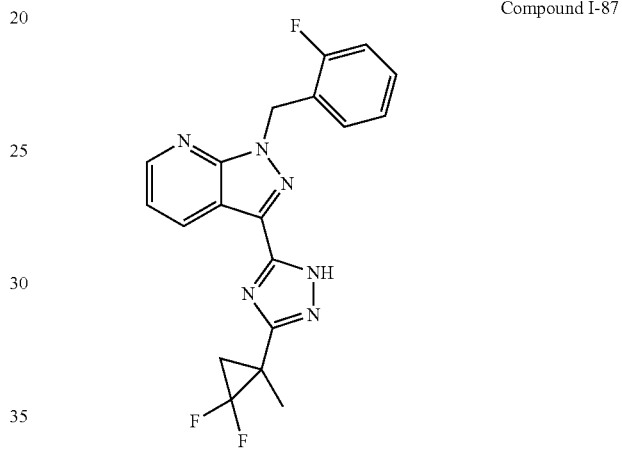

Compound I-87

3-(3-(2,2-Difluoro-1-methylcyclopropyl)-1H-1,2,4-triazol-5-yl)-1-(2-fluorobenzyl)-1H-pyrazolo[3,4-b]pyridine was synthesized according to General Procedure H, with the exception that Hunig's base (3 equiv.) was the base used in the coupling step and phosphoryl trichloride (3 equiv.) in toluene was used in the triazole cyclization step, as a white solid (2.3 mg, 3.4% yield). The reaction conditions (such as reagents ratio, temperature and reaction time) were modified as needed.

$^1$H NMR (500 MHz, methanol-$d_4$) δ (ppm) 8.73 (d, 1H), 8.64 (d, 1H), 7.39 (dd, 1H), 7.27-7.34 (m, 1H), 7.05-7.18 (m, 3H), 5.88 (s, 2H), 2.36-2.43 (m, 1H), 1.64-1.72 (m, 4H).

Compound I-62

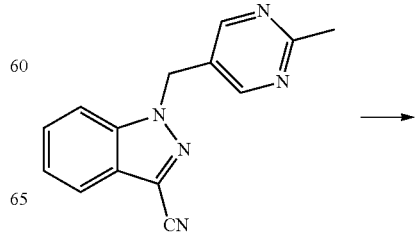

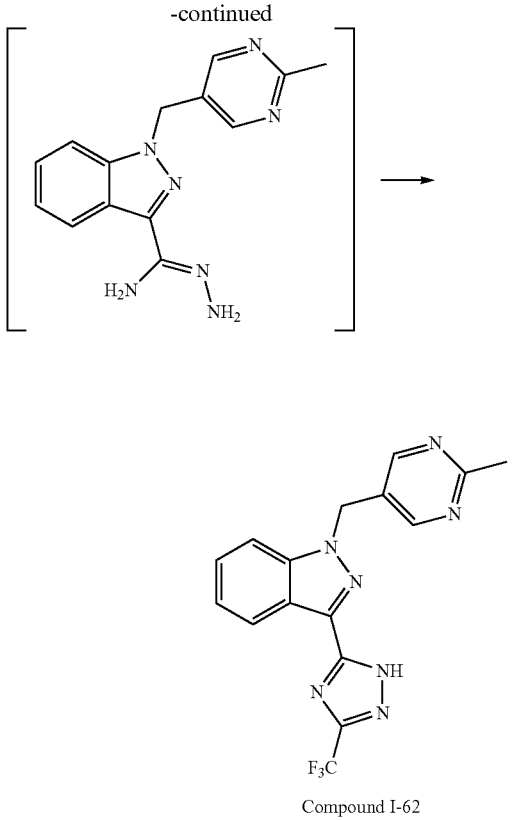

Compound I-62

General Procedure I: 1-((2-methylpyrimidin-5-yl)methyl)-3-(3-(trifluoromethyl)-1H-1,2,4-triazol-5-yl)-1H-indazole 1-((2-Methylpyrimidin-5-yl)methyl)-1H-indazole-3-carbonitrile (270 mg, 1.1 mmol, mixture of a pair of regioisomers) and anhydrous hydrazine (0.37 mL, 12 mmol) in ethanol (4.0 mL) was heated at 60° C. for 5 hours. With complete disappearance of starting material, the reaction was concentrated and dried in vacuo overnight. The crude material was taken up in dichloromethane (2.0 mL) and treated with 2,2,2-trifluoroacetic anhydride (0.15 mL, 1.1 mmol). After stirring at ambient temperature for 1 hour, complete disappearance of starting material was observed. The solvent was removed in vacuo and dried to a yellow residue. The residue was taken up in AcOH (0.3 mL) and EtOH (10 mL) and heated at 120° C. in a microwave for 2.5 hours. The reaction mixture was cooled to ambient temperature and concentrated in vacuo. Purification by reverse phase preparative HPLC (5-95% acetonitrile in water gradient with 0.1% formic acid as additive) yielded the title compound (18 mg, 4.6% yield) as an off-white solid.

$^1$H NMR (500 MHz, DMSO-d$_6$) δ (ppm) 15.6 (s, 1H), 8.74 (s, 2H), 8.26 (d, 1H), 8.00 (d, 1H), 7.58 (t, 1H), 7.39 (t, 1H), 5.85 (s, 2H), 2.58 (s, 3H).

Compound I-96

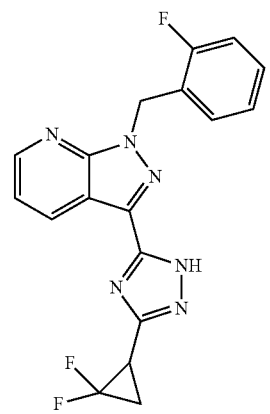

Compound I-96

3-(3-(2,2-Difluorocyclopropyl)-1H-1,2,4-triazol-5-yl)-1-(2-fluorobenzyl)-1H-pyrazolo[3,4-b]pyridine was synthesized according to the coupling method of General Procedure H using 2,2-difluorocyclopropanecarboxylic acid and the triazole cyclization method of General Procedure I, as a white solid (140 mg, 71% yield). The reaction conditions (such as reagents ratio, temperature and reaction time) were modified as needed.

$^1$H NMR (500 MHz, methanol-d$_4$) δ (ppm) 8.73 (d, 1H), 8.65 (d, 1H), 7.39 (m, 1H), 7.34 (m, 1H), 7.22-7.05 (m, 3H), 5.88 (s, 2H), 3.07 (m, 1H), 2.25 (m, 1H), 2.08 (m, 1H).

Compound I-113

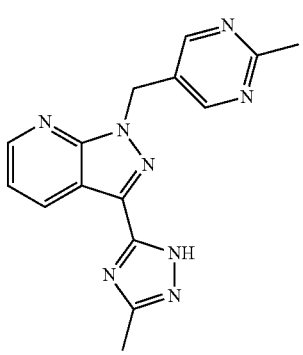

Compound I-113

3-(3-Methyl-1H-1,2,4-triazol-5-yl)-1-((2-methylpyrimidin-5yl)methyl)-1H-pyrazolo[3,4-b]pyridine was synthesized according to the coupling method of General Procedure I, with the exception that acetic anhydride was used, as a white solid (220 mg, 82% yield). The reaction conditions (such as reagents ratio, temperature and reaction time) were modified as needed.

$^1$H NMR (500 MHz, methanol-d$_4$) δ (ppm) 8.80 (s, 2H), 8.71 (d, 1H), 8.65 (m, 1H), 7.37 (m, 1H), 5.82 (s, 2H), 2.65 (s, 3H), 2.54 (br s, 3H).

Compound I-120

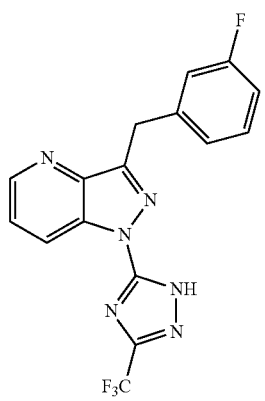

3-(3-Fluorobenzyl)-1-(3-(trifluoromethyl)-1H-1,2,4-triazol-5-yl)-1H-pyrazolo[4,3-b]pyridine was synthesized according to General Procedure I as a white solid (41 mg, 78% yield). The reaction conditions (such as reagents ratio, temperature and reaction time) were modified as needed.

$^1$H NMR (500 MHz, chloroform-d) δ (ppm) 11.6 (br s, 1H), 8.78 (dd, 1H), 8.76 (dd, 1H), 7.57 (dd, 1H), 7.25 (ddd, 1H), 7.19 (d, 1H), 7.12 (dt, 1H), 6.91 (td, 1H), 4.50 (s, 2H).

Compound I-121

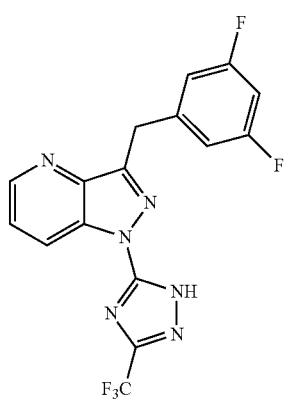

3-(3,5-Difluorobenzyl)-1-(3-(trifluoromethyl)-1H-1,2,4-triazol-5-yl)-1H-pyrazolo[4,3-b]pyridine was synthesized according to General Procedure I as a white solid (68 mg, 77% yield). The reaction conditions (such as reagents ratio, temperature and reaction time) were modified as needed.

$^1$H NMR (500 MHz, chloroform-d) δ (ppm) 11.5 (br s, 1H), 8.79 (s, 1H), 8.78 (d, 1H), 7.59 (dd, 1H), 6.95 (br d, 2H), 6.67 (br t, 1H), 4.48 (s, 2H).

Compound I-122

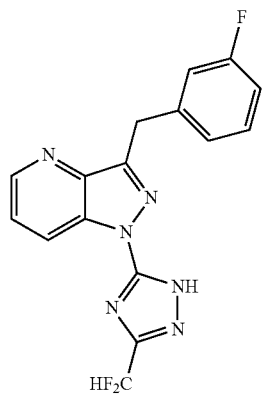

1-(3-(Difluoromethyl)-1H-1,2,4-triazol-5-yl)-3-(3-fluorobenzyl)-1H-pyrazolo[4,3-b]pyridine was synthesized according to General Procedure I, with the exception that 2,2-difluoroacetic anhydride was used, as a white solid (51 mg, 60% yield). The reaction conditions (such as reagents ratio, temperature and reaction time) were modified as needed.

$^1$H NMR (500 MHz, chloroform-d) δ (ppm) 11.4 (br s, 1H), 8.78 (dd, 1H), 8.77 (d, 1H), 7.55 (dd, 1H), 7.25 (ddd, 1H), 7.22 (d, 1H), 7.14 (dt, 1H), 6.91 (dt, 1H), 6.78 (t, 1H), 4.51 (s, 2H).

Compound I-123

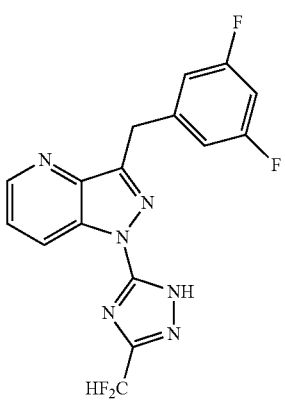

3-(3,5-Difluorobenzyl)-1-(3-(difluoromethyl)-1H-1,2,4-triazol-5-yl)-1H-pyrazolo[4,3-b]pyridine was synthesized according to General Procedure I, with the exception that 2,2-difluoroacetic anhydride was used, as a white solid (65 mg, 77% yield). The reaction conditions (such as reagents ratio, temperature and reaction time) were modified as needed.

$^1$H NMR (500 MHz, chloroform-d) δ (ppm) 11.1 (br s, 1H), 8.81 (dd, 1H), 8.77 (d, 1H), 7.57 (dd, 1H), 6.96 (d, 2H), 6.79 (t, 1H), 6.66 (br t, 1H), 4.49 (s, 2H).

Compound I-127

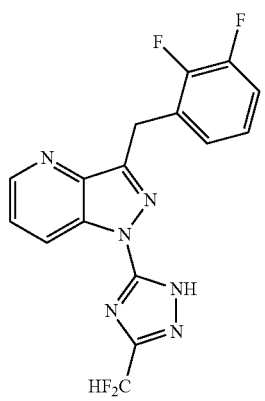

3-(2,3-Difluorobenzyl)-1-(3-(difluoromethyl)-1H-1,2,4-triazol-5-yl)-1H-pyrazolo[4,3-b]pyridine was synthesized according to General Procedure I, with the exception that 2,2-difluoroacetic anhydride was used, as a white solid (160 mg, 93% yield). The reaction conditions (such as reagents ratio, temperature and reaction time) were modified as needed.

$^1$H NMR (500 MHz, chloroform-d) δ (ppm) 11.7 (br s, 1H), 8.79 (d, 1H), 8.78 (d, 1H), 7.56 (dd, 1H), 7.15 (t, 1H), 7.08 (q, 1H), 7.02 (dd, 1H), 6.77 (t, 1H), 4.58 (s, 2H).

Compound I-128

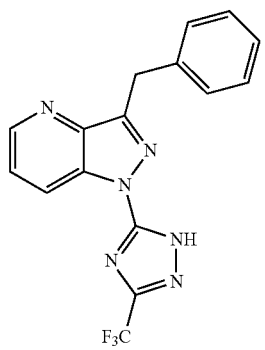

3-Benzyl-1-(3-(trifluoromethyl)-1H-1,2,4-triazol-5-yl)-1H-pyrazolo[4,3-b]pyridine was synthesized according to General Procedure I as a white solid (140 mg, 84% yield). The reaction conditions (such as reagents ratio, temperature and reaction time) were modified as needed.

$^1$H NMR (500 MHz, chloroform-d) δ (ppm) 11.8 (br s, 1H), 8.79 (dd, 1H), 8.75 (dd, 1H), 7.57 (dd, 1H), 7.39 (d, 2H), 7.26 (t, 2H), 7.19 (br t, 1H), 4.51 (s, 2H).

Compound I-129

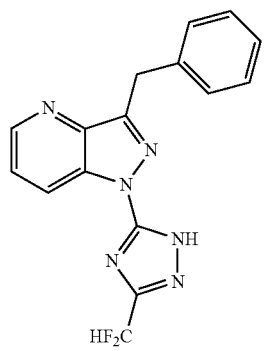

3-Benzyl)-1-(3-(difluoromethyl)-1H-1,2,4-triazol-5-yl)-1H-pyrazolo[4,3-b]pyridine was synthesized according to General Procedure I, with the exception that 2,2-difluoroacetic anhydride was used, as a white solid (110 mg, 92% yield). The reaction conditions (such as reagents ratio, temperature and reaction time) were modified as needed.

$^1$H NMR (500 MHz, chloroform-d) δ (ppm) 10.9 (br s, 1H), 8.77 (d, 2H), 7.52-7.57 (m, 1H), 7.45 (d, 2H), 7.31 (t, 2H), 7.23 (br t, 1H), 6.77 (t, 1H), 4.52 (s, 2H).

Compound I-130

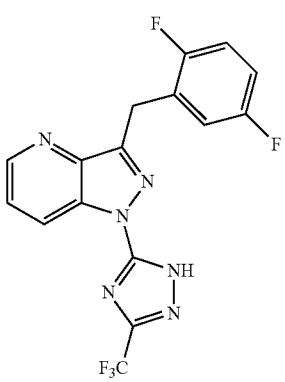

3-(2,5-Difluorobenzyl)-1-(3-(trifluoromethyl)-1H-1,2,4-triazol-5-yl)-1H-pyrazolo[4,3-b]pyridine was synthesized according to General Procedure I as a white solid (110 mg, 95% yield). The reaction conditions (such as reagents ratio, temperature and reaction time) were modified as needed.

$^1$H NMR (500 MHz, chloroform-d) δ (ppm) 11.7 (br s, 1H), 8.80 (d, 1H), 8.78 (d, 1H), 7.59 (dd, 1H), 7.05-7.10 (m, 1H), 6.92-7.03 (m, 1H), 6.86-6.92 (m, 1H), 4.52 (s, 2H).

Compound I-131

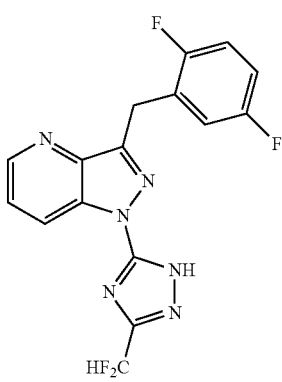

Compound I-131

3-(2,5-Difluorobenzyl)-1-(3-(difluoromethyl)-1H-1,2,4-triazol-5-yl)-1H-pyrazolo[4,3-b]pyridine was synthesized according to General Procedure I, with the exception that 2,2-difluoroacetic anhydride was used, as a white solid (108 mg, 97% yield). The reaction conditions (such as reagents ratio, temperature and reaction time) were modified as needed.

$^1$H NMR (500 MHz, chloroform-d) δ (ppm) 11.4 (br s, 1H), 8.75-8.84 (m, 2H), 7.52-7.60 (m, 1H), 6.85-7.12 (m, 3H), 6.77 (m, 1H), 4.52 (s, 2H).

Compound I-70

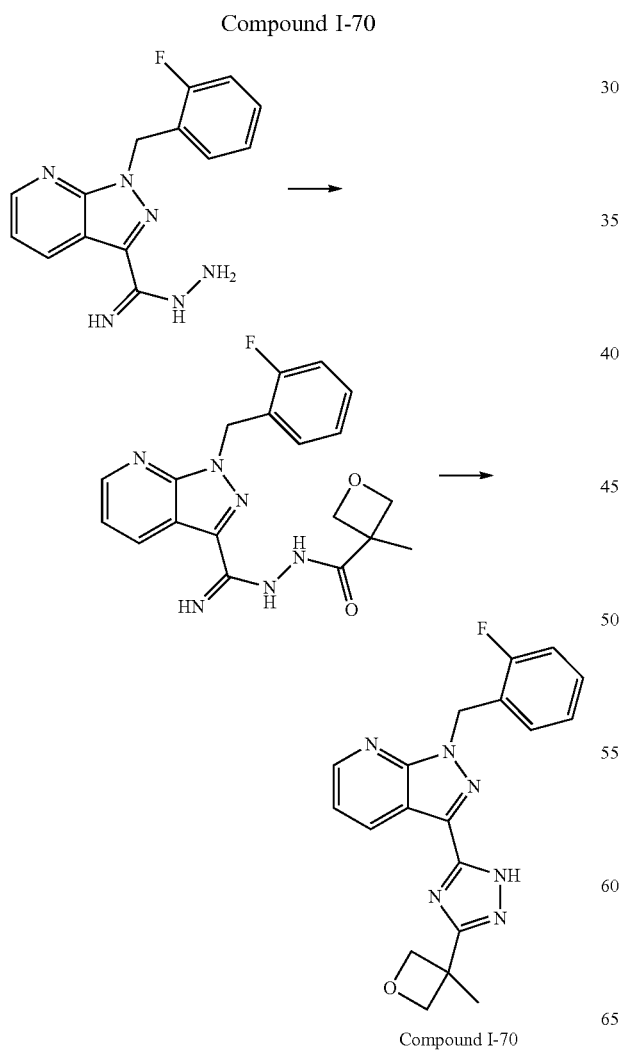

Compound I-70

General Procedure J: 1-(2-fluorobenzyl)-3-(3-(3-methyloxetan-3-yl)-1H-1,2,4-triazol-5-yl)-1H-pyrazolo[3,4-b]pyridine was synthesized in 2 steps.

Step 1: Synthesis of N'-((1-(2-fluorobenzyl)-1H-pyrazolo[3,4-b]pyridin-3-yl)(imino)methyl)-3-methyloxetane-3-carbohydrazide A mixture containing 1-(2-fluorobenzyl)-1H-pyrazolo[3,4-b]pyridine-3-carboximidhydrazide (200 mg, 0.70 mmol), 1-(3-dimethylaminopropyl)-3-ethylcarbodiimide hydrochloride (EDC) (340 mg, 1.8 mmol), HOBt (270 mg, 1.8 mmol) and 3-methyloxetane-3-carboxylic acid (200 mg, 1.8 mmol) in DMF (3.5 mL) was stirred at ambient temperature for 24 hours. The mixture was diluted in EtOAc (100 mL) and washed with water (50 mL). The organic layer was dried over Na$_2$SO$_4$, filtered and evaporated to give an oil. Purification by silica gel chromatography (0 to 100% EtOAc/hexanes gradient) gave N'-((1-(2-fluorobenzyl)-1H-pyrazolo[3,4-b]pyridin-3-yl)(imino)methyl)-3-methyloxetane-3-carbohydrazide (110 mg, 40% yield) as a clear oil.

Step 2: Synthesis of 1-(2-fluorobenzyl)-3-(3-(3-methyloxetan-3-yl)-1H-1,2,4-triazol-5-yl)-1H-pyrazolo[3,4-b]pyridine A mixture containing N'-((1-(2-fluorobenzyl)-1H-pyrazolo[3,4-b]pyridin-3-yl)(imino)methyl)-3-methyloxetane-3-carbohydrazide (110 mg, 0.28 mmol) and sodium hydroxide (1.0 N aqueous solution, 1.4 mL, 1.4 mmol) in 1,4-dioxane (1.4 mL) was heated at 100° C. for 2 days. The mixture was diluted in EtOAc (100 mL) and washed with saturated ammonium chloride solution (50 mL). The organic layer was dried over Na$_2$SO$_4$, filtered and evaporated to give an oil. Purification by silica gel chromatography (0 to 100% EtOAc/hexanes gradient) gave the title compound (27 mg, 26% yield) as a white solid.

$^1$H NMR (500 MHz, methanol-d$_4$) δ (ppm) 8.67-8.80 (m, 1H), 8.62 (s, 1H), 7.33-7.41 (m, 1H), 7.24-7.33 (m, 1H), 7.15 (s, 1H), 7.03-7.13 (m, 2H), 5.86 (s, 2H), 5.05-5.23 (m, 2H), 4.65 (d, 2H), 1.85 (s, 3H).

Compound I-76

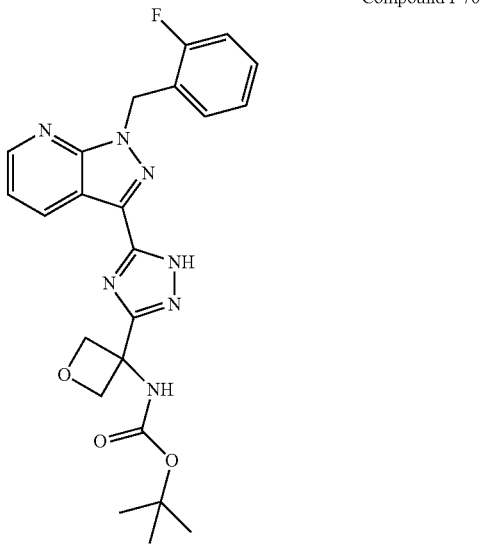

Compound I-76 tert-Butyl (3-(5-(1-(2-fluorobenzyl)-1H-pyrazolo[3,4-b]pyridin-3-yl)-1H-1,2,4-triazol-3-yl)oxetan-3-yl)carbamate was synthesized according to General Procedure J, with the exception that 3-((tert-butoxycarbonyl)amino)oxetane-3-carboxylic acid was used in coupling step, as a white solid (5.5 mg, 13% yield). The reaction conditions (such as reagents ratio, temperature and reaction time) were modified as needed.

LCMS m/z=466.1 [M+H].

Compound I-91

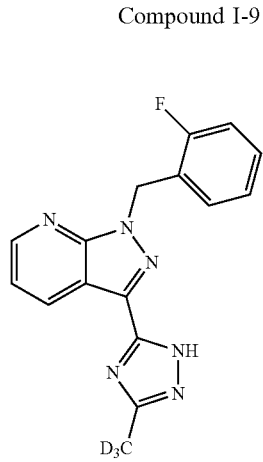

Compound I-91

1-(2-Fluorobenzyl)-3-(3-(methyl-d$_3$)-1H-1,2,4-triazol-5-yl)-1H-pyrazolo[3,4-b]pyridine was synthesized according to General Procedure J, with the exception that acetic acid-d$_4$ was used in coupling step, as a light yellow solid (15 mg, 31% yield). The reaction conditions (such as reagents ratio, temperature and reaction time) were modified as needed.

$^1$H NMR (500 MHz, methanol-d$_4$) δ (ppm) 8.64-8.71 (m, 2H), 7.42 (m, 1H), 7.27-7.36 (m, 1H), 7.21 (m, 1H), 7.02-7.17 (m, 2H), 5.89 (s, 2H).

Compound I-95

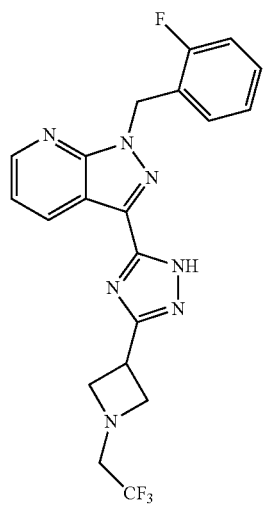

Compound I-95

1-(2-Fluorobenzyl)-3-(3-(1-(2,2,2-trifluoroethyl)azetidin-3-yl)-H-1,2,4-triazol-5-yl)-1H-pyrazolo[3,4-b]pyridine was synthesized according to the coupling method of General Procedure H using sodium 1-(2,2,2-trifluoroethyl)azetidine-3-carboxylate and the triazole cyclization method of General Procedure J as a yellow solid (61 mg, 13% yield). The reaction conditions (such as reagents ratio, temperature and reaction time) were modified as needed.

$^1$H NMR (500 MHz, methanol-d$_4$) δ (ppm) 8.74 (d, 1H), 8.64 (s, 1H), 7.38 (s, 1H), 7.28-7.34 (m, 1H), 7.15 (s, 1H), 7.13 (d, 1H), 7.05-7.10 (m, 1H), 5.88 (s, 2H), 3.99-4.05 (m, 1H), 3.90-3.95 (m, 2H), 3.69-3.78 (m, 2H), 3.64-3.67 (m, 2H).

Compound I-97

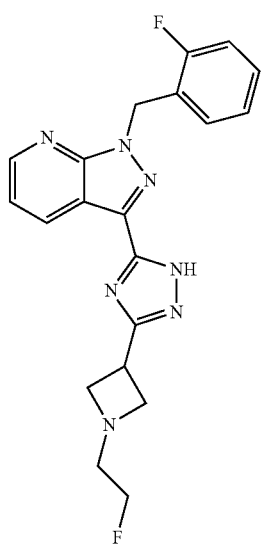

Compound I-97

1-(2-Fluorobenzyl)-3-(3-(1-(2-fluoroethyl)azetidin-3-yl)-1H-1,2,4-triazol-5-yl)-1H-pyrazolo[3,4-b]pyridine was synthesized according to General Procedure J, with the exception that sodium 1-(2-fluoroethyl)azetidine-3-carboxylate was used in the coupling step, as a white solid (32 mg, 4.6% yield, as bis-trifluoroacetate salt). The reaction conditions (such as reagents ratio, temperature and reaction time) were modified as needed.

$^1$H NMR (500 MHz, methanol-d$_4$) δ (ppm) 8.76 (d, 1H), 8.65 (d, 1H), 7.39 (m, 1H), 7.31 (m, 1H), 7.15-7.20 (m, 1H), 7.05-7.15 (m, 2H), 5.87 (s, 2H), 4.71-4.89 (m, 3H), 4.32-4.71 (m, 4H), 3.73-3.86 (m, 2H).

Compound I-104

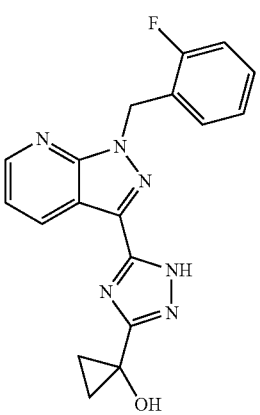

Compound I-104

1-(5-(1-(2-Fluorobenzyl)-1H-pyrazolo[3,4-b]pyridin-3-yl)-1H-1,2,4-triazol-3-yl)cyclopropanol was synthesized according to the coupling method of General Procedure J using 1-hydroxy-1-cyclopropanecarboxylic acid and the triazole cyclization method of General Procedure I, as a white solid (160 mg, 8.2% yield). The reaction conditions (such as reagents ratio, temperature and reaction time) were modified as needed.

$^1$H NMR (500 MHz, methanol-d$_4$) δ (ppm) 8.63 (d, 1H), 8.54 (d, 1H), 7.26 (m, 1H), 7.19-7.24 (m, 1H), 7.04-7.10 (m, 2H), 6.96-7.02 (m, 1H), 5.77-5.83 (m, 2H), 1.35-1.42 (m, 2H), 1.24-1.32 (m, 2H).

Compound I-82

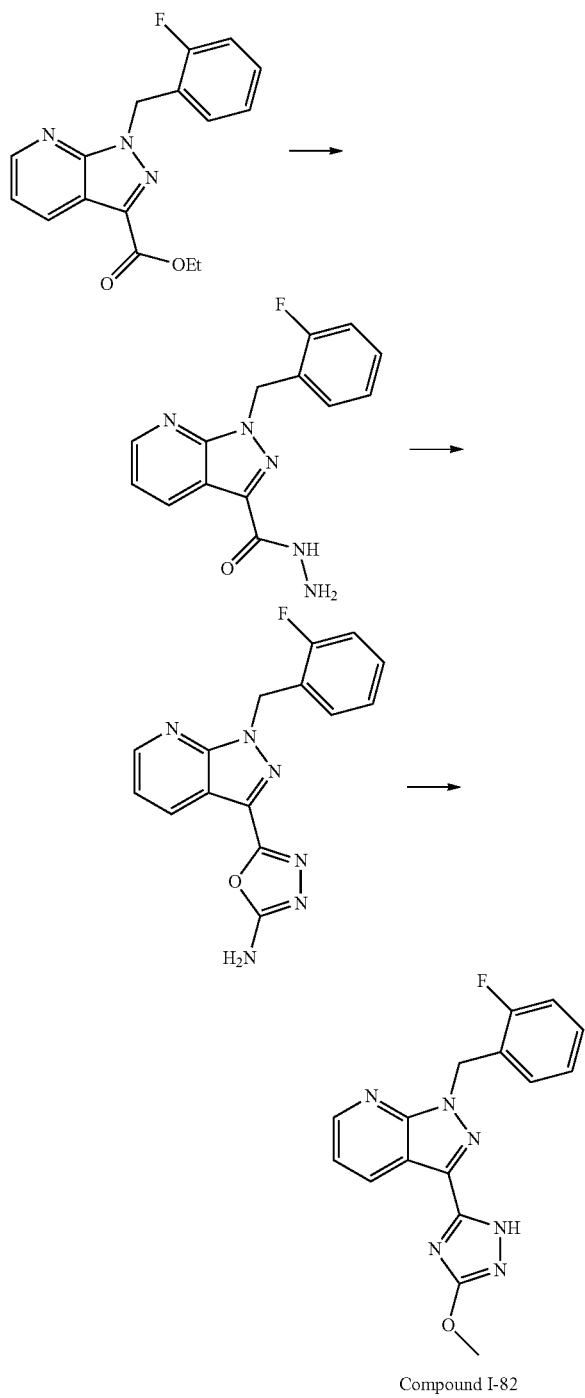

Compound I-82

General Procedure K: 1-(2-fluorobenzyl)-3-(3-methoxy-1H-1,2,4-triazol-5-yl)-1H-pyrazolo[3,4-b]pyridine was synthesized in 3 steps.

Step 1: Synthesis of 1-(2-fluorobenzyl)-1H-pyrazolo[3,4-b]pyridine-3-carbohydrazide To a solution of ethyl 1-(2-fluorobenzyl)-1H-pyrazolo[3,4-b]pyridine-3-carboxylate (85 mg, 0.28 mmol) in ethanol (2.0 mL) was added hydrazine hydrate (140 μL, 2.8 mmol). After heating at 80° C. for 5 hours, complete disappearance of starting material was observed. The reaction was concentrated and dried in vacuo overnight to obtain 1-(2-fluorobenzyl)-1H-pyrazolo[3,4-b]pyridine-3-carbohydrazide (75 mg, 83% yield) as a white solid which was directly carried forward without purification.

Step 2: Synthesis of 5-(1-(2-fluorobenzyl)-1H-pyrazolo[3,4-b]pyridin-3-yl)-1,3,4-oxadiazol-2-amine A solution of sodium hydrogen carbonate (88 mg, 1.1 mmol) in water (6.0 mL) was added to a solution of 1-(2-fluorobenzyl)-1H-pyrazolo[3,4-b]pyridine-3-carbohydrazide (150 mg, 0.53 mmol) in dioxane (4.0 mL). The mixture was stirred at ambient temperature for 5 minutes and then treated with a solution of cyanogen bromide (84 mg, 0.79 mmol) in dioxane (4.0 mL). The reaction mixture was stirred at ambient temperature overnight until complete consumption of starting material was observed. The reaction was diluted with water (75 mL) and the resulting precipitate was filtered to obtain 5-(1-(2-fluorobenzyl)-1H-pyrazolo[3,4-b]pyridin-3-yl)-1,3,4-oxadiazol-2-amine (150 mg, 93% yield) as a cream colored solid after drying in vacuo overnight.

$^1$H NMR (500 MHz, DMSO-d$_6$) δ (ppm) 8.73 (dd, 1H), 8.54 (dd, 1H), 7.42-7.48 (m, 3H), 7.34-7.41 (m, 1H), 7.28 (app. t, 1H), 7.23 (app. t, 1H), 7.16 (app. t, 1H), 5.82 (s, 2H)

Step 3: Synthesis of 1-(2-fluorobenzyl)-3-(3-methoxy-1H-1,2,4-triazol-5-yl)-1H-pyrazolo[3,4-b]pyridine A mixture containing 5-(1-(2-fluorobenzyl)-1H-pyrazolo[3,4-b]pyridin-3-yl)-1,3,4-oxadiazol-2-amine (25 mg, 0.08 mmol) and potassium hydroxide (36 mg, 0.65 mmol) in methanol (1.0 mL) was heated at 90° C. for 15 hours. The mixture was neutralized with 1N aqueous HCl solution to pH ~8, diluted with water (10 mL) and extracted with EtOAc (75 mL). The organic layer was dried, filtered and evaporated. The residue was diluted with dichloromethane (25 mL), washed with 50% aqueous saturated bicarbonate solution (20 mL), dried, filtered and evaporated to give a white solid. The solid was purified by reverse phase preparative HPLC (5-95% acetonitrile in water gradient with 0.1% formic acid as additive) to obtain 1-(2-fluorobenzyl)-3-(3-methoxy-1H-1,2,4-triazol-5-yl)-1H-pyrazolo[3,4-b]pyridine (24 mg, 88% yield) as a white solid after lyophilization.

$^1$H NMR (500 MHz, DMSO-d$_6$) δ (ppm) 13.8 (br s, 1H), 8.68 (d, 1H), 8.63 (d, 1H), 7.33-7.43 (m, 2H), 7.24 (app. t, 1H), 7.12-7.18 (m, 2H), 5.83 (s, 2H), 4.01 (s, 3H).

Compound I-83

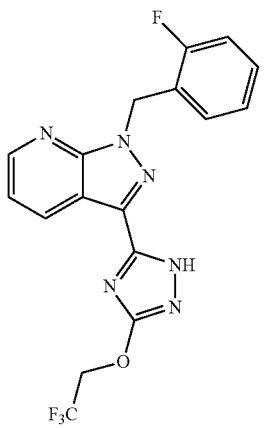

Compound I-83

1-(2-Fluorobenzyl)-3-(3-(2,2,2-trifluoroethoxy)-1H-1,2,4-triazol-5-yl)-1H-pyrazolo[3,4-b]pyridine was synthesized according to General Procedure K, with the exception that 2,2,2-trifluoroethanol was used as the solvent in step 3, as a white solid (20 mg, 60% yield). The reaction conditions (such as reagents ratio, temperature and reaction time) were modified as needed.

$^1$H NMR (500 MHz, DMSO-d$_6$) δ (ppm) 14.3 (br s, 1H), 8.66-8.72 (m, 2H), 7.44 (dd, 1H), 7.33-7.40 (m, 1H), 7.21-7.27 (m, 1H), 7.15 (app. t, 2H), 5.85 (s, 2H), 5.06 (q, 2H).

Compound I-47

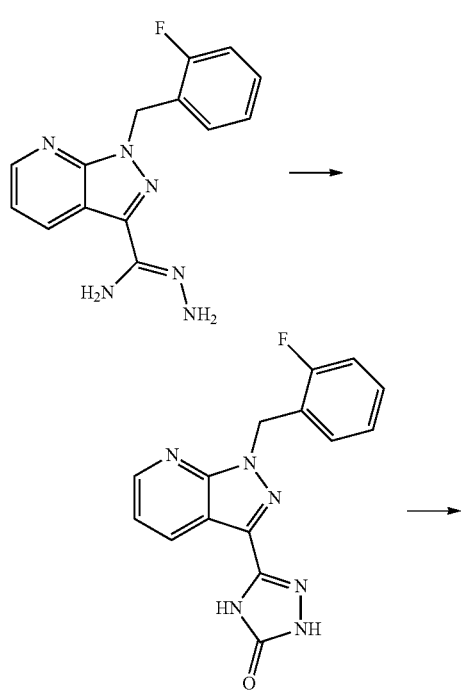

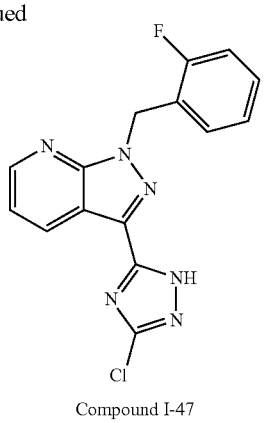

Compound I-47

General Procedure L: 3-(3-Chloro-1H-1,2,4-triazol-5-yl)-1-(2-fluorobenzyl)-1H-pyrazolo[3,4-b]pyridine was synthesized in 2 steps.

Step 1: Synthesis of 3-(1-(2-fluorobenzyl)-1H-pyrazolo[3,4-b]pyridin-3-yl)-1H-1,2,4-triazol-5(4H)-one A mixture containing 1-(2-fluorobenzyl)-1H-pyrazolo[3,4-b]pyridine-3-carboximidhydrazide (280 mg, 0.98 mmol) and 1,1'-carbonyldiimidazole (CDI) (800 mg, 4.9 mmol) in THF (10 mL) was stirred at ambient temperature for 18 hours. After observing complete disappearance of starting material, the reaction was concentrated in vacuo and the residue was purified by reverse phase preparative HPLC (5-95% acetonitrile in water gradient with 0.1% formic acid additive) to obtain 3-(1-(2-fluorobenzyl)-1H-pyrazolo[3,4-b]pyridin-3-yl)-1H-1,2,4-triazol-5(4H)-one (220 mg, 75% yield) as a white solid after lyophilization.

$^1$H NMR (500 MHz, DMSO-d$_6$) δ (ppm) 12.2 (s, 1H), 11.86 (s, 1H), 8.69 (d, 1H), 8.51 (d, 1H), 7.41 (dd, 1H), 7.33-7.39 (m, 1H), 7.23 (t, 1H), 7.11-7.16 (m, 2H), 5.81 (s, 2H).

Step 2: Synthesis of 3-(3-chloro-1H-1,2,4-triazol-5-yl)-1-(2-fluorobenzyl)-1H-pyrazolo[3,4-b]pyridine A mixture of 3-(1-(2-fluorobenzyl)-1H-pyrazolo[3,4-b]pyridin-3-yl)-1H-1,2,4-triazol-5(4H)-one (20 mg, 0.06 mmol) and phosphoryl trichloride (450 µL, 4.8 mmol) was heated at 120° C. for 40 hours. The reaction was carefully poured over ice and extracted with dichloromethane/isopropanol (10:1 ratio, 60 mL). The organic layer was dried over Na$_2$SO$_4$, filtered and concentrated in vacuo. Purification by reverse phase preparative HPLC (5-95% acetonitrile in water gradient with 0.1% formic acid additive) afforded the title compound (17 mg, 78% yield) as a white solid after lyophilization.

$^1$H NMR (500 MHz, DMSO-d$_6$) δ (ppm) 15.2 (br s, 1H), 8.72 (d, 1H), 8.63 (d, 1H), 7.46 (dd, 1H), 7.34-7.39 (m, 1H), 7.22-7.27 (m, 1H), 7.17-7.21 (m, 1H), 7.12-7.16 (m, 1H), 5.86 (s, 2H).

Compound I-86

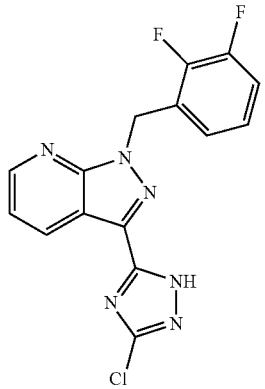

Compound I-86

3-(3-Chloro-1H-1,2,4-triazol-5-yl)-1-(2,3-difluorobenzyl)-1H-pyrazolo[3,4-b]pyridine was synthesized according to General Procedure L as a white solid (33 mg, 69% yield). The reaction conditions (such as reagents ratio, temperature and reaction time) were modified as needed.

$^1$H NMR (500 MHz, DMSO-d$_6$) δ (ppm) 15.2 (br s, 1H), 8.74 (dd, 1H), 8.63 (dd, 1H), 7.47 (dd, 1H), 7.36-7.44 (m, 1H), 7.14-7.19 (m, 1H), 7.03 (app. t, 1H), 5.91 (s, 2H).

Compound I-94

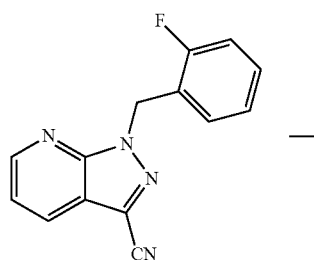

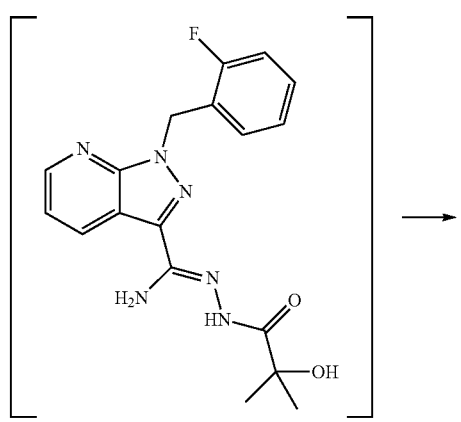

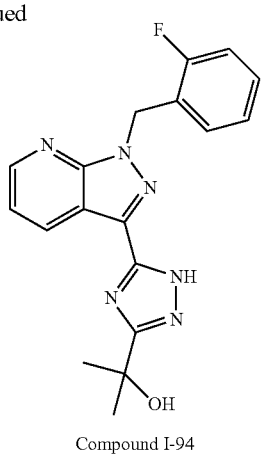

Compound I-94

General Procedure M: 2-(5-(1-(2-fluorobenzyl)-1H-pyrazolo[3,4-b]pyridin-3-yl)-1H-1,2,4-triazol-3-yl)propan-2-ol 1-(2-Fluorobenzyl)-1H-pyrazolo[3,4-b]pyridine-3-carbonitrile (0.12 g, 0.48 mmol) in ethanol (3.0 mL) was treated with sodium methoxide (0.04 g, 0.71 mmol) at 0° C. The resulting solution was allowed to warm to ambient temperature and stirred for 2 hours after which the reaction mixture was concentrated in vacuo. The resulting solid was dissolved in methanol in a sealed tube and 2-hydroxy-2-methylpropanehydrazide (0.24 g, 1.9 mmol) was added. The reaction was heated at 100° C. for 18 hours. The mixture was concentrated in vacuo. Purification by silica gel chromatography (0-80% EtOAc/hexanes gradient) afforded the title compound (41 mg, 24% yield) as a white solid.

$^1$H NMR (500 MHz, DMSO-d$_6$) δ (ppm) 14.0 (s, 1H), 8.63-8.68 (m, 2H), 7.33-7.41 (m, 2H), 7.21-7.26 (m, 1H), 7.12-7.18 (m, 2H), 5.81 (s, 2H), 5.73 (s, 1H), 1.56 (s, 6H).

Compound I-106

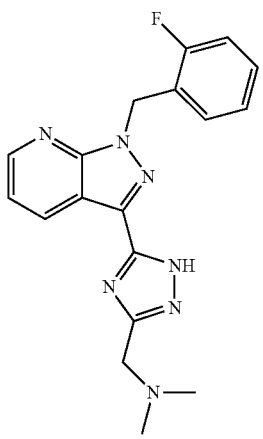

Compound I-106

1-(5-(1-(2-Fluorobenzyl)-1H-pyrazolo[3,4-b]pyridin-3-yl)-1H-1,2,4-triazol-3-yl)-N,N-dimethylmethanamine was synthesized according to General Procedure M, with the exception that 2-(dimethylamino)acetohydrazide was used, as a white solid (7.0 mg, 10% yield). The reaction conditions (such as reagents ratio, temperature and reaction time) were modified as needed.

$^1$H NMR (500 MHz, methanol-$d_4$) δ (ppm) 8.67 (dd, 1H), 8.57-8.60 (m, 1H), 7.32 (dd, 1H), 7.20-7.26 (m, 1H), 7.12 (t, 1H), 6.97-7.05 (m, 2H), 5.80 (s, 2H), 4.46 (s, 2H), 2.93 (s 6H).

Compound I-107

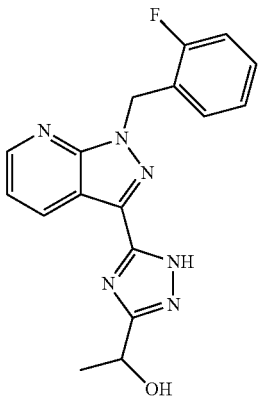

Compound I-107

1-(5-(1-(2-Fluorobenzyl)-1H-pyrazolo[3,4-b]pyridin-3-yl)-1H-1,2,4-triazol-3-yl)ethanol was synthesized according to General Procedure M, with the exception that 2-hydroxypropanehydrazide was used, as a white solid (38 mg, 54% yield). The reaction conditions (such as reagents ratio, temperature and reaction time) were modified as needed.

$^1$H NMR (500 MHz, DMSO-$d_6$) δ (ppm) 14.2 (br s, 1H), 8.64-8.68 (m, 2H), 7.33-7.42 (m, 2H), 7.21-7.27 (m, 1H), 7.12-7.20 (m, 2H), 5.75-5.86 (m, 3H), 4.93 (m, 1H), 1.50 (d, 3H).

Compound I-112

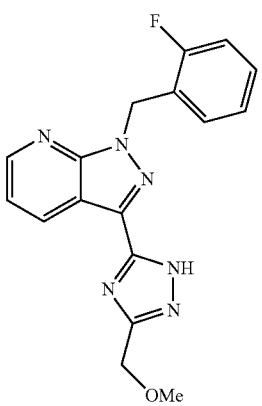

Compound I-112

1-(2-Fluorobenzyl)-3-(3-(methoxymethyl)-1H-1,2,4-triazol-5-yl)-1H-pyrazolo[3,4-b]pyridine was synthesized according to General Procedure M, with the exception that 2-methoxyacetohydrazide was used, as a white solid (35 mg, 50% yield). The reaction conditions (such as reagents ratio, temperature and reaction time) were modified as needed.

$^1$H NMR (500 MHz, chloroform-d) δ (ppm) 10.7 (br s, 1H), 8.59 (d, 1H), 8.55 (d, 1H), 7.17 (dt, 1H), 7.05-7.11 (m, 1H), 6.97-7.03 (m, 1H), 6.82-6.92 (m, 2H), 5.73 (s, 2H), 4.67 (s, 2H), 3.38 (s, 3H).

Compound I-9

Compound I-9

To a suspension of ammonium chloride (160 mg, 3.0 mmol) in toluene (1.5 mL) at 0° C. was added trimethylaluminum (2.0 M solution in toluene, 1.5 mL, 3.0 mmol) dropwise over 5 min. Gas evolution was observed. The reaction mixture was warmed to ambient temperature for 40 minutes and ethyl 1-(3,3,4,4,4-pentafluorobutyl)imidazo[1,5-a]pyridine-3-carboxylate (WO2011/149921A1) (200 mg, 0.60 mmol) was then added. The content was heated at 110° C. for 17 hours. After cooling to 0° C., toluene (10 mL) and Celite was added followed by dropwise addition of methanol (5.0 mL). Gas evolution was observed. The resultant mixture was filtered and the filter cake was washed with methanol. The filtrate was concentrated in vacuo to afford a brown solid. Half of the crude solid was taken up in ethanol/methanol (3:2 ratio, 5 mL) and treated with hydrazine hydrate (0.15 mL, 3.0 mmol). After 14 hours at ambient temperature, additional amount of hydrazine hydrate (0.60 mL, 12 mmol) was added and the reaction was stirred for another 3.5 hours. The reaction mixture was concentrated and dried in vacuo overnight. The residue was suspended in dichloromethane (5.0 mL) and treated with 2,2,2-trifluoroacetic anhydride (0.04 mL, 0.26 mmol) portion-wise. The reaction was stirred at ambient temperature until complete consumption of the amidrazone intermediate. Toluene (5.0 mL) was added followed by phosphoryl trichloride (0.04 mL, 0.46 mmol). The resultant mixture was heated at 75° C. for 3 hours in a sealed vial. After cooling to ambient temperature, water (10 mL) and dichloromethane (15 mL) were added and the mixture was neutralized to pH ~7 with aqueous saturated NaHCO$_3$ solution. The aqueous layer was back-extracted with dichloromethane (15 mL). The combined organic layers were dried over Na$_2$SO$_4$, filtered and concentrated in vacuo. Purification using reverse phase preparative HPLC (35-85% acetonitrile/water gradient with 0.1% formic acid as additive) afforded the title compound (40 mg, 33% yield) as a tan solid.

$^1$H NMR (500 MHz, DMSO-d$_6$) δ (ppm) 15.6 (br s, 1H), 9.21 (m, 1H), 7.95 (m, 1H), 7.09 (m, 2H), 3.25 (m, 2H), 2.73 (m, 2H).

Compound I-17

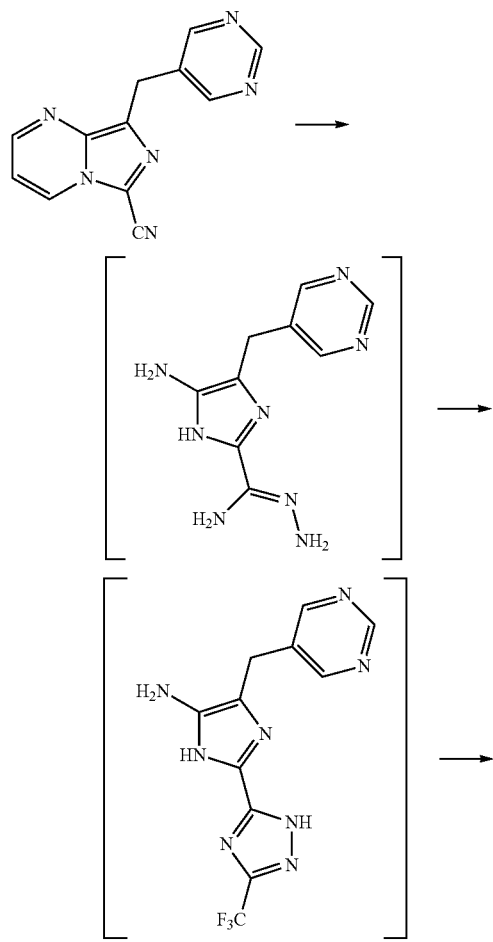

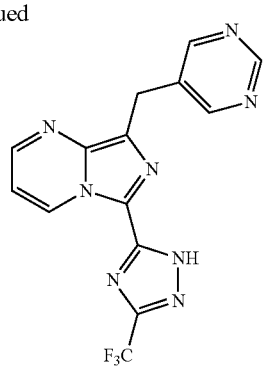

Compound I-17

To a yellow suspension of 8-(pyrimidin-5-ylmethyl)imidazo[1,5-a]pyrimidine-6-carbonitrile (69 mg, 0.29 mmol) in anhydrous methanol (2.0 mL) was added anhydrous hydrazine (0.06 mL, 1.8 mmol). After stirring at ambient temperature for 20 hours, complete disappearance of starting material was observed. The reaction was concentrated in vacuo and the residue was dried in vacuo overnight. The residue (5-amino-4-(pyrimidin-5-ylmethyl)-1H-imidazole-2-carboximidhydrazide) was taken up in dichloromethane/THF (3:2, 2.5 mL) and 2,2,2-trifluoroacetic anhydride (0.05 mL, 0.35 mmol) was added dropwise. Additional amount of 2,2,2-trifluoroacetic anhydride (0.03 mL, 0.23 mmol) was added to drive to complete consumption of the amidrazone intermediate. The reaction was concentrated in vacuo and the residue was dissolved in dichloromethane/toluene (1:1 ratio, 3.0 mL) followed by dropwise addition of phosphoryl trichloride (0.08 mL, 0.88 mmol). The reaction mixture was heated at 75° C. for 15 hours in a sealed vial. After cooling to ambient temperature, aqueous 1N NaOH solution (15 mL) and dichloromethane (20 mL) were added. After stirring for 2 days, the resultant mixture was neutralized to pH ~6-7 with 6N HCl solution and extracted with dichloromethane/isopropanol (5:1 ratio, 6×30 mL). The combined organic layers were dried over Na$_2$SO$_4$, filtered and concentrated to afford a yellow solid. The residue (4-(pyrimidin-5-ylmethyl)-2-(3-(trifluoromethyl)-1H-1,2,4-triazol-5-yl)-1H-imidazol-5-amine) was taken up in absolute ethanol (3.5 mL) and treated with 1,1,3,3-tetramethoxypropane (0.15 mL, 0.93 mmol). After heating at 160° C. for 6 hours in a microwave, additional amount of 1,1,3,3-tetramethoxypropane (0.15 mL, 0.93 mmol) was added and the mixture was heated at 160° C. in a microwave for an additional 6 hours. Finally, a third portion of 1,1,3,3-tetramethoxypropane (0.08 mL, 0.47 mmol) was added and the mixture was heated at 160° C. in a microwave for an additional 6 hours. The reaction mixture was concentrated in vacuo and the residue was purified using reverse phase preparative HPLC (30-80% acetonitrile/water gradient with 0.1% formic acid as additive) to isolate the title compound (20 mg, 31% yield) as a yellow solid.

$^1$H NMR (500 MHz, DMSO-d$_6$) δ (ppm) 15.8 (br s, 1H), 9.41 (dd, 1H), 9.05 (s, 1H), 8.80 (s, 2H), 8.45 (dd, 1H), 7.16 (dd, 1H), 4.42 (s, 2H).

Compound I-25

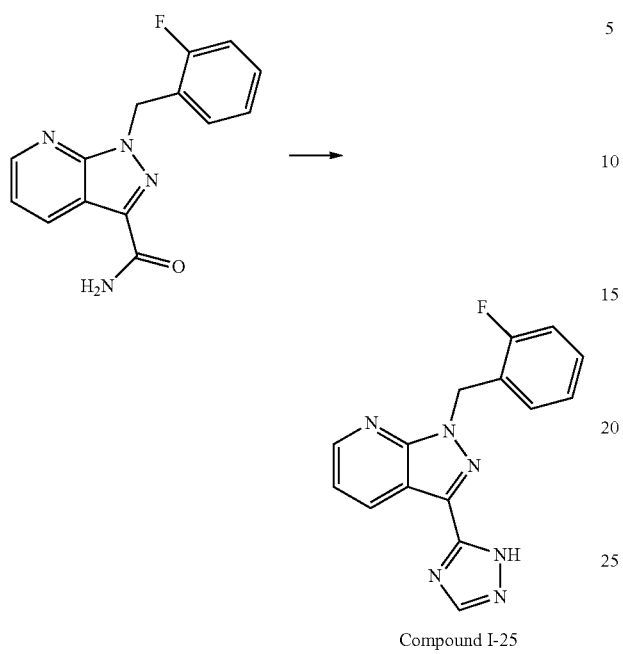

Compound I-25

To a suspension of 1-(2-fluorobenzyl)-1H-pyrazolo[3,4-b]pyridine-3-carboxamide (WO2004/9589A1) (180 mg, 0.67 mmol) in toluene (3.0 mL) was added N,N-dimethylformamide dimethyl acetal (0.27 ml, 2.0 mmol). The reaction mixture was allowed to stir at 50° C. for 2 hours. After cooling to ambient temperature, the mixture was concentrated and the residue was dissolved in AcOH (4.7 mL) and treated with hydrazine hydrate (0.11 mL, 3.3 mmol). After stirring at ambient temperature for 1 hour, the reaction mixture was concentrated twice with toluene to remove most of the AcOH. The residue was dissolved in EtOAc and washed with aqueous 1N NaOH solution. The organic phase was dried over $Na_2SO_4$, filtered and concentrated. The crude material was purified by reverse phase preparative HPLC (5-95% acetonitrile/water gradient with 0.1% TFA as additive) to give the title compound (61 mg, 30% yield) as a white solid.

$^1$H NMR (500 MHz, methanol-$d_4$) δ (ppm) 8.76 (dd, 1H), 8.65-8.68 (m, 1H), 8.49 (br s, 1H), 7.40 (dd, 1H), 7.29-7.36 (m, 1H), 7.07-7.20 (m, 3H), 5.90 (s, 2H).

Compound I-32

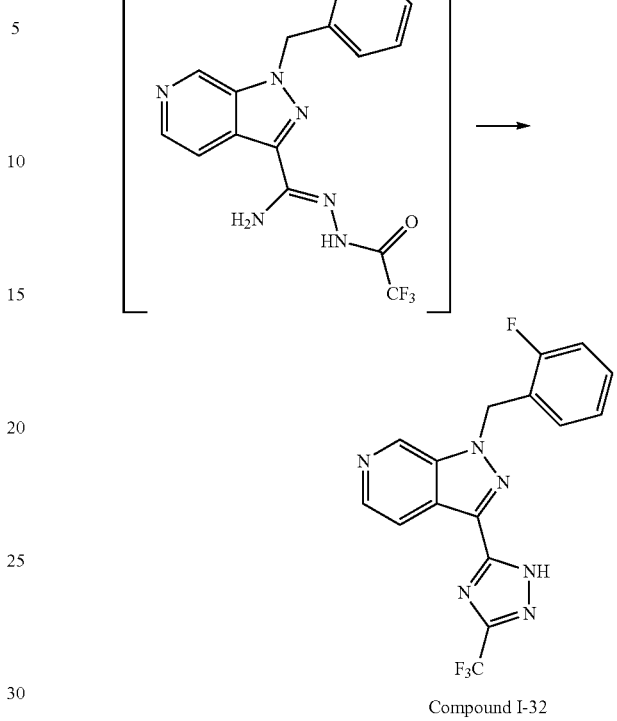

Compound I-32

To a solution of 1-(2-fluorobenzyl)-1H-pyrazolo[3,4-c]pyridine-3-carbonitrile (30 mg, 0.12 mmol) in methanol (0.60 mL) was added sodium methoxide (0.50 M solution in methanol, 0.71 mL, 0.16 mmol). The reaction was heated at 70° C. for 6 hours during which additional amount of sodium methoxide (0.50 M solution in methanol, 0.49 mL, 0.25 mmol) was added portion-wise. 2,2,2-Trifluoroacetohydrazide (76 mg, 0.60 mmol) was added and the reaction was stirred at ambient temperature overnight and then at 70° C. for an hour. The reaction was concentrated in vacuo. Purification using reverse phase preparative HPLC (5-95% acetonitrile/water gradient with 0.1% TFA as additive) gave the title compound (17 mg, 39% yield) as a yellow solid.

$^1$H NMR (500 MHz, chloroform-d) δ (ppm) 9.81 (s, 1H), 8.88 (d, 1H), 8.61 (d, 1H), 7.49 (t, 1H), 7.39 (m, 1H), 7.20 (t, 1H), 7.10 (t, 1H), 5.97 (s, 2H).

Compound I-40

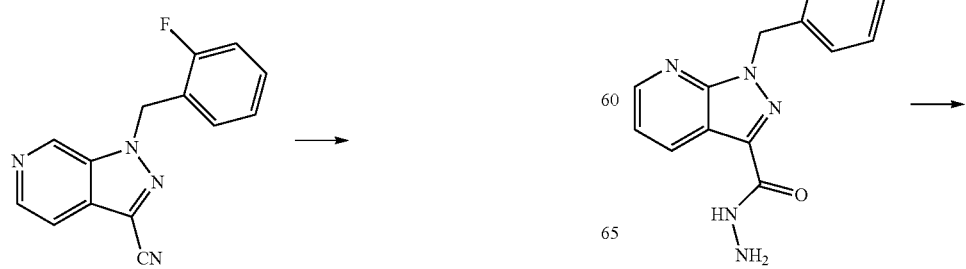

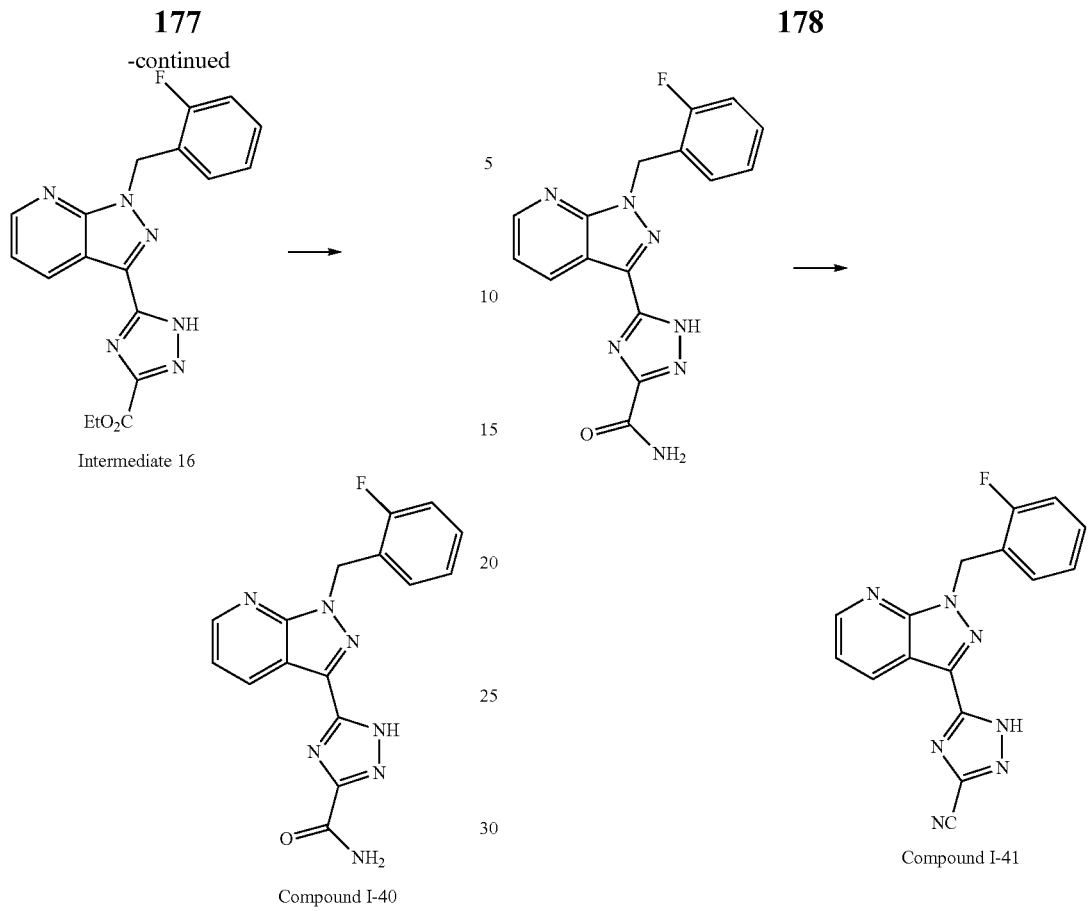

Intermediate 16

Compound I-40

Compound I-41

This compound was synthesized in two steps:

Step 1: Synthesis of Intermediate 16

A suspension of ethyl 2-amino-2-thioxoacetate (160 mg, 1.2 mmol), 1-(2-fluorobenzyl)-1H-pyrazolo[3,4-b]pyridine-3-carbohydrazide (WO2007/124854A1) (300 mg, 1.1 mmol) and ammonium chloride (340 mg, 6.3 mmol) in ethanol (6.0 ml) heated at 160° C. in microwave for 2 hours. The reaction solution was cooled to ambient temperature and concentrated in vacuo. Brine was added. The mixture was adjusted to pH ~6 and extracted with EtOAc. The combined organic phases were dried over $Na_2SO_4$, filtered and concentrated in vacuo. The crude product was purified by silica gel chromatography to afford the title compound as a white solid (75 mg, 18% yield).
$^1$H NMR (500 MHz, chloroform-d) δ (ppm) 8.85 (dd, 1H), 8.70 (dd, 1H), 7.35 (dd, 1H), 7.25-7.31 (m, 1H), 7.18 (t, 1H), 7.01-7.11 (m, 2H), 5.89 (s, 2H), 4.55 (q, 2H), 1.50 (t, 3H).

Step 2: Synthesis of 5-(1-(2-fluorobenzyl)-1H-pyrazolo[3,4-b]pyridin-3-yl)-1H-1,2,4-triazole-3-carboxamide To a solution of ethyl 5-(1-(2-fluorobenzyl)-1H-pyrazolo[3,4-b]pyridin-3-yl)-1H-1,2,4-triazole-3-carboxylate (70 mg, 0.19 mmol) in methanol (2.0 ml) was added ammonia (7.0 M in methanol, 2.7 mL, 19 mmol). The mixture was stirred at 60° C. for 4 days. The reaction mixture was concentrated in vacuo to afford the title compound as a white solid (60 mg, 88% yield).
$^1$H NMR (500 MHz, DMSO-$d_6$) δ (ppm) 15.2 (br s, 1H), 8.83 (d, 1H), 8.70 (d, 1H), 8.32 (s, 1H), 7.90 (s, 1H), 7.43 (dd, 1H), 7.34-7.40 (m, 1H), 7.18-7.27 (m, 2H), 7.13-7.18 (m, 1H), 5.84 (s, 2H).

Compound I-41

A solution of 5-(1-(2-fluorobenzyl)-1H-pyrazolo[3,4-b]pyridin-3-yl)-1H-1,2,4-triazole-3-carboxamide (20 mg, 0.06 mmol) in phosphoryl trichloride (1.1 mL, 11 mmol) was heated at 80° C. overnight. Solvent was removed and the residue was purified by reverse phase preparative HPLC to give the title compound as a white solid (11 mg, 55% yield).
$^1$H NMR (500 MHz, DMSO-$d_6$) δ (ppm) 16.1 (br s, 1H), 8.75 (dd, 1H), 8.68 (dd, 1H), 7.49 (dd, 1H), 7.34-7.41 (m, 1H), 7.18-7.28 (m, 2H), 7.13-7.18 (m, 1H), 5.90 (s, 2H).

Compound I-92

Compound I-92

5-(1-(2,3-Difluorobenzyl)-1H-pyrazolo[3,4-b]pyridin-3-yl)-1H-1,2,4-triazole-3-carbonitrile was prepared as an off-white solid (49 mg, 22% yield, 3 steps from 1-(2,3-difluorobenzyl)-1H-pyrazolo[3,4-b]pyridine-3-carbohydrazide) using a similar procedure for the synthesis of Compound I-41. The reaction conditions (such as reagents ratio, temperature and reaction time) were modified as needed.

$^1$H NMR (500 MHz, DMSO-$d_6$) δ (ppm) 16.1 (br s, 1H), 8.76 (dd, 1H), 8.68 (dd, 1H), 7.51 (dd, 1H), 7.41 (m, 1H), 7.17 (m, 1H), 7.05 (app. t, 1H), 5.94 (s, 2H).

Compound I-42

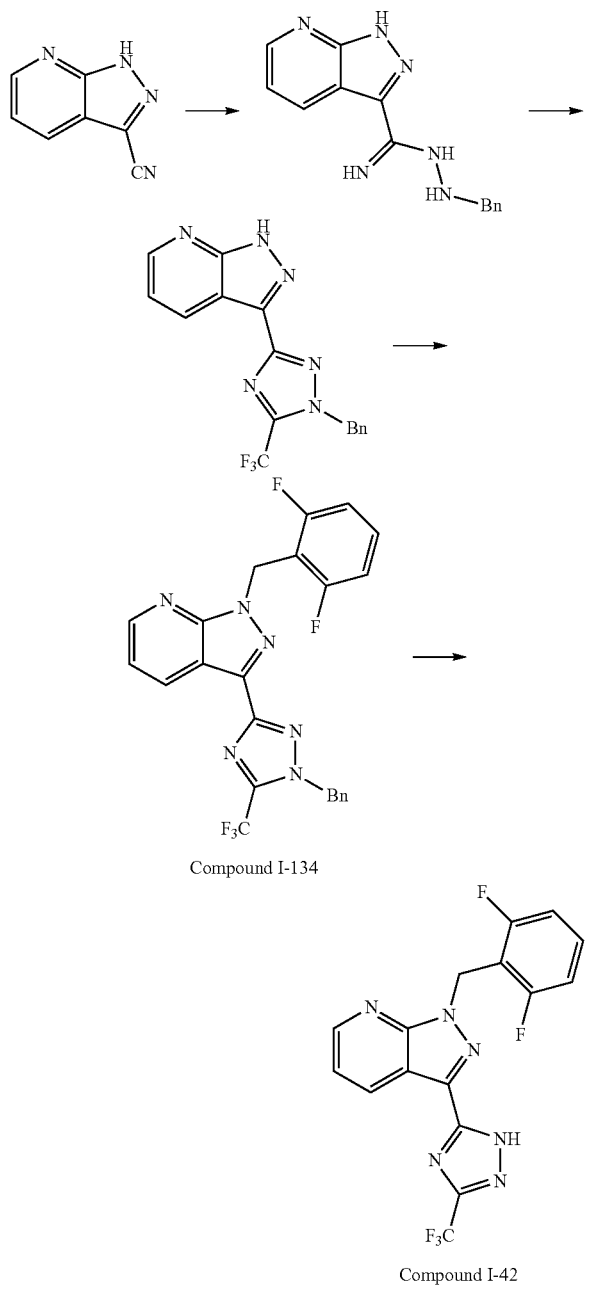

Compound I-134

Compound I-42

The title compound was synthesized in 4 steps:

Step 1: Synthesis of N'-benzyl-1H-pyrazolo[3,4-b]pyridine-3-carboximidhydrazide

To 1H-pyrazolo[3,4-b]pyridine-3-carbonitrile (10 g, 69 mmol) in ethanol (400 mL) in a 1-L pressure bottle was added benzylhydrazine hydrochloride (33 mL, 210 mmol). The vessel was sealed and the reaction was heated at 100° C. for 11 days. After cooling to ambient temperature, the reaction mixture was concentrated in vacuo. The residue was partitioned between EtOAc (400 mL) and 10% aqueous NaHCO$_3$ solution (100 mL). The organic layer was washed with 10% aqueous NaHCO$_3$ solution (20 mL), water (50 mL) and brine, dried over Na$_2$SO$_4$, filtered and concentrated in vacuo. Purification by silica gel chromatography (30 to 100% EtOAc/dichloromethane gradient) afforded N'-benzyl-1H-pyrazolo[3,4-b]pyridine-3-carboximidhydrazide as a light yellow solid (4.4 g, 24% yield). (Note: The structure was tentatively assigned as this regioisomer. The regioselectivity would not affect structure of the title compound at the end of this synthetic sequence).

Step 2: Synthesis of 3-(1-benzyl-5-(trifluoromethyl)-1H-1,2,4-triazol-3-yl)-1H-pyrazolo[3,4-b]pyridine To a solution of N'-benzyl-1H-pyrazolo[3,4-b]pyridine-3-carboximidhydrazide in dichloromethane (20 mL) was added 2,2,2-trifluoroacetic anhydride (0.64 mL, 4.5 mmol) was added dropwise. After 2 hours, the reaction was diluted with EtOAc (100 mL) and washed with 10% aqueous NaHCO$_3$ solution (2×10 mL), water (10 mL) and brine, dried over Na$_2$SO$_4$, filtered and concentrated in vacuo. Purification by silica gel chromatography (15 to 40% EtOAc/dichloromethane gradient) afforded 3-(1-benzyl-5-(trifluoromethyl)-1H-1,2,4-triazol-3-yl)-1H-pyrazolo[3,4-b]pyridine as a white solid (0.63 g, 81% yield).

Step 3: Synthesis of 3-(1-benzyl-5-(trifluoromethyl)-1H-1,2,4-triazol-3-yl)-1-(2,6-difluorobenzyl)-1H-pyrazolo[3,4-b]pyridine (Compound I-134)

2-(Bromomethyl)-1,3-difluorobenzene (120 mg, 0.58 mmol), 3-(1-benzyl-5-(trifluoromethyl)-1H-1,2,4-triazol-3-yl)-1H-pyrazolo[3,4-b]pyridine (100 mg, 0.29 mmol) and freshly ground Li$_2$CO$_3$ (64 mg, 0.87 mmol) were mixed in DMF (3.0 mL) and stirred at ambient temperature for 3 days. The mixture was diluted with EtOAc (70 mL) and washed with water (3×10 mL) and brine. The organic phase was dried over Na$_2$SO$_4$, filtered and concentrated in vacuo. The product was purified by silica gel chromatography (5 to 60% EtOAc/hexanes gradient) to afford 3-(1-benzyl-5-(trifluoromethyl)-1H-1,2,4-triazol-3-yl)-1-(2,6-difluorobenzyl)-1H-pyrazolo[3,4-b]pyridine as a white solid (97 mg, 71% yield).

Step 4: Synthesis of 1-(2,6-difluorobenzyl)-3-(3-(trifluoromethyl)-1H-1,2,4-triazol-5-yl)-1H-pyrazolo[3,4-b]pyridine To a solution of 3-(1-benzyl-5-(trifluoromethyl)-1H-1,2,4-triazol-3-yl)-1-(2,6-difluorobenzyl)-1H-pyrazolo[3,4-b]pyridine (40 mg, 0.09 mmol) in EtOAc (5.0 mL) in a 10-mL round-bottom flask was added palladium hydroxide on carbon (20% w/w, 40 mg). The vessel was purged with hydrogen gas, sealed and kept under positive hydrogen pressure with a balloon filled with hydrogen gas. After stirring rapidly at ambient temperature for 6 hours, the reaction mixture was filtered through Celite and the filter cake was washed with EtOAc. The filtrate was concentrated in vacuo. Purification by silica gel chromatography (5 to 50% EtOAc/hexanes gradient) gave the title compound as a white solid (22 mg, 68% yield).

$^1$H NMR (500 MHz, chloroform-d) δ (ppm) 11.9 (br s, 1H), 8.76-8.72 (m, 2H), 7.36 (dd, 1H), 7.30 (m, 1H), 6.90 (m, 2H), 5.87 (s, 2H).

Compound I-45

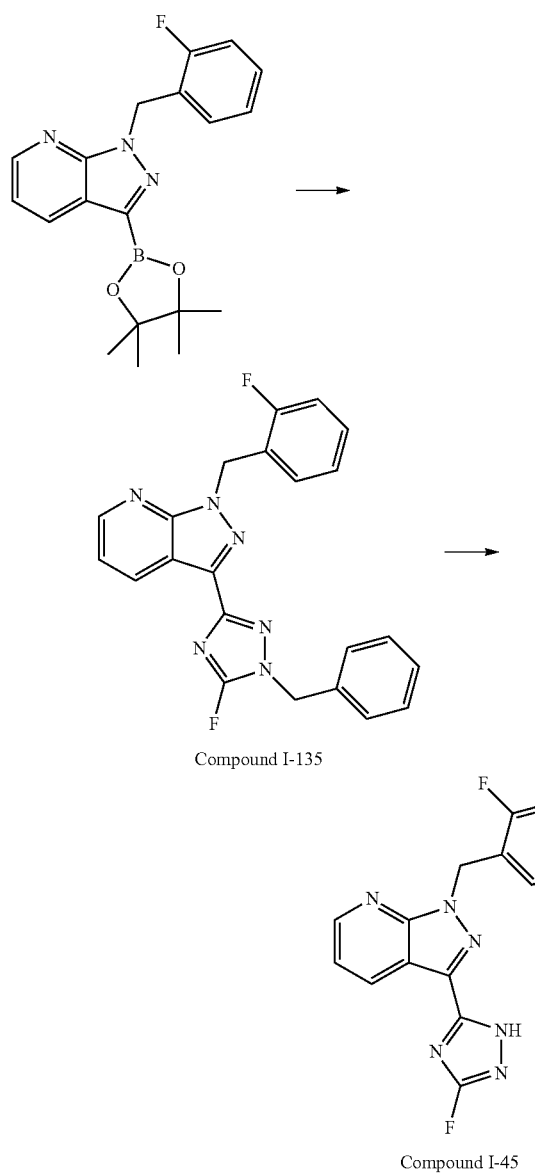

Compound I-135

Compound I-45

The title compound was synthesized in 2 steps:

Step 1: Synthesis of 3-(1-benzyl-5-fluoro-1H-1,2,4-triazol-3-yl)-1-(2-fluorobenzyl)-1H-pyrazolo[3,4-b]pyridine (Compound I-135)

Into a vial was added 1-(2-fluorobenzyl)-3-(4,4,5,5-tetramethyl-1,3,2-dioxaborolan-2-yl)-1H-pyrazolo[3,4-b]pyridine (300 mg, 1.1 mmol), 1-benzyl-3-bromo-5-fluoro-1H-1,2,4-triazole (560 mg, 2.2 mmol) and toluene (7.4 mL). The contents were flushed with argon for 5 minutes. The reaction mixture was treated sequentially with X-Phos (210 mg, 0.44 mmol), potassium carbonate (310 mg, 2.2 mmol) and Pd$_2$dba$_3$ (200 mg, 0.22 mmol). The vial was flushed with argon for another 5 minutes, sealed and heated at 110° C. for 4.5 hours. Additional amount of Pd$_2$dba$_3$ (100 mg, 0.11 mmol) was added and the reaction was stirred at 80° C. for 18 hours. The reaction mixture was concentrated in vacuo. Purification using silica gel chromatography (0-40% acetonitrile/methanol (7:1) in dichloromethane gradient) yield 3-(1-benzyl-5-fluoro-1H-1,2,4-triazol-3-yl)-1-(2-fluorobenzyl)-1H-pyrazolo[3,4-b]pyridine (120 mg) as an impure mixture that was used in the next step without further purification.

Step 2: Synthesis of 3-(3-fluoro-1H-1,2,4-triazol-5-yl)-1-(2-fluorobenzyl)-1H-pyrazolo[3,4-b]pyridine A solution of 3-(1-benzyl-5-fluoro-1H-1,2,4-triazol-3-yl)-1-(2-fluorobenzyl)-1H-pyrazolo[3,4-b]pyridine (120 mg, 0.30 mmol) in methanol (1.5 mL) was treated with Perlman's reagent (42 mg, 0.06 mmol). The reaction vessel was purged with hydrogen and placed under a hydrogen atmosphere with a balloon. After stirring at ambient temperature for 24 hours, additional amount of catalyst (0.2 equiv) was added and the reaction was stirred for another 24 hours under a hydrogen atmosphere. The resultant mixture was filtered through Celite and the filter cake was washed with methanol. The filtrate was concentrated in vacuo. Purification using silica gel chromatography (0-100% EtOAc/hexanes gradient) followed reverse phase preparative HPLC afforded the title compound (8.0 mg, 8.6% yield) as a pale blue solid.

$^1$H NMR (500 MHz, chloroform-d) δ (ppm) 11.3 (br s, 1H), 8.65-8.71 (m, 2H), 7.34 (dd, 1H), 7.22-7.29 (m, 1H), 7.15 (t, 1H), 7.00-7.09 (m, 2H), 5.85 (s, 2H).

Compound I-55

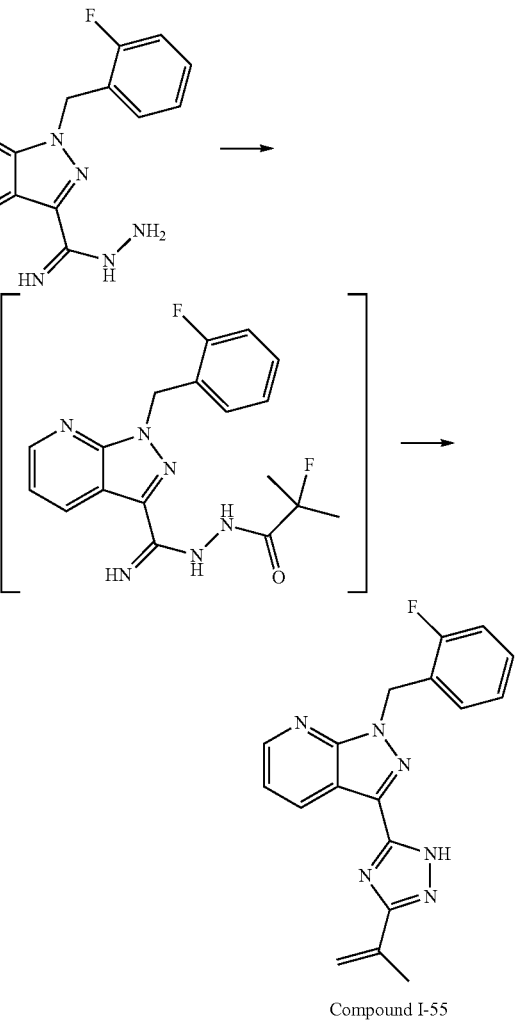

Compound I-55

To a mixture containing oxalyl chloride (38 µL, 0.43 mmol) and 2-fluoro-2-methylpropanoic acid (46 mg, 0.43 mmol) in dichloromethane (1.5 mL) was added DMF (2.0 L, 0.03 mmol). The mixture was stirred at ambient temperature for 2 hours. To this mixture was added a solution of 1-(2-fluorobenzyl)-1H-pyrazolo[3,4-b]pyridine-3-carboximidhydrazide (82 mg, 0.29 mmol) and pyridine (35 µL, 0.43 mmol) in dichloromethane (1.5 mL). The mixture was stirred at ambient temperature for 24 hours. The mixture was diluted in EtOAc (100 mL) and washed with water (50 mL). The organic layer was dried, filtered and evaporated to give an oil. Purification by silica gel chromatography (0 to 50% EtOAc/hexanes gradient) gave crude intermediates (42 mg). Toluene (0.50 mL) and phosphoryl trichloride (52 µL, 0.56 mmol) were added and the reaction was heated at 100° C. for 6 hours. The mixture was cooled to ambient temperature, poured over ice and extracted with EtOAc (100 mL). The organic layer was dried, filtered and evaporated to give an oil. Purification by silica gel chromatography (0 to 100% EtOAc/hexanes gradient) afforded title compound (21 mg, 22% yield) as a clear gum.

$^1$H NMR (500 MHz, methanol-$d_4$) δ (ppm) 8.76 (dd, 1H), 8.70 (dd, 1H), 7.51 (dd, 1H), 7.34 (m, 1H), 7.28 (app. t, 1H), 7.08-7.16 (m, 2H), 6.31 (s, 1H), 5.96 (m, 3H), 2.34 (s, 3H).

Compound I-57

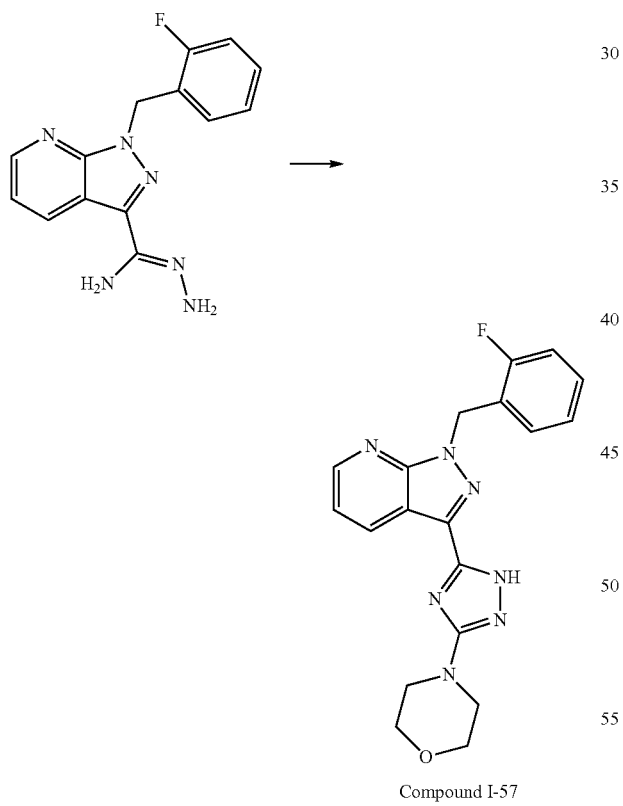

Compound I-57

To a solution of 1-(2-fluorobenzyl)-1H-pyrazolo[3,4-b]pyridine-3-carboximidhydrazide (100 mg, 0.35 mmol) in methanol (3.5 mL) was added triethylamine (120 µL, 0.88 mmol), carbon disulfide (45 µL, 0.74 mmol), iodomethane (57 µL, 0.92 mmol). After heating at reflux for 3 hours, the reaction mixture was concentrated in vacuo. The residue was dissolved in morpholine (1.0 mL) and heated at 150° C. in a microwave for 2 hours. The mixture was concentrated in vacuo and purified by reverse phase preparative HPLC (5-95% acetonitrile in water gradient with 0.1% TFA additive) to afford the Compound I-57 (13 mg, 9.1% yield) as a clear glass.

$^1$H NMR (500 MHz, methanol-$d_4$) δ (ppm) 8.66 (m, 2H), 7.40 (dd, 1H), 7.30 (m, 1H), 7.12 (m, 3H), 5.89 (s, 2H), 3.85 (m, 4H), 3.55 (m, 4H).

Compound I-64

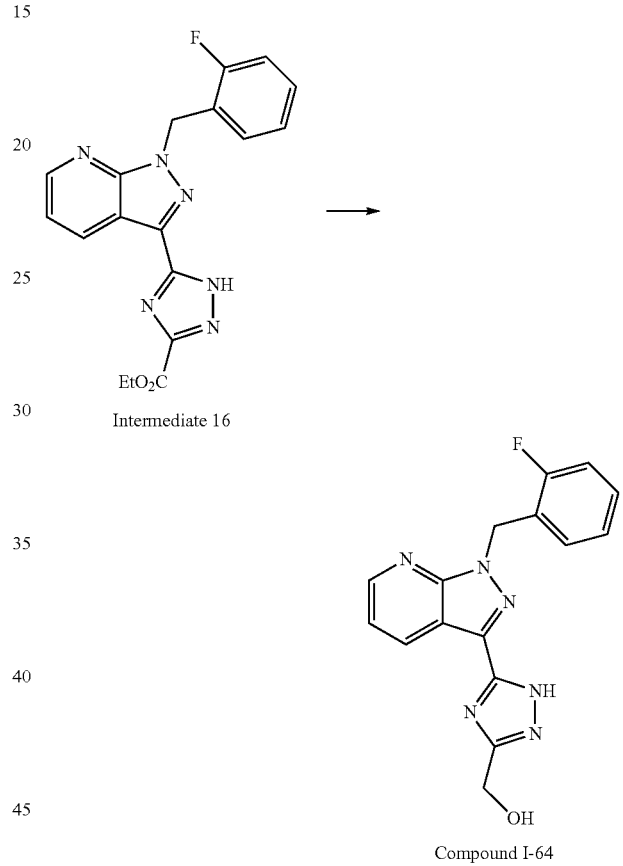

Intermediate 16

Compound I-64

To a solution of ethyl 5-(1-(2-fluorobenzyl)-1H-pyrazolo[3,4-b]pyridin-3-yl)-1H-1,2,4-triazole-3-carboxylate (Intermediate 16, 25 mg, 0.07 mmol) in THF (2.0 ml) was added LiBH$_4$ (2.3 mg, 0.10 mmol). The reaction was stirred at ambient temperature overnight and then heated at 70° C. for 4 hours. The resultant mixture was concentrated in vacuo. Water was added and the pH was adjusted to ~5. The mixture was extracted with EtOAc. The organic layer was washed with brine, dried over MgSO$_4$, filtered and concentrated in vacuo. Purification by reverse phase preparative HPLC afforded the title compound (13 mg, 56% yield) as a white solid.

$^1$H NMR (500 MHz, DMSO-$d_6$) δ (ppm) 14.2 (br s, 1H), 8.57-8.62 (m, 2H), 7.26-7.35 (m, 2H), 7.11-7.20 (m, 2H), 7.05-7.10 (m, 1H), 5.74 (s, 2H), 5.58-5.72 (m, 1H), 4.60 (s, 2H).

Compound I-66

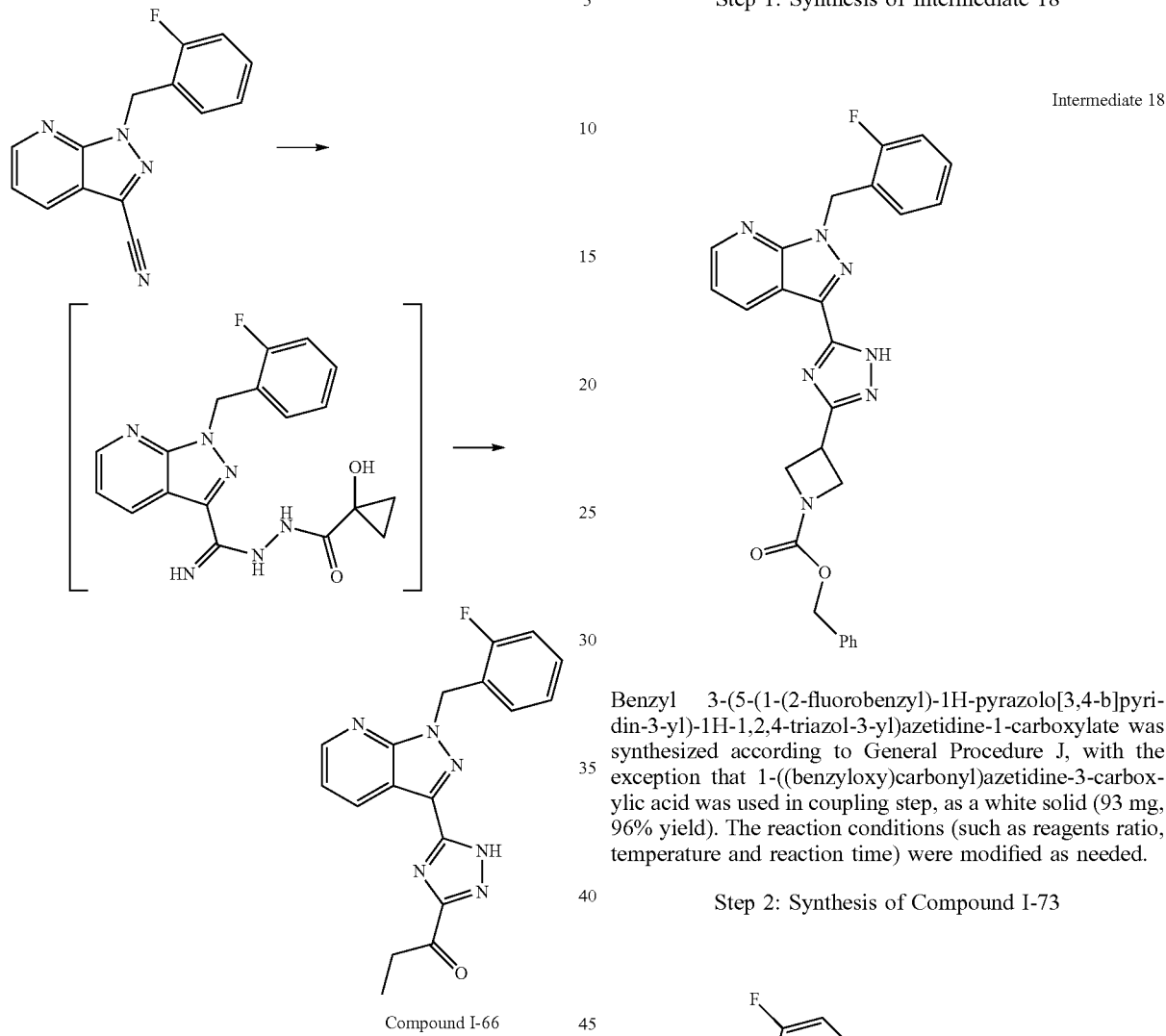

Compound I-66

A mixture containing sodium methoxide (30 wt % in methanol, 880 µL, 4.8 mmol) and 1-(2-fluorobenzyl)-1H-pyrazolo[3,4-b]pyridine-3-carbonitrile (300 mg, 1.2 mmol) in methanol (6.0 mL) was stirred at ambient temperature for 2 hours. Complete conversion to an imidate ester intermediate was observed. 1-Hydroxycyclopropanecarbohydrazide (280 mg, 2.4 mmol) and 1,4-dioxane (2.0 mL) were added and the resultant mixture was heated at 80° C. for 24 hours. After cooling to ambient temperature, the reaction mixture was concentrated in vacuo. Purification by silica gel chromatography (0 to 50% EtOAc/hexanes gradient) gave the title compound (9.5 mg, 2.3% yield) as a white solid.

$^1$H NMR (500 MHz, methanol-$d_4$) δ (ppm) 8.72-8.81 (m, 1H), 8.59-8.66 (m, 1H), 7.36-7.42 (m, 1H), 7.27-7.33 (m, 1H), 7.02-7.16 (m, 3H), 5.89 (s, 2H), 2.99 (m, 2H), 1.39 (m, 3H).

Compound I-73

The title compound was prepared in two steps:

Step 1: Synthesis of Intermediate 18

Intermediate 18

Benzyl 3-(5-(1-(2-fluorobenzyl)-1H-pyrazolo[3,4-b]pyridin-3-yl)-1H-1,2,4-triazol-3-yl)azetidine-1-carboxylate was synthesized according to General Procedure J, with the exception that 1-((benzyloxy)carbonyl)azetidine-3-carboxylic acid was used in coupling step, as a white solid (93 mg, 96% yield). The reaction conditions (such as reagents ratio, temperature and reaction time) were modified as needed.

Step 2: Synthesis of Compound I-73

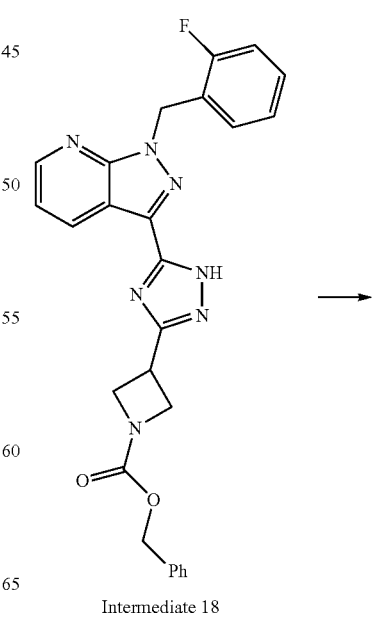

Intermediate 18

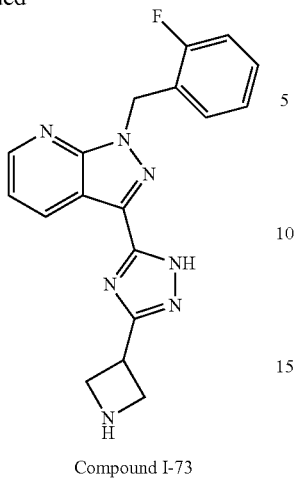

Compound I-73

A solution of benzyl 3-(5-(1-(2-fluorobenzyl)-1H-pyrazolo[3,4-b]pyridin-3-yl)-1H-1,2,4-triazol-3-yl)azetidine-1-carboxylate (Intermediate 18, 93 mg, 0.19 mmol) in methanol (1.0 mL) was treated with palladium on carbon (20 wt %, 20 mg, 0.04 mmol) and stirred under an atmosphere of hydrogen (balloon) for 2 hours. The mixture was filtered through an Acrodisc® syringe filter. The filtrate was concentrated in vacuo to give the title compound (56 mg, 83% yield) as a white solid.

$^1$H NMR (500 MHz, methanol-$d_4$) δ (ppm) 8.73 (m, 1H), 8.60 (m, 1H), 7.33-7.37 (m, 1H), 7.25-7.31 (m, 1H), 7.09-7.16 (m, 2H), 7.02-7.08 (m, 1H), 5.85 (s, 2H), 4.16-4.28 (m, 3H), 4.03-4.13 (m, 2H).

Compound I-74

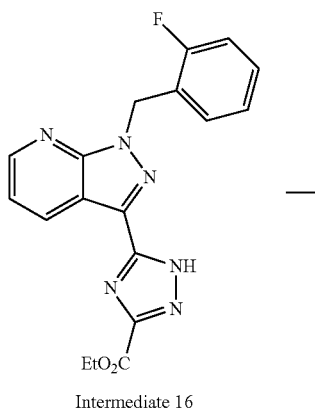

Intermediate 16

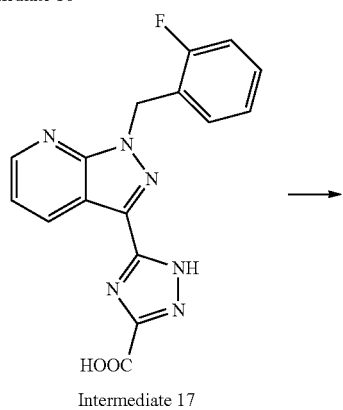

Intermediate 17

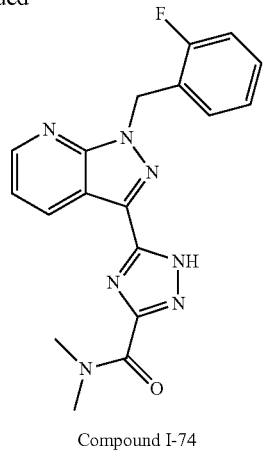

Compound I-74

The title compound was synthesized in 2 steps:

Step 1: Synthesis of 5-(1-(2-fluorobenzyl)-1H-pyrazolo[3,4-b]pyridin-3-yl)-N,N-dimethyl-1H-1,2,4-triazole-3-carboxylic acid (Intermediate 17)

A solution of ethyl 5-(1-(2-fluorobenzyl)-1H-pyrazolo[3,4-b]pyridin-3-yl)-1H-1,2,4-triazole-3-carboxylate (Intermediate 16, 20 mg, 0.06 mmol) in methanol/THF/water (1:3:1 ratio, 5 mL) was treated with lithium hydroxide (4.0 mg, 0.16 mmol) and stirred at ambient temperature overnight. The mixture was concentrated in vacuo and water was added. The pH was adjusted to pH ~5 and the mixture was extracted with EtOAc. The product-containing aqueous layer was concentrated and purified using reverse phase preparative HPLC to afford the acid intermediate (Intermediate 17, 5.0 mg, 27% yield). (Note: A portion of the acid intermediate decarboxylated during manipulation steps of this experiment).

Step 2: Synthesis of 5-(1-(2-fluorobenzyl)-1H-pyrazolo[3,4-b]pyridin-3-yl)-N,N-dimethyl-1H-1,2,4-triazole-3-carboxamide To a stirred solution of 5-(1-(2-fluorobenzyl)-1H-pyrazolo[3,4-b]pyridin-3-yl)-1H-1,2,4-triazole-3-carboxylic acid (Intermediate 17, 15 mg, 0.04 mmol) in DMF (3.0 mL) was added PyAOP (23 mg, 0.04 mmol), dimethylamine (2.0 N solution in THF, 27 mL, 0.05 mmol) and Hunig's base (23 mL, 0.13 mmol). The reaction was stirred at ambient temperature overnight. Water was added and the mixture was extracted with EtOAc. The combined organic layers were washed with water and brine, dried over $Na_2SO_4$, filtered and concentrated in vacuo. Purification by reverse phase preparative HPLC gave the title compound (6.0 mg, 35% yield) as a white solid.

$^1$H NMR (500 MHz, DMSO-$d_6$) δ (ppm) 8.58-8.64 (m, 2H), 7.36 (dd, 1H), 7.26-7.32 (m, 1H), 7.15-7.20 (m, 1H), 7.04-7.14 (m, 2H), 5.78 (s, 2H), 3.33 (s, 3H), 2.99 (s, 3H).

Compound I-75

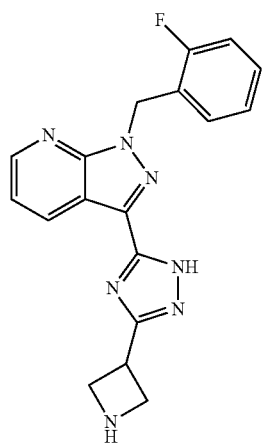

Compound I-73

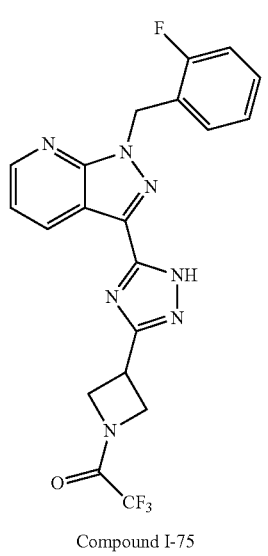

Compound I-75

To 3-(3-(azetidin-3-yl)-1H-1,2,4-triazol-5-yl)-1-(2-fluorobenzyl)-1H-pyrazolo[3,4-b]pyridine (Compound I-73, 37 mg, 0.11 mmol) in dichloromethane (0.50 mL) was added pyridine (22 µL, 0.27 mmol) and 2,2,2-trifluoroacetic anhydride (18 µL, 0.13 mmol). After stirring at ambient temperature for 24 hours, the mixture was diluted with EtOAc (100 mL) and washed with saturated aqueous ammonium chloride solution (50 mL). The organic layer was dried over Na$_2$SO$_4$, filtered and evaporated to give an oil. Purified by silica gel chromatography (0 to 100% EtOAc/hexanes gradient) gave the title compound (26 mg, 55% yield) as a white solid.

$^1$H NMR (500 MHz, methanol-d$_4$) δ (ppm) 8.73 (m, 1H), 8.64 (d, 1H), 7.38 (m, 1H), 7.30 (m, 1H), 7.17 (m, 1H), 7.09-7.14 (m, 1H), 7.04-7.09 (m, 1H), 5.87 (s, 2H), 4.86-4.94 (m, 1H), 4.71-4.82 (m, 1H), 4.59 (m, 1H), 4.44 (m, 1H), 4.25 (m, 1H).

Compound I-79

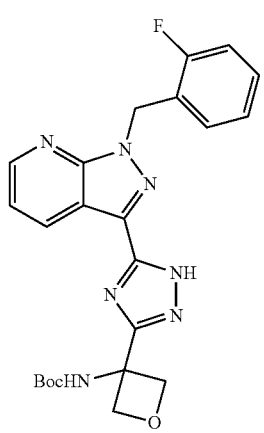

Compound I-76

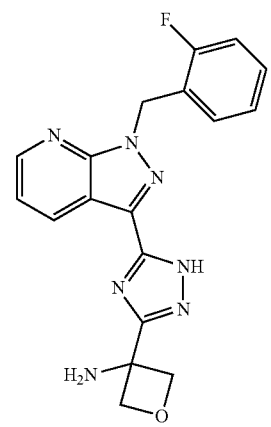

Compound I-79

A mixture containing 2,2,2-trifluoroacetic acid (5.3 µL, 0.07 mmol) and tert-butyl (3-(5-(1-(2-fluorobenzyl)-1H-pyrazolo[3,4-b]pyridin-3-yl)-1H-1,2,4-triazol-3-yl)oxetan-3-yl)carbamate (Compound I-76, 5.5 mg, 0.01 mmol) in dichloromethane (340 µL) was stirred at ambient temperature for 1 hour. The mixture was concentrated in vacuo to give the title compound (3.5 mg, 86% yield, 2,2,2-trifluoroacetate salt) as a light yellow solid.

$^1$H NMR (500 MHz, methanol-d$_4$) δ (ppm) 8.83 (d, 1H), 8.68-8.71 (m, 1H), 7.44 (m, 1H), 7.29-7.37 (m, 1H), 7.23 (m, 1H), 7.07-7.16 (m, 2H), 5.91 (s, 2H), 5.27 (d, 2H), 4.92-4.94 (m, 2H).

Compound I-84

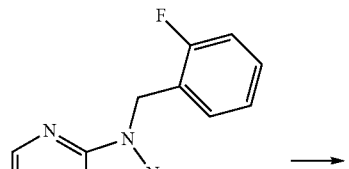

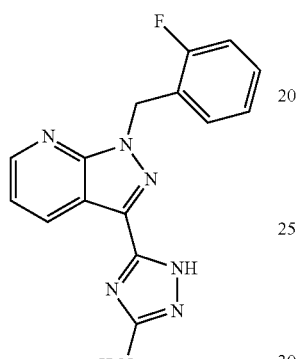

Compound I-84

A suspension of methyl carbamimidothioate sulfate (66 mg, 0.35 mmol) and 1-(2-fluorobenzyl)-1H-pyrazolo[3,4-b]pyridine-3-carboximidhydrazide (100 mg, 0.35 mmol) in water (2.0 mL) and dimethyl sulfoxide (2.0 mL) was heated at 120° C. for 4 hours, after which the reaction was cooled to ambient temperature. Dimethyl sulfoxide and methanol (1:1) were added, and the pink solids were filtered off. The filtrate was purified by reverse phase preparative HPLC (12 to 37% acetonitrile in water gradient with 0.1% TFA as additive) to afford the title compound (9.7 mg, 9.0% yield) as a white solid.

$^1$H NMR (500 MHz, methanol-$d_4$) δ (ppm) 8.69 (dd, 1H), 8.62 (dd, 1H), 7.42 (dd, 1H), 7.30-7.34 (m, 1H), 7.19-7.23 (m, 1H), 7.11-7.14 (m, 1H), 7.08-7.11 (m, 1H), 5.89 (s, 2H).

Compound I-88

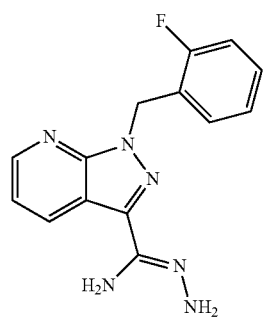

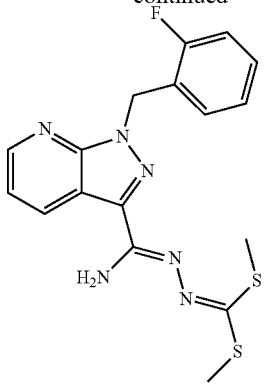

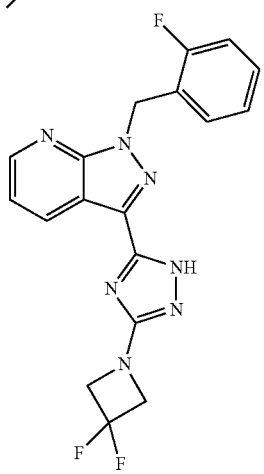

Compound I-88

The title compound was synthesized in 2 steps.

Step 1: Synthesis of dimethyl (amino(1-(2-fluorobenzyl)-1H-pyrazolo[3,4-b]pyridin-3-yl)methylene)carbonohydrazonodithioate To a solution of 1-(2-fluorobenzyl)-1H-pyrazolo[3,4-b]pyridine-3-carboximidhydrazide (0.20 g, 0.70 mmol) in methanol/toluene (1:1 ratio, 7.0 mL) was added carbon disulfide (0.09 mL, 1.5 mmol), iodomethane (0.13 mL, 2.0 mmol) and triethylamine (0.25 ml, 1.8 mmol). The reaction stirred at ambient temperature for 3 days. The resulting yellow precipitate was collected by filtration and dried to give the title intermediate (240 mg, 88% yield) which was carried forward without purification.

Step 2: Synthesis of 3-(3-(3,3-difluoroazetidin-1-yl)-1H-1,2,4-triazol-5-yl)-1-(2-fluorobenzyl)-1H-pyrazolo[3,4-b]pyridine To a solution of dimethyl (amino(1-(2-fluorobenzyl)-1H-pyrazolo[3,4-b]pyridin-3-yl)methylene)carbonohydrazonodithioate (0.03 g, 0.08 mmol) and 3,3-difluoroazetidine, hydrochloride (0.50 g, 3.9 mmol) in NMP (0.50 mL) was added Hunig's base (0.67 mL, 3.9 mmol). The reaction was heated at 200° C. in a microwave for 5 hours. The mixture was concentrated and purified using reverse phase preparative HPLC (5-95% acetonitrile/water gradient with 0.1% formic acid as additive) to isolate the title compound (0.90 mg, 3.0% yield) as an off white solid.

$^1$H NMR (500 MHz, methanol-$d_4$) δ (ppm) 8.70 (m, 2H), 7.40 (dd, 2H), 7.29 (s, 1H), 7.15 (m, 2H), 5.88 (s, 2H), 4.77 (app. t, 2H), 3.75 (app. t, 2H).

Compound I-89

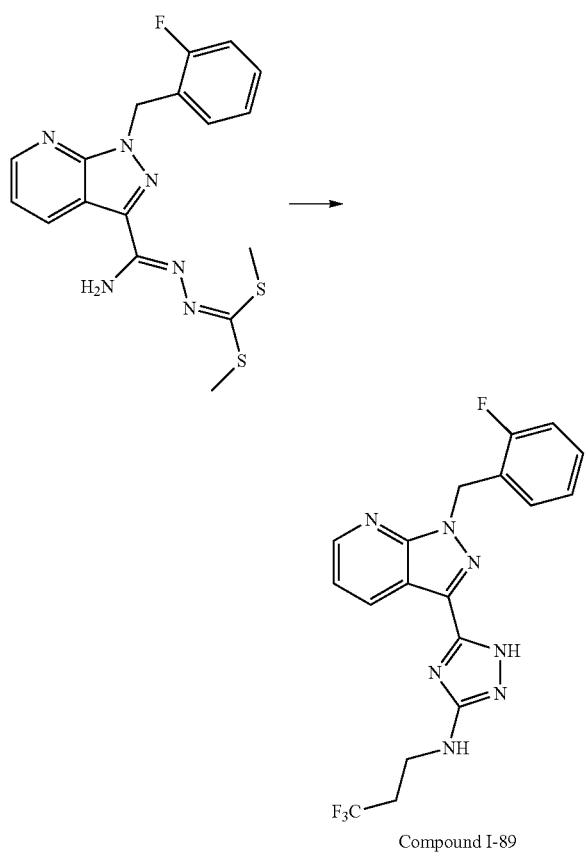

Compound I-89

A solution of dimethyl (amino(1-(2-fluorobenzyl)-1H-pyrazolo[3,4-b]pyridin-3-yl)methylene)carbonohydrazonodithioate (0.04 g, 0.09 mmol) and 3,3,3-trifluoropropan-1-amine (0.31 g, 2.7 mmol) in NMP (0.30 mL) was heated at 200° C. in a microwave for 5 hours. The mixture was concentrated and purified using reverse phase preparative HPLC (5-95% acetonitrile/water gradient with 0.1% TFA as additive) to isolate the title compound (1.0 mg, 2.6% yield) as a clear glassy solid.

$^1$H NMR (500 MHz, methanol-d$_4$) δ (ppm) 8.68 (m, 2H), 7.43 (dd, 1H), 7.34 (d, 1H), 7.14 (m, 3H), 5.91 (s, 2H), 3.70 (t, 2H), 2.62 (m, 2H).

Compound I-90

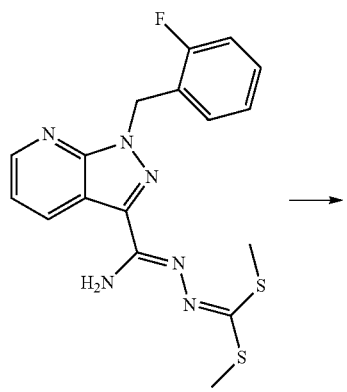

A solution of dimethyl (amino(1-(2-fluorobenzyl)-1H-pyrazolo[3,4-b]pyridin-3-yl)methylene)carbonohydrazonodithioate (0.02 g, 0.06 mmol) and 2,2,2-trifluoroethanamine (1.0 g, 10 mmol) in DMF (0.51 mL) was heated at 200° C. in a microwave for 10 hours. The mixture was concentrated and purified using reverse phase preparative HPLC (5-95% acetonitrile/water gradient with 0.1% TFA as additive) to isolate the title compound (13 mg, 14% yield, side-product) as an orange glassy solid.

$^1$H NMR (500 MHz, methanol-d$_4$) δ (ppm) 8.72 (d, 1H), 8.64 (d, 1H), 7.45 (dd, 1H), 7.34 (m, 1H), 7.22 (app. t, 1H), 7.17-7.08 (m, 2H), 5.93 (s, 2H), 3.26 (s, 6H).

Compound I-99

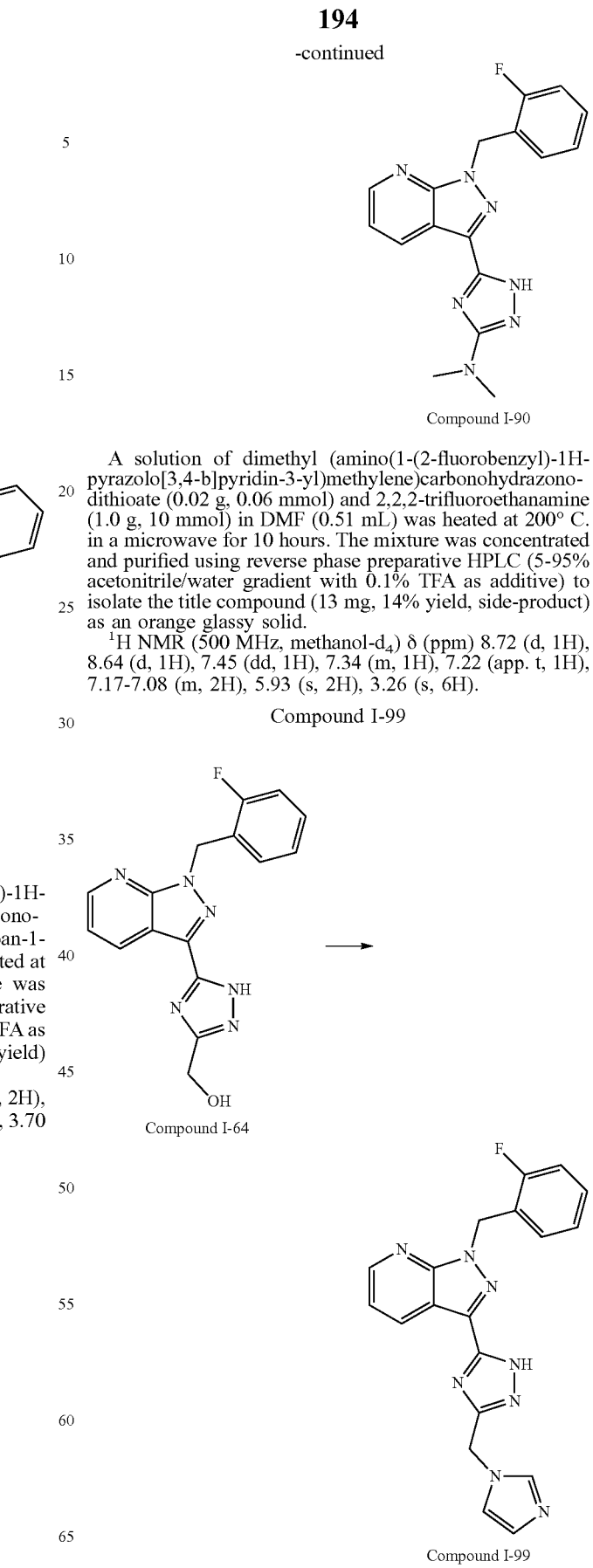

To a stirred solution of (5-(1-(2-fluorobenzyl)-1H-pyrazolo[3,4-b]pyridin-3-yl)-1H-1,2,4-triazol-3-yl)methanol (Compound I-64, 12 mg, 0.04 mmol) in THF (2.0 ml) was added carbonyldiimidazole (CDI) (9.0 mg, 0.06 mmol). After stirring at ambient temperature overnight, $K_2CO_3$ (1.0 mg, 7.4 μmol) was added. After 5 hours, the solvent was evaporated and the residue was purified by reverse phase preparative HPLC to give 3-(3-((1H-imidazol-1-yl)methyl)-1H-1,2,4-triazol-5-yl)-1-(2-fluorobenzyl)-1H-pyrazolo[3,4-b]pyridine (9.0 mg, 62% yield) as a white solid.

$^1$H NMR (500 MHz, methanol-$d_4$) δ (ppm) 9.09 (s, 1H), 8.55-8.61 (m, 2H), 7.69 (s, 1H), 7.52 (s, 1H), 7.30 (dd, 1H), 7.18-7.25 (m, 1H), 7.07-7.12 (m, 1H), 6.95-7.05 (m, 2H), 5.78 (s, 2H), 5.59 (s, 2H).

Compound I-102

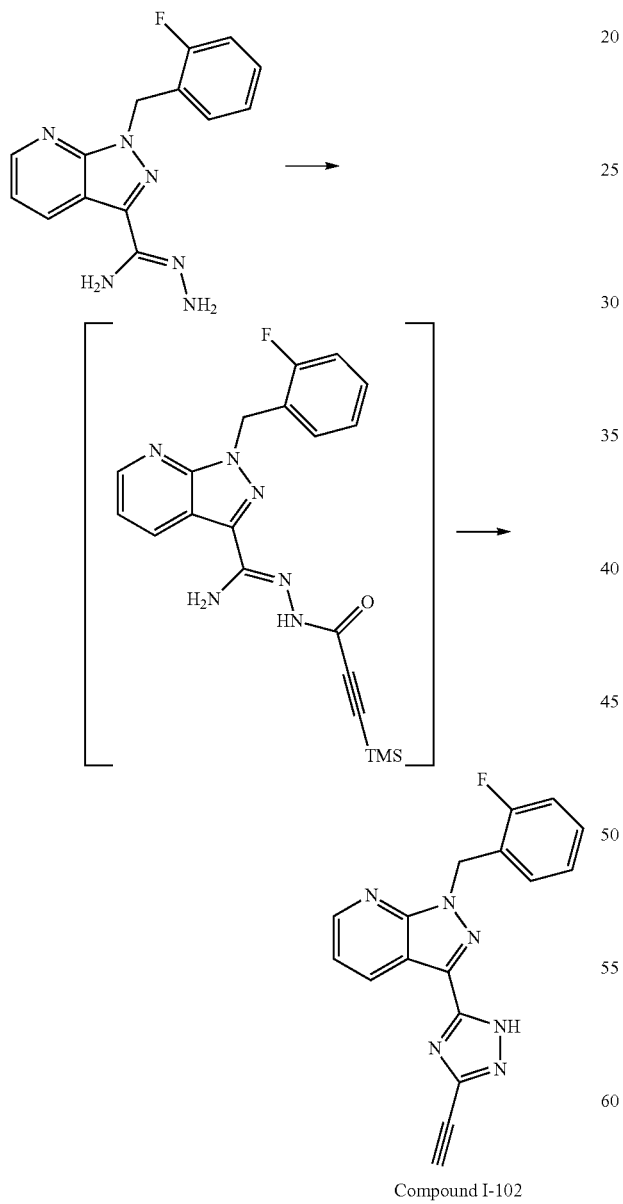

Compound I-102

To a 0° C. solution of 3-(trimethylsilyl)propiolic acid (79 mg, 0.56 mmol) in dichloromethane (3.0 mL) was added (7-azabenzotriazol-1-yloxy)tripyrrolidinophosphonium hexafluorophosphate (PyAOP) (280 mg, 0.53 mmol) followed by Hunig's base (0.28 mL, 1.6 mmol). The resultant yellow color solution was stirred at 0° C. for 5 minutes, after which solid 1-(2-fluorobenzyl)-1H-pyrazolo[3,4-b]pyridine-3-carboximidhydrazide (150 mg, 0.53 mmol) was added. The reaction was stirred for 15 minutes at 0° C. The reaction mixture was diluted with water, extracted with dichloromethane (3×30 mL), dried over $Na_2SO_4$, filtered and concentrated to afford a sticky brown solid. This material was reconstituted in ethanol (8.0 mL), then treated with acetic acid (0.09 mL, 1.6 mmol) and heated at 150° C. for 30 minutes in the microwave. The reaction mixture was concentrated to dryness and purified by silica gel chromatography (0 to 100% EtOAc/hexanes gradient) followed by reverse phase preparative HPLC (10 to 70% acetonitrile/water gradient with 0.1% trifluoroacetic acid as additive) to afford the title compound (2.2 mg, 1.0% yield) as an off-white solid.

$^1$H NMR (500 MHz, methanol-$d_4$) δ (ppm) 8.73 (dd, 1H), 8.66 (dd, 1H), 7.41 (dd, 1H), 7.29-7.33 (m, 1H), 7.17-7.21 (m, 1H), 7.07-7.14 (m, 2H), 5.89 (s, 2H), 3.96 (br. s, 1H).

Compound I-103

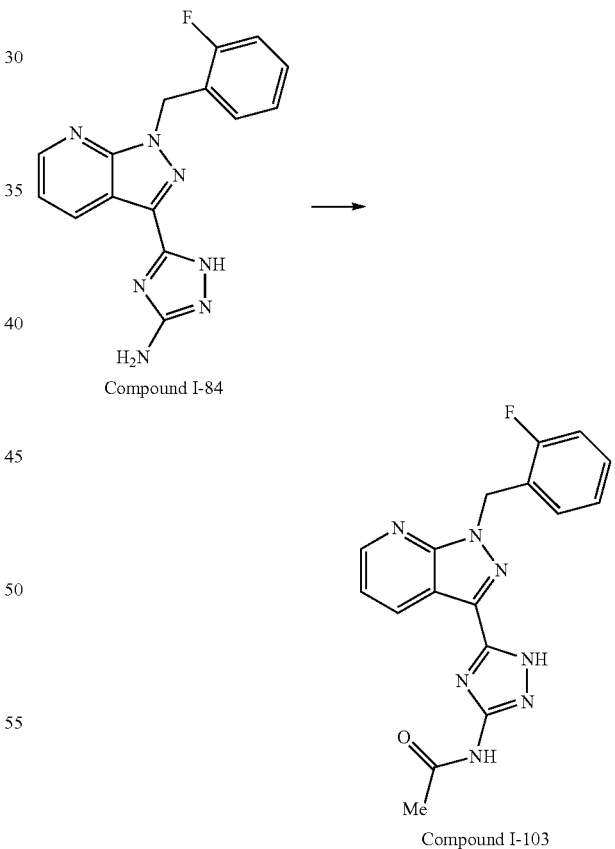

Compound I-84

Compound I-103

To a 0° C. solution of 5-(1-(2-fluorobenzyl)-1H-pyrazolo[3,4-b]pyridin-3-yl)-1H-1,2,4-triazol-3-amine (Compound I-84, 100 mg, 0.33 mmol) in acetonitrile (6.0 mL) was added boron trifluoride diethyl etherate (0.08 mL, 0.66 mmol). The reaction was cooled to −10° C. after which a solution of isoamyl nitrite (0.06 mL, 0.43 mmol) was added. The reaction mixture was allowed to stir for 90 minutes at −10 OC after which a solution of silver trifluoromethylsulfide (90 mg, 0.43 mmol) in acetonitrile (3.0 mL) was added. The reaction mixture was filtered and concentrated to a crude residue. The crude product mixture was purified by silica gel chromatography (0 to 70% of acetonitrile/methanol (7:1) in dichloromethane gradient) followed by a second silica gel chromatography (100% EtOAc eluent) to afford the title compound (1.1 mg, 1.0% yield, side-product) as a white solid.

$^1$H NMR (500 MHz, methanol-$d_4$) δ (ppm) 8.76 (d, 1H), 8.62 (d, 1H), 7.36 (dd, 1H), 7.29-7.32 (m, 1H), 7.05-7.14 (m, 3H), 5.87 (s, 2H), 2.23 (s, 3H).

Compound I-115

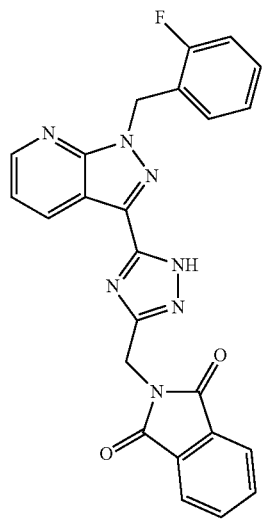

Intermediate 15

The title compound was prepared in two steps:

Step 1: Preparation of Intermediate 15

This intermediate was synthesized according to General Procedure A, with the exception that 2-(1,3-dioxoisoindolin-2-yl)acetyl chloride was used as the acylating agent, as a cream colored solid (0.72 g, 60% yield). The reaction conditions (such as reagents ratio, temperature and reaction time) were modified as needed.

$^1$H NMR (500 MHz, DMSO-$d_6$) δ (ppm) 14.7/14.4 (pair of s, 1H, tautomers), 8.68 (dd, 1H), 8.58 (dd, 1H), 7.94-7.98 (m, 2H), 7.88-7.93 (m, 2H), 7.31-7.44 (m, 2H), 7.10-7.25 (m, 3H), 5.85/5.79 (pair of s, 2H, tautomers), 4.94/5.02 (pair of s, 2H, tautomers).

Step 2: Synthesis of (5-(1-(2-fluorobenzyl)-1H-pyrazolo[3,4-b]pyridin-3-yl)-1H-1,2,4-triazol-3-yl)methanamine To a solution of 2-((5-(1-(2-fluorobenzyl)-1H-pyrazolo[3,4-b]pyridin-3-yl)-1H-1,2,4-triazol-3-yl)methyl)isoindoline-1,3-dione (Intermediate 15, 330 mg, 0.72 mmol) in ethanol (6.0 mL) was added hydrazine hydrate (0.31 mL, 6.5 mmol). After heating at 75° C. for 5 hours, complete disappearance of starting material was observed. The white precipitate formed during the reaction was filtered and washed with methanol. The filtrate was evaporated to a brown solid and purified by reverse phase preparative HPLC (5-95% acetonitrile in water gradient with 0.1% formic acid as additive) to obtain the title compound (90 mg, 39% yield) as a white solid after lyophilization.

$^1$H NMR (500 MHz, DMSO-$d_6$) δ ppm 8.65-8.69 (m, 2H), 8.24 (s, 0.7 H, exchangeable protons), 7.34-7.41 (m, 2H), 7.17-7.25 (m, 2H), 7.12-7.16 (m, 1H), 5.81 (s, 2H), 3.93 (s, 2H).

Compound I-116

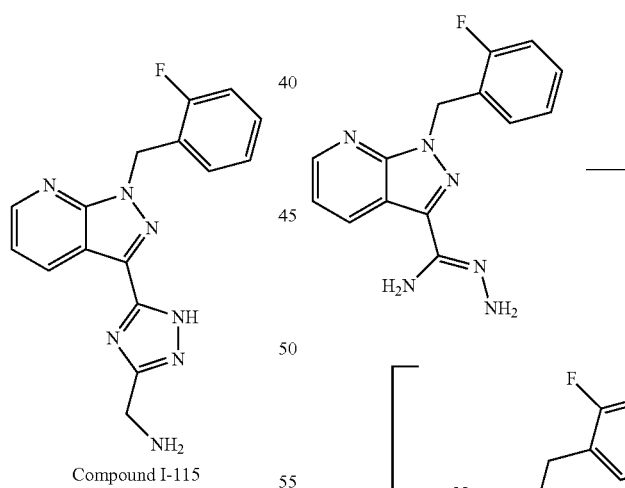

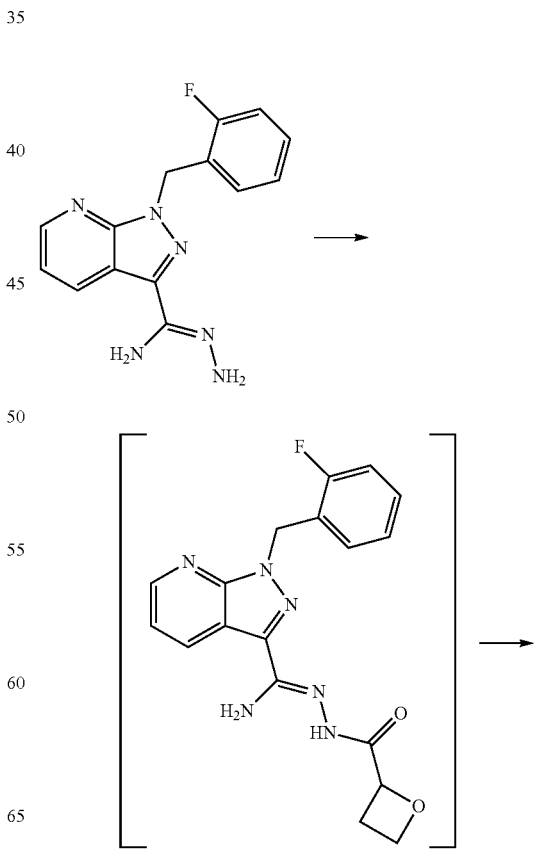

-continued

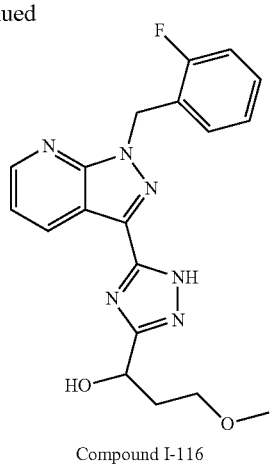

Compound I-116

The title compound was synthesized in 2 steps.

Step 1: Synthesis of N'-((1-(2-fluorobenzyl)-1H-pyrazolo[3,4-b]pyridin-3-yl)(imino)methyl)oxetane-2-carbohydrazide A mixture containing 1-(2-fluorobenzyl)-1H-pyrazolo[3,4-b]pyridine-3-carboximidhydrazide (530 mg, 1.9 mmol), 1-(3-dimethylaminopropyl)-3-ethylcarbodiimide hydrochloride (EDC) (360 mg, 1.9 mmol), HOBt (290 mg, 1.9 mmol) and 2-oxetanecarboxylic acid (190 mg, 1.9 mmol) in DMF (12 mL) was stirred at ambient temperature for 24 hours. The mixture was partitioned between EtOAc (100 mL) and water (100 mL). The organic layer was dried, filtered and evaporated to give an oil. The oil was purified by silica gel chromatography (0 to 10% MeOH/dichloromethane gradient) to give N'-((1-(2-fluorobenzyl)-1H-pyrazolo[3,4-b]pyridin-3-yl)(imino)methyl)oxetane-2-carbohydrazide (158 mg, 23% yield) as a light yellow solid.

Step 2: Synthesis of 1-(5-(1-(2-fluorobenzyl)-1H-pyrazolo[3,4-b]pyridin-3-yl)-1H-1,2,4-triazol-3-yl)-3-methoxypropan-1-ol A mixture containing acetic acid (120 µL, 2.1 mmol) and N'-((1-(2-fluorobenzyl)-1H-pyrazolo[3,4-b]pyridin-3-yl)(imino)methyl)oxetane-2-carbohydrazide (160 mg, 0.43 mmol) in MeOH (2.0 mL) was heated at 120° C. in a microwave for 3 hours. The resulting mixture was cooled to ambient temperature and concentrated in vacuo. The crude product was purified by reverse phase preparative HPLC (5 to 95% acetonitrile/water gradient with 0.1% TFA as additive) to give the title compound (106 mg, 65% yield) as a white solid.

$^1$H NMR (500 MHz, methanol-$d_4$) δ (ppm) 8.72 (m, 1H), 8.63 (m, 1H), 7.37 (m, 1H), 7.26-7.32 (m, 1H), 7.04-7.17 (m, 3H), 5.87 (s, 2H), 4.74 (m, 1H), 3.64-3.78 (m, 2H), 3.36-3.42 (m, 3H), 2.06-2.23 (m, 2H).

Compound I-117

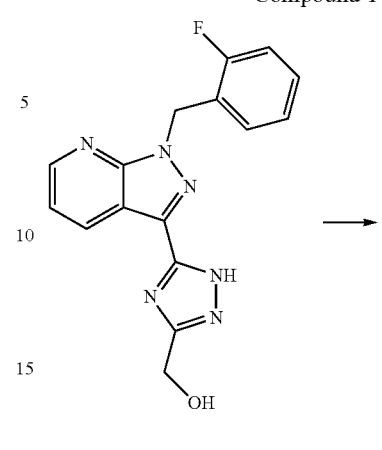

Compound I-117

To a stirred solution of (5-(1-(2-fluorobenzyl)-1H-pyrazolo[3,4-b]pyridin-3-yl)-1H-1,2,4-triazol-3-yl)methanol (Compound I-64, 27 mg, 0.08 mmol) in DMF (2.0 mL) was added potassium carbonate (23 mg, 0.17 mmol) followed by 1,2-dibromoethane (7.3 µL, 0.08 mmol). After stirring at ambient temperature for 15 hours, the mixture was partitioned between EtOAc and water. The organic phase was washed with brine, dried over Na2SO4, filtered and concentrated in vacuo. Purification by reverse phase preparative HPLC gave the title compound (5.8 mg, 19% yield) as a white solid.

$^1$H NMR (500 MHz, chloroform-d) δ (ppm) 8.73 (dd, 1H), 8.64 (dd, 1H), 7.20-7.31 (m, 3H), 7.06 (m, 2H), 7.00 (m, 1H), 6.03 (d, 1H), 5.93 (s, 2H), 5.18 (d, 1H), 4.97 (s, 2H).

Compound I-124 and Compound I-125

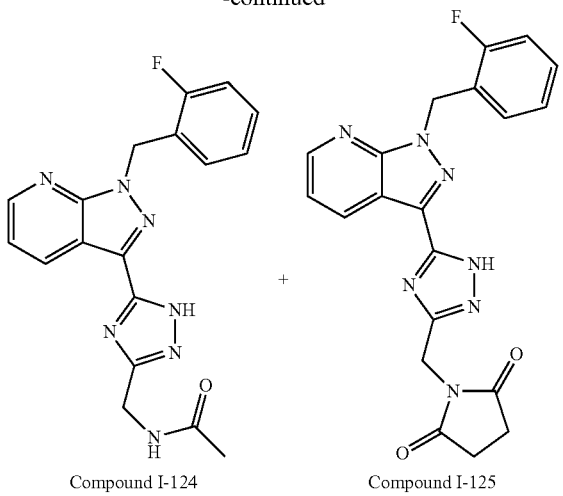

Compound I-124                Compound I-125

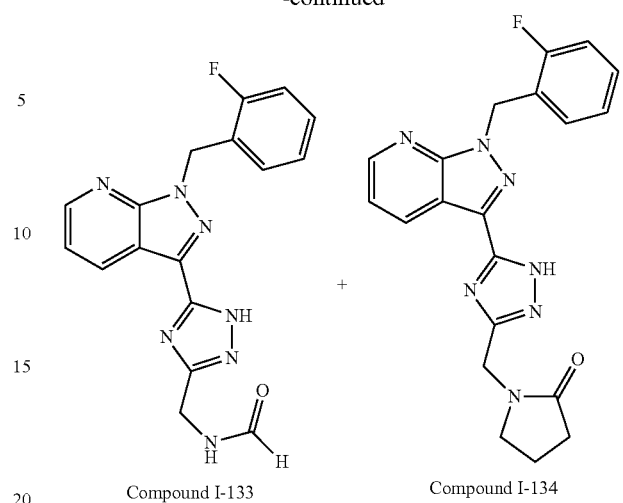

Compound I-133                Compound I-134

Synthesis of N-((5-(1-(2-fluorobenzyl)-1H-pyrazolo[3,4-b]pyridin-3-yl)-1H-1,2,4-triazol-3-yl)methyl)acetamide (Compound I-124) and 1-((5-(1-(2-fluorobenzyl)-1H-pyrazolo[3,4-b]pyridin-3-yl)-1H-1,2,4-triazol-3-yl)methyl)pyrrolidine-2,5-dione (Compound I-125):

A mixture of (5-(1-(2-fluorobenzyl)-1H-pyrazolo[3,4-b]pyridin-3-yl)-1H-1,2,4-triazol-3-yl)methanamine (Compound I-115, 50 mg, 0.16 mmol) and succinic anhydride (15 mg, 0.16 mmol) in toluene (0.30 mL) and acetic acid (0.60 mL) was heated at 100° C. for 2 days. The reaction was cooled to ambient temperature and concentrated in vacuo. The crude material was purified by reverse phase preparative HPLC (5-95% acetonitrile in water gradient with 0.1% formic acid as additive) to obtain Compound I-124 (9.4 mg, 17% yield, side product) as a white solid and Compound I-125 (7.6 mg, 12% yield) as a thin film.

Compound I-124: $^1$H NMR (500 MHz, methanol-$d_4$) δ (ppm) 8.72 (dd, 1H), 8.62 (dd, 1H), 7.36 (dd, 1H), 7.26-7.33 (m, 1H), 7.04-7.17 (m, 3H), 5.86 (s, 2H), 4.58 (s, 2H), 2.04 (s, 3H).

Compound I-125: $^1$H NMR (500 MHz, methanol-$d_4$) δ (ppm) 8.69 (dd, 1H), 8.63 (dd, 1H), 7.37 (dd, 1H), 7.26-7.33 (m, 1H), 7.04-7.17 (m, 3H), 5.86 (s, 2H), 4.87 (s, 2H), 2.80 (s, 4H).

Compound I-133 and Compound I-134 (N-((5-(1-(2-fluorobenzyl)-1H-pyrazolo[3,4-b]pyridin-3-yl)-1H-1,2,4-triazol-3-yl)methyl)formamide (and 1-((5-(1-(2-fluorobenzyl)-1H-pyrazolo[3,4-b]pyridin-3-yl)-1H-1,2,4-triazol-3-yl)methyl)pyrrolidin-2-one)

A mixture of (5-(1-(2-fluorobenzyl)-1H-pyrazolo[3,4-b]pyridin-3-yl)-1H-1,2,4-triazol-3-yl)methanamine (Compound I-115, 50 mg, 0.16 mmol), ethyl 4-bromobutanoate (31 mg, 0.16 mmol) and triethylamine (0.02 mL, 0.16 mmol) in DMF (1.0 mL) was heated at 70° C. for 16 hours. The reaction was then cooled to ambient temperature, neutralized with 1.0 N HCl (20 mL), and extracted with EtOAc (75 mL). The organic layer was washed with brine (10 mL), dried, filtered and evaporated. The crude residue was purified by reverse phase preparative HPLC (5-95% acetonitrile in water gradient with 0.1% formic acid additive) to obtain Compound I-133 (5.6 mg, 10% yield) as a white solid and Compound I-134 (16 mg, 27% yield) as a thin film.

Compound I-133: $^1$H NMR (500 MHz, methanol-$d_4$) δ (ppm) 8.73 (d, 1H), 8.63 (d, 1H), 8.22 (s, 1H), 7.37 (dd, 1H), 7.30 (q, 1H), 7.04-7.19 (m, 3H), 5.87 (s, 2H), 4.63 (s, 2H).

Compound I-134: $^1$H NMR (500 MHz, methanol-$d_4$) δ (ppm) 8.70 (d, 1H), 8.63 (d, 1H), 7.36 (dd, 1H), 7.29 (q, 1H), 7.04-7.18 (m, 3H), 5.86 (s, 2H), 4.69 (s, 2H), 3.55 (t, 2H), 2.45 (t, 2H), 2.09 (quin, 2H).

Compound I-126

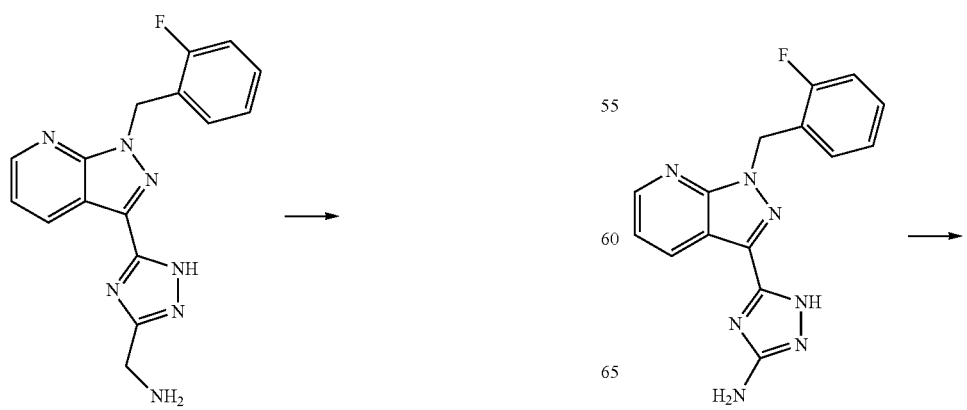

-continued

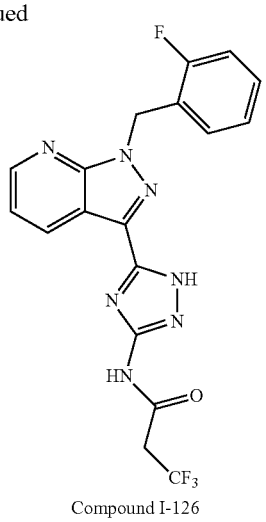

Compound I-126

A suspension of 5-(1-(2-fluorobenzyl)-1H-pyrazolo[3,4-b]pyridin-3-yl)-H-1,2,4-triazol-3-amine (Compound I-84, 130 mg, 0.30 mmol), 3,3,3-trifluoropropanoyl chloride (0.03 mL, 0.30 mmol), and triethylamine (0.06 mL, 0.40 mmol) in dichloromethane (10 mL) was stirred at ambient temperature for 2 hours. The reaction mixture was concentrated and purified directly by silica gel chromatography (0 to 100% EtOAc/hexanes gradient) and then with reverse phase preparative HPLC (5 to 95% acetonitrile in water gradient with 0.1% TFA as additive) to afford the title compound (1.3 mg, 1.0% yield) as a flocculent white solid.

$^1$H NMR (500 MHz, acetone-$d_6$) δ (ppm) 8.76 (d, 1H), 8.66 (m, 1H), 7.32-7.39 (m, 4H), 7.23-7.27 (m, 1H), 7.15-7.19 (m, 1H), 7.12-7.15 (m, 1H), 5.89 (s, 2H), 4.39 (q, 2H).

Example 2: Biological Activity Measurement by the cGMP GloSensor Cell-Based Assay, 384-Well Format Human embryonic kidney cells (HEK293) cells expressing GloSensor™ 40F cGMP (Part No: CS 182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GloSensor cells were maintained in Dulbecco's Modification of Eagle's Medium (DMEM) supplemented with fetal bovine serum (FBS, 10% final) and hygromycine (200 ug/ml). The day before assay, cells were plated in DMEM with 10% FBS in a 50 μL volume at a density of 1.5×10$^4$ cells/well in a poly-D-lysine coated 384-well flat white-bottom plate (Corning Cat No 35661). Cells were incubated overnight at 37° C. in a humidified chamber with 5% $CO_2$. The next day, medium was removed and cells were replaced with 40 ul/well of GloSensor™, 2 mM (Promega Cat No E1291). Cells were treated for 90 minutes at 25° C. to allow the substrate to equilibrate in the cells. Test compounds and Diethylenetriamine NONOate (DETA-NONOate) was diluted to 3 mM (20×) in serum-free $CO_2$ independent medium and serially diluted at 4> dilutions to create 5× dose curve from which 10 ul was added to the wells (×M concentration for test compound solution and 10 μM concentration for DETA-NONOate solution; wherein x is one of the following final concentrations: 30 μM, 7.5 μM, 1.9 μM, 469 nM, 117 nM, 29.3 nM, 7.3 nM, 1.83 nM, 0.46 nM, 0.11 nM, 0.03 nM) For the kinetics studies, luminescence was measured right away for 0.2 sec per well with Envision (Perkin Elmer). For endpoint SAR screening, data were collected after 55 min incubation at room temperature.

Data were normalized to a high control using the following equation: 100*(Sample−Low Control)/(High Control−Low Control), where the low control is the average of 16 samples treated with 1% DMSO, and the high control is the average of 16 samples treated with 30 μM of Compound Y depicted below. Data were fit using a 4-parameter fit (log (agonist) vs. response−variable slope) using GraphPad Prism Software v.5. n=2 for all compounds. The Absolute (Abs) $EC_{50}$ was interpolated from the curve fit and is defined as the concentration at which a given compound elicits 50% of the high control response after data normalization as indicated above. Compounds failing to elicit a minimum response of 50% are reported as >30 μM or ND. For compounds run in duplicate or n higher than 2, the result herein given is the geometric mean of the several results obtained. Tables 2A and 2B summarize results obtained for selected compounds of the invention in this assay.

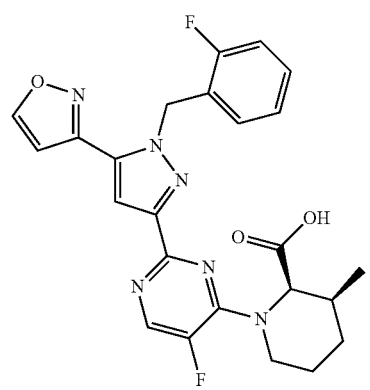

Compound Y

TABLE 2A

Whole cell activity in the GloSensor cell-based assay, 384-well format (Example 2) for compounds in Table IA.

| Compound | Glo-sensor AbsEC50 (nM) |
|---|---|
| I-48 | A |
| I-21 | A |
| I-16 | A |
| I-22 | A |
| I-20 | A |
| I-51 | A |
| I-49 | A |
| I-52 | A |
| I-42 | A |
| I-8 | A |
| I-14 | A |
| I-4 | A |
| I-67 | A |
| I-26 | A |
| I-36 | A |
| I-72 | A |
| I-41 | A |
| I-50 | A |
| I-1 | A |
| I-62 | A |
| I-65 | A |
| I-113 | A |
| I-86 | A |

TABLE 2A-continued

Whole cell activity in the GloSensor cell-based assay, 384-well format (Example 2) for compounds in Table IA.

| Compound | Glo-sensor AbsEC50 (nM) |
|---|---|
| I-89 | A |
| I-92 | A |
| I-37 | A |
| I-53 | A |
| I-58 | A |
| I-54 | A |
| I-73 | A |
| I-60 | A |
| I-107 | A |
| I-47 | A |
| I-64 | A |
| I-96 | A |
| I-105 | A |
| I-130 | A |
| I-63 | A |
| I-104 | A |
| I-131 | A |
| I-91 | A |
| I-68 | A |
| I-61 | A |
| I-101 | A |
| I-85 | A |
| I-94 | B |
| I-95 | B |
| I-112 | B |
| I-127 | B |
| I-90 | B |
| I-70 | B |
| I-31 | B |
| I-124 | B |
| I-2 | B |
| I-87 | B |
| I-45 | B |
| I-55 | B |
| I-69 | B |
| I-48 | B |
| I-103 | B |
| I-25 | B |
| I-46 | B |
| I-3 | B |
| I-59 | B |
| I-120 | B |
| I-75 | B |
| I-121 | B |
| I-117 | B |
| I-116 | B |
| I-84 | B |
| I-125 | B |
| I-97 | B |
| I-100 | B |
| I-77 | B |
| I-32 | B |
| I-40 | B |
| I-13 | B |
| I-123 | B |
| I-82 | B |
| I-77 | B |
| I-122 | B |
| I-76 | B |
| I-57 | B |
| I-115 | B |
| I-128 | B |
| I-99 | B |
| I-74 | B |
| I-129 | C |
| I-43 | C |
| I-66 | C |
| I-70 | C |
| I-79 | C |
| I-39 | C |
| I-98 | C |
| I-7 | C |
| I-78 | C |
| I-73 | C |
| I-126 | C |
| I-88 | C |
| I-83 | C |
| I-19 | C |
| I-35 | C |
| I-81 | C |
| I-38 | C |
| I-30 | ND | sGC enzyme activity values in HEK cells, determined by the GloSensor assay.
(~) Code definitions for the sGC enzyme activity values, expressed as Absolute $EC_{50}$ which is defined as the concentration at which a given compound elicits 50% of the high control response (Compound Y) after data normalization:
Abs $EC_{50} \leq 100$ nM = A;
100 nM < Abs $EC_{50} \leq 1000$ nM = B;
1000 nM < Abs $EC_{50}$ = C.
Compounds failing to elicit a minimum response of 50% are reported as >30 μM or ND.

TABLE 2B

Whole cell activity in the GloSensor cell-based assay, 384-well format (Example 2) for compounds in Table IB.

| Compound | Glo-sensor Abs EC50 (nM) |
|---|---|
| I-12 | A |
| I-6 | A |
| I-15 | A |
| I-27 | C |
| I-28 | A |
| I-29 | B |
| I-34 | C |
| I-24 | C |
| I-5 | B |
| I-9 | B |
| I-44 | C |
| I-17 | A |
| I-18 | B |
| I-23 | B | sGC enzyme activity values in HEK cells, determined by the GloSensor assay.
(~) Code definitions for the sGC enzyme activity values, expressed as Absolute $EC_{50}$ which is defined as the concentration at which a given compound elicits 50% of the high control response (Compound Y) after data normalization:
Abs $EC_{50} \leq 100$ nM = A;
100 nM < Abs $EC_{50} \leq 1000$ nM = B;
1000 nM < Abs $EC_{50}$ = C.
Compounds failing to elicit a minimum response of 50% are reported as >30 μM or ND.

Example 3. Biological Activity Measurement by the cGMP Neuronal Cell-Based Assay Rat primary neurons were isolated from fetuses of 18-day pregnant Sprague-Dawley females. The fetuses were collected in Hanks' balanced salt solution (HBSS) and brains were rapidly removed. The cerebral hippocampi were isolated and mechanically fragmented. Further tissue digestion was performed with 0.25% (wt/vol) trypsin solution in HBSS without Ca2+ and Mg2+ for 15 min at 37° C. After trypsination, cells were washed and resuspended in neurobasal medium supplemented with 0.5 mM L-glutamine, 12.5 uM glutamic acid, 2% B-27 and 100 U/mL penicillin, and 100 g/mL streptomycin. Cells were plated at a density of $4 \times 10^4$ cells/well in a poly-D-lysine coated 384-well flat clear-bottom plate (Corning Cat No 354662). Cells were incubated 6-7 days at 37° C. in a humidified chamber with 5% $CO_2$. Media was removed and cells were washed 1× with HBSS containing Ca2+ and Mg2+, and replaced with 40 uL HBSS containing 0.5 mM IBMX, and incubated for 15 minutes at 37° C. 10 uL of a 5× stock of test compounds with diethylenetriamine NONOate (DETA-NO) was added. Final concentration of DETA-NO was 30 µM. Cells were incubated for 20 min at 37° C. Medium was removed, 50 uL of ice-cold 10% acetic acid was added, and incubated for 60 minutes at 4° C. Following centrifugation at 4° C. for 5 minutes at 1000×g to pellet cell debris, the supernatant was aspirated to a clean plate and the samples were analyzed for cGMP content. cGMP concentrations were determined from each sample using LC-MS/MS.

Data were normalized to a high control using the following equation: 100*(Sample−Low Control)/(High Control−Low Control), where the low control is the average of 15 samples treated with 1% DMSO, and the high control is the average of 15 samples treated with 10 µM of the known sGC stimulator Compound Y (depicted in Example 2). Data were fit using a 4-parameter fit (log(agonist) vs. response–variable slope) using GraphPad Prism Software v.5. n=2 for all compounds. The Absolute $EC_{50}$ was interpolated from the curve fit and is defined as the concentration at which a given compound elicits 50% of the high control response after data normalization. Compounds failing to elicit a minimum response of 50% are reported as >30 µM. For compounds run in duplicate or n higher than 2, the result herein given is the geometric mean of the several results obtained. Tables 3A and 3B summarize results obtained for selected compounds of the invention in this assay.

TABLE 3A

Biological activity in the cGMP neuronal cell-based assay (Example 3) for compounds in Table IA.

| Compound | sGC-neuron Abs EC50 (nM) |
|---|---|
| I-48 | A |
| I-49 | A |
| I-8 | A |
| I-4 | A |
| I-41 | A |
| I-62 | A |
| I-86 | A |
| I-64 | A |
| I-96 | A |
| I-105 | A |
| I-130 | A |
| I-131 | A |
| I-101 | A |
| I-127 | A |
| I-31 | A |
| I-2 | A |

Neuronal-based cell assay.
Abs $EC_{50}$ ≤ 100 nM = A;
100 nM < Abs $EC_{50}$ ≤ 1000 nM = B;
1000 nM < Abs $EC_{50}$ = C.
Compounds failing to elicit a minimum response of 50% are reported as >30 µM or ND.

TABLE 3B

Biological activity in the cGMP neuronal cell-based assay (Example 3) for compounds in Table IB.

| Compound | sGC-Neuron Abs EC50 (nM) |
|---|---|
| I-6 | A |
| I-9 | B |

Neuronal-based cell assay.
Abs $EC_{50}$ ≤ 100 nM = A;
100 nM < Abs $EC_{50}$ ≤ 1000 nM = B;
1000 nM < Abs $EC_{50}$ = C.
Compounds failing to elicit a minimum response of 50% are reported as >30 µM or ND.

Example 4: Rat Cerebrospinal Fluid (CSF) Pharmacokinetic Properties

Protocol:

PK in rats was determined following oral dosing. For the oral (PO) experiments, a group of 6 male Sprague-Dawley rats with an indwelling catheter placed in the cisterna magna were used. The PO group was dosed with 3 or 10 mg/kg of a compound formulated as a solution in PEG400. PO doses were administered by oral gavage and delivered to the stomach using a syringe and gavage tube. Following oral dosage administration, the gavage tube was flushed with approximately 0.5 mL of water to ensure complete delivery of the full dose.

Plasma and CSF samples were collected as follows: samples of CSF and blood were collected at 1 hour and 2 hours post-dosing. CSF samples (0.05 mL) were collected through the intracisternal catheter. Blood samples (0.25 mL) were collected through retro-orbital sampling. These samples were kept on ice until processed for plasma. Blood samples were centrifuged at 3200 rpm for 5 minutes at approximately 5° C. within 1 hour of collection. Plasma was directly transferred to a 96-well plate tube (0.125 mL). Plug caps were placed on the tubes and the tubes frozen at approximately −70° C. and stored until analysis.

Plasma was collected and analyzed for the presence of compound.

Quantitation of Compounds

The compound in question and the internal standard were extracted from plasma and CSF by precipitation. Samples were analyzed using liquid chromatography (LC) with tandem mass spectrometric detection (MS/MS) using electrospray ionization. The standard curve range was from 1 to 1000 ng/mL. Results of the compounds described herein in this assay are illustrated in Tables 4A (for compounds in Table IA) and 4B (for compounds in Table IB) below.

Kp,uu is defined as the concentration ratio of unbound drug in CSF to unbound drug in plasma. Unbound drug in plasma (or free plasma concentration) is calculated by multiplying the total plasma concentration by the unbound fraction as determined by plasma protein binding. The CSF concentration is then divided by the free plasma concentration to determine the Kp,uu. (See e.g., Di et al., *J. Med. Chem.*, 56, 2-12 (2013))

TABLE 4A

CSF PK properties of select compounds described herein (Example 4) for compounds in Table IA (10 mg/kg dose)

| Compound | CSF Conc. (nM @ 1 h) | Kp, uu (@ 1 h) |
|---|---|---|
| I-48 | 41.57 | 2.52 |
| I-20 | 206.87 | 3.37 |
| I-49 | 172.05 | 1.57 |
| I-41 | 26.57 | 0.36 |
| I-1 | 164.06 | 0.24 |
| I-62 | 83 | 0.62 |
| I-86 | 31.53 | 2.41 |
| I-92 | 10.78 | 0.52 |
| I-64 | 13.13 | 0.54 |
| I-96 | 21.51 | 1.54 |
| I-105 | 17.43 | 2.20 |
| I-101 | 104.12 | 2.81 |
| I-4 | 79.46 | 1.98 |
| I-31 | 66.62 | 3.84 |
| I-2 | 16.55 | 0.24 |

TABLE 4B

CSF PK properties of select compounds described herein
(Example 4) for compounds in Table IB (10 mg/kg dose)

| Compound | CSF Conc. (nM @ 1 h) | Kp, uu (@ 1 h) |
| --- | --- | --- |
| I-12 | 44.99 | 0.16 |
| I-5 | 30.43 | 1.08 |

Various embodiments of the invention can be described in the text below:

[1]. A compound of formula I, or a pharmaceutically acceptable salt thereof:

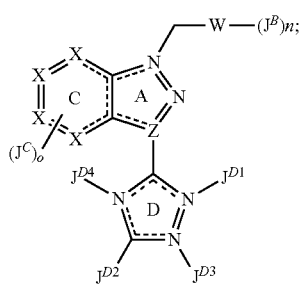

Formula I wherein rings A and C constitute the core of the molecule; rings A and D are heteroaryl rings; ring C may be a phenyl or a heteroaryl ring; each bond in these rings is either a single or a double bond depending on the substituents, so that each of said rings has aromatic character;

one instance of Z on ring A is N and the other instance of Z is C;

each instance of X on ring C is independently selected from C or N; wherein 0, 1 or 2 instances of X can simultaneously be N;

o is an integer selected from 2, 3 or 4;

each $J^C$ is a substituent on a carbon atom independently selected from hydrogen, halogen, —CN, $C_{1-4}$ aliphatic, $C_{1-4}$ haloalkyl or $C_{1-4}$ alkoxy;

W is either:
i) absent, and $J^B$ is connected directly to the methylene group linked to the core; n is 1; and $J^B$ is a $C_{1-7}$ alkyl chain optionally substituted by up to 9 instances of fluorine; or
ii) a ring B selected from phenyl or a 5 or 6-membered heteroaryl ring, containing 1 or 2 ring heteroatoms independently selected from N, O or S; wherein when W is ring B, n is 0 or an integer selected from 1, 2 or 3;

each $J^B$ is independently selected from halogen, —CN, a $C_{1-6}$ aliphatic, —$OR^B$ or a $C_{3-8}$ cycloaliphatic ring; wherein each said $C_{1-6}$ aliphatic and each said $C_{3-8}$ cycloaliphatic ring is optionally and independently substituted with up to 3 instances of $R^3$;

each $R^B$ is independently selected from a methyl, propyl, butyl, isopropyl, isobutyl or a $C_{3-8}$ cycloaliphatic ring; wherein each of said $R^B$ is optionally and independently substituted with up to 3 instances of $R^{3a}$;

each $R^3$ and each $R^{3a}$ is independently selected in each instance from halogen, —CN, $C_{1-4}$ alkyl, $C_{1-4}$ haloalkyl, —O($C_{1-4}$ alkyl) or —O($C_{1-4}$ haloalkyl);

$J^{D1}$ and $J^{D4}$ are independently selected from a lone pair on the nitrogen atom to which they are attached or hydrogen, wherein $J^{D1}$ and $J^{D4}$ are not both simultaneously hydrogen or both simultaneously a lone pair;

$J^{D3}$ is either a lone pair on the nitrogen atom to which it is attached, hydrogen, or a substituent selected from —C(O)$R^D$, a $C_{1-6}$ aliphatic, —($C_{1-6}$ aliphatic)-$R^D$, a $C_{3-8}$ cycloaliphatic ring, a phenyl ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^D$ moiety, said $C_{3-8}$ cycloaliphatic ring, said 4 to 8-membered heterocyclic ring, and said 5 or 6-membered heteroaryl ring is optionally and independently substituted with up to 5 instances of $R^5$; and wherein said phenyl ring is optionally and independently substituted with up to 5 instances of $R^{5a}$;

$J^{D1}$ and $J^{D3}$ cannot both simultaneously be hydrogen;

$J^{D2}$ is hydrogen, or a substituent selected from halogen, —CN, —$NO_2$, —$OR^{D1}$, —C(O)$R^D$, —C(O)N($R^D$)$_2$, —N($R^D$)$_2$, —N($R^D$)C(O)$R^D$, —N($R^D$)C(O)O$R^D$, —N($R^D$)C(O)N($R^D$)$_2$, —OC(O)N($R^D$)$_2$, a $C_{1-6}$ aliphatic, —($C_{1-6}$ aliphatic)-$R^D$, a $C_{3-8}$ cycloaliphatic ring, a phenyl ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^D$ moiety, said $C_{3-8}$ cycloaliphatic ring, said 4 to 8-membered heterocyclic ring and said 5 or 6-membered heteroaryl ring is optionally and independently substituted with up to 5 instances of $R^5$; and wherein said phenyl ring is optionally and independently substituted with up to 5 instances of $R^{5a}$;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring and each said 5 to 6-membered heteroaryl ring is optionally and independently substituted with up to 5 instances of $R^5$; and wherein each said phenyl ring is optionally and independently substituted with up to 5 instances of $R^{5a}$;

$R^{D1}$ is selected from a $C_{1-6}$ aliphatic, —($C_{1-6}$ aliphatic)-$R^f$, a $C_{3-8}$ cycloaliphatic ring, a 4 to 8-membered heterocyclic ring, a phenyl ring or a 5 to 6-membered heteroaryl ring; wherein said 4 to 8-membered heterocyclic ring and said 5 to 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^f$ moiety, said $C_{3-8}$ cycloaliphatic ring, said 4 to 8-membered heterocyclic ring and said 5 to 6-membered heteroaryl ring is optionally and independently substituted with up to 5 instances of $R^5$; wherein said phenyl ring is optionally and independently substituted with up to 5 instances of $R^{5a}$;

each $R^f$ is independently selected from a a $C_{3-8}$ cycloaliphatic ring, a 4 to 8-membered heterocyclic ring, a phenyl ring or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{3-8}$ cycloaliphatic ring, each said 4 to 8-membered heterocyclic ring and each said 5 to 6-membered heteroaryl ring is optionally and independently substituted by up to 5 instances of $R^5$; and wherein each said phenyl is optionally and independently substituted by up to 5 instances of $R^{5a}$;

each $R^5$ is independently selected from halogen, —CN, $C_{1-6}$ aliphatic, —($C_{1-6}$ alkyl)-$R^6$, —$OR^6$, —$COR_6$, —C(O)N($R^6$)$_2$, —N($R^6$)C(O)$R^6$, —N($R^6$)C(O)O$R^6$, —N($R^6$)C(O)N($R^6$)$_2$, —N($R^6$)$_2$, a $C_{3-8}$ cycloalkyl ring, a 4 to 8-membered heterocyclic ring, a 5 or 6-membered heteroaryl ring, phenyl, benzyl or an oxo group; wherein if two instances of $R^5$ are oxo and —OH or oxo and —$OR^6$, they are not substituents on the same carbon atom; wherein each of said 5 or 6-membered heteroaryl ring or 4 to 8-membered heterocyclic ring contains up to 3 ring heteroatoms independently selected from N, O and S; and wherein each of said $C_{1-6}$ aliphatic, each said $C_{1-6}$ alkyl portion of the —($C_{1-6}$ alkyl)-$R^6$ moiety, each said $C_{3-8}$ cycloalkyl ring, each said 5 or 6-membered heteroaryl ring and each said 4 to 8-membered heterocyclic ring, is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —$CONH_2$, —O($C_{1-4}$ alkyl), —O($C_{1-4}$ haloalkyl) or oxo; wherein if two instances of a substituent on $R^5$ are a) oxo and —OH or b) oxo and —O($C_{1-4}$ alkyl) or c) oxo and —O($C_{1-4}$ haloalkyl), they are not substituents on the same carbon atom; wherein each said benzyl or phenyl is optionally and independently substituted with up to 3 instances of halogen, $C_{1-4}$ alkyl, —$NH_2$, —NH($C_{1-4}$ alkyl), —N($C_{1-4}$ alkyl)$_2$, —CN, —$CONH_2$, —O($C_{1-4}$ alkyl), —O($C_{1-4}$ haloalkyl);

each $R^{5a}$ is independently selected from halogen, —CN, $C_{1-6}$ aliphatic, —($C_{1-6}$ alkyl)-$R^6$, —$OR^{6a}$, —$COR_6$, —C(O)N($R^6$)$_2$, —N($R^6$)C(O)$R^6$, —N($R^6$)C(O)O$R^6$, —N($R^6$)C(O)N($R^6$)$_2$, —N($R^6$)$_2$, a $C_{3-8}$ cycloalkyl ring, a 4 to 8-membered heterocyclic ring, a 5 or 6-membered heteroaryl ring, phenyl, benzyl or an oxo group; wherein each of said 5 or 6-membered heteroaryl ring and each of said 4 to 8-membered heterocyclic ring contains up to 3 ring heteroatoms independently selected from N, O and S; and wherein each of said $C_{1-6}$ aliphatic, each of said $C_{1-6}$ alkyl portion of the —($C_{1-6}$ alkyl)-$R^6$ moiety, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl, —OH, —$NH_2$, —NH($C_{1-4}$ alkyl), —N($C_{1-4}$ alkyl)$_2$, —CN, —$CONH_2$, —O($C_{1-4}$ alkyl), —O($C_{1-4}$ haloalkyl) or oxo; wherein if two instances of a substituent on $R^{5a}$ are a) oxo and —OH or b) oxo and —O($C_{1-4}$ alkyl) or c) oxo and —O($C_{1-4}$ haloalkyl), they are not substituents on the same carbon atom; and wherein each of said benzyl and each of said phenyl is optionally and independently substituted with up to 3 instances of halogen, $C_{1-4}$ alkyl, $C_{1-4}$ haloalkyl —$NH_2$, —NH($C_{1-4}$ alkyl), —N($C_{1-4}$ alkyl)$_2$, —CN, —$CONH_2$, —O($C_{1-4}$ alkyl) or —O($C_{1-4}$ haloalkyl);

each $R^6$ is independently selected from hydrogen, a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring or 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo; wherein if two instances of a substituent on $R^6$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, $C_{1-4}$ haloalkyl, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo;

each $R^{6a}$ is independently selected from a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring and each of said 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo; wherein if two instances of $R^{6a}$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, $C_{1-4}$ haloalkyl, —$NH_2$, —NH($C_{1-4}$ alkyl), —N($C_{1-4}$ alkyl)$_2$, —CN, —C(O)$NH_2$, —O($C_{1-4}$ alkyl), —O($C_{1-4}$ haloalkyl) or oxo;

alternatively, $J^{D2}$ and $J^{D3}$, together with the atoms to which they are attached, form a 5 or 6-membered heteroaryl ring or a 5 to 8-membered heterocyclic ring; wherein said heteroaryl ring or heterocyclic ring contains between 1 and 3 heteroatoms independently selected from N, O or S, including the N to which $J^{D3}$ is attached; wherein said heterocyclic or heteroaryl ring can be substituted by up to three instances of $J^E$; and $J^E$ is selected from halogen, $C_{1-4}$ alkyl, $C_{1-4}$ haloalkyl or oxo; provided the compound is not one of the two depicted below:

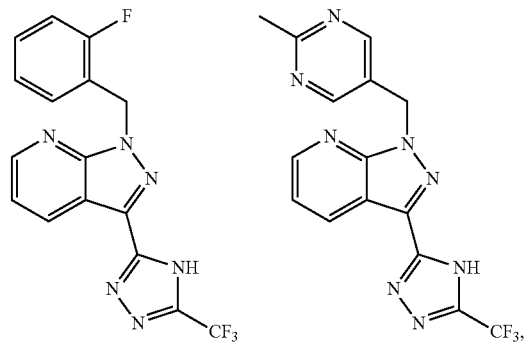 [SMILES: Fc1ccccc1Cn1nc(-c2nnc(C(F)(F)F)[nH]2)c2cccnc21 ; Cc1ncc(Cn2nc(-c3nnc(C(F)(F)F)[nH]3)c3cccnc32)cn1]

[2]. A compound, or a pharmaceutically acceptable salt of the compound, of [1] above, or according to other embodiments of the invention, wherein the compound is one of Formula IIA, Formula IIB or Formula IIC, or a pharmaceutically acceptable salt thereof:

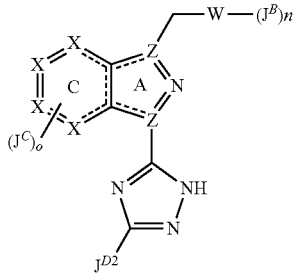

Formula IIA

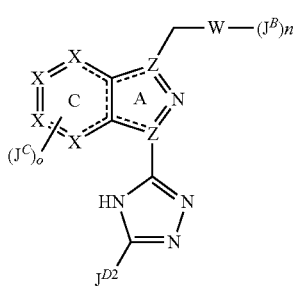

Formula IIB

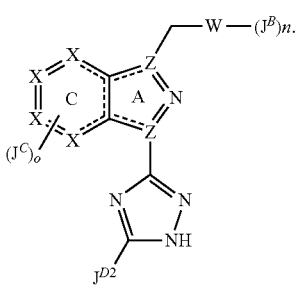

Formula IIC

[3] A compound, or a pharmaceutically acceptable salt of the compound, of [1] or [2] above, or according to other embodiments of the invention, wherein $J^{D2}$ is selected from: hydrogen, halogen, —CN, —OR$^{D1}$, —C(O)R$^D$, —C(O)N (R$^D$)$_2$, —N(R$^D$)$_2$, —N(R$^D$)C(O)R$^D$, a C$_{1-6}$ aliphatic, —(C$_{1-6}$ aliphatic)-R$^D$, a C$_{3-8}$ cycloaliphatic ring, a phenyl ring, and a 4 to 8-membered heterocyclic ring containing between 1 and 3 heteroatoms independently selected from O, N or S; and wherein said C$_{1-6}$ aliphatic, said C$_{1-6}$ aliphatic portion of the —(C$_{1-6}$ aliphatic)-R$^D$ moiety, said C$_{3-8}$ cycloaliphatic ring, said 4 to 8-membered heterocyclic ring and said 5 or 6-membered heteroaryl ring is optionally and independently substituted with up to 5 instances of R$^5$; and wherein each said phenyl ring is optionally and independently substituted with up to 5 instances of R$^{5a}$.

[4]. A compound, or a pharmaceutically acceptable salt of the compound, of [1], [2] or [3] above, or according to other embodiments of the invention, wherein R$^5$ is selected in each instance from halogen, C$_{1-6}$ haloalkyl, —OH, —OCH$_3$, —C(=O)CF$_3$, —NH(CO)O(C$_{1-6}$ aliphatic), —NH$_2$, phenyl, —CH$_2$_heteroaryl, —N(CH$_3$)$_2$, C$_{1-6}$ aliphatic, —NH (CO)R$^6$, or oxo.

[5]. A compound, or a pharmaceutically acceptable salt of the compound, of [1], [2], [3] or [4] above, or according to other embodiments of the invention, wherein wherein the compound is one of Formula III, or a pharmaceutically acceptable salt thereof:

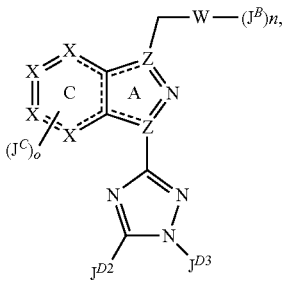

Formula III wherein $J^{D3}$ is not hydrogen or a lone pair on the N atom to which it is attached.

[6] A compound, or a pharmaceutically acceptable salt of the compound, of [1], [2], [3], [4] or [5] above, or according to other embodiments of the invention, wherein wherein $J^{D2}$ and $J^{D3}$, together with the atoms to which they are attached, form a 5 or 6-membered heteroaryl ring or a 5 to 8-membered heterocyclic ring; wherein said heteroaryl ring or heterocyclic ring contains between 1 and 3 heteroatoms independently selected from N, O or S, including the N to which $J^{D3}$ is attached; wherein said heterocyclic or heteroaryl ring can be substituted by up to three instances of $J^E$; and $J^E$ is selected from halogen, C$_{1-4}$ alkyl, C$_{1-4}$ haloalkyl or oxo

[7]. A compound, or a pharmaceutically acceptable salt of the compound, of [1], [2], [3], [4], [5] or [6] above, or according to other embodiments of the invention, wherein $J^{D2}$ and $J^{D3}$ together with the atoms to which they are attached, form a ring selected from pyrrole, pyridine, oxazine, pyrimidine, diazepine, pyrazine, pyridazine, and imidazole; wherein said ring is partially or fully saturated; and wherein said ring is optionally substituted by up to three instances of $J^E$.

[8]. A compound, or a pharmaceutically acceptable salt of the compound, of [7] above, or according to other embodiments of the invention, wherein $J^{D2}$ is selected from hydrogen, halogen, —NH$_2$, —CF$_3$, —CH$_3$, or —CH$_2$OH.

[9]. A compound, or a pharmaceutically acceptable salt of the compound, of [1], [2], [3], [4] or [5] above, or according to other embodiments of the invention, wherein $J^{D3}$ is selected from a C$_{1-6}$ aliphatic optionally and independently substituted with up to 5 instances of R$^5$.

[10]. A compound, or a pharmaceutically acceptable salt of the compound, of [9] above, or according to other embodiments of the invention, wherein each R$^5$ is independently selected from halogen, —CN, —OR$^6$, —C(O)N(R$^6$)$_2$, a 4 to 8-membered heterocyclic ring, or phenyl; wherein each 4 to 8-membered heterocyclic ring contains up to 3 ring heteroatoms independently selected from N, O and S, and is optionally and independently substituted with up to 3 instances of halogen, —O(C$_{1-4}$ alkyl), or oxo; and wherein said phenyl is optionally and independently substituted with up to 3 instances of halogen.

[11]. A compound, or a pharmaceutically acceptable salt of the compound, of [9] or [10] above, or according to other embodiments of the invention, wherein $J^{D3}$ is selected from —C$_{1-4}$ alkyl, —CH$_2$CF$_3$, —(CH$_2$)$_2$OH, —CH$_2$C(O)NH$_2$, —CH$_2$CN, —CH$_2$C(OH)CF$_3$, —(CH$_2$)$_2$ pyrrolidin-2-one, or benzyl optionally substituted with methoxy or halogen.

[12]. A compound, or a pharmaceutically acceptable salt of the compound, of [1], [2], [3], [4], [5], [6], [7], [8], [9], [10] or [11] above, or according to other embodiments of the invention, wherein W is absent, and $J^B$ is connected directly to the methylene group linked to the core; n is 1; and $J^B$ is a $C_{1-7}$ alkyl chain optionally substituted by up to 9 instances of fluorine.

[13]. A compound, or a pharmaceutically acceptable salt of the compound, of [1], [2], [3], [4], [5], [6], [7], [8], [9], [10] or [11] above, or according to other embodiments of the invention, wherein W is a ring B selected from phenyl or a 5 or 6-membered heteroaryl ring, and the compound is one of Formula IV, or a pharmaceutically acceptable salt thereof:

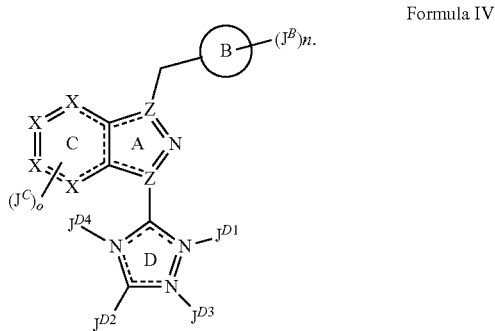

Formula IV

[14]. A compound, or a pharmaceutically acceptable salt of the compound, of [1], [2], [3], [4], [5], [6], [7], [8], [9], [10], [11] or [13] above, or according to other embodiments of the invention, wherein ring B is selected from phenyl, pyridine, pyridazine, pyrazine, and pyrimidine.

[15]. A compound, or a pharmaceutically acceptable salt of the compound, of [1], [2], [3], [4], [5], [6], [7], [8], [9], [10], [11], [13] or [14] above, or according to other embodiments of the invention, wherein ring B is phenyl.

[16]. A compound, or a pharmaceutically acceptable salt of the compound, of [1], [2], [3], [4], [5], [6], [7], [8], [9], [10], [11], [13] or [14] above, or according to other embodiments of the invention, wherein ring B is pyridine or pyrimidine.

[17]. A compound, or a pharmaceutically acceptable salt of the compound, of [1], [2], [3], [4], [5], [6], [7], [8], [9], [10], [11], [12], [13], [14], [15] or [16] above, or according to other embodiments of the invention, wherein n is 1.

[18]. A compound, or a pharmaceutically acceptable salt of the compound, of [1], [2], [3], [4], [5], [6], [7], [8], [9], [10], [11], [12], [13], [14], [15] or [16] above, or according to other embodiments of the invention, wherein n is 2.

[19]. A compound, or a pharmaceutically acceptable salt of the compound, of [1], [2], [3], [4], [5], [6], [7], [8], [9], [10], [11], [12], [13], [14], [15] or [16] above, or according to other embodiments of the invention, wherein n is 0.

[20]. A compound, or a pharmaceutically acceptable salt of the compound, of [1], [2], [3], [4], [5], [6], [7], [8], [9], [10], [11], [12], [13], [14], [15] or [16] above, or according to other embodiments of the invention, wherein n is 3.

[21]. A compound, or a pharmaceutically acceptable salt of the compound, of [1], [2], [3], [4], [5], [6], [7], [8], [9], [10], [11], [13], [14], [15], [16], [17], [18] or [20] above, or according to other embodiments of the invention, wherein each $J^B$ is independently selected from halogen and a $C_{1-6}$ aliphatic.

[22]. A compound, or a pharmaceutically acceptable salt of the compound, of [1], [2], [3], [4], [5], [6], [7], [8], [9], [10], [11], [13], [14], [15], [16], [17], [18], [20] or [21] above, or according to other embodiments of the invention, wherein each $J^B$ is independently selected from halogen atoms.

[23]. A compound, or a pharmaceutically acceptable salt of the compound, of [1], [2], [3], [4], [5], [6], [7], [8], [9], [10], [11], [13], [14], [15], [16], [17], [18], [20], [21] or [22] above, or according to other embodiments of the invention, wherein each $J^B$ is independently selected from fluoro or chloro.

[24]. A compound, or a pharmaceutically acceptable salt of the compound, of [1], [2], [3], [4], [5], [6], [7], [8], [9], [10], [11], [13], [14], [15], [16], [17], [18], [20], [21], [22] or [23] above, or according to other embodiments of the invention, wherein each $J^B$ is fluoro.

[25]. A compound, or a pharmaceutically acceptable salt of the compound, of [1], [2], [3], [4], [5], [6], [7], [8], [9], [10], [11], [13], [14], [15], [16], [17], [18], [20] or [21] above, or according to other embodiments of the invention, wherein each $J^B$ is a $C_{1-6}$ aliphatic.

[26]. A compound, or a pharmaceutically acceptable salt of the compound, of [1], [2], [3], [4], [5], [6], [7], [8], [9], [10], [11], [13], [14], [15], [16], [17], [18], [20], [21] or [25] above, or according to other embodiments of the invention, wherein each $J^B$ is methyl.

[27]. A compound, or a pharmaceutically acceptable salt of the compound, of [1], [2], [3], [4], [5], [6], [7], [8], [9], [10], [11], [13], [14], [15], [16], [17], [18], [20], [21], [22], [23], [24], [25] or [26] above, or according to other embodiments of the invention, wherein at least one $J^B$ is ortho to the attachment of the methylene linker between ring B and ring A.

[28]. A compound, or a pharmaceutically acceptable salt of the compound, of [1], [2], [3], [4], [5], [6], [7], [8], [9], [10], [11], [13], [14], [15], [16], [17], [18], [20] [21], [22], [23], [24], [25], [26] or [27] above, or according to other embodiments of the invention, wherein one $J^B$ is ortho to the attachment of the methylene linker between rings B and Ring A and is fluoro.

[29]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27] or [28] above, or according to other embodiments of the invention, wherein the core formed by rings C and A is selected from:

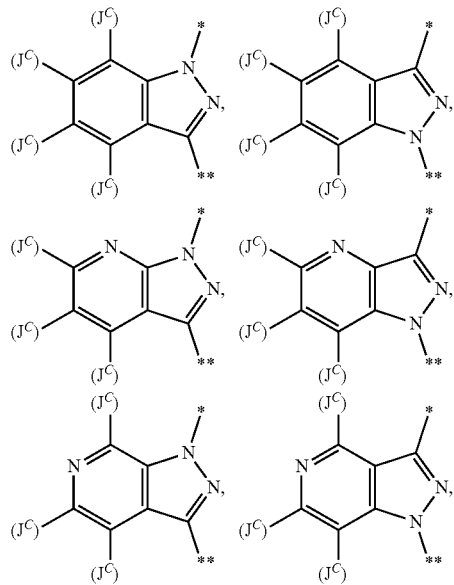

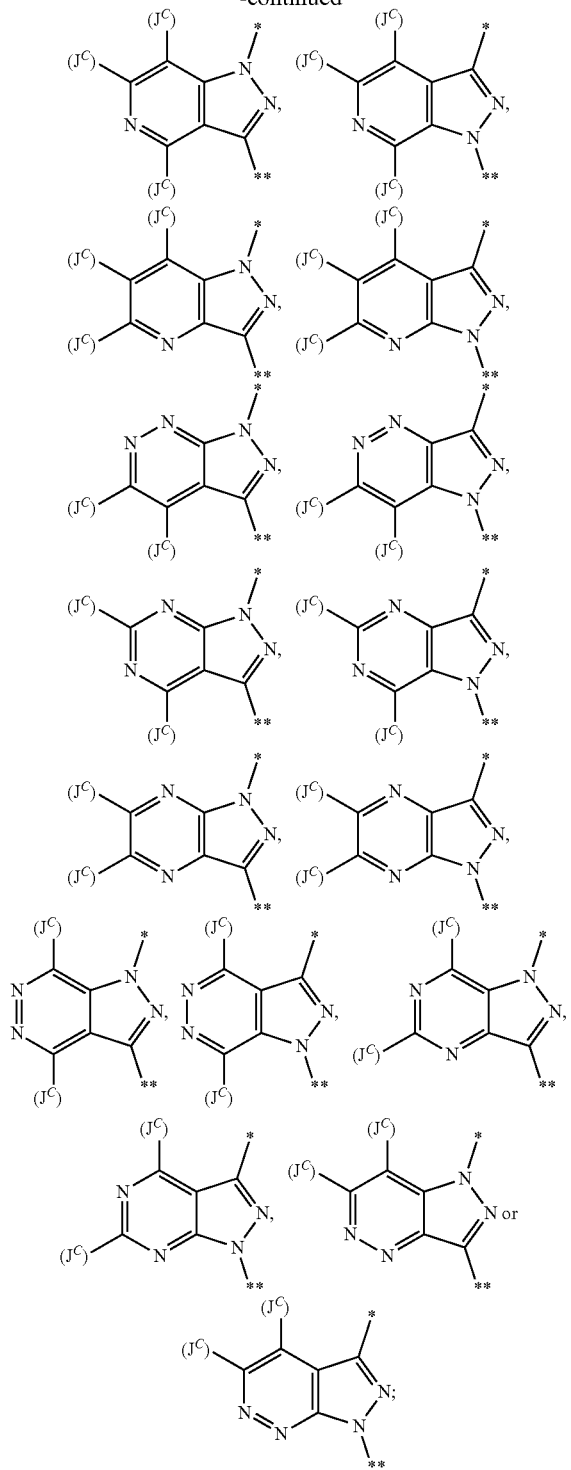

wherein the atom with a symbol * represents the attachment point to the methylene linker to W-(J$^B$)$_n$; and the atom with a symbol ** represents the point of attachment to ring D.

[30]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28] or [29] above, or according to other embodiments of the invention, wherein the core formed by rings C and A is selected from:

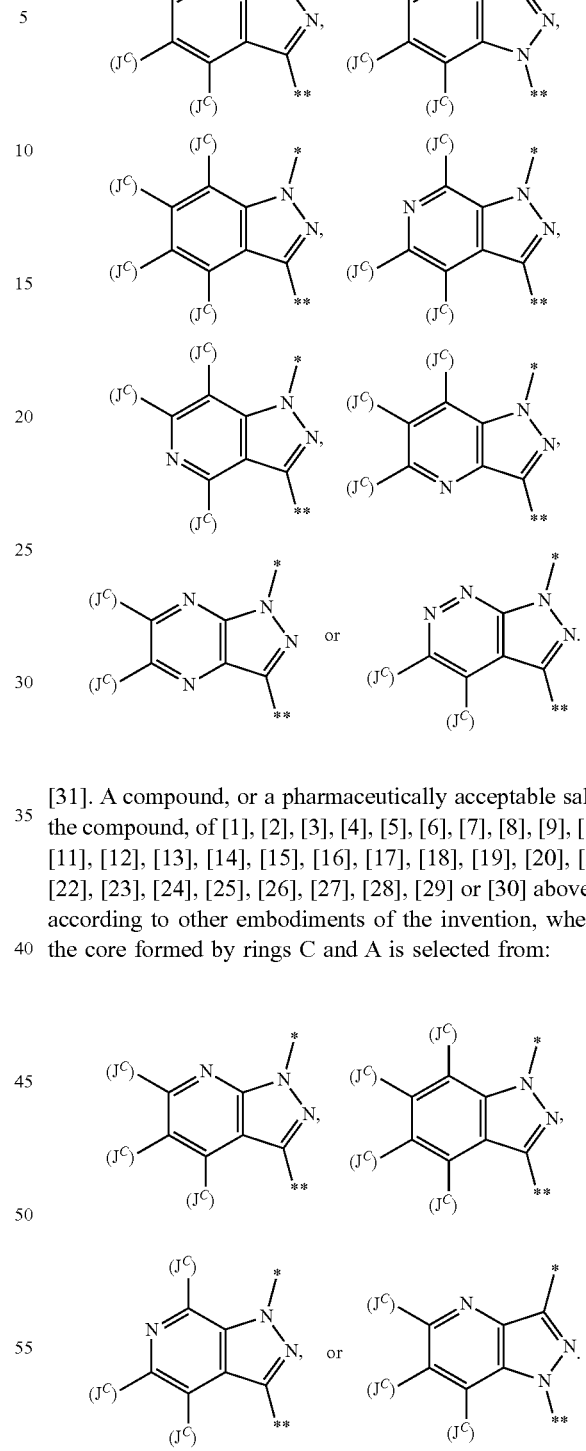

[31]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28], [29] or [30] above, or according to other embodiments of the invention, wherein the core formed by rings C and A is selected from:

[32]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28], [29], [30] or [31] above, or according to other embodiments of the invention, wherein the core formed by rings C and A is selected from:

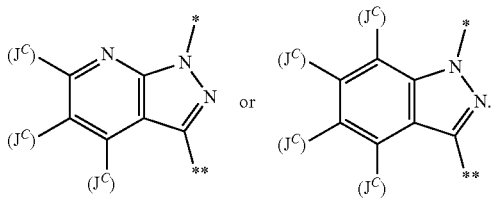

[33]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28], [29], [30] or [31] above, or according to other embodiments of the invention, wherein the core formed by rings C and A is selected from:

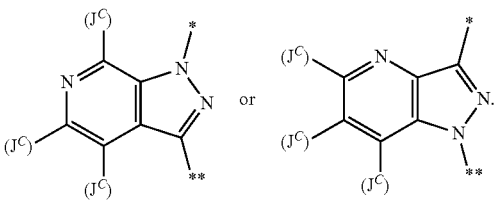

[34]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28], [29], [30], [31], [32] or [33] above, or according to other embodiments of the invention, wherein each $J^C$ is independently selected from hydrogen, halogen, or $C_{1-4}$ aliphatic.

[35]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28], [29], [30], [31], [32], [33] or [34] above, or according to other embodiments of the invention, wherein each $J^C$ is independently selected from hydrogen, fluoro, chloro, or methyl.

[36]. A compound, or a pharmaceutically acceptable salt of the compound, of [1], [2], [3], [4], [5], [6], [7], [8], [9], [10], [11], [12], [13], [14], [15], [16], [17], [18], [19], [20], [21], [22], [23], [24], [25], [26], [27], [28], [29], [30], [31], [32], [33], [34] or [35] above, or according to other embodiments of the invention, wherein the compound is selected from those listed in Table IA.

[37]. A compound selected from those listed in Table IB, or a pharmaceutically acceptable salt thereof.

[38]. A pharmaceutical composition comprising at least one pharmaceutically acceptable excipient or carrier and a compound, or a pharmaceutically acceptable salt thereof, of [1], [2], [3], [4], [5], [6], [7], [8], [9], [10], [11], [12], [13], [14], [15], [16], [17], [18], [19], [20], [21], [22], [23], [24], [25], [26], [27], [28], [29], [30], [31], [32], [33], [34], [35], [36] or [37] above, or according to other embodiments of the invention.

[39]. A method for treating a disease, health condition or disorder selected from a CNS disease, health condition or disorder, the method comprising administering to a subject in need of treatment a therapeutically effective amount of a compound, or a pharmaceutically acceptable salt thereof, of any of [1] to [37] above, or a pharmaceutical composition of [38] above, or according to other embodiments of the invention.

[40]. A method according to [39] above, or according to other embodiments of the invention, wherein the CNS disease, health condition or disorder is selected from: Alzheimer's disease, amyotrophic lateral sclerosis, Down's syndrome, dementia, vascular dementia, vascular cognitive impairment, Binswanger's dementia, cerebral autosomal-dominant arteriopathy with subcortical infarcts and leuko-encephalopathy, frontotemporal lobar degeneration or dementia, HIV-associated dementia, Lewy body dementia, pre-senile dementia, glaucoma, Huntington's disease, multiple sclerosis, multiple system atrophy, Parkinson's disease, Parkinsonism Plus, spinocerebellar ataxias, Steel-Richardson-Olszewski disease, attention deficit disorder, and attention deficit hyperactivity disorder.

[41]. A method according to [39] above, or according to other embodiments of the invention, wherein the CNS disease, health condition or disorder is selected from: traumatic penetrating head injury, traumatic brain injury, non-traumatic injury to the brain, stroke, aneurism, hypoxia, and cognitive impairment or dysfunction resulting from brain injury or neurodegenerative disorder.

[42]. A method according to [39] above, or according to other embodiments of the invention, wherein the CNS disease, health condition or disorder is selected from: a dystonia or a dyskinesia.

[43]. A method according to [39] or [42] above, or according to other embodiments of the invention, wherein said dystonia is selected from generalized, focal, segmental, sexual, intermediate, genetic/primary dystonia or acute dystonic reaction.

[44]. A method according to [39] or [42] above, or according to other embodiments of the invention, wherein said dyskinesia is selected from acute, chronic/tardive, or non-motor or levo-dopa induced dyskinesia (LID).

[45]. A method according to [39] above, or according to other embodiments of the invention, wherein the CNS disease, health condition or disorder is selected from a relative reduction in synaptic plasticity and synaptic processes.

[46]. A method according to [9] or [45] above, or according to other embodiments of the invention, wherein the CNS disease, health condition or disorder is selected from: Fragile X, Rhett's disorder, Williams syndrome, Renpenning's syndrome, an autism spectrum disorder (ASD), autism, Asperger's syndrome, pervasive development disorder or childhood disintegrative disorder.

[47]. A method according to [39] above, or according to other embodiments of the invention, wherein the CNS disease, health condition or disorder is neuropathic pain.

[48]. A method according to [39] above, or according to other embodiments of the invention, wherein the CNS disease, health condition or disorder is a psychiatric, mental, mood or affective disorder.

[49]. A method according to [39] or [48] above, or according to other embodiments of the invention, wherein the psychiatric, mental, mood or affective disorder is selected from: a bipolar disorder, schizophrenia, general psychosis, drug-induced psychosis, a delusional disorder, a schizoaffective disorder, obsessive compulsive disorder (OCD), a depressive disorder, an anxiety disorder, a panic disorder, or post-traumatic stress disorder (PTSD).

[50]. A method according to [39] above, or according to other embodiments of the invention, wherein the CNS disease, health condition or disorder is selected from: chemo brain, levo-dopa induced addictive behavior, alcoholism, narcotic dependence or substance abuse.

[51]. A method according to [39] above, or according to other embodiments of the invention, wherein said CNS disease, health condition or disorder is selected from: Alzheimer's disease or pre-Alzheimer's disease, mild to moderate Alzheimer's disease or moderate to severe Alzheimer's disease.

[52]. A method according to [39] above, or according to other embodiments of the invention, wherein said CNS disease, health condition or disorder is selected from: dementia, vascular dementia or cerebral vasospasm.

[53]. A method according to [39] above, or according to other embodiments of the invention, wherein said CNS disease, health condition or disorder is selected from Huntington's disease or Huntington's chorea.

[54]. A method according to [39] above, or according to other embodiments of the invention, wherein said CNS disease, health condition or disorder is selected from Parkinson's disease or Parkinsonism Plus.

[55]. A method according to [39] above, or according to other embodiments of the invention, wherein said CNS disease, health condition or disorder is mild cognitive impairment.

[56]. A method according to [39] above, or according to other embodiments of the invention, wherein said CNS disease, health condition or disorder is cerebral autosomal-dominant arteriopathy with subcortical infarcts and leukoencephalopathy (CADASIL).

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A compound of Formula IIA, Formula IIB or Formula IIC, or a pharmaceutically acceptable salt thereof:

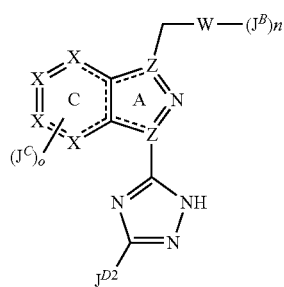

Formula IIA

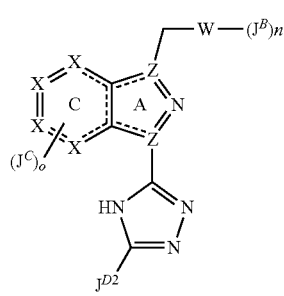

Formula IIB

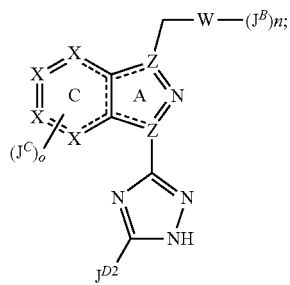

Formula IIC wherein
rings A and C constitute the core of the molecule having the following structure:

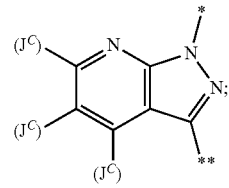

wherein the atom with a symbol * represents the attachment point to the methylene linker to W-($J^B$)$_n$; and the atom with a symbol ** represents the point of attachment to ring D;

each $J^C$ is a substituent on a carbon atom independently selected from hydrogen, halogen, or $C_{1-4}$ aliphatic;

W is either:
  i) absent, and $J^B$ is connected directly to the methylene group linked to the core; n is 1; and $J^B$ is a $C_{1-7}$ alkyl chain optionally substituted by up to 9 instances of fluorine; or
  ii) a ring B selected from phenyl, pyridine and pyrimidine wherein n is 0 or an integer selected from 1, 2 or 3;

each $J^B$ is independently selected from halogen, —CN, a $C_{1-6}$ aliphatic, —$OR^B$ or a $C_{3-8}$ cycloaliphatic ring; wherein each said $C_{1-6}$ aliphatic and each said $C_{3-8}$ cycloaliphatic ring is optionally and independently substituted with up to 3 instances of $R^3$;

each $R^B$ is independently selected from a methyl, propyl, butyl, isopropyl, isobutyl or a $C_{3-8}$ cycloaliphatic ring; wherein each of said $R^B$ is optionally and independently substituted with up to 3 instances of $R^{3a}$;

each $R^3$ and each $R^{3a}$ is independently selected in each instance from halogen, —CN, $C_{1-4}$ alkyl, $C_{1-4}$ haloalkyl, —O($C_{1-4}$ alkyl) or —O($C_{1-4}$ haloalkyl);

$J^{D2}$ is hydrogen, or a substituent selected from halogen, —CN, —$NO_2$, —$OR^{D1}$, —C(O)$R^D$, —N($R^D$)C(O)$R^D$, —N($R^D$)C(O)N($R^D$)$_2$, —OC(O)N($R^D$)$_2$, a $C_{1-6}$ aliphatic, a $C_{3-8}$ cycloaliphatic ring, a 4 to 8-membered heterocyclic ring or a 5 or 6-membered heteroaryl ring; wherein said 4 to 8-membered heterocyclic ring and said 5 or 6-membered heteroaryl ring contains between 1 and 3 heteroatoms independently selected from O, N or S; and wherein said $C_{1-6}$ aliphatic, said $C_{3-8}$ cycloaliphatic ring, said 4 to 8-membered heterocyclic ring and said 5 or 6-membered heteroaryl ring is independently substituted with up to 5 instances of $R^5$;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring and each said 5 to 6-membered heteroaryl ring is optionally and independently substituted with up to 5 instances of $R^5$; and wherein each said phenyl ring is optionally and independently substituted with up to 5 instances of $R^{5a}$;

$R^{D1}$ is selected from a $C_{1-6}$ aliphatic, —($C_{1-6}$ aliphatic)-$R^f$, a $C_{3-8}$ cycloaliphatic ring, a 4 to 8-membered heterocyclic ring, a phenyl ring or a 5 to 6-membered heteroaryl ring; wherein said 4 to 8-membered heterocyclic ring and said 5 to 6-membered heteroaryl ring contains between 1 and 3 heteroatoms independently selected from O, N or S; and wherein said $C_{1-6}$ aliphatic, said $C_{1-6}$ aliphatic portion of the —($C_{1-6}$ aliphatic)-$R^f$ moiety, said $C_{3-8}$ cycloaliphatic ring, said 4 to 8-membered heterocyclic ring and said 5 to 6-membered heteroaryl ring is optionally and independently substituted with up to 5 instances of $R^5$; wherein said phenyl ring is optionally and independently substituted with up to 5 instances of $R^{5a}$;

each $R^f$ is independently selected from a $C_{3-8}$ cycloaliphatic ring, a 4 to 8-membered heterocyclic ring, a phenyl ring or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{3-8}$ cycloaliphatic ring, each said 4 to 8-membered heterocyclic ring and each said 5 to 6-membered heteroaryl ring is optionally and independently substituted by up to 5 instances of $R^5$; and wherein each said phenyl is optionally and independently substituted by up to 5 instances of $R^{5a}$;

each $R^5$ is independently selected from halogen, —CN, $C_{1-6}$ aliphatic, —($C_{1-6}$ alkyl)-$R^6$, —N($R^6$)C(O)$R^6$, —N($R^6$)C(O)O$R^6$, —N($R^6$)C(O)N($R^6$)$_2$, a $C_{3-8}$ cycloalkyl ring, a 4 to 8-membered heterocyclic ring, a 5 or 6-membered heteroaryl ring, phenyl, benzyl; wherein each of said 5 or 6-membered heteroaryl ring or 4 to 8-membered heterocyclic ring contains up to 3 ring heteroatoms independently selected from N, O and S; and wherein each of said $C_{1-6}$ aliphatic, each said $C_{1-6}$ alkyl portion of the —($C_{1-6}$ alkyl)-$R^6$ moiety, each said $C_{3-8}$ cycloalkyl ring, each said 5 or 6-membered heteroaryl ring and each said 4 to 8-membered heterocyclic ring, is independently substituted with 1 to 3 instances of halogen, $C_{1-4}$ alkyl, —OH, —NH$_2$, —NH($C_{1-4}$ alkyl), —N($C_{1-4}$ alkyl)$_2$, —CN, —CONH$_2$, —O($C_{1-4}$ alkyl), —O($C_{1-4}$ haloalkyl); wherein each said benzyl or phenyl is optionally and independently substituted with up to 3 instances of halogen, $C_{1-4}$ alkyl, —NH$_2$, —NH($C_{1-4}$ alkyl), —N($C_{1-4}$ alkyl)$_2$, —CN, —CONH$_2$, —O($C_{1-4}$ alkyl), —O($C_{1-4}$ haloalkyl);

each $R^{5a}$ is independently selected from halogen, —CN, $C_{1-6}$ aliphatic, —($C_{1-6}$ alkyl)-$R^6$, —O$R^{6a}$, —CO$R^6$, —C(O)N($R^6$)$_2$, —N($R^6$)C(O)$R^6$, —N($R^6$)C(O)O$R^6$, —N($R^6$)C(O)N($R^6$)$_2$, —N($R^6$)$_2$, a $C_{3-8}$ cycloalkyl ring, a 4 to 8-membered heterocyclic ring, a 5 or 6-membered heteroaryl ring, phenyl, benzyl or an oxo group; wherein each of said 5 or 6-membered heteroaryl ring and each of said 4 to 8-membered heterocyclic ring contains up to 3 ring heteroatoms independently selected from N, O and S; and wherein each of said $C_{1-6}$ aliphatic, each of said $C_{1-6}$ alkyl portion of the —($C_{1-6}$ alkyl)-$R^6$ moiety, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —CONH$_2$, —O($C_{1-4}$ alkyl), —O($C_{1-4}$ haloalkyl) or oxo; wherein if two instances of a substituent on $R^{5a}$ are a) oxo and —OH or b) oxo and —O($C_{1-4}$ alkyl) or c) oxo and —O($C_{1-4}$ haloalkyl), they are not substituents on the same carbon atom; and wherein each of said benzyl and each of said phenyl is optionally and independently substituted with up to 3 instances of halogen, $C_{1-4}$ alkyl, $C_{1-4}$ haloalkyl —NH$_2$, —NH($C_{1-4}$ alkyl), —N($C_{1-4}$ alkyl)$_2$, —CN, —CONH$_2$, —O($C_{1-4}$ alkyl) or —O($C_{1-4}$ haloalkyl);

each $R^6$ is independently selected from hydrogen, a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring or 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo; wherein if two instances of a substituent on $R^6$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, $C_{1-4}$ haloalkyl, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo;

each $R^{6a}$ is independently selected from a $C_{1-6}$ aliphatic, phenyl, benzyl, a $C_{3-8}$ cycloalkyl ring, a 4 to 8-membered heterocyclic ring or a 5 or 6-membered heteroaryl ring; wherein each of said 5 or 6-membered heteroaryl ring and each of said 4 to 8-membered heterocyclic ring contains up to 3 ring heteroatoms independently selected from N, O and S; wherein each of said $C_{1-6}$ aliphatic, each of said $C_{3-8}$ cycloalkyl ring, each of said 4 to 8-membered heterocyclic ring and each of said 5 or 6-membered heteroaryl ring is optionally and independently substituted with up to 3 instances of halogen, $C_{1-4}$ alkyl, $C_{1-4}$ haloalkyl —OH, —NH$_2$, —NH($C_{1-4}$ alkyl), —N($C_{1-4}$ alkyl)$_2$, —CN, —C(O)NH$_2$, —O($C_{1-4}$ alkyl), —O($C_{1-4}$ haloalkyl) or oxo; wherein if two instances of $R^{6a}$ are a) oxo and —OH or b) oxo and —O($C_{1-4}$ alkyl) or c) oxo and —O($C_{1-4}$ haloalkyl), they are not substituents on the same carbon atom; wherein each of said phenyl and each of said benzyl is optionally and independently substituted with up to 3 instances of halogen, $C_{1-4}$ alkyl, C$_{1-4}$ haloalkyl, —NH$_2$, —NH(C$_{1-4}$ alkyl), —N(C$_{1-4}$ alkyl)$_2$, —CN, —C(O)NH$_2$, —O(C$_{1-4}$ alkyl), —O(C$_{1-4}$ haloalkyl) or oxo;

provided the compound is not one of the two depicted below, or any of their tautomers:

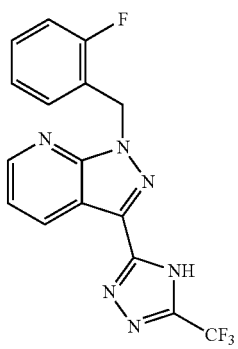 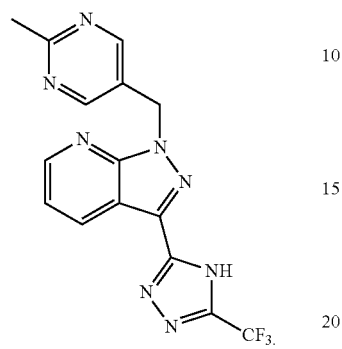

2. The compound according to claim 1, or a pharmaceutically acceptable salt thereof, wherein J$^{D2}$ is selected from hydrogen, halogen, or —CF$_3$.

3. The compound according to claim 1, or a pharmaceutically acceptable salt thereof, wherein W is absent, and J$^B$ is connected directly to the methylene group linked to the core; n is 1; and J$^B$ is a C$_{1-7}$ alkyl chain optionally substituted by up to 9 instances of fluorine.

4. The compound according to claim 1, wherein J$^{D2}$ is halogen, or a C$_{1-6}$ aliphatic; and wherein said C$_{1-6}$ aliphatic is independently substituted with 1 to 5 instances of R$^5$.

5. The compound according to claim 4, wherein R$^5$ is halogen.

6. The compound according to claim 1, or a pharmaceutically acceptable salt thereof, wherein J$^{D2}$ is selected from halogen or —CF$_3$.

7. The compound according to claim 1, or a pharmaceutically acceptable salt thereof, wherein W is a ring B selected from phenyl, pyridine and pyrimidine, wherein n is 0 or an integer selected from 1, 2 or 3.

8. A compound, or a pharmaceutically acceptable salt thereof, wherein said compound is selected from those listed in the table below:

TABLE IA

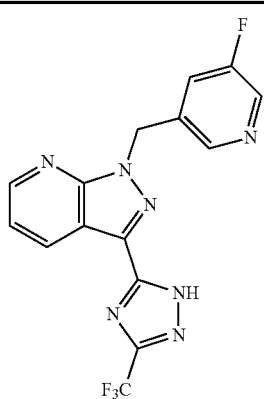

I-1

TABLE IA-continued

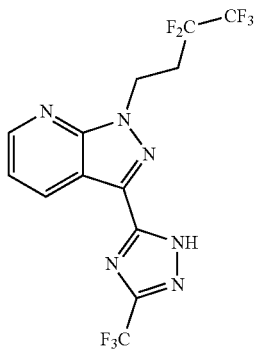 [SMILES: FC(F)(F)c1n[nH]c(-c2nn(CCC(F)(F)C(F)(F)F)c3ncccc23)n1]

I-2

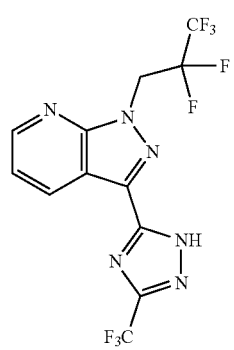 [SMILES: FC(F)(F)c1n[nH]c(-c2nn(CC(F)(F)C(F)(F)F)c3ncccc23)n1]

I-19

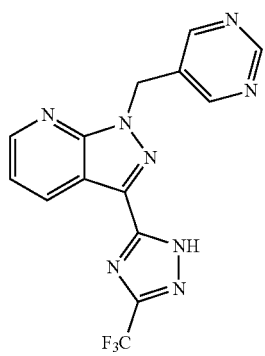 [SMILES: FC(F)(F)c1n[nH]c(-c2nn(Cc3cncnc3)c3ncccc23)n1]

I-4

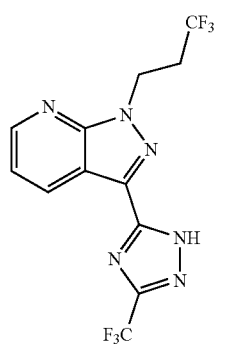 [SMILES: FC(F)(F)CCn1nc(-c2nc(C(F)(F)F)n[nH]2)c2cccnc21]

I-7

TABLE IA-continued
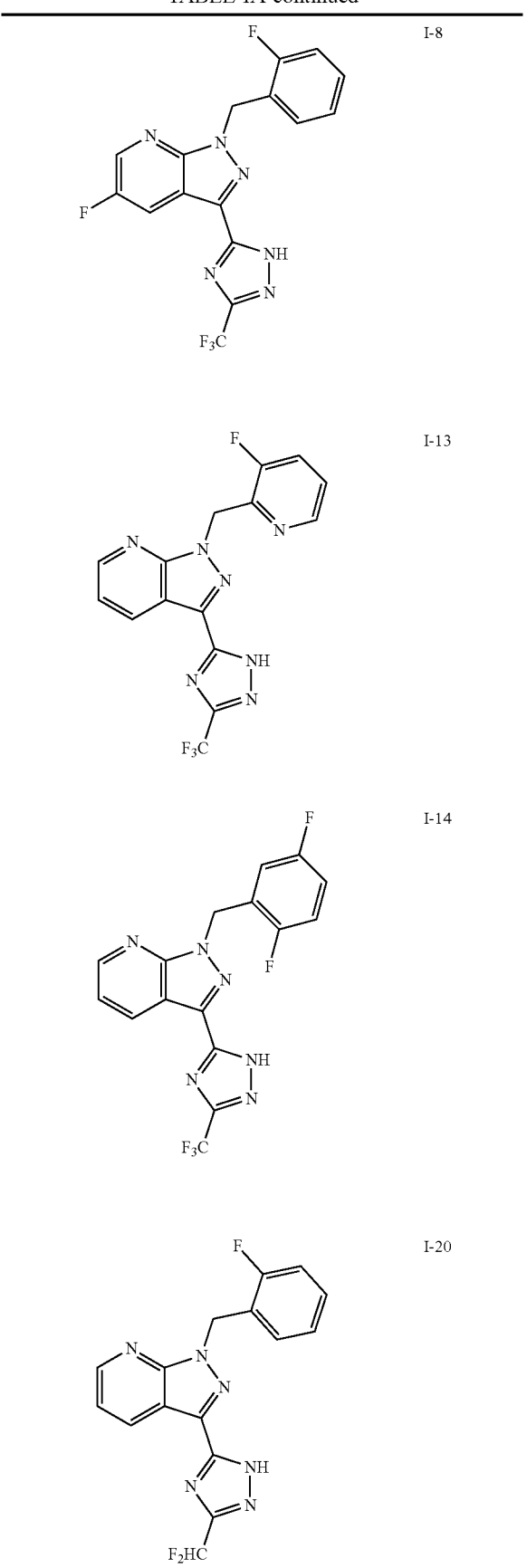
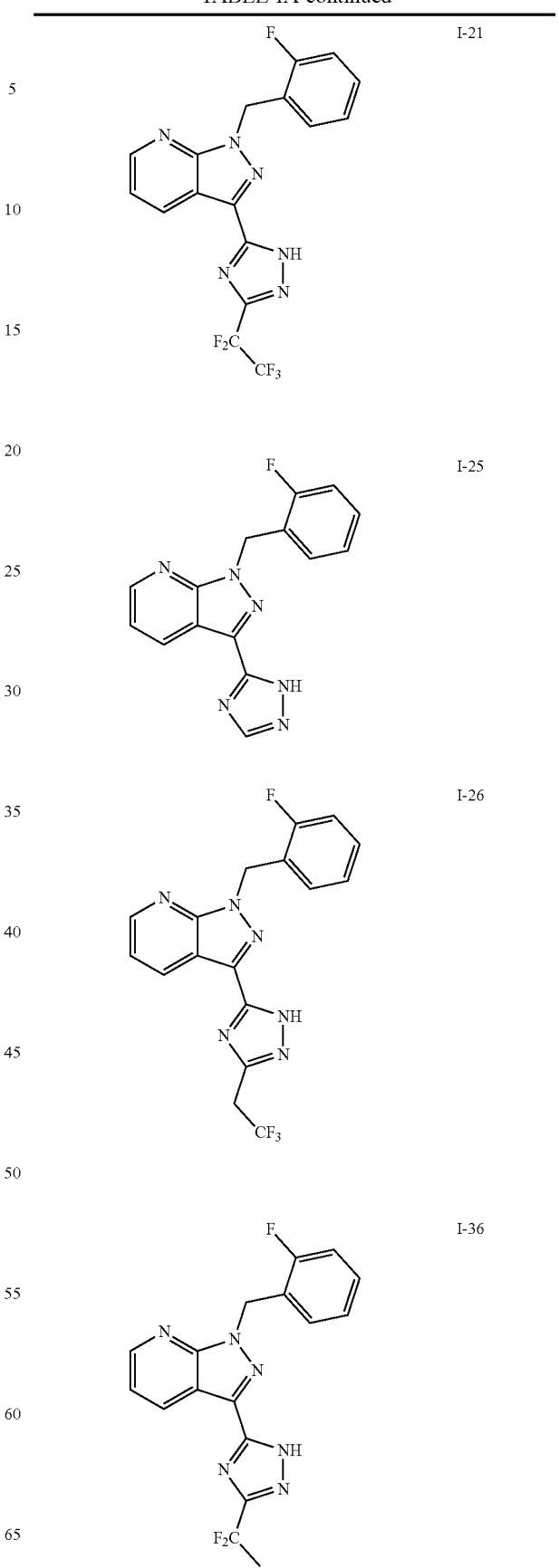

TABLE IA-continued
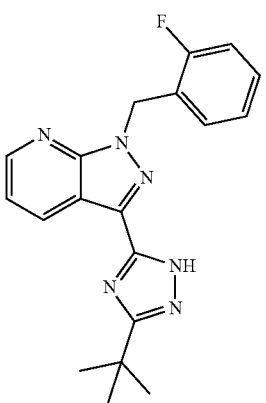 [SMILES: CC(C)(C)c1n[nH]c(-c2nn(Cc3ccccc3F)c3ncccc23)n1]
I-37
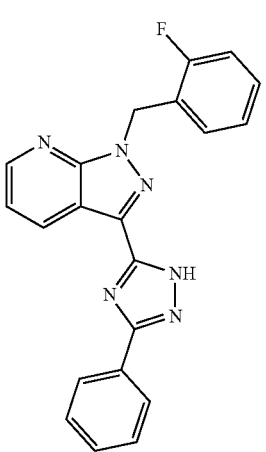 [SMILES: Fc1ccccc1Cn1nc(-c2nc(-c3ccccc3)n[nH]2)c2cccnc21]
I-39
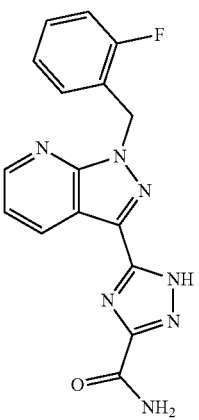 [SMILES: NC(=O)c1n[nH]c(-c2nn(Cc3ccccc3F)c3ncccc23)n1]
I-40
TABLE IA-continued
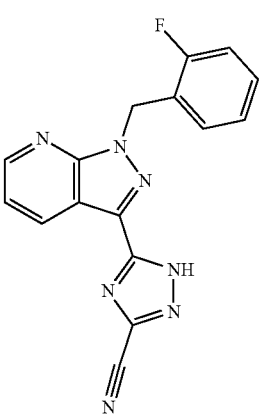 [SMILES: N#Cc1n[nH]c(-c2nn(Cc3ccccc3F)c3ncccc23)n1]
I-41
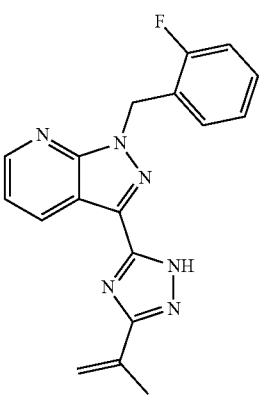 [SMILES: C=C(C)c1n[nH]c(-c2nn(Cc3ccccc3F)c3ncccc23)n1]
I-55
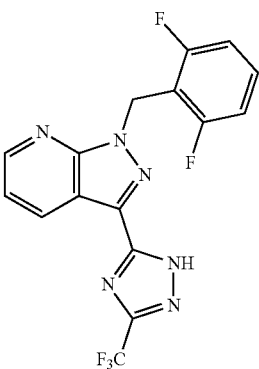 [SMILES: Fc1cccc(F)c1Cn1nc(-c2nc(C(F)(F)F)n[nH]2)c2cccnc21]
I-42
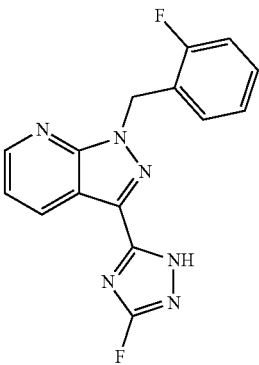 [SMILES: Fc1n[nH]c(-c2nn(Cc3ccccc3F)c3ncccc23)n1]
I-45

TABLE IA-continued
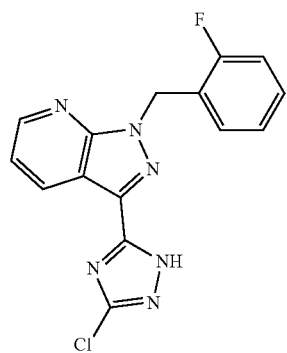 [SMILES: Fc1ccccc1Cn1nc(-c2nc(Cl)n[nH]2)c2cccnc21]
I-47
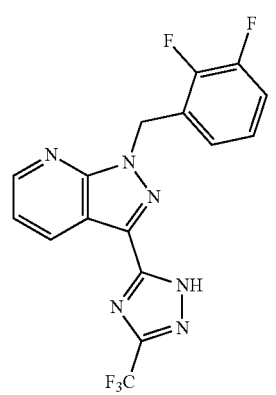 [SMILES: Fc1cccc(Cn2nc(-c3nc(C(F)(F)F)n[nH]3)c3cccnc32)c1F]
I-48
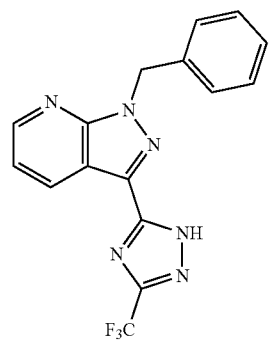 [SMILES: FC(F)(F)c1n[nH]c(-c2nn(Cc3ccccc3)c3ncccc23)n1]
I-49
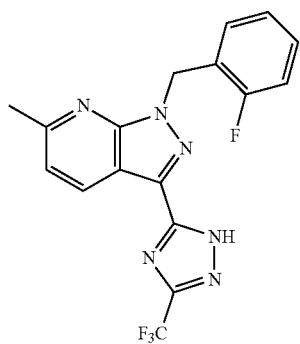 [SMILES: Cc1ccc2c(-c3nc(C(F)(F)F)n[nH]3)nn(Cc3ccccc3F)c2n1]
I-50
TABLE IA-continued
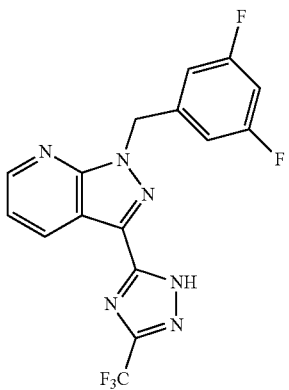 [SMILES: Fc1cc(F)cc(Cn2nc(-c3nc(C(F)(F)F)n[nH]3)c3cccnc32)c1]
I-51
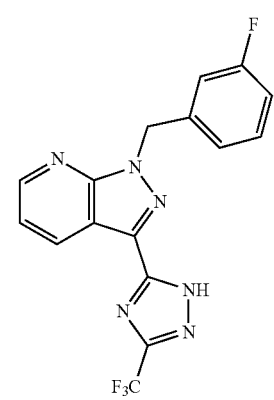 [SMILES: Fc1cccc(Cn2nc(-c3nc(C(F)(F)F)n[nH]3)c3cccnc32)c1]
I-52
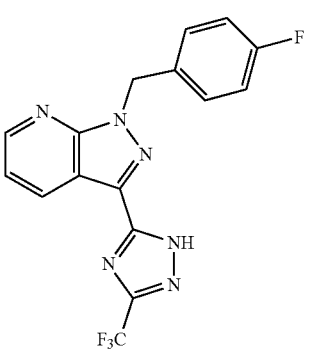 [SMILES: Fc1ccc(Cn2nc(-c3nc(C(F)(F)F)n[nH]3)c3cccnc32)cc1]
I-53
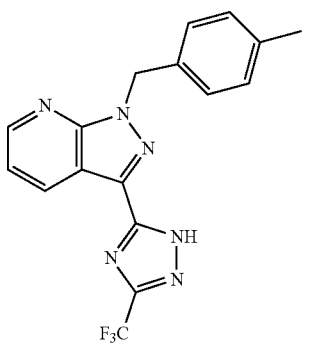 [SMILES: Cc1ccc(Cn2nc(-c3nc(C(F)(F)F)n[nH]3)c3cccnc32)cc1]
I-54

TABLE IA-continued
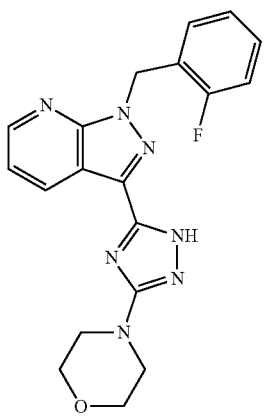 [SMILES: Fc1ccccc1Cn1nc(-c2nc(N3CCOCC3)n[nH]2)c2cccnc21]
I-57
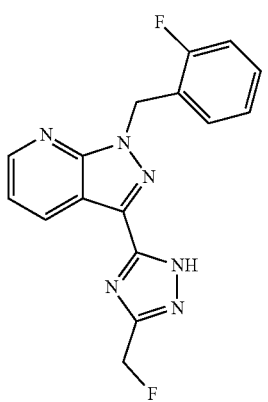 [SMILES: FCc1n[nH]c(-c2nn(Cc3ccccc3F)c3ncccc23)n1]
I-58
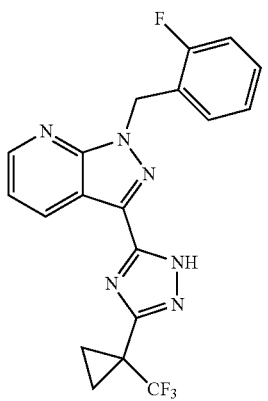 [SMILES: Fc1ccccc1Cn1nc(-c2nc(C3(C(F)(F)F)CC3)n[nH]2)c2cccnc21]
I-59
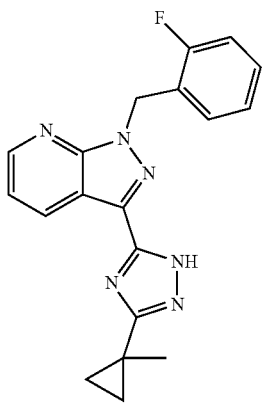 [SMILES: CC1(c2n[nH]c(-c3nn(Cc4ccccc4F)c4ncccc34)n2)CC1]
I-63
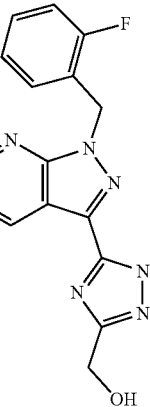
I-64
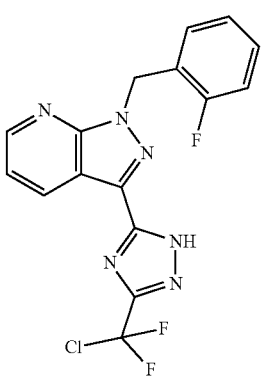 [SMILES: Fc1ccccc1Cn1nc(-c2nc(C(F)(F)Cl)n[nH]2)c2cccnc21]
I-65
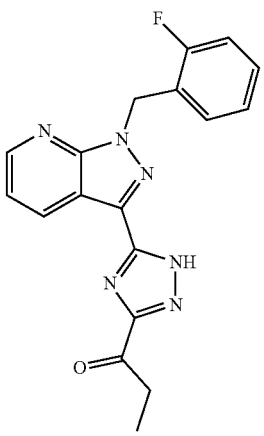 [SMILES: CCC(=O)c1n[nH]c(-c2nn(Cc3ccccc3F)c3ncccc23)n1]
I-66
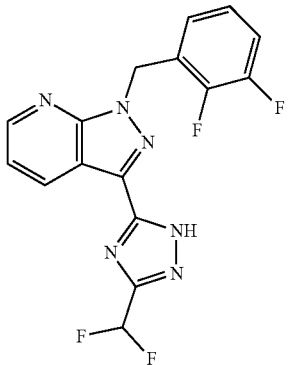 [SMILES: Fc1cccc(Cn2nc(-c3nc(C(F)F)n[nH]3)c3cccnc32)c1F]
I-67

TABLE IA-continued
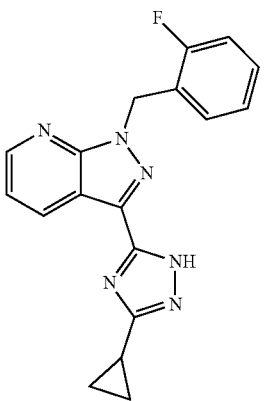 [SMILES: Fc1ccccc1Cn1nc(-c2nc(C3CC3)n[nH]2)c2cccnc21]
I-68
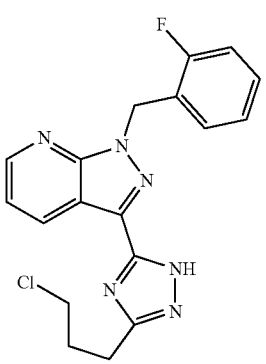 [SMILES: Fc1ccccc1Cn1nc(-c2nc(CCCCl)n[nH]2)c2cccnc21]
I-69
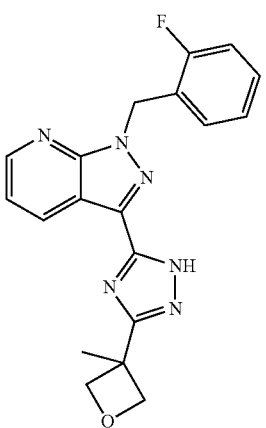 [SMILES: CC1(c2n[nH]c(-c3nn(Cc4ccccc4F)c4ncccc34)n2)COC1]
I-70
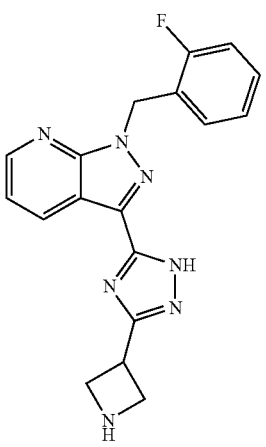 [SMILES: Fc1ccccc1Cn1nc(-c2nc(C3CNC3)n[nH]2)c2cccnc21]
I-73
TABLE IA-continued
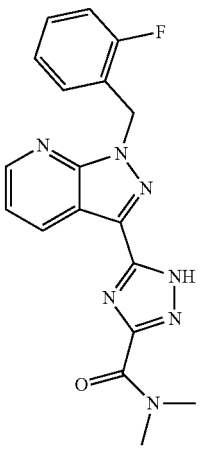 [SMILES: CN(C)C(=O)c1n[nH]c(-c2nn(Cc3ccccc3F)c3ncccc23)n1]
I-74
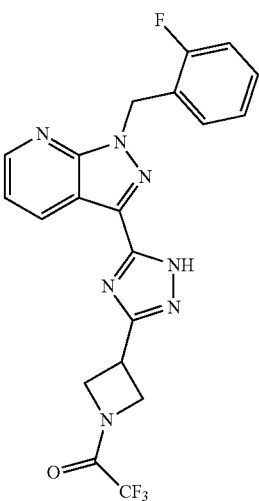 [SMILES: O=C(N1CC(c2n[nH]c(-c3nn(Cc4ccccc4F)c4ncccc34)n2)C1)C(F)(F)F]
I-75
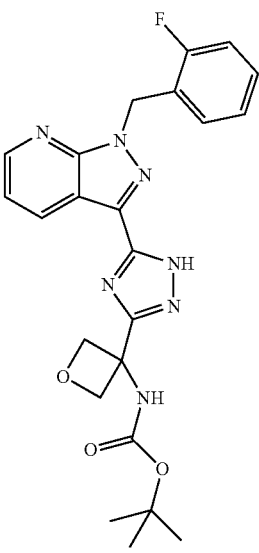 [SMILES: CC(C)(C)OC(=O)NC1(c2n[nH]c(-c3nn(Cc4ccccc4F)c4ncccc34)n2)COC1]
I-76

TABLE IA-continued
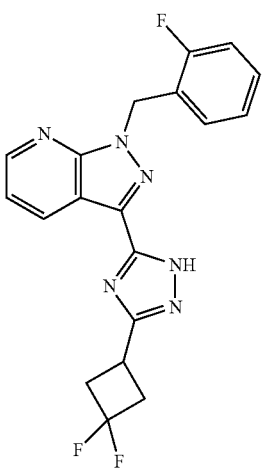 [SMILES: Fc1ccccc1Cn1nc(-c2nc(C3CC(F)(F)C3)n[nH]2)c2cccnc21]
I-77
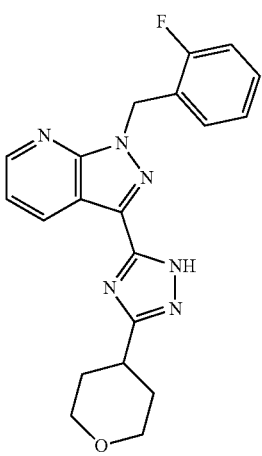 [SMILES: Fc1ccccc1Cn1nc(-c2nc(C3CCOCC3)n[nH]2)c2cccnc21]
I-78
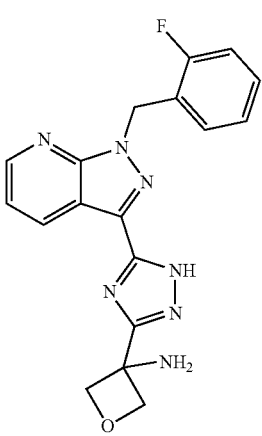 [SMILES: NC1(c2n[nH]c(-c3nn(Cc4ccccc4F)c4ncccc34)n2)COC1]
I-79
TABLE IA-continued
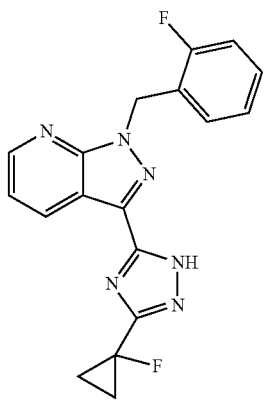 [SMILES: Fc1ccccc1Cn1nc(-c2nc(C3(F)CC3)n[nH]2)c2cccnc21]
I-80
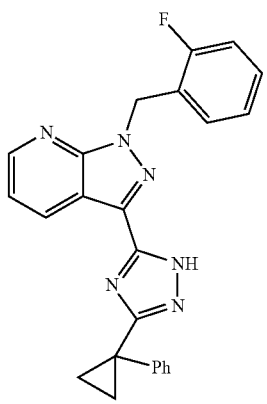 [SMILES: Fc1ccccc1Cn1nc(-c2nc(C3(c4ccccc4)CC3)n[nH]2)c2cccnc21]
I-81
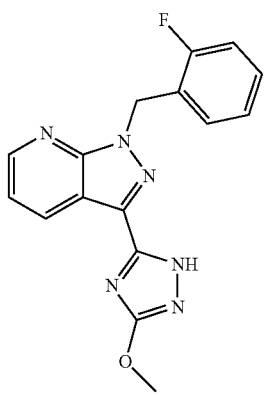 [SMILES: COc1n[nH]c(-c2nn(Cc3ccccc3F)c3ncccc23)n1]
I-82

TABLE IA-continued
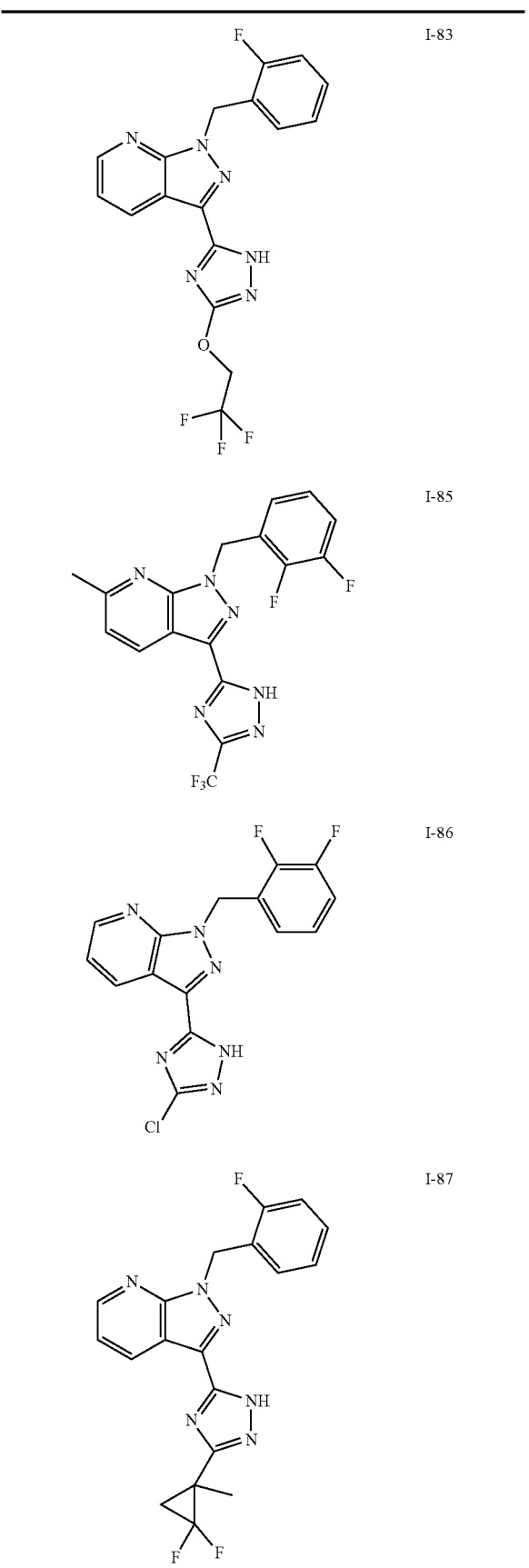
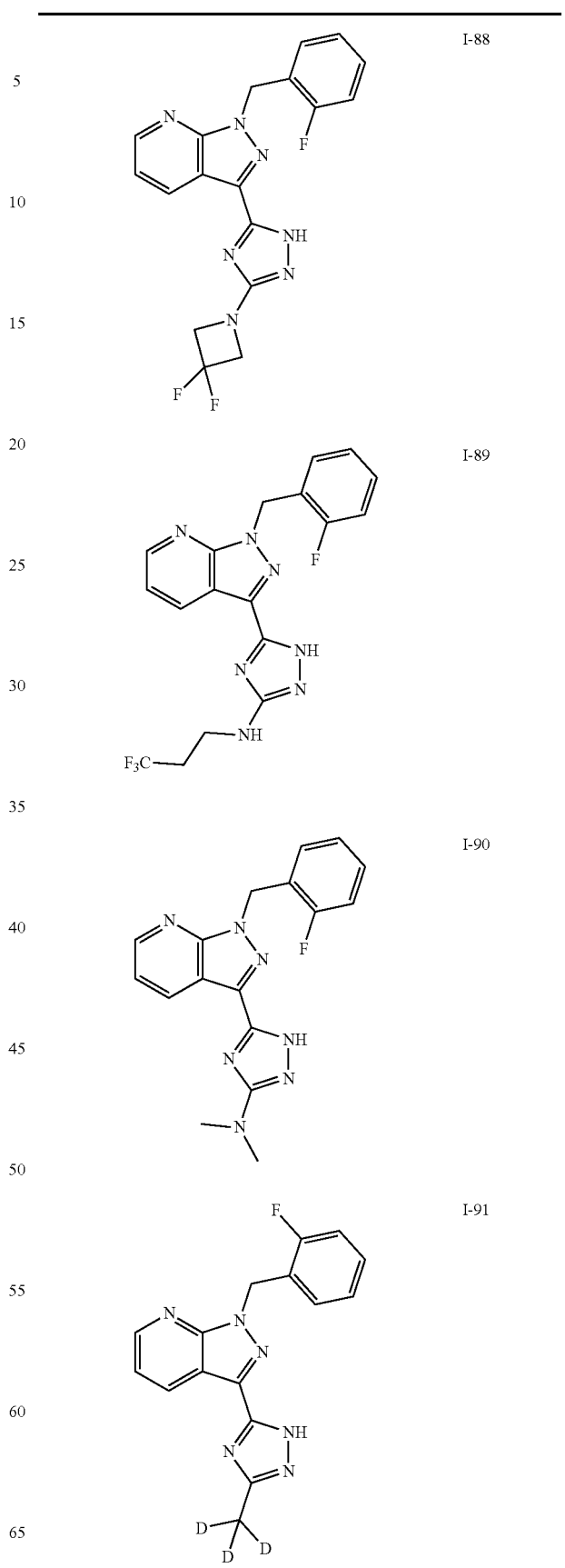

TABLE IA-continued
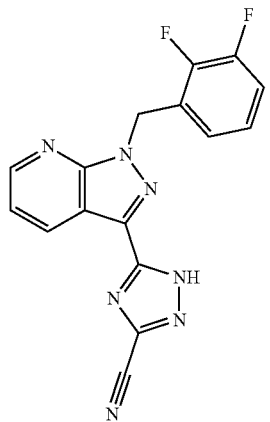 [SMILES: N#Cc1n[nH]c(-c2nn(Cc3cccc(F)c3F)c3ncccc23)n1]
I-92
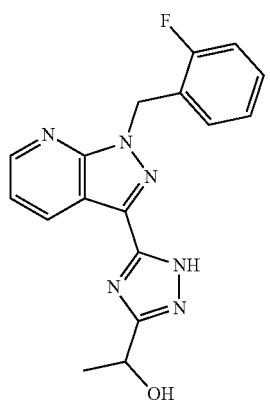 [SMILES: CC(O)c1n[nH]c(-c2nn(Cc3ccccc3F)c3ncccc23)n1]
I-107
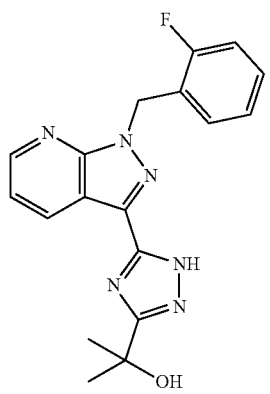 [SMILES: CC(C)(O)c1n[nH]c(-c2nn(Cc3ccccc3F)c3ncccc23)n1]
I-94
TABLE IA-continued
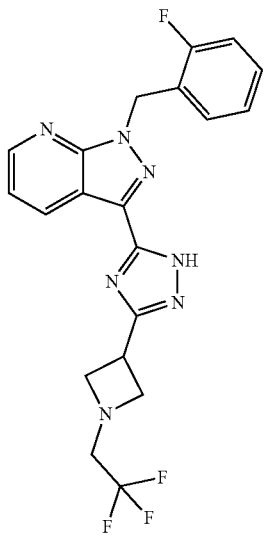 [SMILES: Fc1ccccc1Cn1nc(-c2nc(C3CN(CC(F)(F)F)C3)n[nH]2)c2cccnc21]
I-95
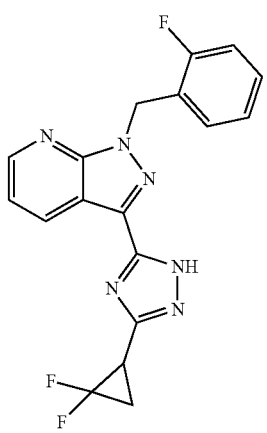 [SMILES: Fc1ccccc1Cn1nc(-c2nc(C3CC3(F)F)n[nH]2)c2cccnc21]
I-96
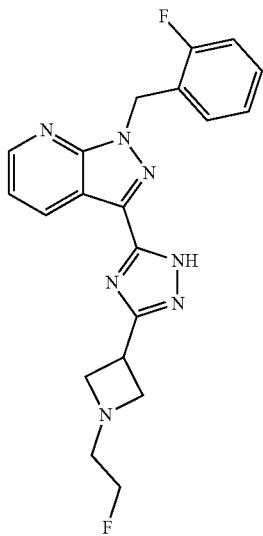 [SMILES: FCCN1CC(c2n[nH]c(-c3nn(Cc4ccccc4F)c4ncccc34)n2)C1]
I-97

TABLE IA-continued
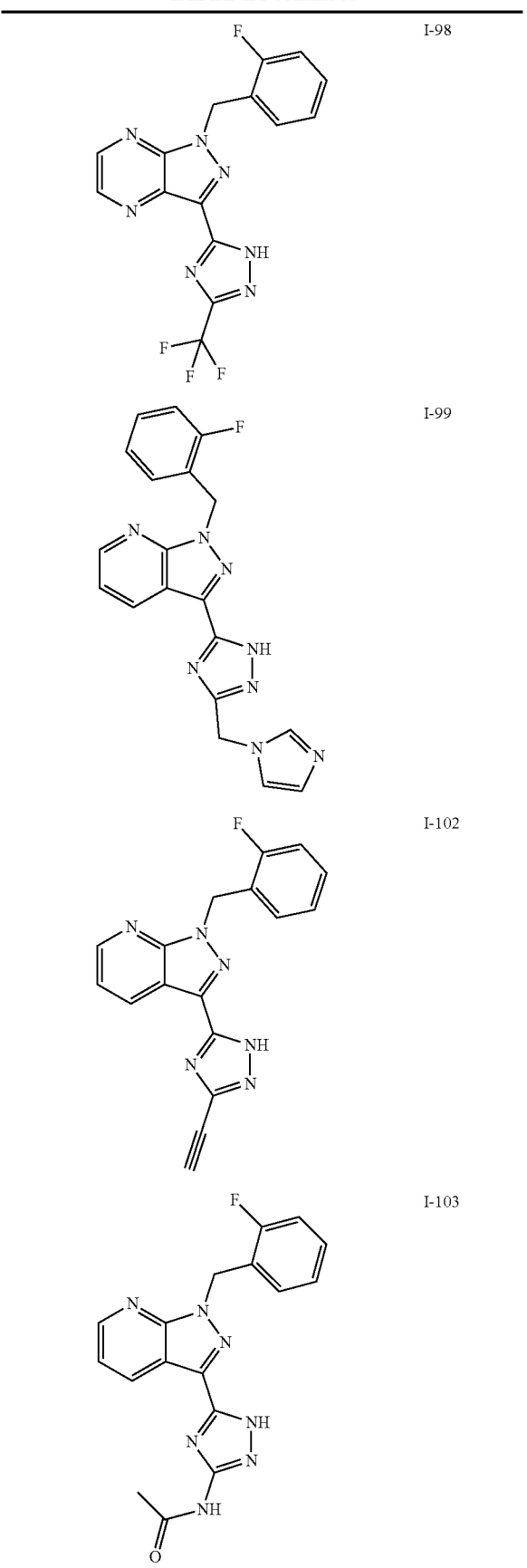
I-98
I-99
I-102
I-103
TABLE IA-continued
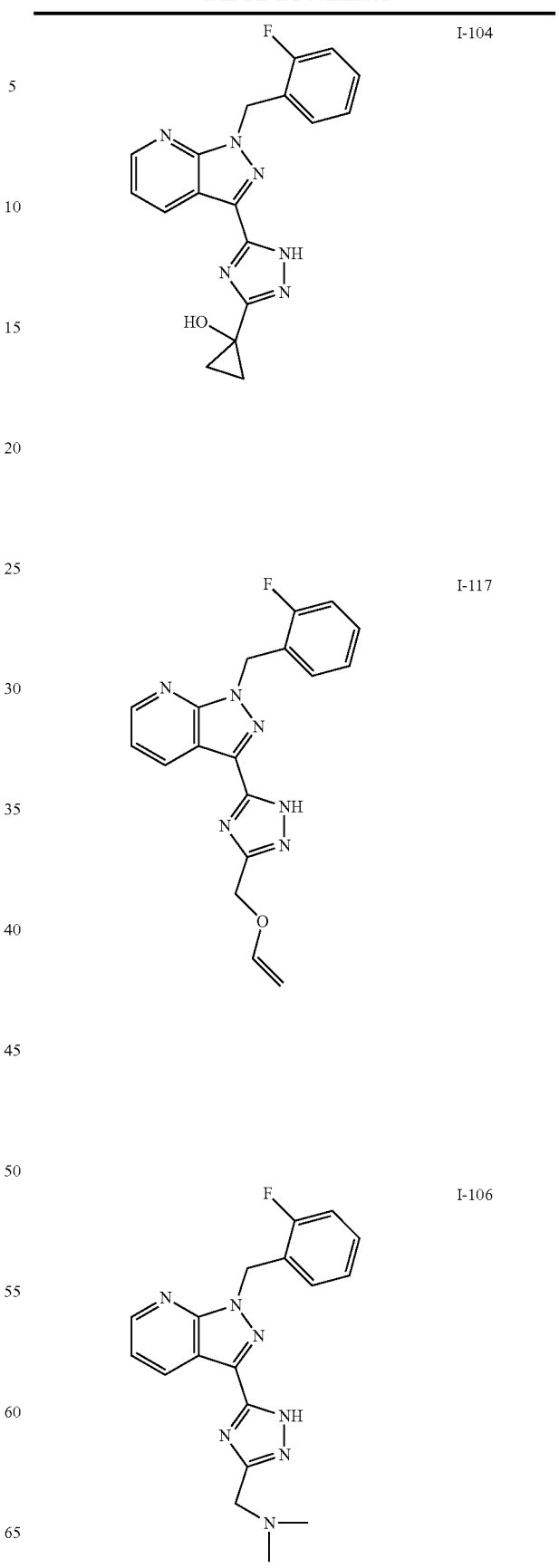
I-104
I-117
I-106

TABLE IA-continued
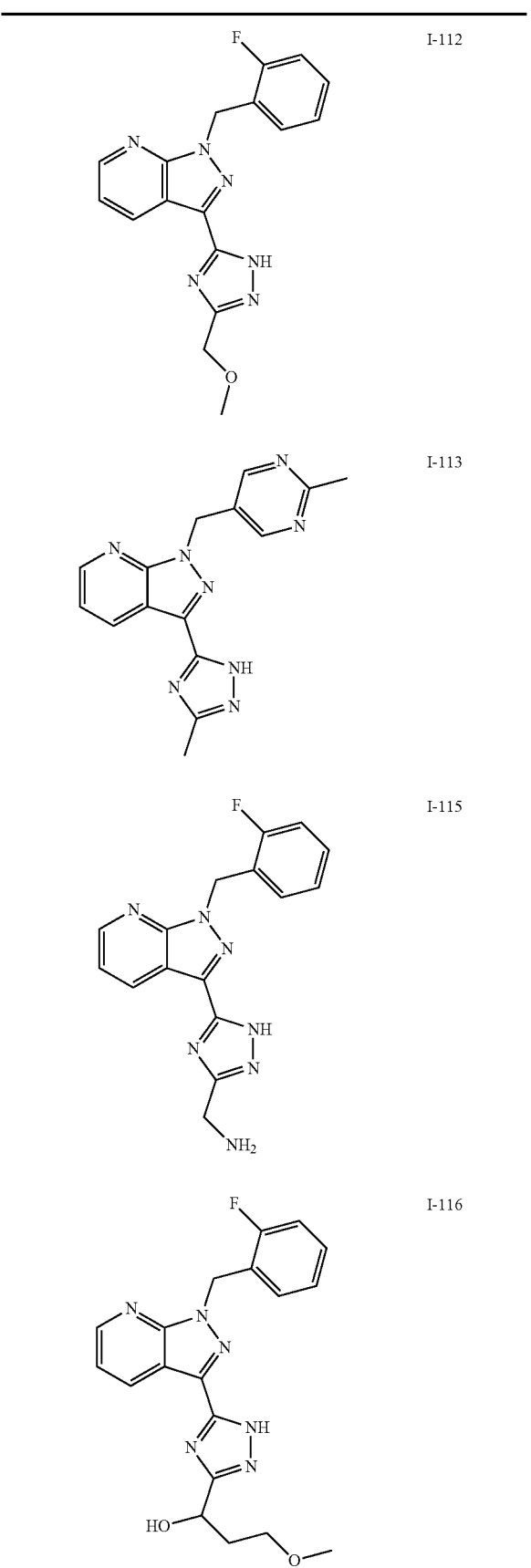
TABLE IA-continued
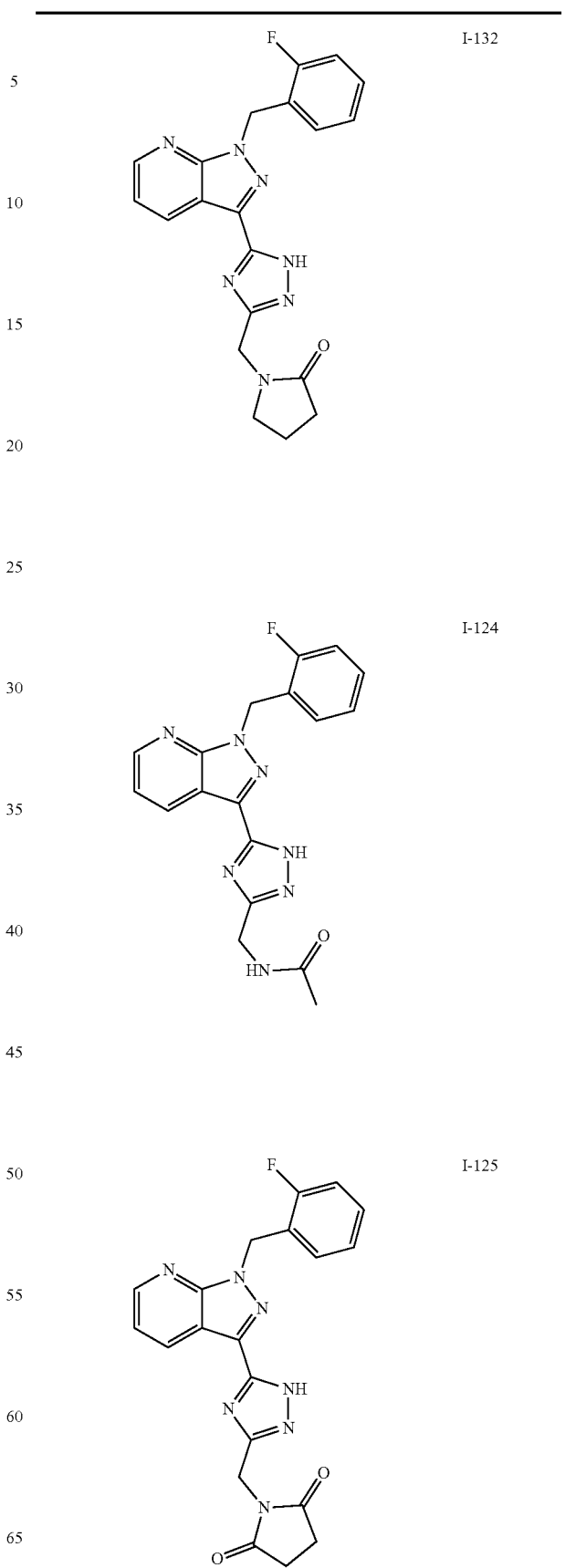

TABLE IA-continued

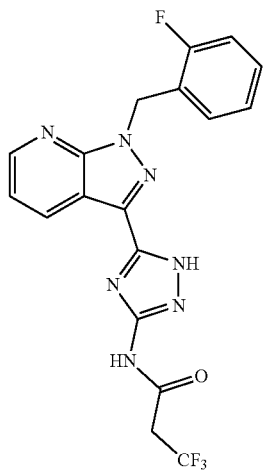 [SMILES: O=C(CC(F)(F)F)Nc1n[nH]c(-c2nn(Cc3ccccc3F)c3ncccc23)n1]

I-126

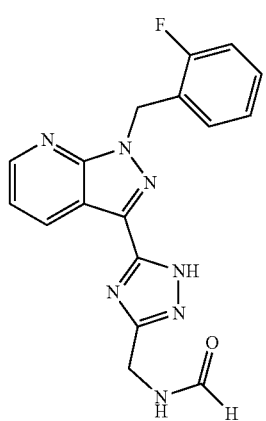 [SMILES: O=CNCc1n[nH]c(-c2nn(Cc3ccccc3F)c3ncccc23)n1]

I-133

TABLE IA-continued

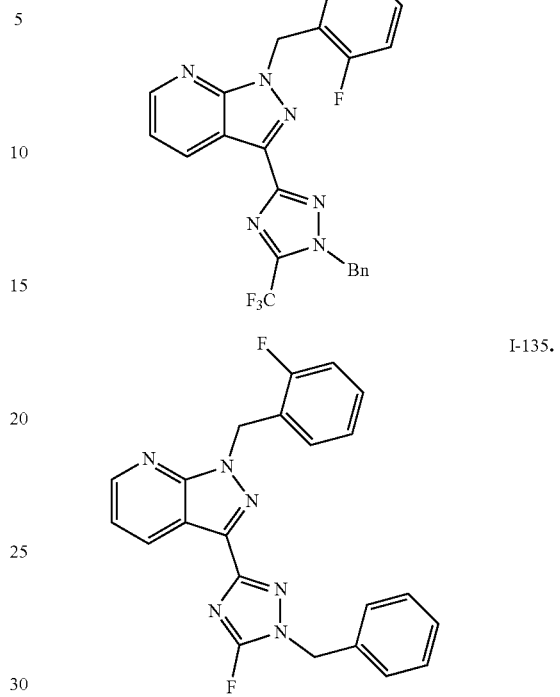

I-134

I-135.

9. A pharmaceutical composition comprising a compound according to claim 1, or a pharmaceutically acceptable salt thereof, and at least one pharmaceutically acceptable excipient or carrier.

10. A pharmaceutical composition comprising a compound according to claim 8, or a pharmaceutically acceptable salt thereof, and at least one pharmaceutically acceptable excipient or carrier.

* * * * *

UNITED STATES PATENT AND TRADEMARK OFFICE
CERTIFICATE OF CORRECTION

PATENT NO. : 11,180,493 B2
APPLICATION NO. : 16/348377
DATED : November 23, 2021
INVENTOR(S) : Rennie et al.

Page 1 of 1

It is certified that error appears in the above-identified patent and that said Letters Patent is hereby corrected as shown below:

In the Claims

In Claim 1, Column 221, Line 45, to Column 222, Line number 14, please replace the formulas:

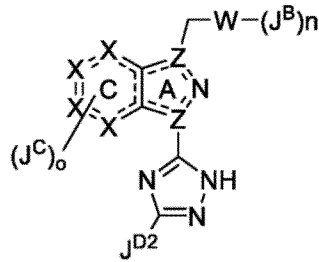 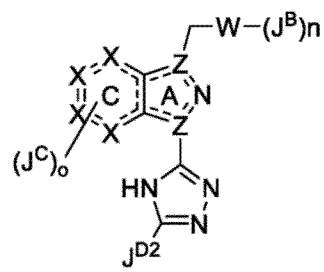 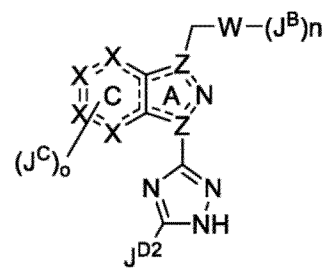

"        Formula IIA                     Formula IIB                     Formula IIC        "

With the formulas:

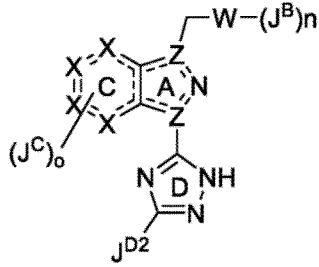 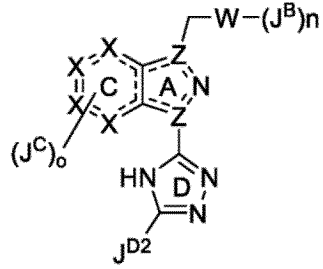 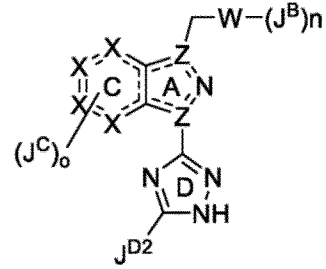

"        Formula IIA                     Formula IIB                     Formula IIC        ".

In Claim 1, Column 222, Line number 67, please replace the term "up" with the number "1".

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*